(12) United States Patent
Lunniss et al.

(10) Patent No.: US 8,906,902 B2
(45) Date of Patent: Dec. 9, 2014

(54) ANTIBACTERIAL COMPOUNDS

(71) Applicant: Biota Europe Ltd., Yarnton, Oxfordshire (GB)

(72) Inventors: Christopher James Lunniss, Notting Hill (AU); James T. Palmer, Notting Hill (AU); Gary Robert William Pitt, Notting Hill (AU); David Davies, Yarnton (GB); Lorraine Claire Axford, Notting Hill (AU)

(73) Assignee: Biota Europe Limited, Yarnton, Oxfordshire (GB)

( * ) Notice: Subject to any disclaimer, the term of this patent is extended or adjusted under 35 U.S.C. 154(b) by 0 days.

(21) Appl. No.: 13/848,118

(22) Filed: Mar. 21, 2013

(65) Prior Publication Data

US 2013/0252938 A1      Sep. 26, 2013

Related U.S. Application Data

(60) Provisional application No. 61/614,044, filed on Mar. 22, 2012.

(51) Int. Cl.
| | |
|---|---|
| *A61K 31/397* | (2006.01) |
| *A61K 31/5377* | (2006.01) |
| *A61K 31/4427* | (2006.01) |
| *C07D 413/02* | (2006.01) |
| *C07D 413/14* | (2006.01) |
| *C07D 403/02* | (2006.01) |
| *C07D 403/14* | (2006.01) |
| *C07D 401/02* | (2006.01) |
| *C07D 401/14* | (2006.01) |
| *C07D 417/02* | (2006.01) |
| *C07D 417/14* | (2006.01) |
| *C07D 417/04* | (2006.01) |

(52) U.S. Cl.
CPC ............ *C07D 417/14* (2013.01); *C07D 417/04* (2013.01)

USPC ............ 514/210.21; 514/233.8; 514/256; 514/333; 514/338; 544/122; 544/296; 544/333; 546/256; 546/270.1

(58) Field of Classification Search
USPC ............... 514/210.21, 233.8, 256, 333, 338; 544/122, 296, 333; 546/256, 270.1
See application file for complete search history.

(56) References Cited

FOREIGN PATENT DOCUMENTS

| JP | WO 2006/028226 | * | 3/2006 |
|---|---|---|---|
| WO | 2007/148093 | | 12/2007 |
| WO | 2009/074812 | | 6/2009 |
| WO | 2009/156966 | | 12/2009 |

OTHER PUBLICATIONS

[Ito, Nobuyuki. Cancer Science 94(1), (2003) 3-8.].*
PCT/AU2013/000286, Notification of Transmittal of the International Search Report and the Written Opinion, dated Jul. 25, 2013.

* cited by examiner

*Primary Examiner* — Samantha Shterengarts
(74) *Attorney, Agent, or Firm* — Banner & Witcoff, Ltd.

(57) ABSTRACT

The present invention provides a compound of the following formula, salts, racemates, diastereomers, enantiomers, esters, carbamates, phosphates, sulfates, deuterated forms and prodrugs thereof.

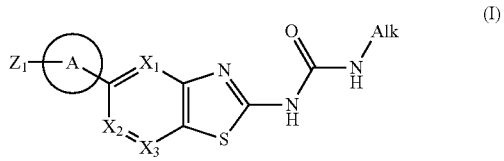

(I)

Also provided is the use of these compounds as antibacterials, compositions comprising them and processes for their manufacture.

22 Claims, 2 Drawing Sheets

A

B

ANTIBACTERIAL COMPOUNDS

FIELD OF THE INVENTION

The present invention relates to a novel class of compounds, their use as antibacterials, compositions comprising them and processes for their manufacture.

BACKGROUND

Type II topoisomerases catalyse the interconversion of DNA topoisomers by transporting one DNA segment through another. Bacteria encode two type II topoisomerase enzymes, DNA gyrase and DNA topoisomerase IV. Gyrase controls DNA supercoiling and relieves topological stress. Topoisomerase IV decatenates daughter chromosomes following replication and can also relax supercoiled DNA. Bacterial type II topoisomerases form a heterotetrameric complex composed of two subunits. Gyrase forms an $A_2B_2$ complex comprised of GyrA and GyrB whereas topoisomerase forms a $C_2E_2$ complex comprised of ParC and ParE. In contrast eukaryotic type II topoisomerases are homodimers. Ideally, an antibiotic based on the inhibition of bacterial type II topoisomerases would be selective for the bacterial enzymes and be relatively inactive against the eukaryotic type II isomerases.

The type II topoisomerases are highly conserved enzymes allowing the design of broad-spectrum inhibitors. Furthermore, the GyrB and ParE subunits are functionally similar, having an ATPase domain in the N-terminal domain and a C-terminal domain that interacts with the other subunit (GyrA and ParC respectively) and the DNA. The conservation between the gyrase and topoisomerase IV active sites suggests that inhibitors of the sites might simultaneously target both type II topoisomerases. Such dual-targeting inhibitors are attractive because they have the potential to reduce the development of target-based resistance.

Type II topoisomerases are the target of a number of antibacterial agents. The most prominent of these agents are the quinolones. The original quinolone antibiotics included nalidixic acid, cinoxacin and oxolinic acid. The addition of fluorine yielded a new class of drugs, the fluoroquinolones, which have a broader antimicrobial spectrum and improved pharmacokinetic properties. The fluoroquinolones include norfloxacin, ciprofloxacin, and fourth generation quinolones gatifloxacin and moxifloxacin. The coumarins and the cyclothialidines are further classes of antibiotics that inhibit type II topoisomerases, however they are not widely used because of poor permeability in bacteria, eukaryotic toxicity, and low water solubility. Examples of such antibiotics include novobiocin and coumermycin A1, cyclothialidine, cinodine, and clerocidin.

Linezolid is currently the standard treatment for acute bacterial skin and skin structure infections (ABSSSI) caused by Gram-positive bacteria. It belongs to the class of oxazolidinones and is a protein synthesis inhibitor.

However, the continual emergence of antibiotic resistance demands that novel classes of antibiotics continue to be developed and alternative compounds that inhibit bacterial topoisomerases are required.

WO2007/148093, WO2009/074812, WO2009/074810 and WO2012/045124 describe the applicant's earlier compounds that inhibit bacterial gyrase activity. The applicant has now discovered a class of related compounds that includes a carbocyclic or heterocyclic ring comprising a branched i.e. secondary or tertiary alcohol substituent and prodrugs thereof which appears to confer advantage(s) to the compounds. One or more advantage(s) include desirable pharmacokinetic properties, prodrugability, solubility and introduced chirality to provide a further subclass of active enantiomers.

SUMMARY

According to a first aspect there is provided a compound of Formula (I)

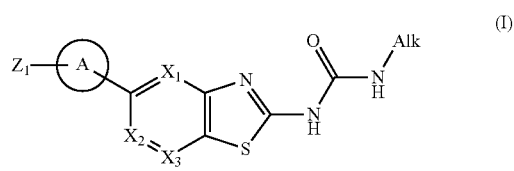

salts, racemates, diastereomers, enantiomers, esters, carbamates, phosphates, sulfates, deuterated forms and prodrugs thereof
wherein
$X_1$ is N or C—$R_1$, preferably C—$R_1$ where $R_1$ is selected from H, OH, optionally substituted $C_{1-3}$alkyl, optionally substituted $C_{2-3}$alkenyl, optionally substituted $C_{2-3}$alkynyl, optionally substituted $C_{1-3}$alkoxyl, halo, halo$C_{1-3}$alkyl, $NH_2$, optionally substituted $NHC_{1-3}$alkyl, optionally substituted $N(C_{1-3}alkyl)_2$, optionally substituted $SC_{1-3}$alkyl and CN;

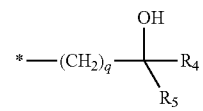

represents Ring A which is selected from saturated or unsaturated monocyclic $C_{3-7}$cycloalkyl, saturated or unsaturated monocyclic 3-7 membered heterocycle, saturated or unsaturated fused bicyclic $C_{8-10}$cycloalkyl, saturated or unsaturated fused bicyclic 8-10 membered-heterocyclyl, $C_{6-10}$aryl and 5-10 membered heteroaryl and may be optionally substituted;
$Z_1$ is a secondary or tertiary alcohol of general formula

an ester, carbamate, phosphate, sulfate or prodrug thereof as defined below or $Z_1$ is selected from H, OH, optionally substituted $C_{1-6}$alkyl, optionally substituted $C_{2-6}$alkenyl, optionally substituted $C_{2-6}$alkynyl, optionally substituted $(CH_2)_m OC_{1-6}$alkyl, optionally substituted $(CH_2)_m SC_{1-6}$alkyl, optionally substituted $(CH_2)_m S(=O)C_{1-6}$alkyl halo, optionally substituted halo$C_{1-3}$alkyl, CN and optionally substituted $(CH_2)_m NR^a R^b$ where each $R^a$ and $R^b$ is independently selected from H, optionally substituted $C_{1-6}$alkyl, optionally substituted $C_{3-6}$cycloalkyl and optionally substituted 4-6-membered heterocyclyl or $R^a$ and $R^b$ join together to form an optionally substituted 4-6-membered heterocyclyl and where each m is an integer independently selected from 0, 1, 2 and 3;
$X_2$ is N or C—$R_2$, preferably C—$R_2$ where $R_2$ is selected from H, OH, optionally substituted $C_{1-6}$alkyl, optionally substituted $C_{2-6}$alkenyl, optionally substituted $C_{2-6}$alkynyl, optionally substituted $(CH_2)_m OC_{1-6}$alkyl, optionally substituted $(CH_2)_mSC_{1-6}$alkyl, optionally substituted $(CH_2)_mS(=O)C_{1-6}$alkyl, optionally substituted $(CH_2)_m(CH_2)_mC_{3-7}$cycloalkyl, optionally substituted $(CH_2)_mC_{3-7}$cycloalkyl, optionally substituted $(CH_2)_mO(CH_2)_m$phenyl, optionally substituted $(CH_2)_m$phenyl, optionally substituted $(CH_2)_mO(CH_2)_m$-5-10-membered heterocycle, optionally substituted $(CH_2)_m$-5-10-membered heterocyclyl, halo, optionally substituted haloC$_{1-3}$alkyl, CN and optionally substituted $(CH_2)_mNR^aR^b$;

$X_3$ is N or C—$R_3$, preferably C—$R_3$ where $R_3$ is selected from H, OH, optionally substituted $C_{1-6}$alkyl, optionally substituted $C_{2-6}$alkenyl, optionally substituted $C_{2-6}$alkynyl, optionally substituted $(CH_2)_mOC_{1-6}$alkyl, optionally substituted $(CH_2)_mSC_{1-6}$alkyl, optionally substituted $(CH_2)_mS(=O)C_{1-6}$alkyl, optionally substituted $(CH_2)_mO(CH_2)_mC_{3-7}$cycloalkyl, optionally substituted $(CH_2)_mC_{3-7}$cycloalkyl, optionally substituted $(CH_2)_mO(CH_2)_m$phenyl, optionally substituted $(CH_2)_m$phenyl, optionally substituted $(CH_2)_mO(CH_2)_m$-5-10-membered heterocycle, optionally substituted $(CH_2)_m$-5-10-membered heterocyclyl, halo, optionally substituted haloC$_{1-3}$alkyl, CN and optionally substituted $(CH_2)_mNR^aR^b$ or $R_3$ is a group of formula

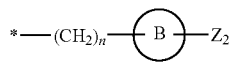

where * represents the point of attachment to the C ring atom; n is an integer selected from 0, 1, 2 and 3;

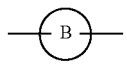

represents Ring B which is selected from saturated or unsaturated monocyclic $C_{3-7}$cycloalkyl, saturated or unsaturated monocyclic 3-7 membered heterocycle, saturated or unsaturated fused bicyclic $C_{8-10}$cycloalkyl, saturated or unsaturated fused bicyclic 8-10 membered-heterocyclyl, $C_{6-10}$aryl and 5-10 membered heteroaryl and may be optionally substituted; and $Z_2$ is a secondary or tertiary alcohol of general formula

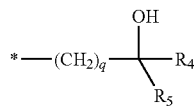

an ester, carbamate, phosphate, sulfate or prodrug thereof as defined below or $Z_2$ is selected from H, OH, optionally substituted $C_{1-6}$alkyl, optionally substituted $C_{2-6}$alkenyl, optionally substituted $C_{2-6}$alkynyl, optionally substituted $(CH_2)_mOC_{1-6}$alkyl, optionally substituted $(CH_2)_mSC_{1-6}$alkyl, optionally substituted $(CH_2)_mS(=O)C_{1-6}$alkyl, halo, optionally substituted haloC$_{1-3}$alkyl, CN, optionally substituted $(CH_2)_mNR^aR^b$, optionally substituted $(CH_2)_p$-4-6-membered heterocylyic ring, optionally substituted $(CH_2)_p$-spiro-bi-cyclic-7-11-membered heterocyclic ring and optionally substituted

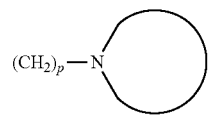

where p is an integer selected from 0, 1, 2 and 3 and

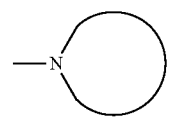

represents an optionally substituted 4-6 membered heterocyclic ring or an optionally substituted spiro bicyclic 7-11-membered heterocyclic ring; and Alk is optionally substituted $C_{1-6}$alkyl, $C_{2-6}$alkenyl, $C_{2-6}$alkynyl, $C_{3-6}$cycloalkyl; and with the proviso that $Z_1$ or $Z_2$ is a secondary or tertiary alcohol of general formula

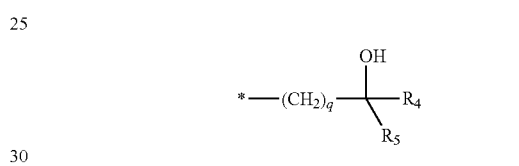

an ester, carbamate, phosphate, sulfate or prodrug thereof wherein q is an integer selected from 0, 1, 2 and 3, preferably q is 0;

$R_4$ is H or is selected from optionally substituted $C_{1-6}$alkyl, optionally substituted $C_{2-6}$alkenyl, optionally substituted $C_{2-6}$alkynyl, optionally substituted $(CH_2)_tOC_{1-6}$alkyl, optionally substituted $(CH_2)_tOC(=O)C_{1-6}$alkyl, optionally substituted $(CH_2)_tSC_{1-6}$alkyl, optionally substituted $(CH_2)_tS(=O)C_{1-6}$alkyl, halo, optionally substituted haloC$_{1-3}$alkyl and optionally substituted $(CH_2)_tNR^aR^b$;

$R_5$ is selected from optionally substituted $C_{1-6}$alkyl, optionally substituted $C_{2-6}$alkenyl, optionally substituted $C_{2-6}$alkynyl, optionally substituted $C_{3-7}$cycloalkyl ring, optionally substituted phenyl, optionally substituted 4-6-membered heterocyclyl ring, optionally substituted 5-6-membered heteroaryl ring, optionally substituted $(CH_2)_tOC_{1-6}$alkyl, optionally substituted $(CH_2)_tOC(=O)C_{1-6}$alkyl, optionally substituted $(CH_2)_tSC_{1-6}$alkyl, optionally substituted $(CH_2)_tS(=O)C_{1-6}$alkyl, halo, optionally substituted haloC$_{1-3}$alkyl and optionally substituted $(CH_2)_tNR^aR^b$;

t is an integer selected from 1, 2, 3, 4, 5 and 6;

or $R_4$ and $R_5$ together with the carbon atom to which they are attached form an optionally substituted 4-6-membered heterocyclic ring or $C_{3-7}$cycloalkyl ring; and

* represents the point of attachment to Ring A or Ring B respectively; and further wherein each (CH$_2$) entity when present may be independently optionally substituted.

In one embodiment there is provided a compound of Formula (I), salts and prodrugs thereof.

In one embodiment $Z_1$ is a secondary or tertiary alcohol of general formula

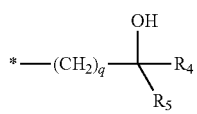

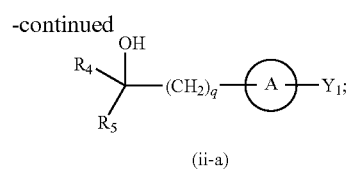

(ii-a)

or prodrug thereof wherein the prodrug is selected from an ester, carbamate, phosphate or sulfate formed from the hydroxyl moiety. According to a second aspect there is provided a method for the treatment of a bacterial infection comprising administration of a compound of Formula (I) or a pharmaceutically acceptable salt, racemate, diastereomer, enantiomer, ester, carbamate, phosphate, sulphate, deuterated form or prodrug thereof to a subject suffering from said infection. In one embodiment, the infection is a Gram positive bacterial infection. In a further embodiment the Gram positive infection is caused by a bacterial strain selected from S. aureus, E. faecalis and S. pyogenes, even more preferably S. aureus. In another embodiment, the infection is a Gram negative bacterial infection. In a further embodiment the Gram negative infection is caused by a bacterial strain of H. influenzae, A. baumannii, E. coli, K. pneumoniae, Legionella pneumophila, Moraxella catarrhalis and Neisseria gonorrhoeae.

According to a third aspect there is provided a compound of Formula (I) or a pharmaceutically acceptable salt, racemate, diastereomer, enantiomer, ester, carbamate, phosphate, sulphate, deuterated form or prodrug thereof for use in the treatment of a bacterial infection.

According to a fourth aspect there is provided an antibacterial agent comprising a compound of Formula (I) or a pharmaceutically acceptable salt, racemate, diastereomer, enantiomer, ester, carbamate, phosphate, sulphate, deuterated form or prodrug thereof.

According to a fifth aspect there is provided a composition comprising a compound of Formula (I) or a salt, racemate, diastereomer, enantiomer, ester, carbamate, phosphate, sulphate, deuterated form or prodrug thereof and an excipient or carrier. In one embodiment the composition is a pharmaceutical composition, the salt is a pharmaceutically acceptable salt and the excipient or carrier is pharmaceutically acceptable.

According to a sixth aspect there is provided a compound of Formula (I) or a pharmaceutically acceptable salt, racemate, diastereomer, enantiomer, ester, carbamate, phosphate, sulphate, deuterated form or prodrug thereof for use as a gyrase inhibitor. In one embodiment the compound of Formula (I) is active against the ATPase enzyme.

According to a seventh aspect there is provided a process for the manufacture of a compound of Formula (I), salt, racemate, diastereomer, enantiomer, ester, carbamate, phosphate, sulphate, deuterated form or prodrug thereof comprising the step(s) of:

coupling an intermediate of formula (i-a) with a precursor of formula (ii-a):

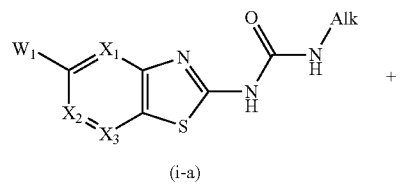

(i-a)

or alternatively coupling an intermediate of formula (i-b) with a precursor of formula (ii-b):

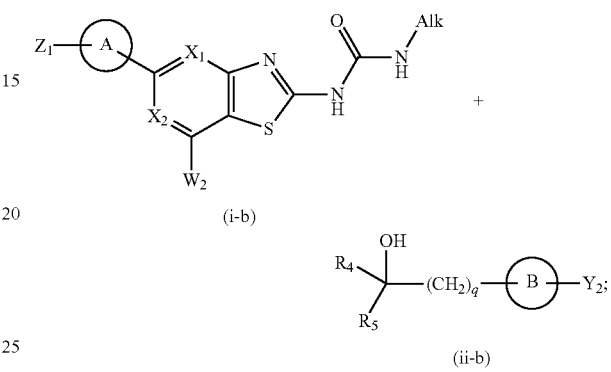

(i-b)

$$R_4 \underset{R_5}{\overset{OH}{-}} (CH_2)_q - B - Y_2;$$

(ii-b)

under coupling conditions wherein $W_1$ and $W_2$ are selected from halo (preferably Cl, Br and I), boronic acid or a boronate ester thereof, a stannylated moiety and triflate;

$Y_1$ and $Y_2$ are selected from H, halo (preferably Cl, Br and I), boronic acid or a boronate ester thereof, a stannylated moiety and triflate; and ring A, ring B, Alk, $X_1$, $X_2$, $X_3$, $R_4$, $R_5$ and q are as previously defined.

In one embodiment, the process comprises the additional step of forming an ester, carbamate, phosphate or sulphate of the hydroxyl (alcohol) moiety.

According to an eighth aspect, there is provided a method of treating bacterial contamination of a substrate comprising applying to the site of such contamination an amount of a compound of Formula (I) or a pharmaceutically acceptable salt, racemate, diastereomer, enantiomer, ester, carbamate, phosphate, sulphate, or deuterated form thereof sufficient to inhibit bacterial growth.

According to a ninth aspect, there is provided the use of a compound of Formula (I) or a pharmaceutically acceptable salt, racemate, diastereomer, enantiomer, ester, carbamate, phosphate, sulphate, deuterated form or prodrug thereof in the preparation of a medicament for the treatment of a bacterial infection in a subject.

DETAILED DESCRIPTION

Figure 1:
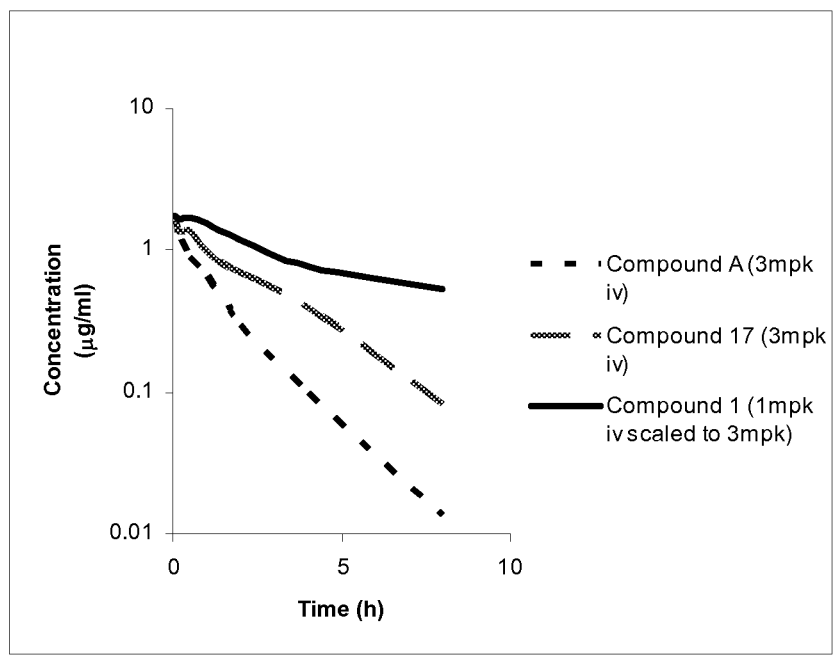
FIG. 1: Shows the intravenous (IV) pharmacokinetic profile in the rat assay, where the X axis denotes the time (hours) and the Y axis denotes the plasma concentration (μg/mL), of (A) comparative Compound A against Compounds 1 and 17 of the invention; and (B) comparative Compound B against Compound 27 of the invention.
Figure 1:
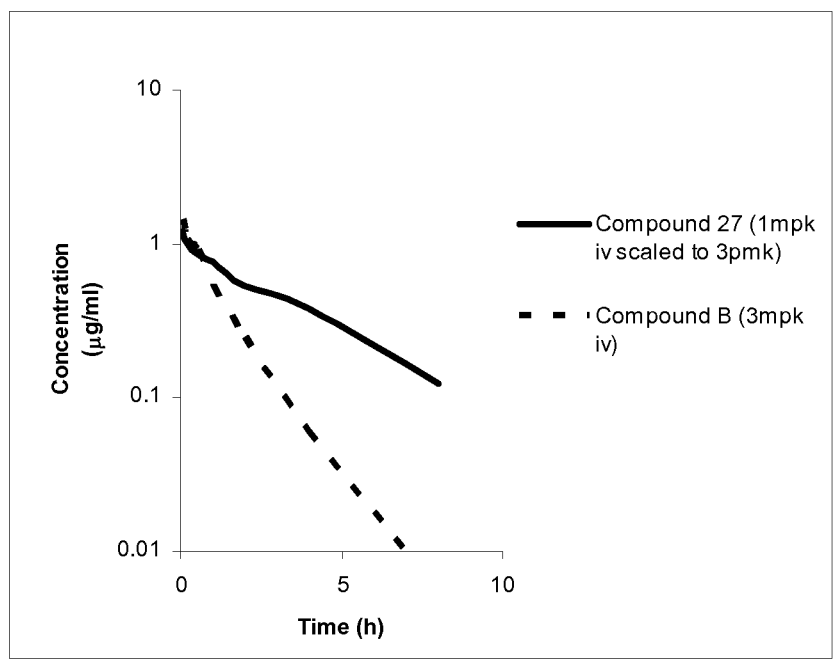

The present invention is predicated on the discovery of a new class of compounds that have shown on-target gyrase enzyme activity. Accordingly, in one embodiment the compounds of Formula (I) are useful in modulating the activity of gyrase, more particularly as gyrase inhibitors.

Compounds of this class also exhibit antibacterial activity, more particularly antibacterial activity against strains of Gram-positive and/or Gram-negative classes, such as staphylococci, enterococci, streptococci and haemophili for example *Staphylococcus aureus, Staphylococcus epidermidis, Enterococcus faecalis, Enterococcus faecium, Streptococcus pyogenes, Streptococcus pneumoniae, Haemophilus influenzae, Acinetobacter baumannii, Escherichia coli, Klebsiella pneumoniae, Legionella pneumophila, Moraxella catarrhalis* and *Neisseria gonorrhoeae*. The compounds with which the invention is concerned are therefore useful for the treatment of bacterial infection or contamination, for example in the treatment of, inter alia, Gram-positive infections, Gram-negative infections and community acquired bacterial pneumonias (CABPs), hospital acquired bacterial pneumonias (HABPs) and ventilator acquired bacterial pneuomias (VABPs). Accordingly, in one embodiment the compounds of Formula (I) are useful in the treatment of bacterial infections caused by Gram positive bacterial strains. In another embodiment, the compounds of Formula (I) are useful in the treatment of bacterial infections caused by Gram negative bacterial strains. The sites of bacterial infections are many and include respiratory infections, particularly lung infections, skin and skin structure infections, urinary tract infections, intra-abdominal infections and blood stream (septicaemia) infections.

The development of antibacterial resistance is particularly common in a hospital setting. Hospital patients are therefore especially at risk of infection by resistant strains of bacteria.

DEFINITIONS

Unless otherwise herein defined, the following terms will be understood to have the general meanings which follow.

The term "$C_{1-6}$alkyl" encompasses optionally substituted straight chain or branched chain hydrocarbon groups having from 1, 2, 3, 4, 5 or 6 carbon atoms or a range comprising any of two of those integers. Examples include methyl (Me), ethyl (Et), propyl (Pr), isopropyl (i-Pr), butyl (Bu), isobutyl (i-Bu), sec-butyl (s-Bu), tert-butyl (t-Bu), pentyl, neopentyl, hexyl and the like. Unless the context requires otherwise, the term "$C_{1-6}$alkyl" also encompasses alkyl groups containing one less hydrogen atom such that the group is attached via two positions i.e. divalent. Such groups are also referred to as "$C_{1-6}$alkylene" groups. $C_{1-3}$alkyl and $C_{1-3}$alkylene groups are preferred.

The term "$C_{2-6}$alkenyl" refers to optionally substituted straight chain or branched chain hydrocarbon groups having at least one double bond of either E or Z stereochemistry where applicable and 2, 3, 4, 5 or 6 carbon atoms or a range comprising any of two of those integers. Examples include vinyl, 1-propenyl, 1- and 2-butenyl, 2-methyl-2-propenyl, hexenyl, butadienyl, hexadienyl, hexatrienyl and the like. Unless the context requires otherwise, the term "$C_{1-6}$alkenyl" also encompasses alkenyl groups containing one less hydrogen atom such that the group is attached via two positions i.e. divalent. Such groups are also referred to as "$C_{2-6}$alkenylene" groups. $C_{2-3}$alkenyl and $C_{2-3}$alkenylene groups are preferred.

The term "$C_{2-6}$alkynyl" refers to optionally substituted straight chain or branched chain hydrocarbon groups having at least one triple bond and 2, 3, 4, 5 or 6 carbon atoms or a range comprising any of two of those integers. Examples include ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl, 5-hexynyl and the like. Unless the context indicates otherwise, the term "$C_{2-6}$alkynyl" also encompasses alkynyl groups containing one less hydrogen atom such that the group is attached via two positions i.e. divalent. Such groups are also referred to as "$C_{2-6}$alkynylene" groups. $C_{2-3}$alkynyl and $C_{2-3}$alkynylene groups are preferred.

The term "$C_{3-8}$cycloalkyl" refers to non-aromatic cyclic hydrocarbon groups having from 3, 4, 5, 6, 7 or 8 carbon atoms or a range comprising any of two of those integers, including cyclopropyl, cyclobutyl, cyclopentyl, cyclohexyl, cyclohexenyl, cycloheptyl and the like. It will be understood that cycloalkyl groups may be saturated such as cyclohexyl or unsaturated such as cyclohexenyl. $C_{3-6}$cycloalkyl groups are preferred.

The terms "hydroxy" and "hydroxyl" refer to the group —OH.

The term "oxo" refers to the group =O.

The term "$C_{1-6}$alkoxyl" refers to the group $OC_{1-6}$alkyl. Examples include methoxy, ethoxy, propoxy, isoproxy, butoxy, tert-butoxy, pentoxy and the like. The oxygen atom may be located along the hydrocarbon chain, and need not be the atom linking the group to the remainder of the compound. $C_{1-3}$alkoxyl groups are preferred.

The term "aryloxy" refers to the group —Oaryl and may include variations thereof such as "alkoxyaryl", wherein aryl is defined herein. Examples include, but are not limited to, phenoxy and naphthoxy and benzyloxy.

The terms "halo", "halogen", "halogenated" and similar terms refers to fluoro, chloro, bromo and iodo (F, Cl, Br, I).

The term "$C_{1-6}$alkylhalo" refers to a $C_{1-6}$alkyl which is substituted with one or more halogens. $C_{1-3}$alkylhalo groups are preferred, such as for example, —$CHF_2$ and —$CF_3$. The term "$C_{1-6}$alkoxylhalo" refers to a $C_{1-6}$alkoxyl which is substituted with one or more halogens. $C_{1-3}$alkoxylhalo groups are preferred, such as for example, —$OCHF_2$ and —$OCF_3$.

The term "carboxylate" or "carboxyl" refers to the group —COO⁻ or —COOH.

The term "ester" refers to a carboxyl group having the hydrogen replaced with, for example a $C_{1-6}$alkyl group ("carboxyl$C_{1-6}$alkyl" or "alkylester"), an aryl or aralkyl group ("arylester" or "aralkylester") and so on. Examples include but are not limited to $CO_2C_{1-3}$alkyl, such as for example, methylester ($CO_2Me$), ethylester ($CO_2Et$) and propylester ($CO_2Pr$) and includes reverse esters thereof (e.g. —OCOMe, —OCOEt and —OCOPr).

The term "cyano" refers to the group —CN.

The term "nitro" refers to the group —$NO_2$.

The term "amino" refers to the group —$NH_2$.

The term "substituted amino" or "secondary amino" refers to an amino group having a hydrogen replaced with, for example a $C_{1-6}$alkyl group ("$C_{1-6}$alkylamino"), an aryl or aralkyl group ("arylamino", "aralkylamino") and so on. $C_{1-3}$alkylamino groups are preferred, such as for example, methylamino (NHMe), ethylamino (NHEt) and propylamino (NHPr).

The term "disubstituted amino" or "tertiary amino" refers to an amino group having the two hydrogens replaced with, for example a $C_{1-6}$alkyl group, which may be the same or different ("dialkylamino"), an aryl and alkyl group ("aryl(alkyl)amino") and so on. Di($C_{1-3}$alkyl)amino groups are preferred, such as for example, dimethylamino ($NMe_2$), diethylamino ($NEt_2$), dipropylamino ($NPr_2$) and variations thereof (e.g. N(Me)(Et) and so on).

The term "acyl" or "aldehyde" refers to the group —C(=O)H.

The term "substituted acyl" or "ketone" refers to an acyl group having a hydrogen replaced with, for example a $C_{1-6}$alkyl group ("$C_{1-6}$alkylacyl" or "alkylketone" or "ketoalkyl"), an aryl group ("arylketone"), an aralkyl group ("aralkylketone") and so on. $C_{1-3}$alkylacyl groups are preferred.

The term "amido" or "amide" refers to the group —C(O)NH$_2$.

The term "aminoacyl" refers to the group —NHC(O)H.

The term "substituted amido" or "substituted amide" refers to an amido group having a hydrogen replaced with, for example a $C_{1-6}$alkyl group ("$C_{1-6}$alkylamido" or "$C_{1-6}$alkylamide"), an aryl ("arylamido"), aralkyl group ("aralkylamido") and so on. $C_{1-3}$alkylamide groups are preferred, such as for example, methylamide (—C(O)NHMe), ethylamide (—C(O)NHEt) and propylamide (—C(O)NHPr) and includes reverse amides thereof (e.g.—NHMeC(O)—, —NHEtC(O)— and —NHPrC(O)—).

The term "disubstituted amido" or "disubstituted amide" refers to an amido group having the two hydrogens replaced with, for example a $C_{1-6}$alkyl group ("di($C_{1-6}$alkyeamido") or "di($C_{1-6}$alkyeamide"), an aralkyl and alkyl group ("alkyl(aralkyl)amido") and so on. Di($C_{1-3}$alkyeamide groups are preferred, such as for example, dimethylamide (—C(O)NMe$_2$), diethylamide (—C(O)NEt$_2$) and dipropylamide (—C(O)NPr$_2$) and variations thereof (e.g. —C(O)N(Me)Et and so on) and includes reverse amides thereof.

The term "carbamic acid" refers to the group NH$_2$CO$_2$H.

The term "carbamate" refers to a carbamic acid group having one or both amino hydrogens independently replaced with, for example a $C_{1-6}$alkyl group ("$C_{1-6}$alkyl carbamate"), an aryl ("arylcarbamate"), aralkyl group ("aralkylcarbamate") and so on.

The term "thiol" refers to the group —SH.

The term "$C_{1-6}$alkylthio" refers to a thiol group having the hydrogen replaced with a $C_{1-6}$alkyl group. $C_{1-3}$alkylthio groups are preferred, such as for example, thiolmethyl, thiolethyl and thiolpropyl.

The term "thioxo" refers to the group =S.

The term "sulfinyl" refers to the group —S(=O)H.

The term "substituted sulfinyl" or "sulfoxide" refers to a sulfinyl group having the hydrogen replaced with, for example a $C_{1-6}$alkyl group ("$C_{1-6}$alkylsulfinyl" or "$C_{1-6}$alkylsulfoxide"), an aryl ("arylsulfinyl"), an aralkyl ("aralkyl sulfinyl") and so on. $C_{1-3}$alkylsulfinyl groups are preferred, such as for example, —SOmethyl, —SOethyl and —SOpropyl.

The term "sulfonyl" refers to the group —SO$_2$H.

The term "substituted sulfonyl" refers to a sulfonyl group having the hydrogen replaced with, for example a $C_{1-6}$alkyl group ("sulfonyl$C_{1-6}$alkyl"), an aryl ("arylsulfonyl"), an aralkyl ("aralkylsulfonyl") and so on. Sulfonyl$C_{1-3}$alkyl groups are preferred, such as for example, —SO$_2$Me, —SO$_2$Et and —SO$_2$Pr.

The term "sulfonylamido" or "sulfonamide" refers to the group —SO$_2$NH$_2$.

The term "substituted sulfonamido" or "substituted sulphonamide" refers to an sulfonylamido group having a hydrogen replaced with, for example a $C_{1-6}$alkyl group ("sulfonylamido$C_{1-6}$alkyl"), an aryl ("arylsulfonamide"), aralkyl ("aralkylsulfonamide") and so on. Sulfonylamido$C_{1-3}$alkyl groups are preferred, such as for example, —SO$_2$NHMe, —SO$_2$NHEt and —SO$_2$NHPr and includes reverse sulfonamides thereof (e.g. —NHSO$_2$Me, —NHSO$_2$Et and —NHSO$_2$Pr).

The term "disubstituted sulfonamido" or "disubstituted sulphonamide" refers to a sulfonylamido group having the two hydrogens replaced with, for example a $C_{1-6}$alkyl group, which may be the same or different ("sulfonylamidodi($C_{1-6}$alkyl)"), an aralkyl and alkyl group ("sulfonamido(aralkyl)alkyl") and so on. Sulfonylamidodi($C_{1-3}$alkyl) groups are preferred, such as for example, —SO$_2$NMe$_2$, —SO$_2$NEt$_2$ and —SO$_2$NPr$_2$ and variations thereof (e.g. —SO$_2$N(Me)Et and so on) and includes reverse sulfonamides thereof.

The term "sulfate" refers to the group OS(O)$_2$OH and includes groups having the hydrogen replaced with, for example a $C_{1-6}$alkyl group ("alkylsulfates"), an aryl ("arylsulfate"), an aralkyl ("aralkylsulfate") and so on. $C_{1-3}$sulfates are preferred, such as for example, OS(O)$_2$OMe, OS(O)$_2$OEt and OS(O)$_2$OPr.

The term "sulfonate" refers to the group SO$_3$H and includes groups having the hydrogen replaced with, for example a $C_{1-6}$alkyl group ("alkylsulfonate"), an aryl ("arylsulfonate"), an aralkyl ("aralkylsulfonate") and so on. $C_{1-3}$sulfonates are preferred, such as for example, SO$_3$Me, SO$_3$Et and SO$_3$Pr.

The term "phosphate" refers to a group —OP(O)(OH)$_2$ and includes groups having each hydrogen independently replaced with, for example a $C_{1-6}$alkyl group ("alkylphosphate"), an aryl ("arylphosphate"), an aralkyl ("aralkylphosphate") and so on.

The term "phosphonate" refers to a group —P(O)(OH)$_2$ and includes groups having each hydrogen independently replaced with, for example a $C_{1-6}$alkyl group ("alkylphosphonate"), an aryl ("arylphosphonate"), an aralkyl ("aralkylphosphphmate") and so on.

The term "aryl" refers to any group containing a carbocyclic (non-heterocyclic) aromatic ring and may be a mono-, bi- or tri-cyclic ring system. The aromatic ring or ring system is generally composed of 6 or 10 carbon atoms. Such groups may contain fused ring systems (such as naphthyl, tetrahydronaphthyl, fluorenyl, indenyl, azulenyl, anthracenyl and the like), linked ring systems (such as biphenyl groups), and may be substituted or unsubstituted. Examples of aryl groups include, but are not limited to, phenyl, biphenyl, naphthyl and tetrahydronaphthyl. Phenyl is preferred.

The term "aralkyl" refers to an aryl group substituted with a $C_{1-6}$alkyl group. Examples include benzyl and phenethyl.

The term "heterocyclyl" refers to a moiety obtained by removing a hydrogen atom from a ring atom of a heterocyclic compound which moiety has from 3 to 10 ring atoms (unless otherwise specified), of which 1, 2, 3 or 4 are ring heteroatoms each heteroatom being independently selected from O, S and N.

In this context, the prefixes 3-, 4-, 5-, 6-, 7-, 8-, 9- and 10-membered denote the number of ring atoms, or range of ring atoms, whether carbon atoms or heteroatoms. For example, the term "3-10 membered heterocyclyl", as used herein, pertains to a heterocyclyl group having 3, 4, 5, 6, 7, 8, 9 or 10 ring atoms or a range comprising any of two of those integers. Examples of heterocyclyl groups include 5-6-membered monocyclic heterocyclyls and 9-10 membered fused bicyclic heterocyclyls.

Examples of monocyclic heterocyclyl groups include, but are not limited to, those containing one nitrogen atom such as aziridine (3-membered ring), azetidine (4-membered ring), pyrrolidine (tetrahydropyrrole), pyrroline (e.g., 3-pyrroline, 2,5-dihydropyrrole), 2H-pyrrole or 3H-pyrrole (isopyrrole, isoazole) or pyrrolidinone (5-membered rings), piperidine, dihydropyridine, tetrahydropyridine (6-membered rings), and azepine (7-membered ring); those containing two nitrogen atoms such as imidazoline, pyrazolidine (diazolidine), imidazoline, pyrazoline (dihydropyrazole) (5-membered rings), piperazine (6-membered ring); those containing one oxygen atom such as oxirane (3-membered ring), oxetane (4-membered ring), oxolane (tetrahydrofuran), oxole (dihydrofuran) (5-membered rings), oxane (tetrahydropyran), dihydropyran, pyran (6-membered rings), oxepin (7-membered ring); those containing two oxygen atoms such as dioxolane (5-membered ring), dioxane (6-membered ring), and dioxepane (7-membered ring); those containing three oxygen atoms such as trioxane (6-membered ring); those containing one sulfur atom such as thiirane (3-membered ring), thietane (4-membered ring), thiolane (tetrahydrothiophene) (5-membered ring), thiane (tetrahydrothiopyran) (6-membered ring), thiepane (7-membered ring); those containing one nitrogen and one oxygen atom such as tetrahydrooxazole, dihydrooxazole, tetrahydroisoxazole, dihydroisoxazole (5-membered rings), morpholine, tetrahydrooxazine, dihydrooxazine, oxazine (6-membered rings); those containing one nitrogen and one sulfur atom such as thiazoline, thiazolidine (5-membered rings), thiomorpholine (6-membered ring); those containing two nitrogen and one oxygen atom such as oxadiazine (6-membered ring); those containing one oxygen and one sulfur such as: oxathiole (5-membered ring) and oxathiane (thioxane) (6-membered ring); and those containing one nitrogen, one oxygen and one sulfur atom such as oxathiazine (6-membered ring).

Heterocyclyls also encompass aromatic heterocyclyls and non-aromatic heterocyclyls. Such groups may be substituted or unsubstituted.

The term "aromatic heterocyclyl" may be used interchangeably with the term "heteroaromatic" or the term "heteroaryl" or "hetaryl". The heteroatoms in the aromatic heterocyclyl group may be independently selected from N, S and O.

"Heteroaryl" is used herein to denote a heterocyclic group having aromatic character and embraces aromatic monocyclic ring systems and polycyclic (e.g. bicyclic) ring systems containing one or more aromatic rings. The term aromatic heterocyclyl also encompasses pseudoaromatic heterocyclyls. The term "pseudoaromatic" refers to a ring system which is not strictly aromatic, but which is stabilized by means of delocalization of electrons and behaves in a similar manner to aromatic rings. The term aromatic heterocyclyl therefore covers polycyclic ring systems in which all of the fused rings are aromatic as well as ring systems where one or more rings are non-aromatic, provided that at least one ring is aromatic. In polycyclic systems containing both aromatic and non-aromatic rings fused together, the group may be attached to another moiety by the aromatic ring or by a non-aromatic ring.

Examples of heteroaryl groups are monocyclic and bicyclic groups containing from five to ten ring members. The heteroaryl group can be, for example, a five membered or six membered monocyclic ring or a bicyclic structure formed from fused five and six membered rings or two fused six membered rings or two fused five membered rings. Each ring may contain up to about four heteroatoms typically selected from nitrogen, sulfur and oxygen. The heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Aromatic heterocyclyl groups may be 5-membered or 6-membered monocyclic aromatic ring systems.

Examples of 5-membered monocyclic heteroaryl groups include but are not limited to furanyl, thienyl, pyrrolyl, oxazolyl, oxadiazolyl (including 1,2,3 and 1,2,4oxadiazolyls and furazanyl i.e. 1,2,5-oxadiazolyl), thiazolyl, isoxazolyl, isothiazolyl, pyrazolyl, imidazolyl, triazolyl (including 1,2,3, 1,2,4 and 1,3,4triazolyls), oxatriazolyl, tetrazolyl, thiadiazolyl (including 1,2,3 and 1,3,4thiadiazolyls) and the like.

Examples of 6-membered monocyclic heteroaryl groups include but are not limited to pyridinyl, pyrimidinyl, pyridazinyl, pyrazinyl, triazinyl, pyranyl, oxazinyl, dioxinyl, thiazinyl, thiadiazinyl and the like. Examples of 6-membered heteroaryl groups containing nitrogen include pyridyl (1 nitrogen), pyrazinyl, pyrimidinyl and pyridazinyl (2 nitrogens). It will be understood that, such as in the case of pyridyl when substituted with an oxo (=O) substituted the group may be interchangeably referred to as a pyridinone group.

Aromatic heterocyclyl groups may also be bicyclic or polycyclic heteroaromatic ring systems such as fused ring systems (including purine, pteridinyl, napthyridinyl, 1H thieno[2,3-c] pyrazolyl, thieno[2,3-b]furyl and the like) or linked ring systems (such as oligothiophene, polypyrrole and the like). Fused ring systems may also include aromatic 5-membered or 6-membered heterocyclyls fused to carbocyclic aromatic rings such as phenyl, naphthyl, indenyl, azulenyl, fluorenyl, anthracenyl and the like, such as 5- or 6-membered aromatic heterocyclyls fused to a phenyl ring including 5-membered aromatic heterocyclyls containing nitrogen fused to a phenyl ring, 5-membered aromatic heterocyclyls containing 1 or 2 nitrogens fused to a phenyl ring and such as 5- or 6-membered aromatic heteroaryls fused to a 6-membered aromatic or non-aromatic heterocyclyls.

A bicyclic heteroaryl group may be, for example, a group selected from: a) a benzene ring fused to a 5- or 6-membered ring containing 1, 2 or 3 ring heteroatoms; b) a pyridine ring fused to a 5- or 6-membered ring containing 1, 2 or 3 ring heteroatoms; c) a pyrimidine ring fused to a 5- or 6-membered ring containing 1 or 2 ring heteroatoms; d) a pyrrole ring fused to a 5- or 6-membered ring containing 1, 2 or 3 ring heteroatoms; e) a pyrazole ring fused to a 5- or 6-membered ring containing 1 or 2 ring heteroatoms; f) an imidazole ring fused to a 5- or 6-membered ring containing 1 or 2 ring heteroatoms; g) an oxazole ring fused to a 5- or 6-membered ring containing 1 or 2 ring heteroatoms; h) an isoxazole ring fused to a 5- or 6-membered ring containing 1 or 2 ring heteroatoms; i) a thiazole ring fused to a 5- or 6-membered ring containing 1 or 2 ring heteroatoms; j) an isothiazole ring fused to a 5- or 6-membered ring containing 1 or 2 ring heteroatoms; k) a thiophene ring fused to a 5- or 6-membered ring containing 1, 2 or 3 ring heteroatoms; l) a furan ring fused to a 5- or 6-membered ring containing 1, 2 or 3 ring heteroatoms; m) a cyclohexyl ring fused to a 5- or 6-membered ring containing 1, 2 or 3 ring heteroatoms; and n) a cyclopentyl ring fused to a 5- or 6-membered ring containing 1, 2 or 3 ring heteroatoms.

Particular examples of bicyclic heteroaryl groups containing a five membered ring fused to another five membered ring i.e. 8-membered fused bicyclic rings include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring i.e. 9-membered fused bicyclic rings include but are not limited to benzofuran, benzothiophene, benzimidazole, benzoxazole, isobenzoxazole, benzisoxazole, benzothiazole, benzisothiazole, isobenzofuran, indole, isoindole, indolizine, indoline, isoindoline, purine (e.g., adenine, guanine), indazole, imidazopyridine (e.g. imidazo[1,2-a]pyridine and imidazo[4,5-b]pyridine], pyrazolopyrimidine (e.g. pyrazolo[1,5-a]pyrimidine), benzodioxole and pyrazolopyridine (e.g. pyrazolo[1,5-a]pyridine) groups. A further example of a six membered ring fused to a five membered ring is a pyrrolopyridine group such as a pyrrolo[2,3-b]pyridine group.

Particular examples of bicyclic heteroaryl groups containing two fused six membered rings i.e. 10-membered fused bicyclic rings include but are not limited to quinoline, isoquinoline, chroman, thiochroman, chromene (including optionally substituted with oxo (═O) i.e. oxochromene), isochromene, isochroman, benzodioxan, quinolizine, benzoxazine, benzodiazine, pyridopyridine, quinoxaline, quinazoline, cinnoline, phthalazine, naphthyridine and pteridine groups.

Examples of heteroaryl groups containing an aromatic ring and a non-aromatic ring include tetrahydronaphthalene, tetrahydroisoquinoline, tetrahydroquinoline, dihydrobenzothiophene, dihydrobenzofuran, 2,3-dihydro-benzo[1,4]dioxine, benzo[1,3]dioxole, 4,5,6,7-tetrahydrobenzofuran, indoline, isoindoline and indane groups.

Examples of aromatic heterocyclyls fused to carbocyclic aromatic rings may therefore include but are not limited to benzothiophenyl, indolyl, isoindolyl, benzofuranyl, isobenzofuranyl, benzimidazolyl, indazolyl, benzoxazolyl, benzisoxazolyl, isobenzoxazoyl, benzothiazolyl, benzisothiazolyl, quinolinyl, isoquinolinyl, quinoxalinyl, quinazolinyl, cinnolinyl, benzotriazinyl, phthalazinyl, carbolinyl and the like.

The term "non-aromatic heterocyclyl" encompasses optionally substituted saturated and unsaturated rings which contain at least one heteroatom selected from the group consisting of N, S and O.

Non-aromatic heterocyclyls may be 3-7 membered monocyclic rings. The term "3-7 membered monocyclic", as used herein, pertains to a mono-cyclic group having 3, 4, 5, 6 or 7 ring atoms or a range comprising any of two of those integers. Examples of 5-membered non-aromatic heterocyclyl rings include 2H-pyrrolyl, 1-pyrrolinyl, 2-pyrrolinyl, 3-pyrrolinyl, pyrrolidinyl, 1-pyrrolidinyl, 2-pyrrolidinyl, 3-pyrrolidinyl, tetrahydrofuranyl, tetrahydrothiophenyl, pyrazolinyl, 2-pyrazolinyl, 3-pyrazolinyl, pyrazolidinyl, 2-pyrazolidinyl, 3-pyrazolidinyl, imidazolidinyl, 3-dioxalanyl, thiazolidinyl, isoxazolidinyl, 2-imidazolinyl and the like.

Examples of 6-membered non-aromatic heterocyclyls include piperidinyl, piperidinonyl, pyranyl, dihyrdopyranyl, tetrahydropyranyl, 2H pyranyl, 4H pyranyl, thianyl, thianyl oxide, thianyl dioxide, piperazinyl, diozanyl, 1,4-dioxinyl, 1,4-dithianyl, 1,3,5-triozalanyl, 1,3,5-trithianyl, 1,4-morpholinyl, thiomorpholinyl, 1,4-oxathianyl, triazinyl, 1,4-thiazinyl and the like.

Examples of 7-membered non-aromatic heterocyclyls include azepanyl, oxepanyl, thiepanyl and the like.

Non-aromatic heterocyclyl rings may also be bicyclic heterocyclyl rings such as linked ring systems (for example uridinyl and the like) or fused ring systems. Fused ring systems include non-aromatic 5-membered, 6-membered or 7-membered heterocyclyls fused to carbocyclic aromatic rings such as phenyl, naphthyl, indenyl, azulenyl, fluorenyl, anthracenyl and the like. Examples of non-aromatic 5-membered, 6-membered or 7-membered heterocyclyls fused to carbocyclic aromatic rings include indolinyl, benzodiazepinyl, benzazepinyl, dihydrobenzofuranyl and the like.

The term "spiro ring system" means a bicyclic ring system in which the rings are connected via a single shared atom or "spiroatom" more particularly a quaternery carbon ("spiro carbon") and encompasses spiro bicyclic 7-11-membered carbocyclic rings and spiro bicyclic 7-11-membered heterocyclic rings containing one, two, three or four heteroatoms independently selected from O, N and S.

The term "derived from an amino acid" refers to any side chain that may be present in natural (L-) or unnatural (D-) amino acids. Examples of amino acid side chain moieties derived from natural amino acids, with the amino acids from which they are derived shown in brackets, are —H (Glycine), —CH$_3$ (Alanine), —CH(CH$_3$)$_2$ (Valine), —CH$_2$CH(CH$_3$)$_2$ (Leucine), —CH(CH$_3$)CH$_2$CH$_3$ (Isoleucine), —(CH$_2$)$_4$NH$_2$ (Lysine), —(CH$_2$)$_3$NHC(═NH)NH$_2$ (Arginine), —CH$_2$-(5-1H-imidazolyl) (Histidine), —CH$_2$CONH$_2$ (Asparagine), —CH$_2$CH$_2$CONH$_2$ (Glutamine), —CH$_2$COOH (Aspartic acid), —CH$_2$CH$_2$COOH (Glutamic acid), —CH$_2$-phenyl (Phenylalanine), —CH$_2$-(4-OH-phenyl) (Tyrosine), —CH$_2$-(3-1H-indolyl) (Tryptophan), —CH$_2$SH (Cysteine), —CH$_2$CH$_2$SCH$_3$ (Methioine), —CH$_2$OH (Serine), —CH(OH)CH$_3$ (Threonine) and the cyclic side chain pyrrolidinyl (Proline) whereby the covalent bond between the nitrogen and carbon in the pyrrolidinyl ring forms the backbone. Examples of amino acid side chain moieties derived from unnatural amino acids, with the amino acids from which they are derived shown in brackets, are —(CH$_2$)$_2$—C(O)—O—C(CH$_3$)$_3$ (glutamic acid t-butyl ester), —(CH$_2$)$_4$—NH—C(O)—O—C(CH$_3$)$_3$ (N$_c$(tert-butoxycarbonyl)-lysine), —(CH$_2$)$_3$—NH—C(O)NH$_2$ (citrulline), —CH$_2$—CH$_2$OH (homoserine) and —(CH$_2$)$_2$—CH$_2$NH$_2$ (ornithine). Examples can also include alkyl, alkenyl, alkynyl, aryl, saturated and unsaturated heterocycles (functionalized and unfunctionalized). The term "amino-acid side chain moiety" can also include a number of unnatural amide and sulfonamide, aryl and heteroaryl side chains.

Unless otherwise defined, the term "optionally substituted" or "optional substituent" as used herein refers to a group which may or may not be further substituted with 1, 2, 3, 4 or more groups, preferably 1, 2 or 3, more preferably 1 or 2 groups selected from the group consisting of $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, $C_{1-6}$alkoxyaryl, halo, $C_{1-6}$alkylhalo (such as CF$_3$ and CHF$_2$), $C_{1-6}$alkoxyhalo (such as OCF$_3$ and OCHF$_2$), carboxylic acid, carboxyl, esters, cyano, nitro, amino, mono substituted amino, disubstituted amino, acyl, ketones, amides, aminoacyl, substituted amides, disubstituted amides, carbamic acid, carbamates, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, phosphates, phosphonates, aryl, ar$C_{1-6}$alkyl, heterocyclyl, heteroaryl and spiro ring systems wherein each alkyl, alkenyl, alkynyl, cycloalkyl, aryl, heterocyclyl, heteroaryl and spiro ring system and groups containing them may be further optionally substituted. Unless otherwise defined, particularly preferred optional substituents in one embodiment of the invention include 1, 2, 3 or 4, preferably 1 or 2 substituents each independently selected from the group consisting of $C_{1-4}$alkyl (particularly methyl), halo (particularly F), halo$C_{1-3}$alkyl (particularly CHF$_2$ and CF$_3$), OH, $C_{1-4}$alkoxyl (particularly OCH$_3$), CO$_2$H, CO$_2$C$_{1-4}$alkyl (particularly CO$_2$CH$_3$), NH$_2$, NHC$_{1-4}$alkyl (particularly NHCH$_3$), N(C$_{1-4}$alkyl)$_2$ (particularly N(CH$_3$)$_2$), NHC(═O)C$_{1-4}$alkyl, NHC(═O)-4-6-membered heterocyclyl, OP(═O)(OR)$_2$ (where each R is independently H or C$_{1-4}$alkyl), P(═O)(OR)$_2$ (where each R is independently H or C$_{1-4}$alkyl), C$_{3-6}$cycloalkyl (particularly cyclopropyl, cyclobutyl, cyclopenyl and cyclohexyl), phenyl, 4-6-membered heterocylyl (particularly oxetanyl, azetidinyl, tetrahydrofuranyl, pyrrolidinyl, tetrahydropyranyl, morpholinyl, thiomorpholinyl, oxothiazinyl, dioxothiazinyl, thianyl (also known as tetrahydrothiopyranyl), oxothianyl, dioxothianyl, piperidinyl, and piperazinyl) and further where $C_{1-4}$alkyl either alone or as part of a substituent group includes methyl, ethyl, n-propyl, iso-propyl, n-butyl, iso-butyl, sec-butyl and tert-butyl and may be further optionally substituted.

Optional substituents in the case of heterocycles, heteroaryls and spiro bicyclic heterocyclic ring systems containing N may also include but are not limited to alkyl i.e. N—$C_{1-3}$ alkyl, more preferably methyl, particularly N-methyl.

It will be understood that suitable derivatives of aromatic heterocyclyls containing nitrogen include N-oxides thereof.

Embodiments will now be described with reference to the following non-limiting examples.
Compounds In one embodiment Alk is optionally substituted $C_{1-6}$alkyl, preferably $C_{1-3}$alkyl and even more preferably is unsubstituted ethyl.

In one embodiment $X_1$ is C—$R_1$, $X_2$ is C—$R_2$ and $X_3$ is C—$R_3$.

In one embodiment $X_1$ is C—$R_1$ and $R_1$ is H or halo, preferably H.

In one embodiment ring A is an optionally substituted 5-6-membered heteroaryl, preferably containing at least one N heteroatom. In one embodiment ring A is a 5-membered heteroaryl. Preferred 5-membered heteoaryl include triazolyl, imidazolyl and thiazolyl rings. In one embodiment, ring A is a 6-membered heteoaryl with pyrimidine, pyridine and pyrazine rings being most preferred.

In one embodiment $Z_1$ is a secondary or tertiary alcohol of general formula

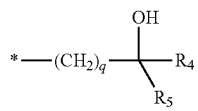

an ester, carbamate, phosphate, sulfate or prodrug thereof wherein q, $R_4$ and $R_5$ are as previously defined.

In one embodiment $X_2$ is C—$R_2$ where $R_2$ is H. In another embodiment $X_2$ is C—$R_2$ where $R_2$ is selected from $H_2OH$, optionally substituted $C_{1-6}$alkyl, optionally substituted $C_{2-6}$alkenyl, optionally substituted $OC_{1-6}$ alkyl, optionally substituted $SC_{1-6}$alkyl, optionally substituted $S(=O)C_{1-6}$ alkyl, an optionally substituted 5-6-membered heterocycle, halo, halo$C_{1-3}$alkyl, CN and optionally substituted $(CH_2)_m$N-$R^a R^b$.

In one embodiment $R_2$ is selected from H, halo preferably F, OH, optionally substituted $NHC_{1-3}$alkyl (preferably $NHCH_3$ or $NHCH_2CH_3$), optionally substituted $N(C_{1-3}$ alkyl$)_2$ (preferably $N(CH_3)_2$ or $N(CH_3)CH_2CH_3$), optionally substituted $SC_{1-3}$alkyl (preferably $SCH_2CH_3$), optionally substituted $S(=O)C_{1-3}$alkyl (preferably $S(=O)CH_2CH_3$), an optionally substituted 6-membered heterocycle (preferably 6-membered such as morpholine) and optionally substituted $OC_{1-3}$alkyl (preferably methoxy or ethoxy) wherein the optional substituents may be, for example OH, methoxy, $C_{3-6}$cycloalkyl (e.g. such as cyclopropyl), phenyl or a 5-6-membered heterocycle (e.g. such as tetrahydrofuran, tetrahydropyran, pyrrolidine, pyrazolidine, imidazolidine, piperidine, piperazine and morpholine).

In one embodiment $X_3$ is C—$R_3$ where $R_3$ is H.

In another embodiment $X_3$ is C—$R_3$ where $R_3$ is selected from optionally substituted $C_{1-6}$alkyl, optionally substituted $(CH_2)_mOC_{1-6}$alkyl, optionally substituted $(CH_2)_mNR^a R^b$ or is a group of formula

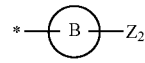

where * represents the point of attachment to the carbon ring atom;

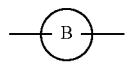

represents Ring B which is selected from saturated or unsaturated monocyclic 3-7 membered heterocycle, saturated or unsaturated fused bicyclic 8-10 membered-heterocyclyl, $C_{6-10}$aryl and 5-10 membered heteroaryl and may be optionally substituted; and $Z_2$ is a secondary or tertiary alcohol or $Z_2$ is selected from H, OH, optionally substituted $C_{1-6}$alkyl, optionally substituted $C_{2-6}$alkenyl, optionally substituted $C_{2-6}$alkynyl, optionally substituted $(CH_2)_mOC_{1-6}$alkyl, optionally substituted $(CH_2)_mNR^a R^b$, optionally substituted $(CH_2)_p$-4-6-membered heterocyclylic ring, optionally substituted $(CH_2)_p$-spiro-bicyclic-7-11-membered heterocyclic ring and optionally substituted

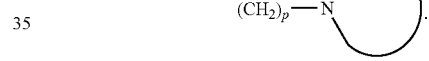

In a further embodiment $R_3$ is selected from optionally substituted $C_{1-3}$alkyl, optionally substituted $OC_{1-3}$alkyl, optionally substituted $(CH_2)_mNH_2$, optionally substituted $(CH_2)_mNHC_{1-3}$alkyl and optionally substituted $(CH_2)_mN(C_{1-3}$ alkyl$)_2$. In still a further particular embodiment $R_3$ is selected from optionally substituted methyl (such as optionally substituted with methoxy, dimethylamino or a 6-membered heterocyclic group such as morpholinyl) or optionally substituted methoxy (such as optionally substituted with pyridyl wherein pyridyl is further optionally substituted with methyl).

In another embodiment $R_3$ is a group of formula

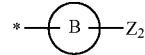

where * represents the point of attachment to the carbon ring atom;

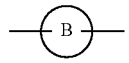

represents Ring B which is selected from saturated or unsaturated monocyclic 5-6 membered heterocycle (such as pyrrolidinyl and morpholinyl), $C_6$aryl and 5-6 membered heteroaryl and may be optionally substituted.

In a preferred embodiment Ring B is an optionally substituted 5-6 membered heteroaryl, with 6-membered heteroaryl being particularly preferred and 6-membered heteroaryl selected from pyridine, pyridazine, pyrimidine and pyrazine being most preferred.

In one embodiment $Z_2$ is H.

In one embodiment $Z_2$ is selected from OH, optionally substituted $C_{1-6}$alkyl, optionally substituted $C_{2-6}$alkenyl, optionally substituted $C_{2-6}$alkynyl, optionally substituted $(CH_2)_mOC_{1-6}$alkyl, optionally substituted $(CH_2)_mSC_{1-6}$alkyl, optionally substituted $(CH_2)_mS(=O)C_{1-6}$alkyl, halo, optionally substituted haloC$_{1-3}$alkyl, $(CH_2)_mNH_2$, optionally substituted $(CH_2)_mNHC_{1-6}$alkyl, optionally substituted $(CH_2)_mN(C_{1-6}$alkyl$)_2$, optionally substituted $(CH_2)_p$-4-6-membered heterocyclic ring, optionally substituted $(CH_2)_p$-spiro-bicyclic-7-11-membered heterocyclic ring and optionally substituted

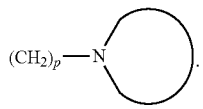

In a further embodiment $Z_2$ is selected from OH, halo (particularly F), an optionally substituted $C_{1-6}$alkyl (particularly methyl, ethyl and propyl, most preferably methyl), optionally substituted $OC_{1-6}$alkyl (particularly methoxy, ethoxy and propoxy), halo (particularly F), $(CH_2)_mNH_2$ (particularly NH$_2$), optionally substituted $(CH_2)_mNHC_{1-3}$alkyl (particularly NHCH$_3$ and NHCH$_2$CH$_3$), optionally substituted $(CH_2)_mNHC_{3-6}$cycloalkyl (particularly CH$_2$NHC$_{3-6}$cycloalkyl such as CH$_2$NHcyclopropyl and NHC$_{3-6}$cycloalkyl such as NH-cyclohexyl) optionally substituted $(CH_2)_mN(C_{1-3}$ alkyl$)_2$ (particularly N(CH$_3$)$_2$ and N(CH$_3$)CH$_2$CH$_3$), optionally substituted $(CH_2)_p$-4-6-membered heterocyclic ring, optionally substituted $(CH_2)_p$-spiro-bicyclic-7-11 membered heterocyclic ring and optionally substituted

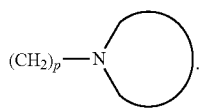

In still another embodiment $Z_2$ is optionally substituted

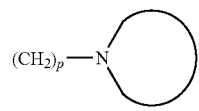

where p is 0, 1 or 2, preferably 0 or 1, even more preferably is 1.

In a particularly preferred embodiment $Z_2$ is an optionally substituted $(CH_2)_p$-4-6-membered heterocyclic ring or optionally substituted $(CH_2)_p$-spiro-bicyclic-7-11-membered heterocyclic ring where p is an integer selected from 0, 1 and 2, preferably 0 or 1. Particularly preferred 4-6-membered heterocyclic rings contain at least one nitrogen heteroatom and include azetidinyl, pyrrolidinyl, piperidinyl, piperazinyl, morpholinyl, thiomorpholinyl, oxothiazinyl and dioxothiazinyl and further may be optionally substituted. Particularly preferred spiro-bicyclic-7-11-membered heterocyclic rings include oxa-azaspiroheptane and oxa-azaspirononane and may be optionally substituted.

Suitable optional substituents for $Z_2$ include but are not limited to one or more substituents, preferably 1 or 2 substituents independently selected from OH, $C_{1-3}$alkyl (particularly methyl), $C_{1-3}$alkoxyl (particularly methoxy), halo (particularly F), $CO_2H$, $CO_2C_{1-3}$alkyl (particularly $CO_2CH_3$), $P(=O)(OH)_2$ and $P(=O)(OC_{1-3}$alkyl$)_2$.

In one embodiment the compound is of Formula (Ia)

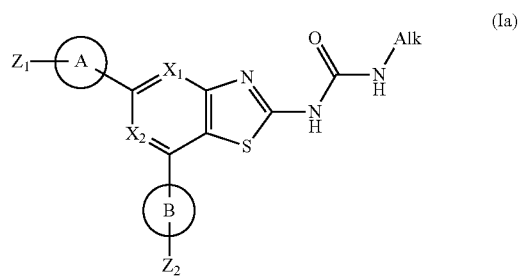

(Ia)

salts, isomers, racemates, diastereomers, enantiomers, esters, carbamates, phosphates, sulfates, deuterated forms and prodrugs thereof
wherein $X_1$, $X_2$, Alk, Ring A, Ring B, $Z_1$ and $Z_2$ are as previously defined.

In one embodiment $Z_1$ is a secondary or tertiary alcohol of general formula

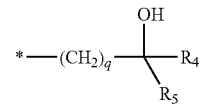

or an ester, carbamate, phosphate, sulfate or prodrug thereof
wherein q is an integer selected from 0, 1, 2 or 3 and each (CH$_2$) entity when present may be independently optionally substituted;

$R_4$ is H or is selected from optionally substituted $C_{1-6}$alkyl, optionally substituted $C_{2-6}$alkenyl, optionally substituted $C_{2-6}$alkynyl, optionally substituted $(CH_2)_tOC_{1-6}$alkyl, optionally substituted $(CH_2)_tC(=O)C_{1-6}$alkyl, optionally substituted $(CH_2)_tSC_{1-6}$alkyl, optionally substituted $(CH_2)_tS(=O)C_{1-6}$alkyl, halo, optionally substituted haloC$_{1-3}$alkyl and optionally substituted $(CH_2)_tNR^aR^b$;

$R_5$ is selected from optionally substituted $C_{1-6}$alkyl, optionally substituted $C_{2-6}$alkenyl, optionally substituted $C_{2-6}$alkynyl, optionally substituted $C_{3-7}$cycloalkyl ring, optionally substituted phenyl, optionally substituted 4-6-membered heterocyclyl ring, optionally substituted 5-6-membered heteroaryl ring, optionally substituted $(CH_2)_tOC_{1-6}$alkyl, optionally substituted $(CH_2)_tOC(=O)C_{1-6}$alkyl, optionally substituted $(CH_2)_tSC_{1-6}$alkyl, optionally substituted $(CH_2)_tOC(=O)C_{1-6}$alkyl, halo, optionally substituted haloC$_{1-3}$alkyl and optionally substituted $(CH_2)_tNR^aR^b$;

t is selected from 1, 2, 3, 4, 5 and 6 preferably 1, 2 or 3;

$R^a$ and $R^b$ are each independently selected from H or optionally substituted $C_{1-6}$alkyl; or $R_4$ and $R_5$ together with the carbon atom to which they are attached form an optionally substituted 4-6-membered heterocyclic ring or $C_{3-6}$cycloalkyl ring; and

* represents the point of attachment to Ring A.

In one embodiment q is 0 or 1, preferably 0.

In one embodiment $R_4$ is H or optionally substituted $C_{1-3}$alkyl (particularly methyl and ethyl); and $R_5$ is selected from optionally substituted $C_{1-3}$alkyl (particularly methyl and ethyl), optionally substituted halo$C_{1-3}$alkyl (particularly $CHF_2$, $CH_2CHF_2$, $CF_3$ and $CH_2CF_3$), optionally substituted $C_{3-7}$cycloalkyl ring (particularly cyclopropyl, cyclobutyl, cyclopentyl and cyclohexyl), optionally substituted 4-6-membered heterocyclyl ring (particularly morpholinyl), optionally substituted 5-6-membered heteroaryl ring (particularly containing at least one nitrogen heteroatom such as imidazolyl and pyridinyl); or $R_4$ and $R_5$ together with the carbon atom to which they are attached form an optionally substituted 4-6-membered heterocyclic ring or $C_{3-6}$cycloalkyl ring.

4-6-membered heterocyclic rings $R_4$ and $R_5$ together with the carbon atom to which they are attached include 4-membered rings such as oxetane and azetidine, 5-membered rings such as pyrrolidine, pyrazolidine, imidazole, tetrahydrofuran and thiophene and 6-membered rings such as piperidine, piperazine, morpholine, tetrahydropyran, and tetrahydrothiopyran. Heteroatom ring substituents in the case of heterocyclic rings include =O, e.g. S=O (e.g. to form oxo-thianes and dioxothianes from tetrahydrothiopyran), oxides e.g. N-oxides and $C_{1-3}$alkyl e.g. N-methyl. $C_{3-6}$cycloalkyl rings $R_4$ and $R_5$ together with the carbon atom to which they are attached include saturated cyclopropyl, cyclobutyl, cyclopentyl and cyclohexyl rings, particularly cyclopentyl and cyclohexyl.

Suitable optional substituents for $R_4$ and $R_5$ may include but are not limited to, for example, one or more preferably 1 or 2 substituents independently selected from OH, $C_{1-3}$alkyl such as methyl, halo$C_{1-3}$alkyl such as $CHF_2$ and $CF_3$, $CO_2H$, $CO_2C_{1-4}$alkyl, $C_{1-3}$alkoxyl such as methoxy, oxo (=O), $NH_2$, $NHC_{1-3}$alkyl and $N(C_{1-3}$alkyl$)_2$.

In a further embodiment $Z_1$ or $Z_2$, preferably $Z_1$, is a chiral alcohol of general formula

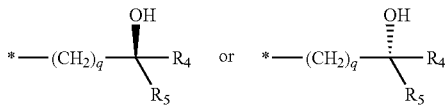

or an ester, carbamate, phosphate, sulfate or prodrug thereof wherein q, $R_4$, $R_5$ and * are as previously defined provided that $R_4$ and $R_5$ are different. In a preferred embodiment q is 0 or 1, preferably 0.

In one embodiment when $Z_1$ is a chiral alcohol, the compound of Formula (I) or (Ia) as previously defined may exist in the form of a racemic mixture, a single enantiomer and/or mixtures thereof.

In one embodiment the compound is of Formula (II):

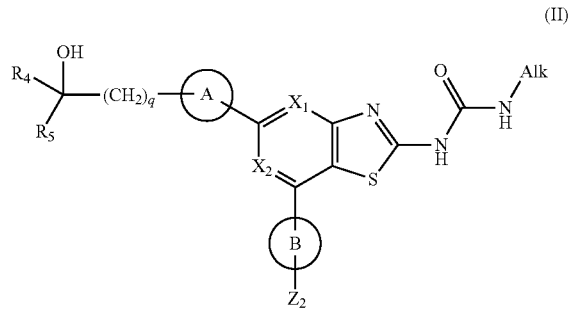

salts, racemates, diastereomers, enantiomers, esters, carbamates, phosphates, sulfates, deuterated forms and prodrugs thereof
wherein $X_1$, $X_2$, Alk, Ring A, Ring B, $Z_2$, $R_4$, $R_5$ and q are as previously defined. In a preferred embodiment q is 0 or 1, preferably 0.

In a preferred embodiment $X_1$ is C—H, q is 0 or 1, preferably 0 and Alk is ethyl.

In still another embodiment, $R_4$ is H or optionally substituted $C_{1-6}$alkyl and $R_5$ is optionally substituted $C_{1-6}$alkyl. In a further more particular embodiment $R_4$ is H or an optionally substituted methyl, ethyl or propyl and $R_5$ is an optionally substituted methyl, ethyl or propyl.

In one embodiment the compound of Formula (II) is in the form of a single enantiomer of Formula (IIa):

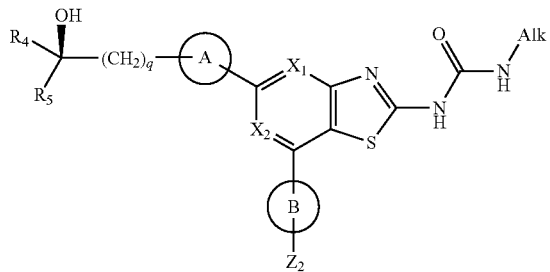

salts, esters, carbamates, phosphates, sulfates, deuterated forms and prodrugs thereof wherein $X_1$, $X_2$, Alk, Ring A, Ring B, $Z_2$, $R_4$, $R_5$ and q are as previously defined provided that $R_4$ and $R_5$ are different. In a preferred embodiment q is 0 or 1, preferably 0.

In another embodiment the compound of formula I is in the form of a single enantiomer of Formula (IIb):

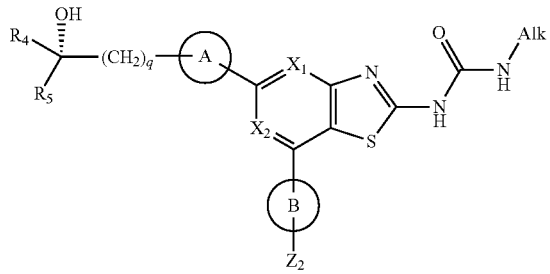

salts, esters, carbamates, phosphates, sulfates, deuterated forms and prodrugs thereof wherein $X_1$, $X_2$, Alk, Ring A, Ring B, $Z_2$, $R_4$, $R_5$ and q are as previously defined provided that $R_4$ and $R_5$ are different. In a preferred embodiment q is 0 or 1, preferably 0.

In one embodiment the compound is of Formula (III)

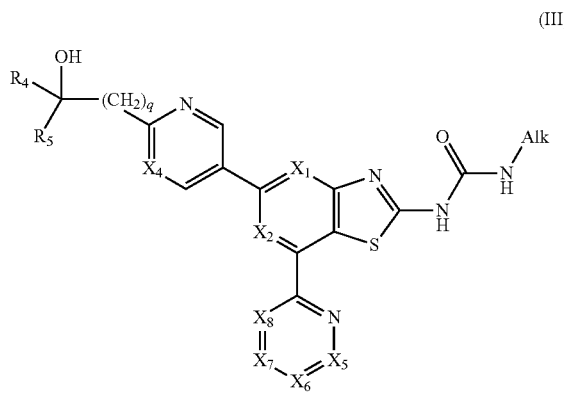

salts, racemates, diastereomers, enantiomers, esters, carbamates, phosphates, sulfates, deuterated forms and prodrugs thereof
wherein $X_1$, $X_2$, Alk, $R_4$, $R_5$ and q are as previously defined; $X_4$ is N, CH, C-halo or C—$C_{1-3}$alkoxy, preferably N or CH; $X_5$, $X_6$, $X_7$ and $X_8$ are each independently selected from N, C—H or C—$Z_2$ where $Z_2$ is as previously defined provided that no more than one of $X_5$, $X_6$, $X_7$ or $X_8$ is N.

In a preferred embodiment $X_1$ is C—H, q is 0 or 1, preferably 0 and Alk is ethyl.

In one embodiment any one of $X_5$, $X_6$, $X_7$ or $X_8$ is C—$Z_2$ where $Z_2$ is selected from OH, optionally substituted $C_{1-6}$alkyl, optionally substituted $(CH_2)_m$—$OC_{1-6}$alkyl, optionally substituted $(CH_2)_mSC_{1-6}$alkyl, optionally substituted $(CH_2)_mS(\!=\!O)C_{1-6}$alkyl, halo, optionally substituted halo$C_{1-3}$alkyl, optionally substituted $(CH_2)_mNR^aR^b$, optionally substituted $(CH_2)_p$-4-6-membered heterocyclic ring, optionally substituted $(CH_2)_p$-spiro-bicyclic-7-11-membered heterocyclic ring and optionally substituted

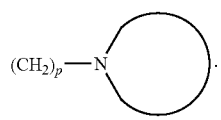

In one embodiment $X_5$, $X_6$, $X_7$ and $X_8$ are each independently C—H or C—$Z_2$.

In another embodiment one of $X_5$, $X_6$, $X_7$ and $X_8$ is N and each of the remainder independently selected from C—H or C—$Z_2$.

In still another embodiment, $R_4$ is H or optionally substituted $C_{1-6}$alkyl and $R_5$ is optionally substituted $C_{1-6}$alkyl. In a further more particular embodiment $R_4$ is H or an optionally substituted methyl, ethyl or propyl and $R_5$ is an optionally substituted methyl, ethyl or propyl.

In one embodiment of the compounds of any one of Formula (I), (Ia), (II), (IIa), (IIb) or (III), the $Z_1$ and/or $Z_2$ secondary or tertiary alcohol is in the form of an ester including those derived from amino acids and dipeptides, a carbamate, a phosphate or sulphate.

In one embodiment of the compounds of any one of Formula (I), (Ia), (II), (IIa), (IIb) or (III), the ester of the $Z_1$ and/or $Z_2$ secondary or tertiary alcohol is of general formula OC(=O)$R_6$ where $R_6$ is a 5-6-membered heterocycle or an optionally substituted $C_{1-6}$alkyl wherein the optional substituents are independently selected from 1, 2, 3 or 4 moieties selected from $C_{1-3}$ alkyl, $C_{1-3}$alkoxyl, OH, $OC_{1-3}$alkyl, $CO_2H$, $CO_2C_{1-3}$ alkyl, optionally substituted 5-6-membered heterocycles, NHC(O)$C_{1-6}$alkyl, NHC(O)-5-6-membered heterocycles, C(O)NHC$_{1-6}$ alkyl, $NH_2$, NHC$_{1-3}$ alkyl and N(C$_{1-3}$alkyl)$_2$ wherein NHC(O)C$_{1-6}$ alkyl, C(O)NHC$_{1-6}$ alkyl, NHC$_{1-3}$alkyl and N(C$_{1-3}$alkyl)$_2$ may be further optionally substituted with, for example, $CO_2H$, $CO_2CH_3$, a 5-6-membered heterocycle, $NH_2$, NHC$_{1-3}$alkyl and N(C$_{1-3}$alkyl)$_2$ and OP(=O)(OR$_9$)$_2$ where each $R_9$ is independently selected from H or $C_{1-3}$alkyl. Preferred 5-6 membered heterocycles include optionally substituted morpholino and optionally substituted pyrrolidine, pyrazolidine, imidazoline, piperidine and piperazine (such as N-methyl piperazine). In a particular embodiment there is provided a succinate ester of the $Z_1$ and/or $Z_2$ secondary or tertiary alcohol.

In another embodiment there is provided an ester of the $Z_1$ and/or $Z_2$ secondary or tertiary alcohol wherein the ester is derived from an amino acid or a dipeptide moiety. In one embodiment of the compounds of any one of Formula (I), (Ia), (II), (IIa), (IIb) or (III), the carbamate of the $Z_1$ and/or $Z_2$ secondary or tertiary alcohol is of general formula OC(=O)NR$_7$R$_8$ where $R_2$ and $R_8$ are each independently selected from H and optionally substituted $C_{1-6}$ alkyl or join together with the N to which they are attached to form an optionally substituted 5-6-membered heterocycle. Preferred 5-6 membered heterocycle include optionally substituted morpholino and optionally substituted pyrrolidine, pyrazolidine, imidazoline, piperidine and piperazine (such as N-methyl piperazine).

In another embodiment of the compounds of any one of Formula (I), (Ia), (II), (IIa), (IIb) or (III), the phosphate of the $Z_1$ and/or $Z_2$ secondary or tertiary alcohol is of general formula OP(O)(OR$_9$)$_2$ where each $R_9$ is independently selected from H or an optionally substituted $C_{1-6}$ alkyl.

In still another embodiment of the compounds of any one of Formula (I), (Ia), (II), (IIa), (IIb) or (III), the sulphate of the $Z_1$ and/or $Z_2$ secondary or tertiary alcohol is of general formula OSO$_2$OR$_{10}$ where $R_{10}$ is H or an optionally substituted $C_{1-6}$alkyl. In one embodiment of the compounds of any one of Formula (I), (Ia), (II), (IIa), (IIb) or (III), the prodrug is selected from an ester, carbamate, phosphate or sulphate formed from the hydroxyl moiety of the secondary or tertiary alcohol as previously defined.

In a particularly preferred embodiment of the compounds of any one of Formula (I), (Ia), (II), (IIa), (IIb) or (III), $Z_1$ is a secondary or tertiary alcohol of general formula

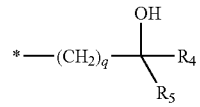

or an ester or phosphate thereof as previously defined.

Accordingly, in one embodiment of the compounds of any one of Formula (I), (Ia), (II), (IIa), (IIb) or (III) there is provided an ester of the $Z_1$ secondary or tertiary alcohol of general formula:

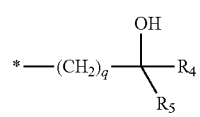

wherein the ester is derived from an amino acid, a dipeptide, a carbamate, a phosphate or a sulphate.

In one embodiment of the compounds of any one of Formula (I), (Ia), (II), (IIa), (IIb) or (III) there is provided an ester of the $Z_1$ secondary or tertiary alcohol of general formula:

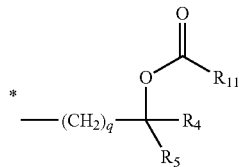

wherein $R_{11}$ is $R_6$ or $NR_7R_8$ and wherein $R_6$, $R_7$, $R_8$, q, $R_4$ and $R_5$ are as previously defined. In one embodiment, $R_{11}$ is selected from the group consisting of an optionally substituted 5-6-membered heterocyclyl or an optionally substituted $C_{1-6}$alkyl. Particularly preferred 5-6-membered heterocyclyl include pyrrolidinyl, morpholinyl and piperazinyl and may be optionally substituted with $C_{1-3}$ alkyl, preferably methyl. In one embodiment $R_{11}$ is an optionally substituted $C_{1-6}$ alkyl wherein particularly preferred optional substituents are independently selected from methyl, methoxy, OH, $CO_2H$, $CO_2C_{1-3}$ alkyl (particularly $CO_2CH_3$), optionally substituted 5-6-membered heterocycles, $NHC(=O)$-5-6-membered heterocycles, $NH_2$, $NHC_{1-3}$ alkyl and $N(C_{1-3}alkyl)_2$ (particularly $N(CH_3)_2$) and wherein $NHC_{1-3}$ alkyl may be further optionally substituted with $NH_2$, $CO_2H$, $CO_2CH_3$, 5-6-membered heterocyclyls and $OP(=O)(OR_9)_2$ where each $R_9$ is independently selected from H or $C_{1-3}$ alkyl and wherein particularly preferred 5-6-membered heterocycles include pyrrolidinyl, piperazinyl and morpholinyl.

In yet another embodiment of the compounds of any one of Formula (I), (Ia), (II), (IIa), (IIb) or (III) there is provided a phosphate of the $Z_1$ secondary or tertiary alcohol of general formula:

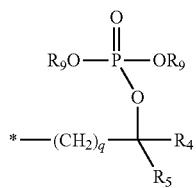

wherein each $R_9$ is independently selected from H or an optionally substituted $C_{1-3}$alkyl and q, $R_4$ and $R_5$ are as previously defined. In one embodiment each $R_9$ is H.

In one embodiment the compound is selected from the group consisting of any one of compounds 1 to 202:

1

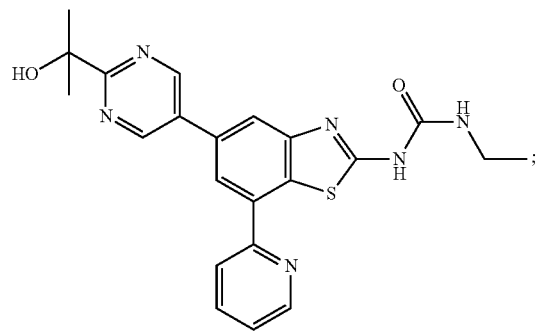

2

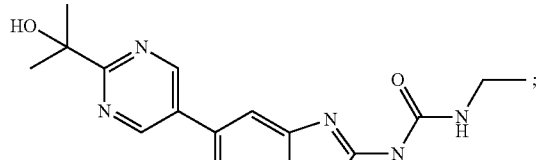

3

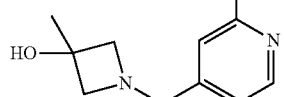

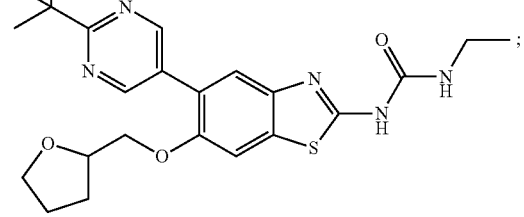

4

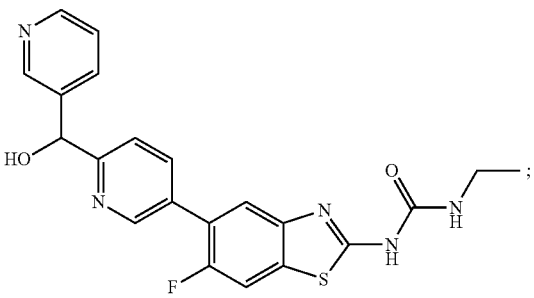

5

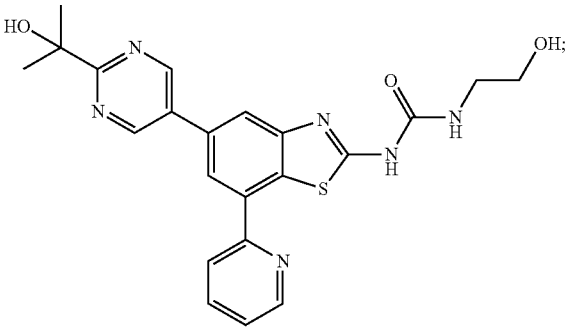

6

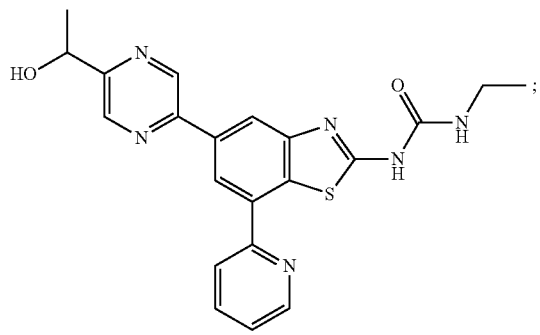

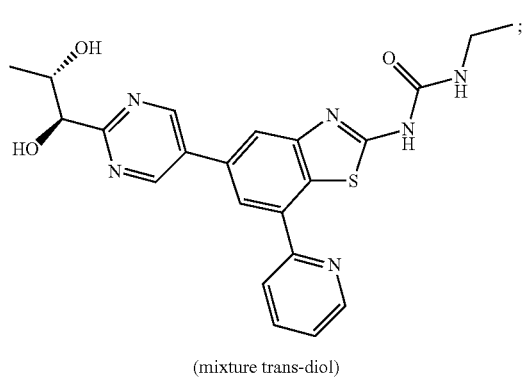
7
(mixture trans-diol)
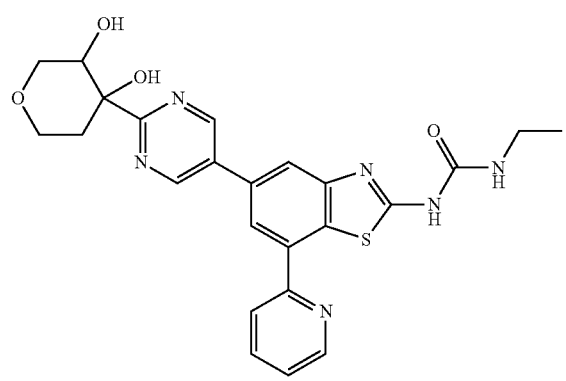
8
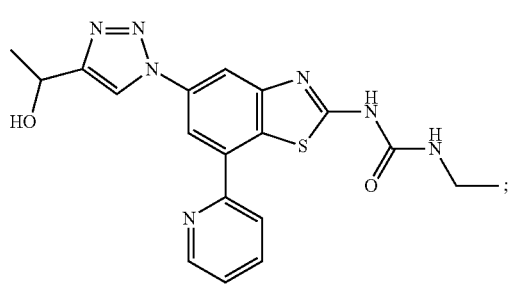
9
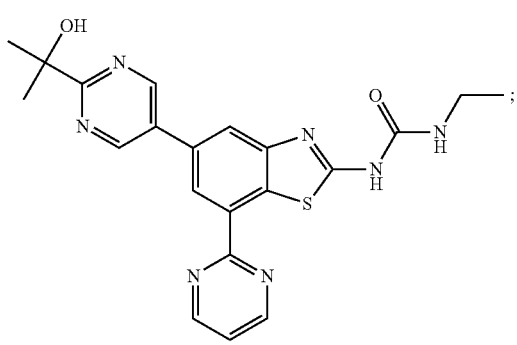
10
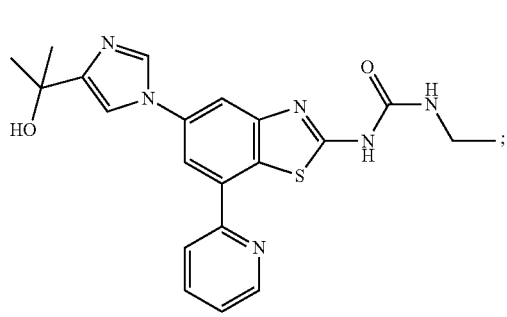
11
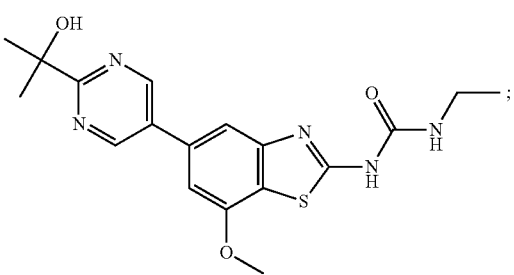
12
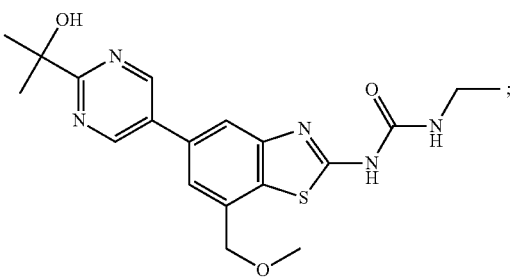
13
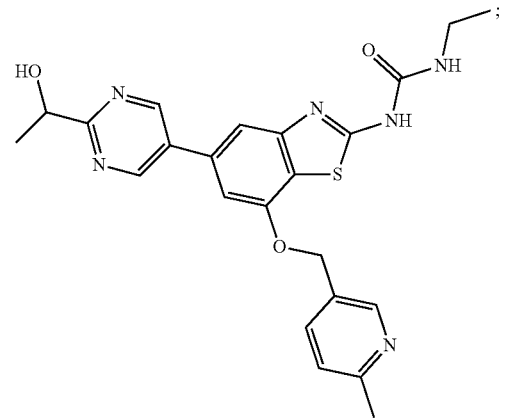
14

-continued
15
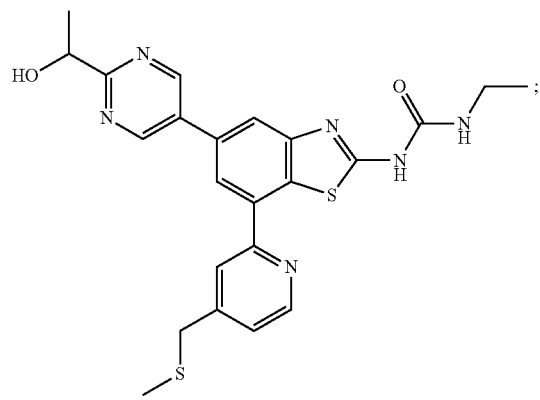
16
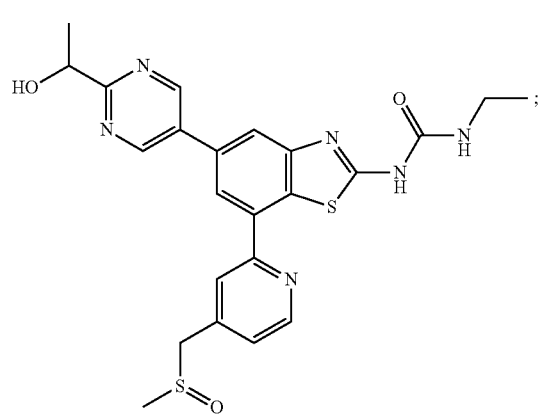
17
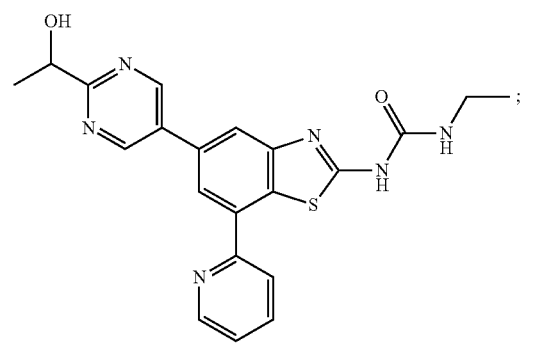
18
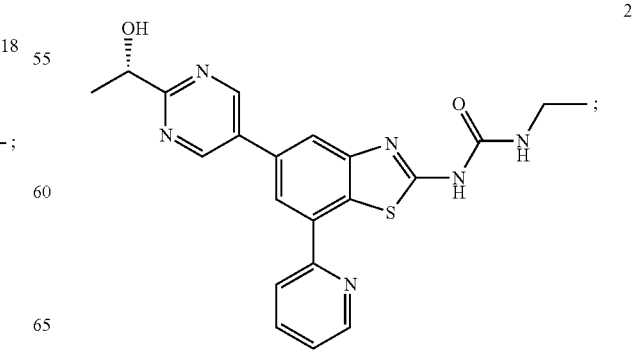
-continued
19
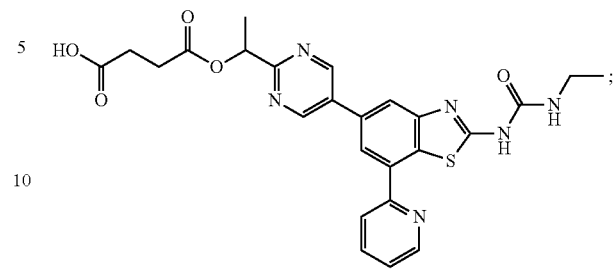
20
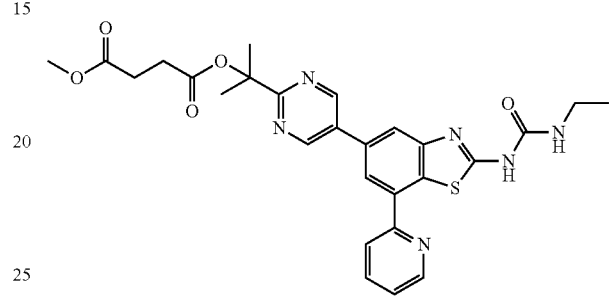
21
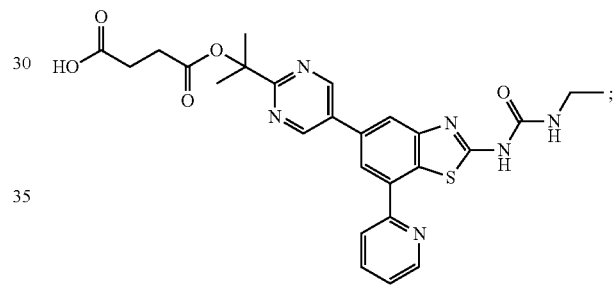
22
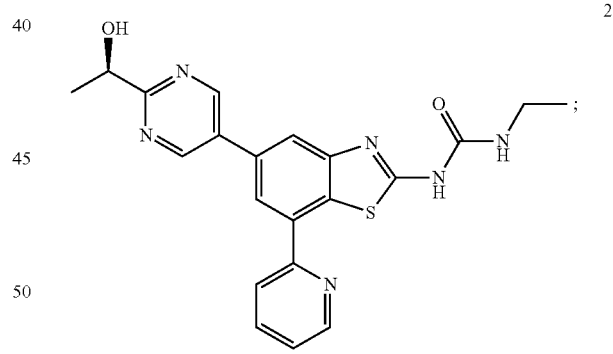
23

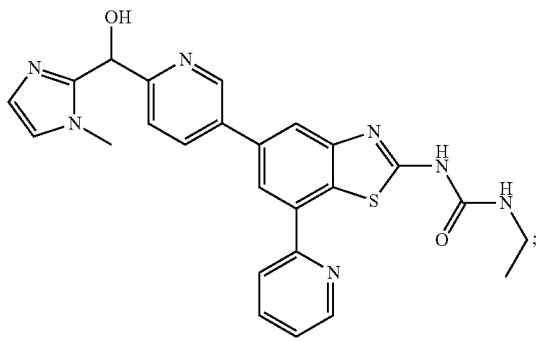
24
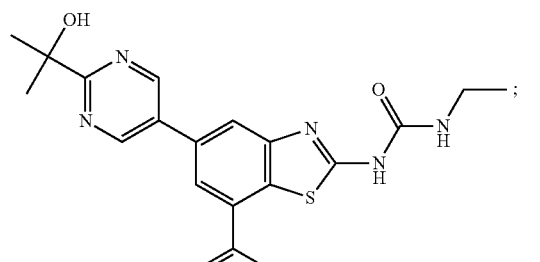
25
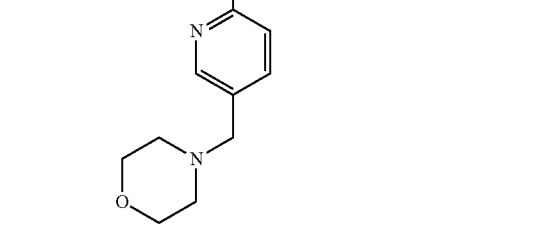
26
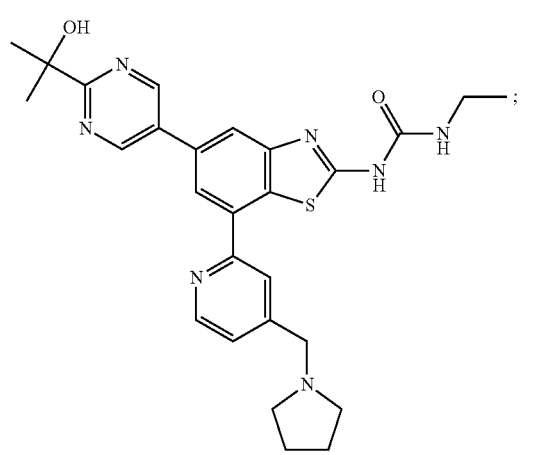
27
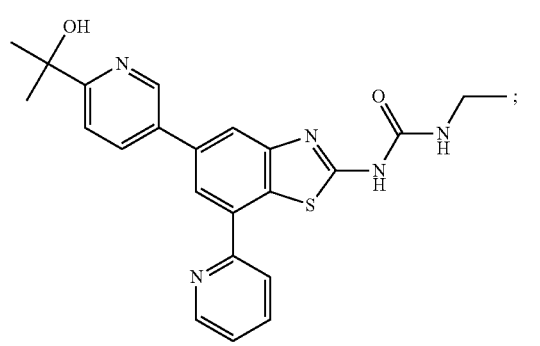
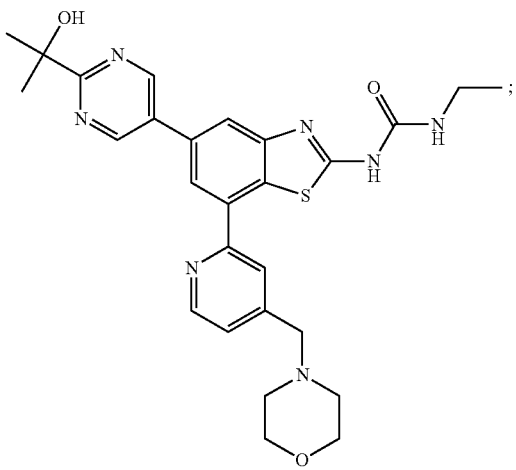
28
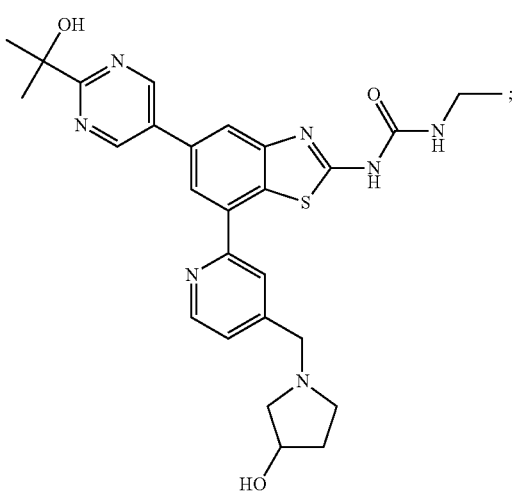
29
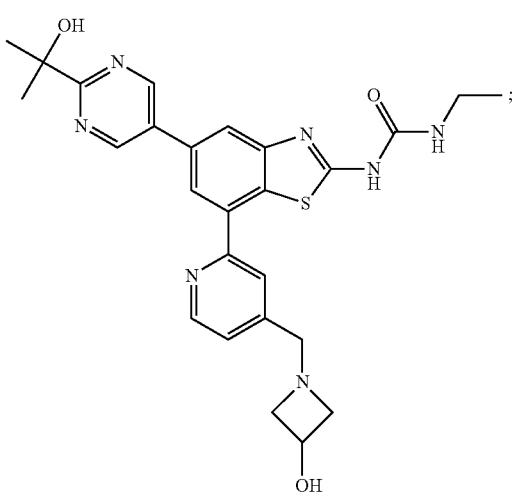
30

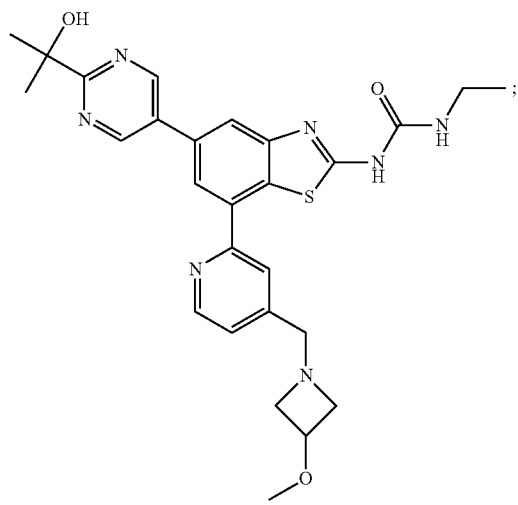
31
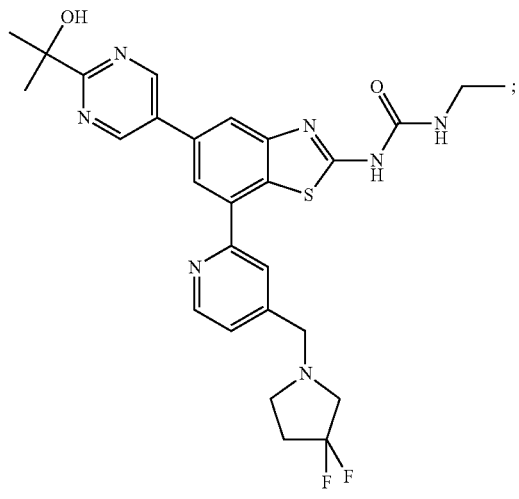
34
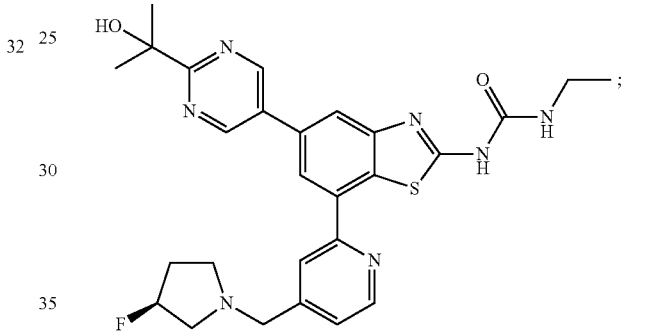
35
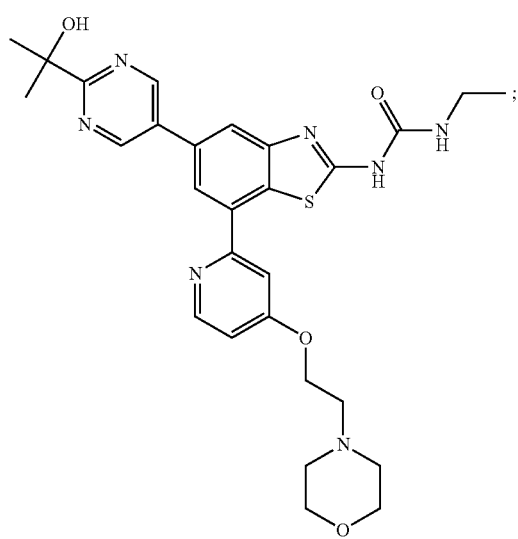
32
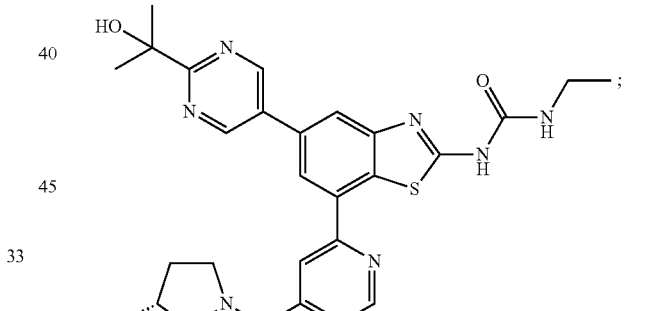
36
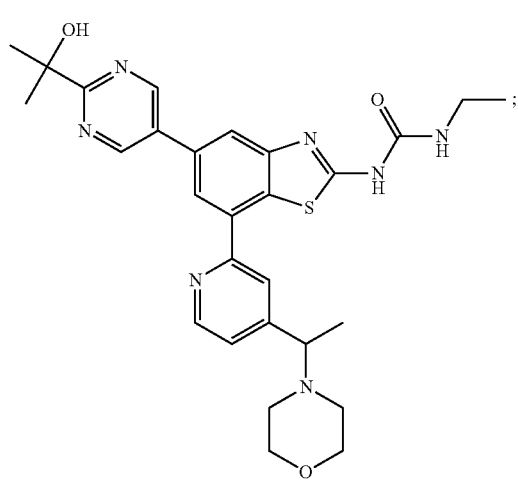
33
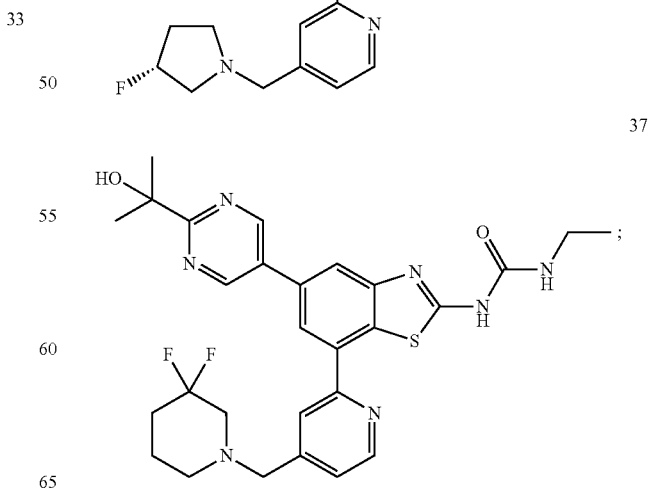
37

38
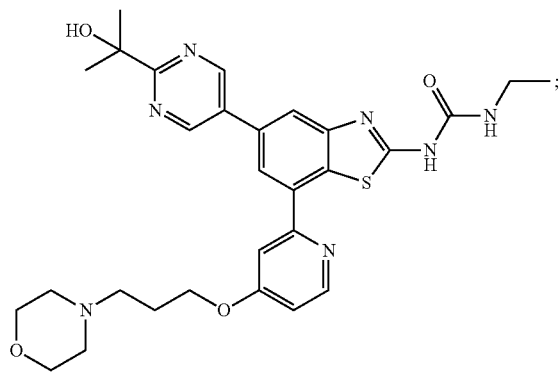
39
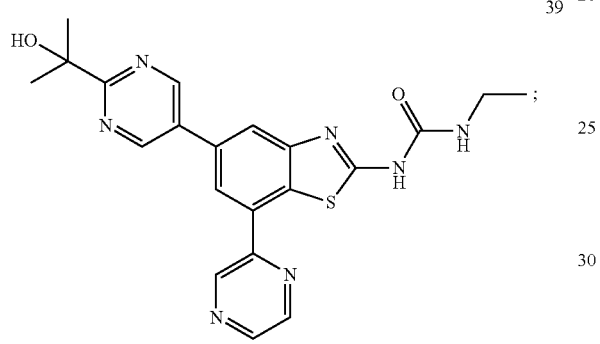
40
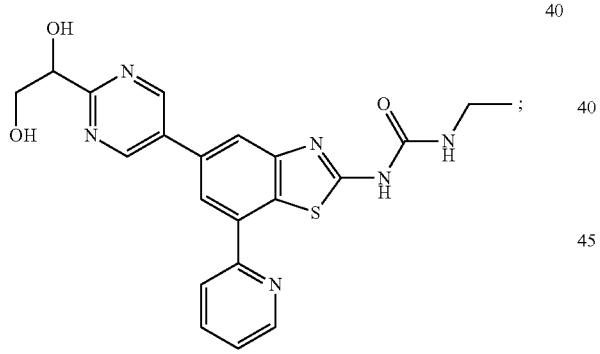
41
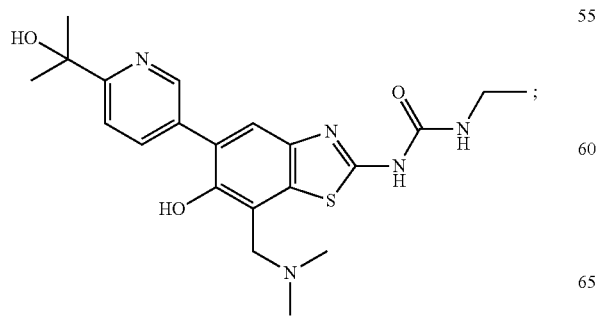
42
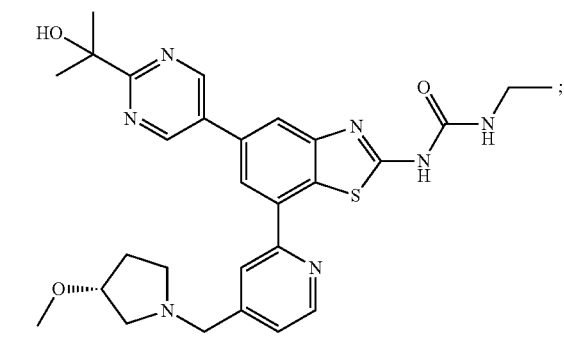
43
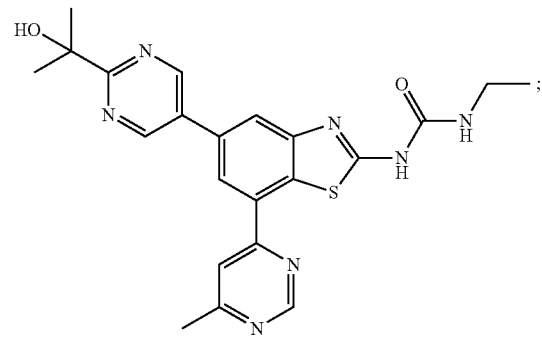
44
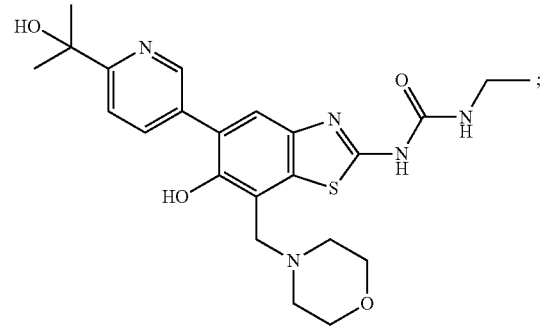
45
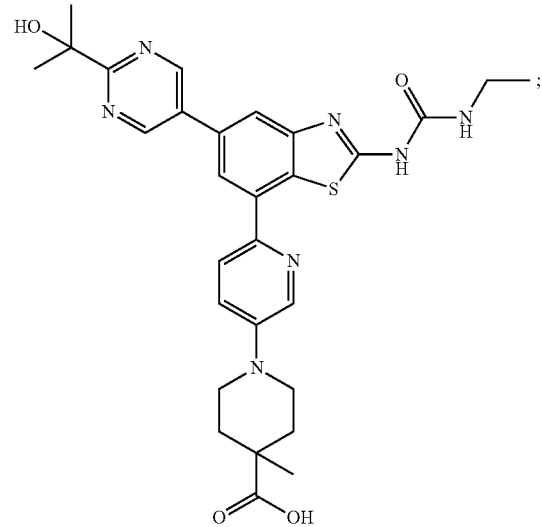

46
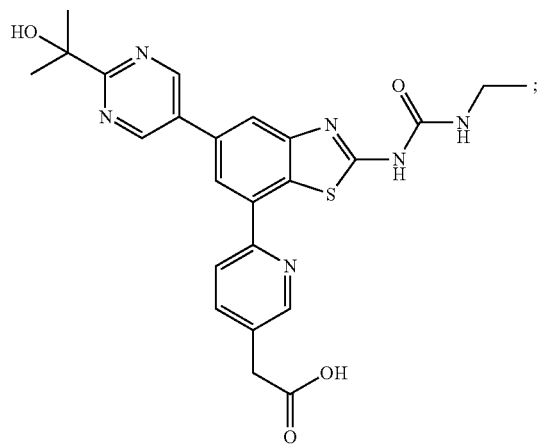
47
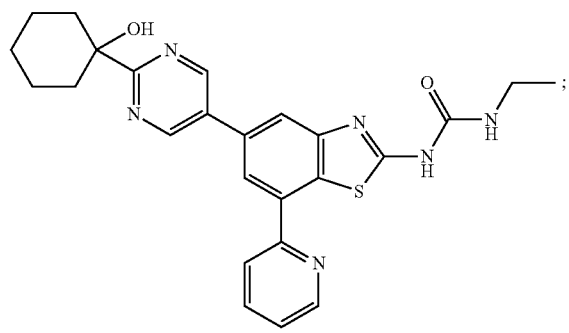
48
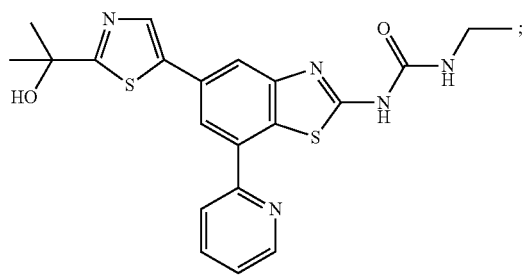
49
50
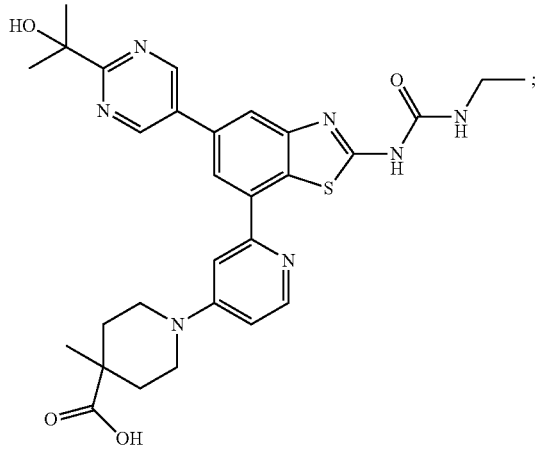
51
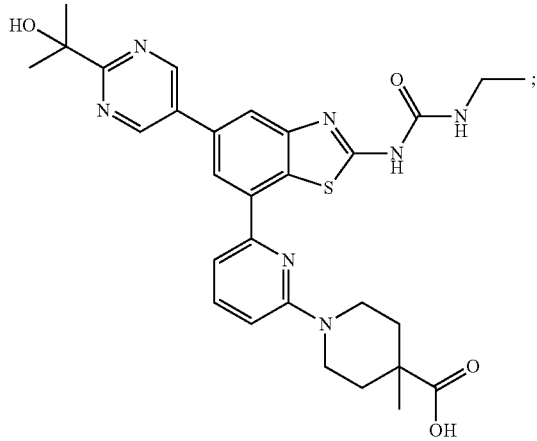
52
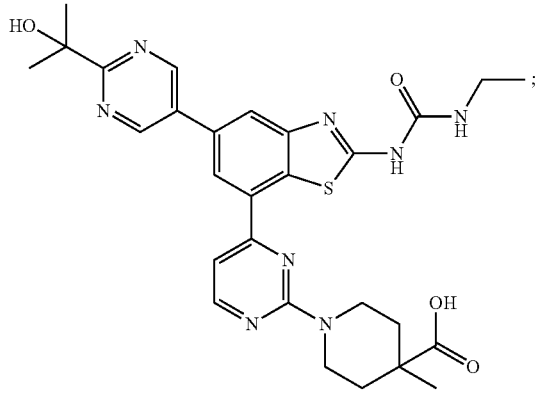

53
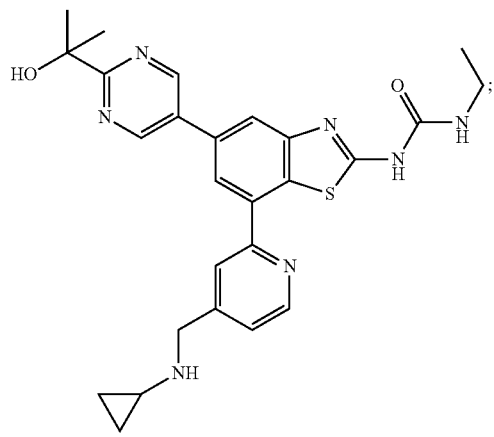
54
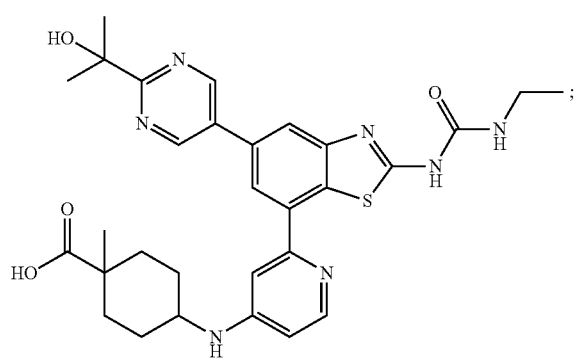
55
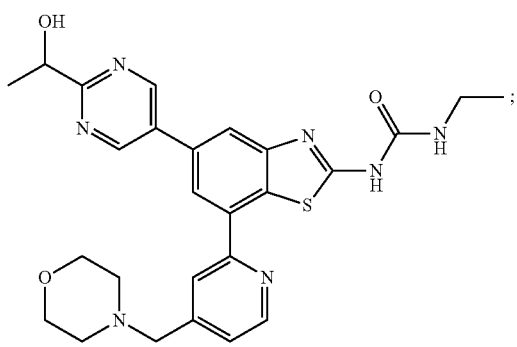
56
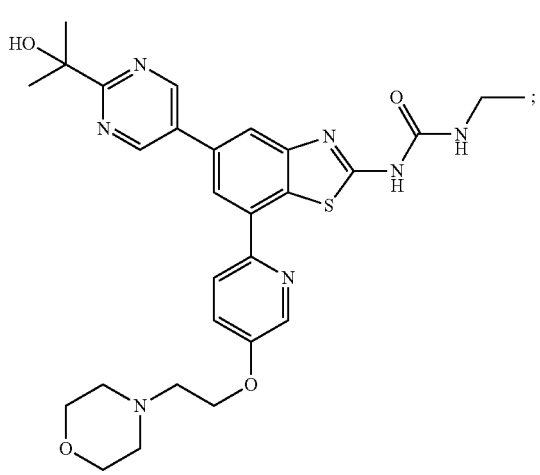
57
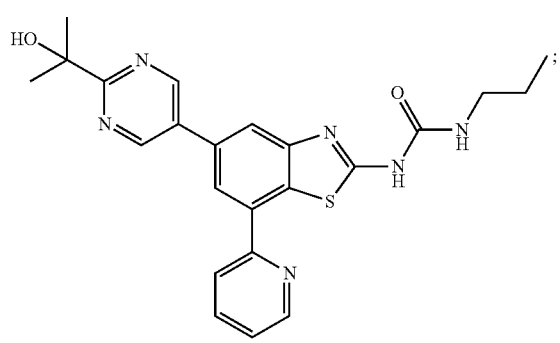
58
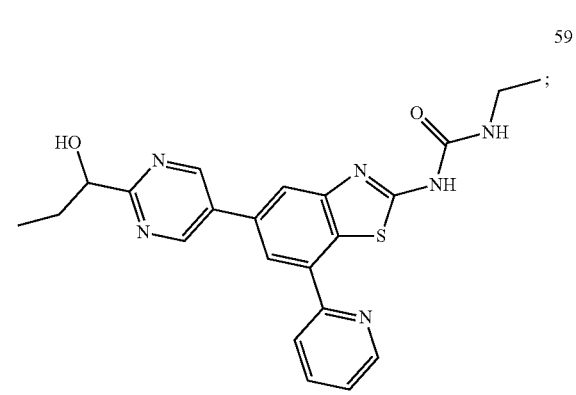
59
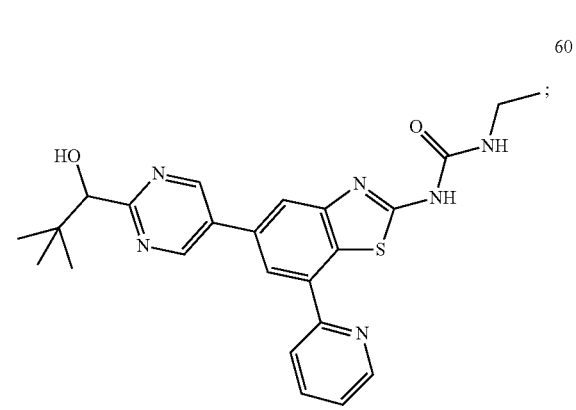
60

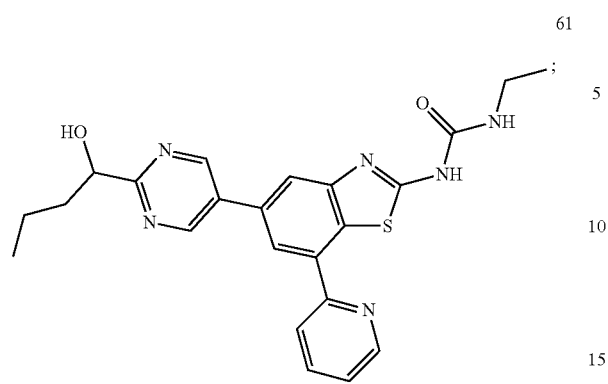
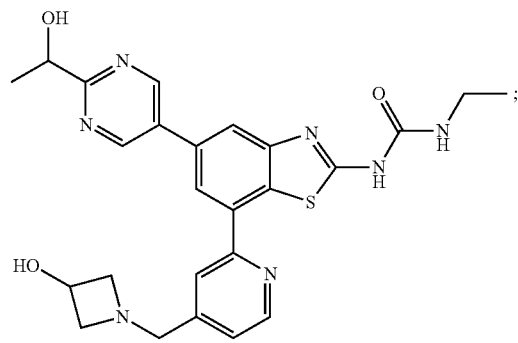
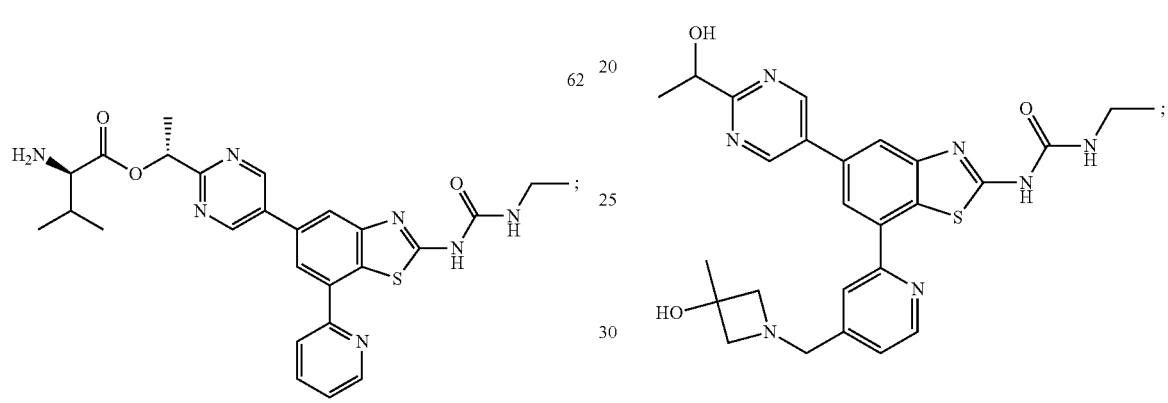
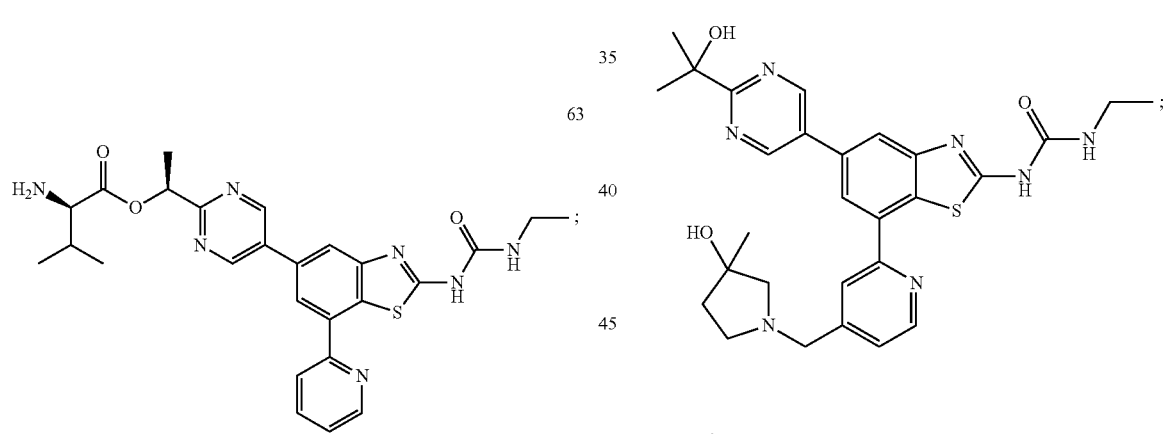
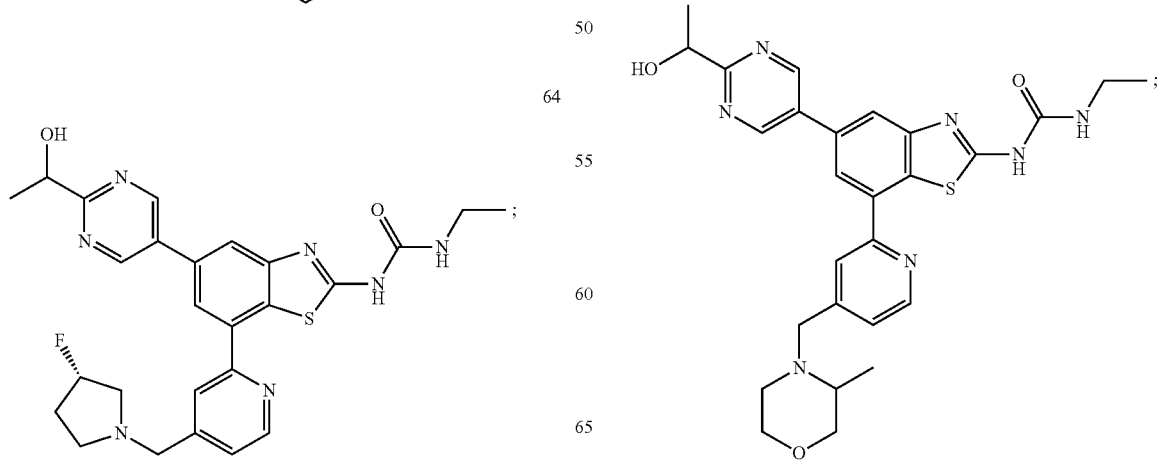

69
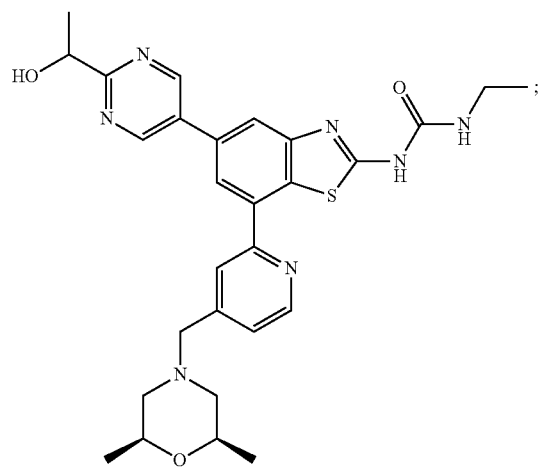
70
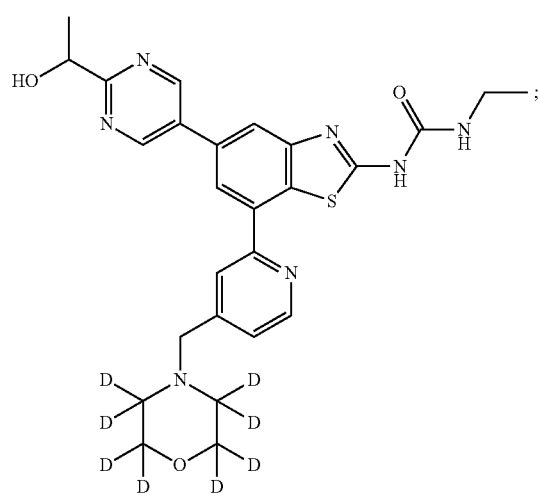
71
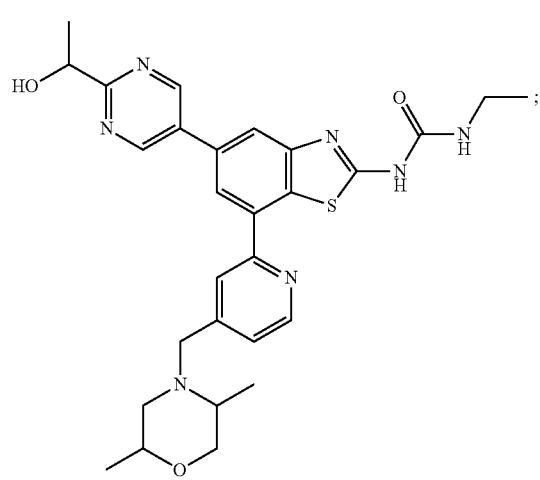
72
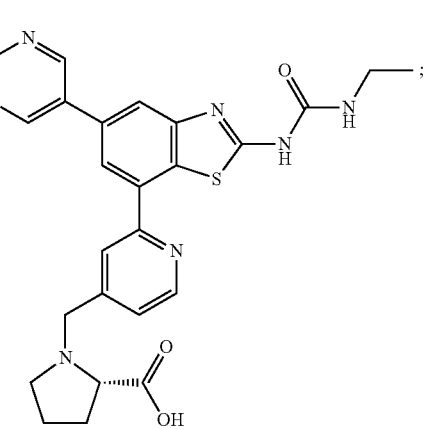
73
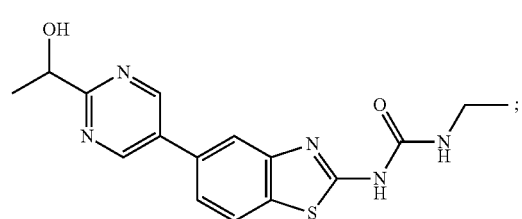
74
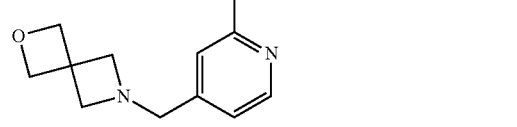
75
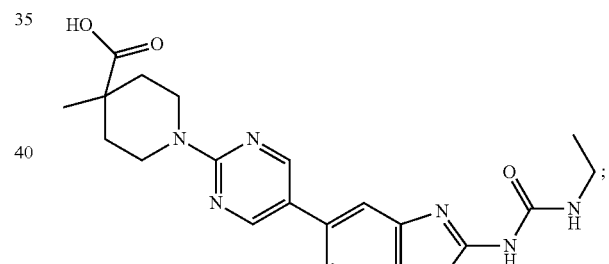

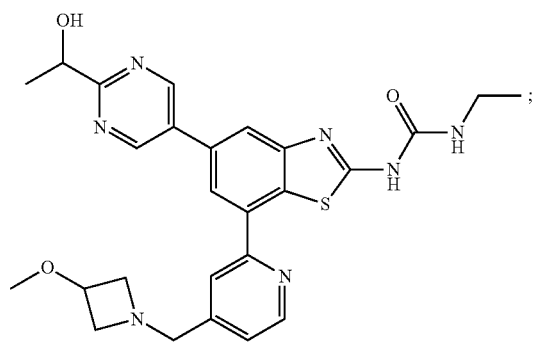
76
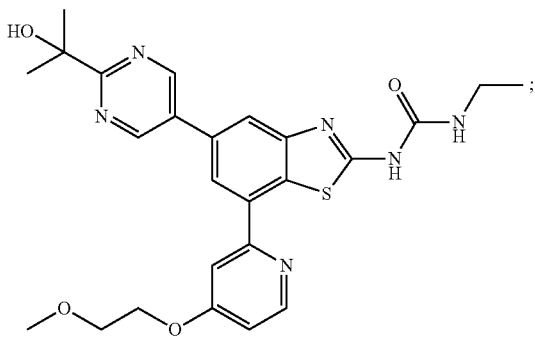
80
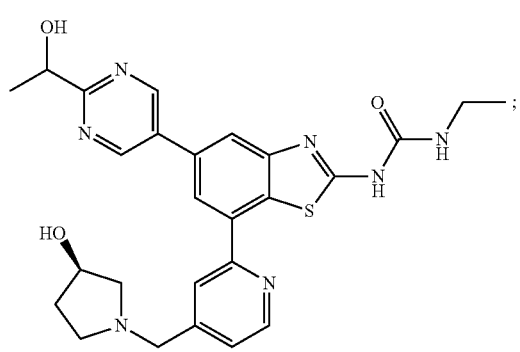
77
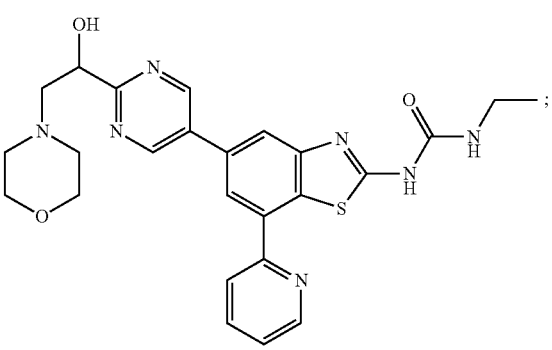
81
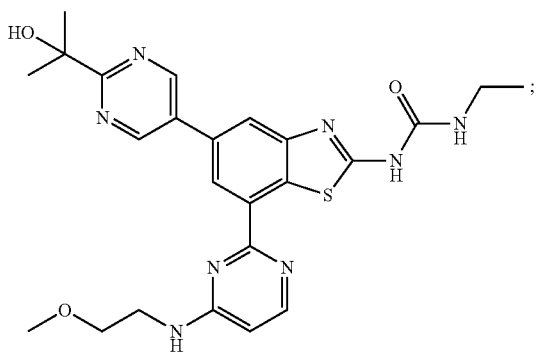
78
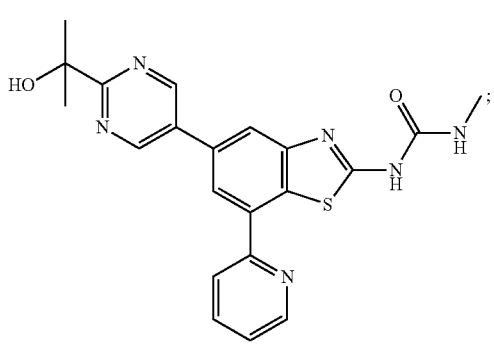
82
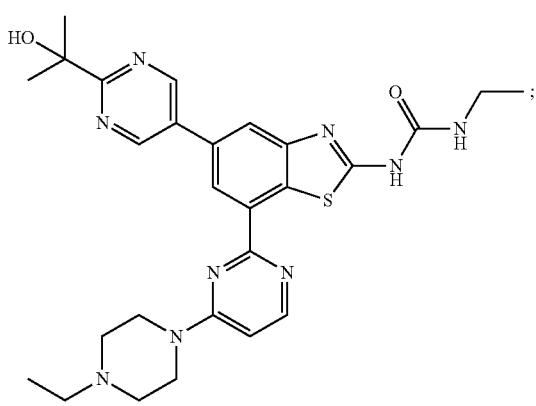
79
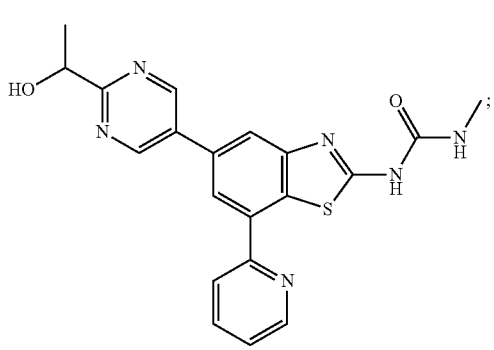
83

84
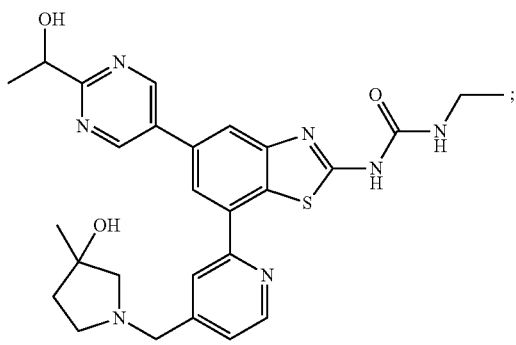
85
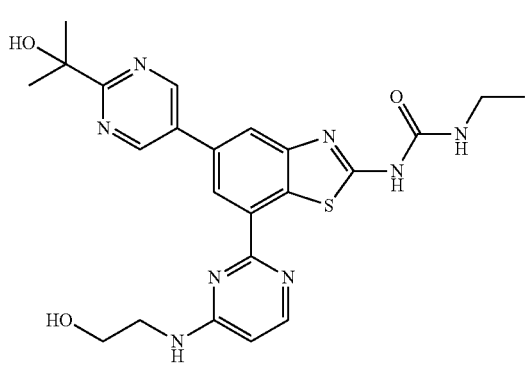
86
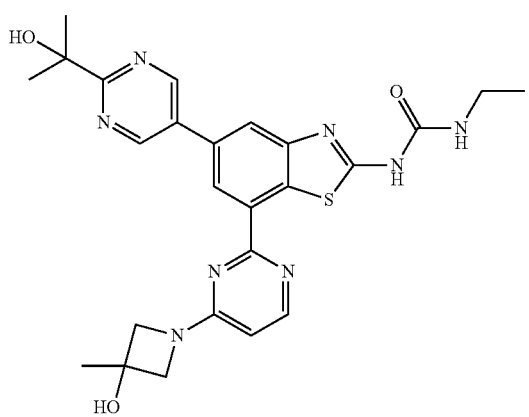
87
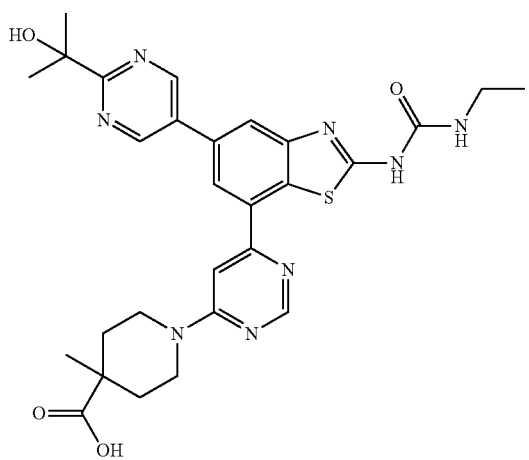
88
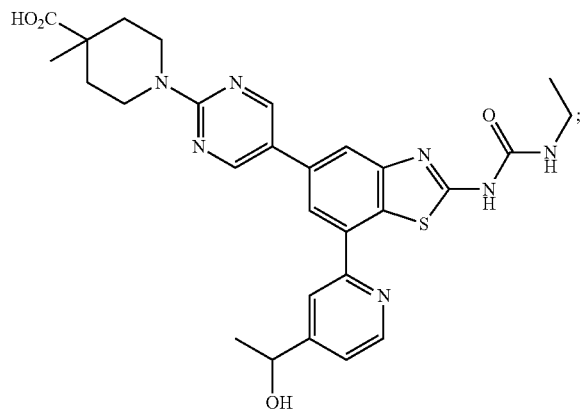
89
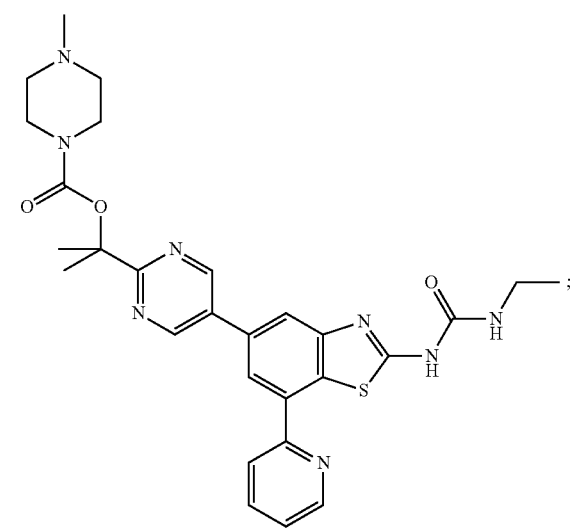
90
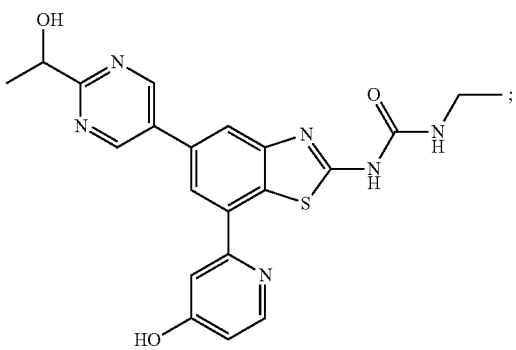

47
-continued
91
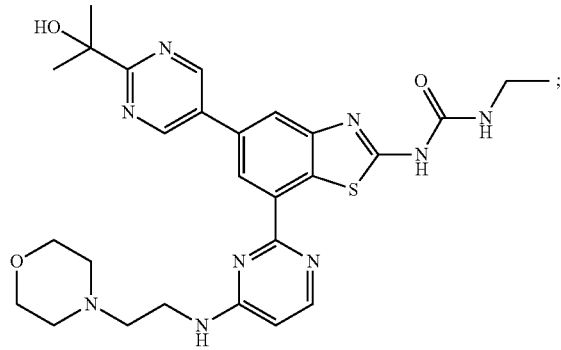
92
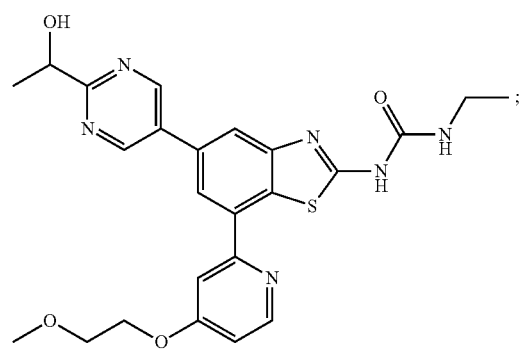
93
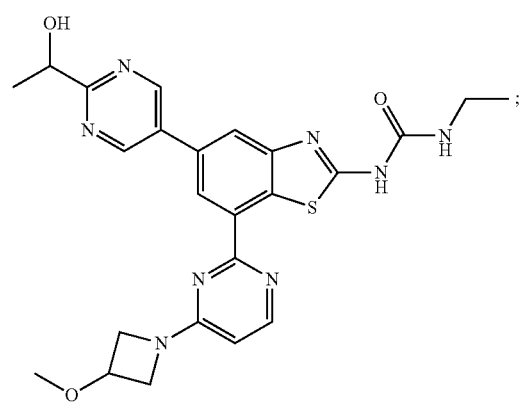
94
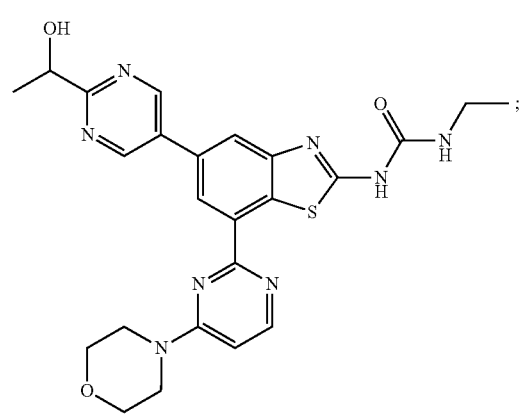
48
-continued
95
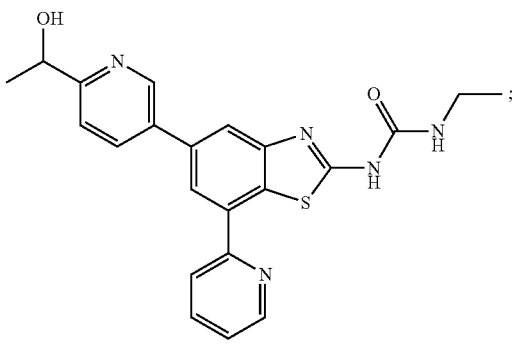
96
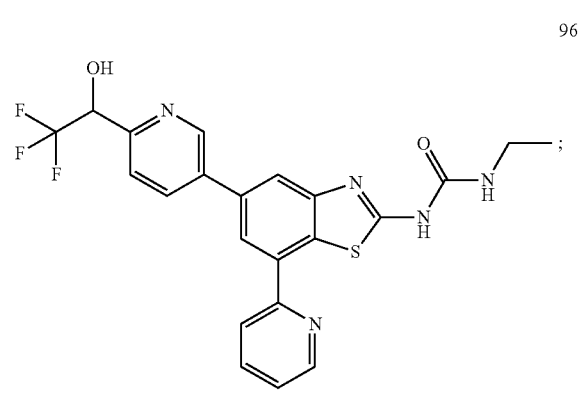
97
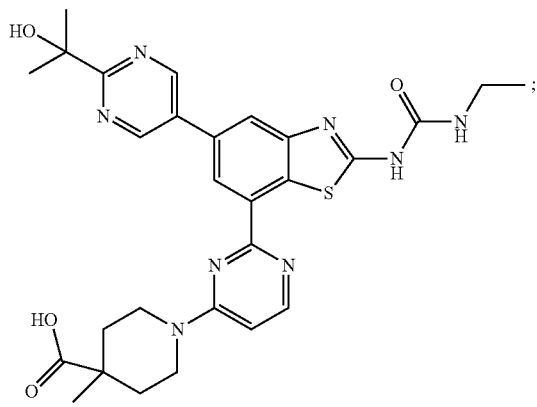
98
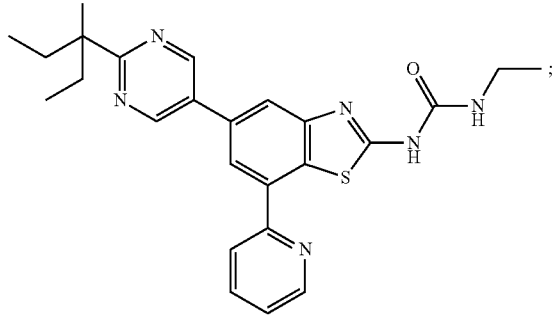

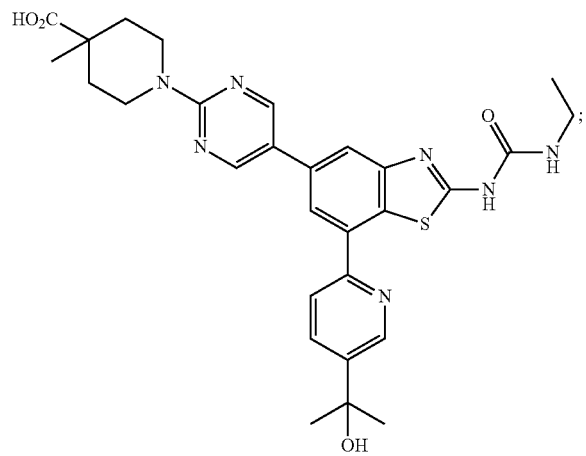
99
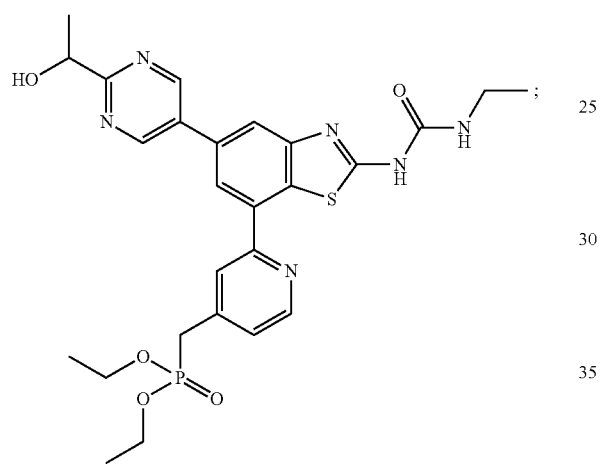
100
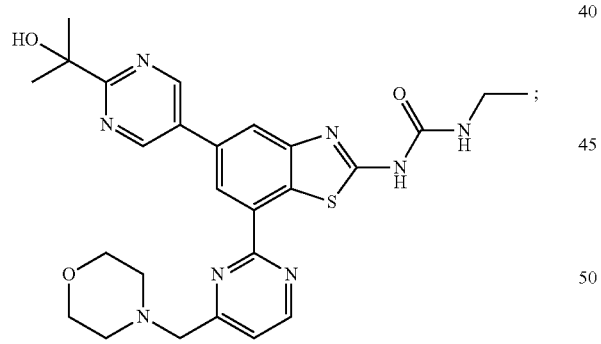
101
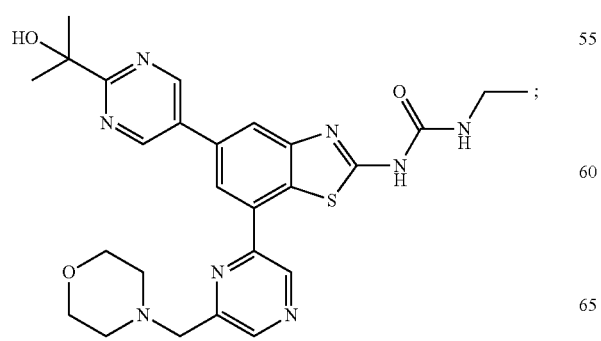
102
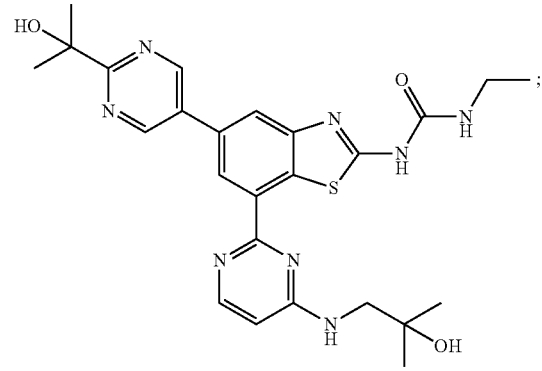
103
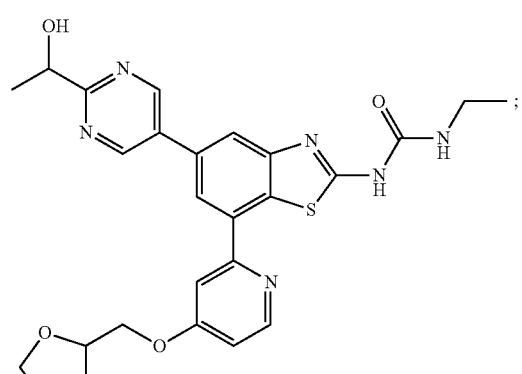
104
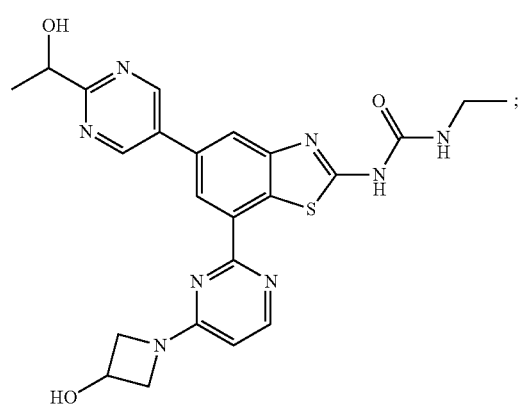
105
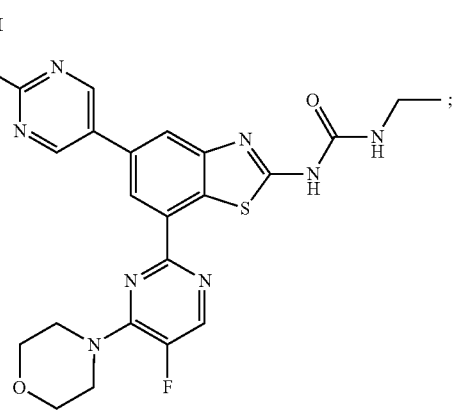
106

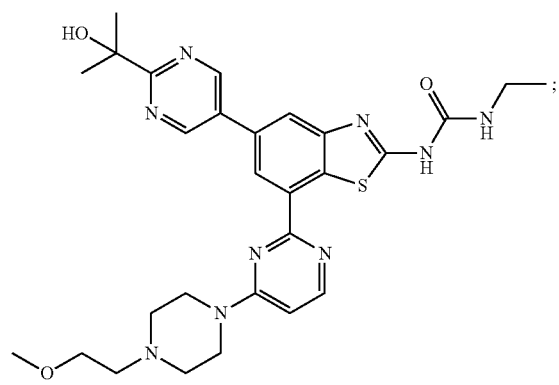
107
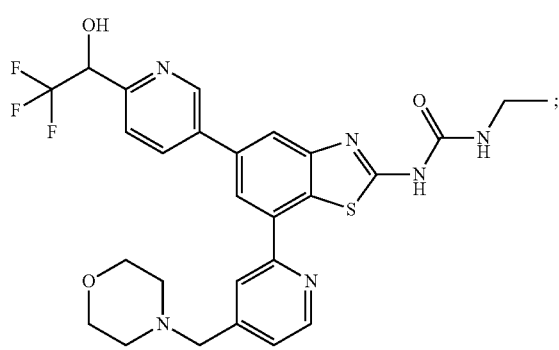
108
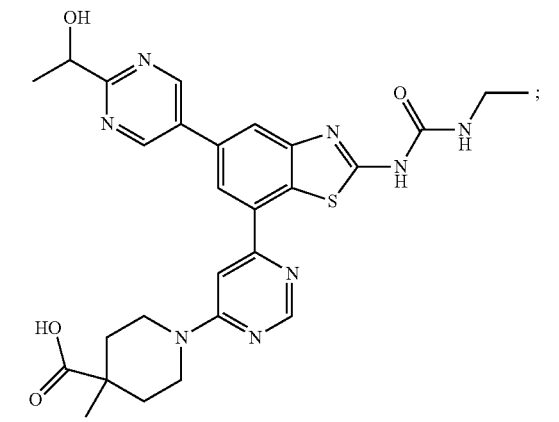
109
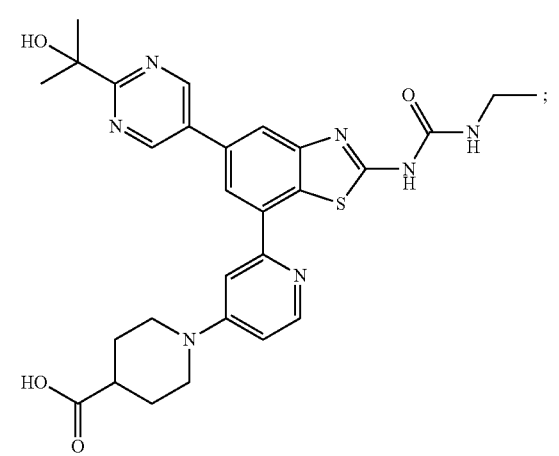
110
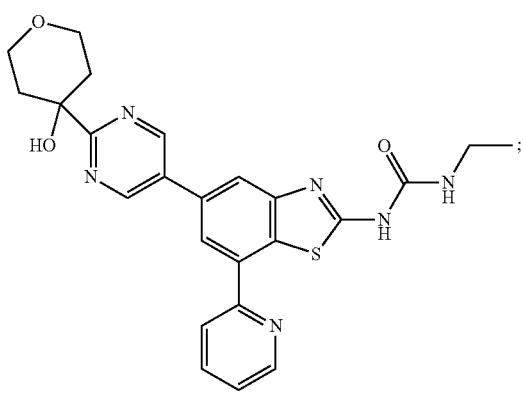
111
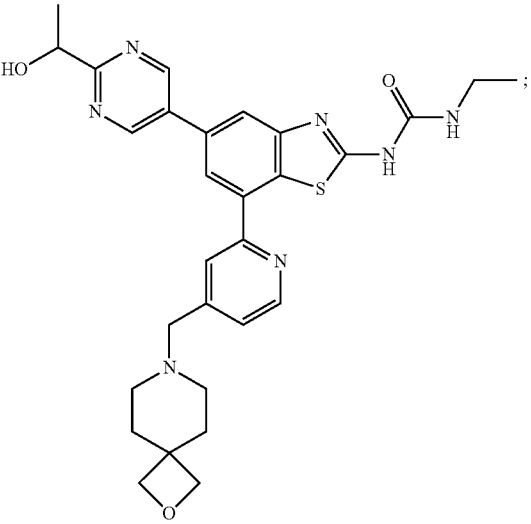
112
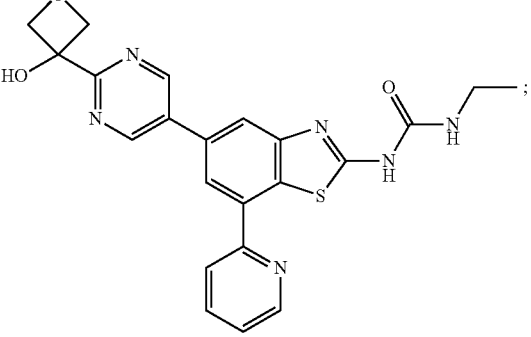
113
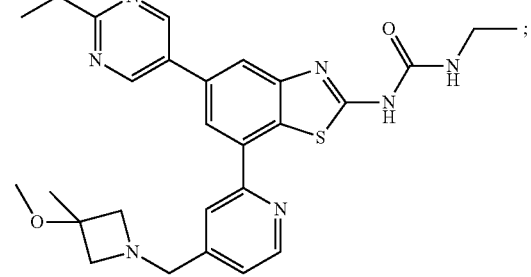
114

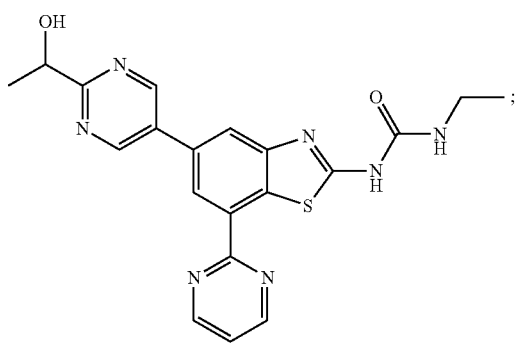
115
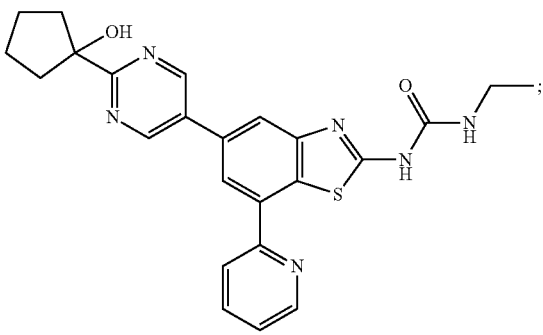
119
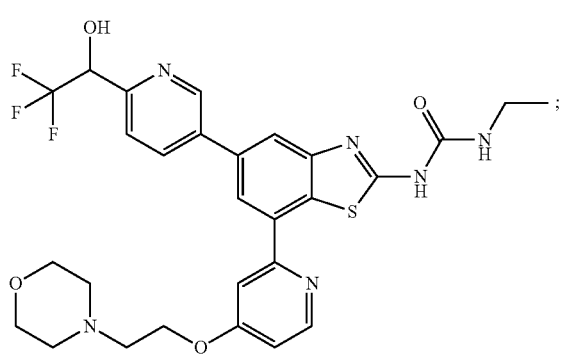
116
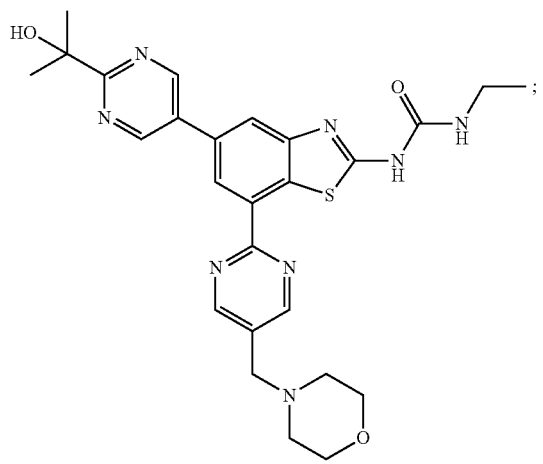
120
117
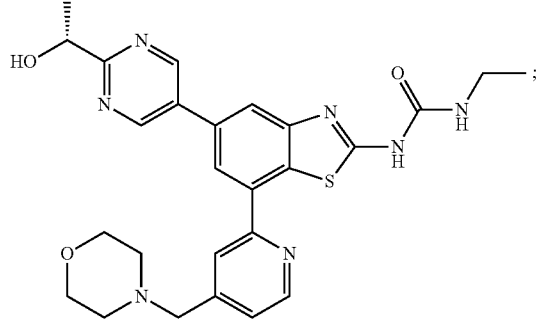
121
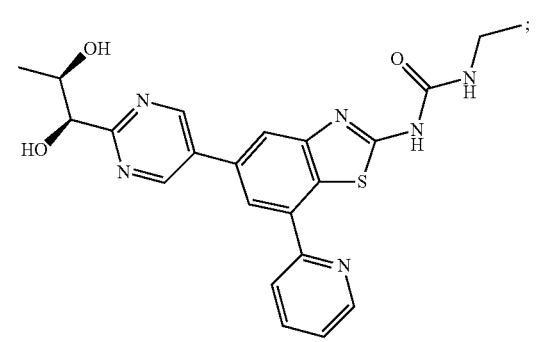
(mixture cis-diols)
118
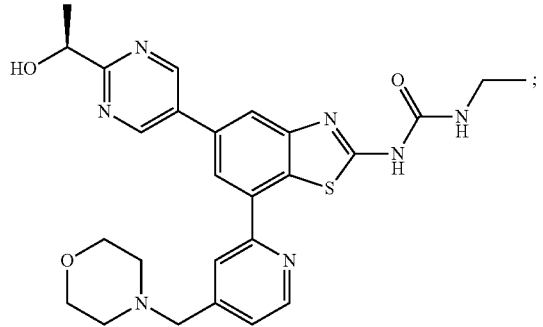
122

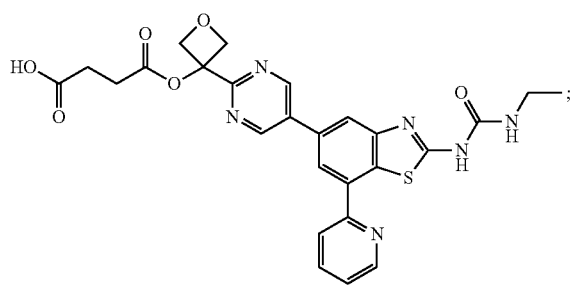
123
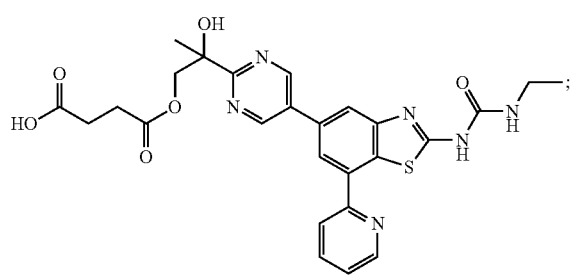
124
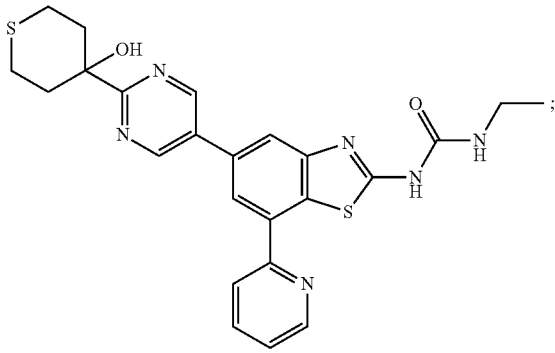
127
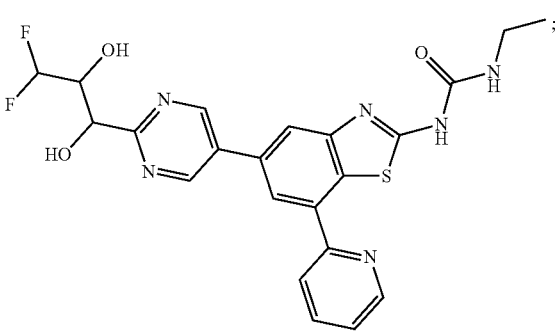
128
125
129
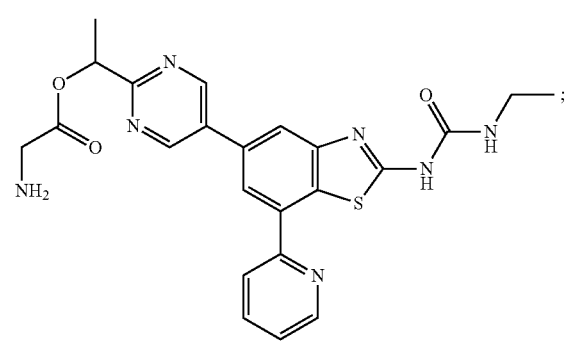
126
130

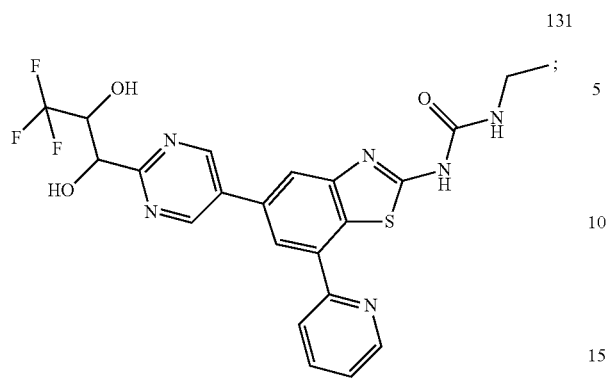
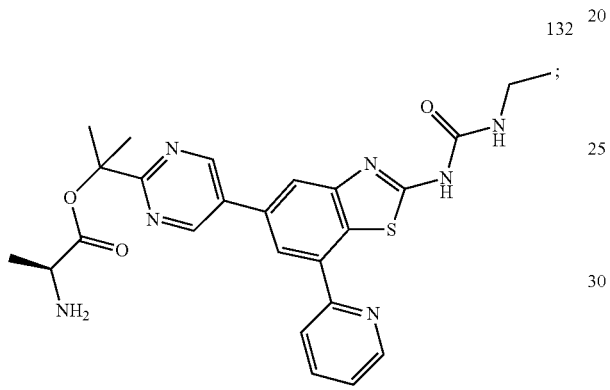
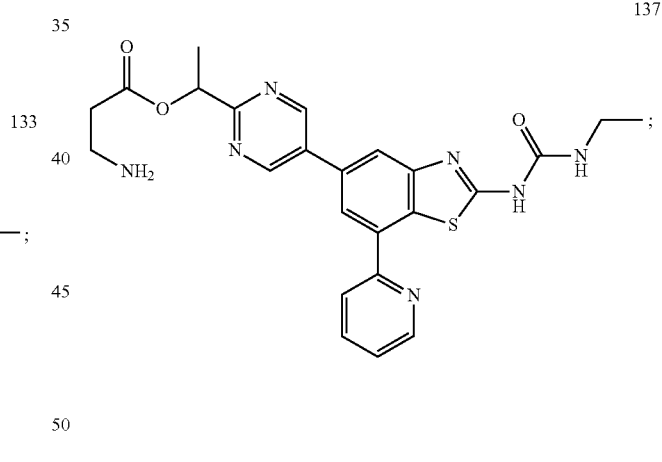
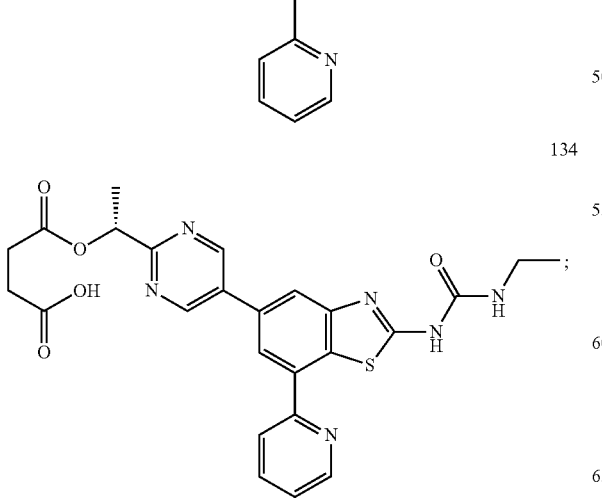
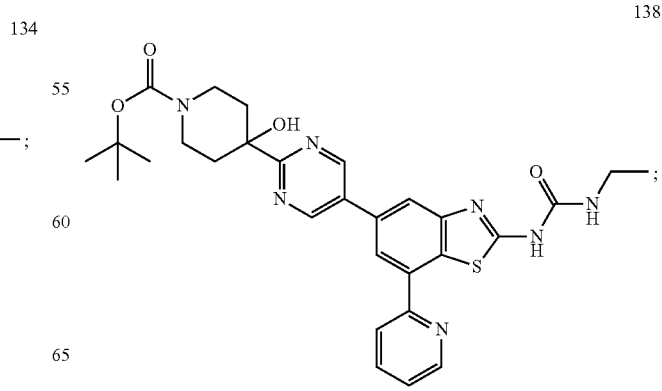

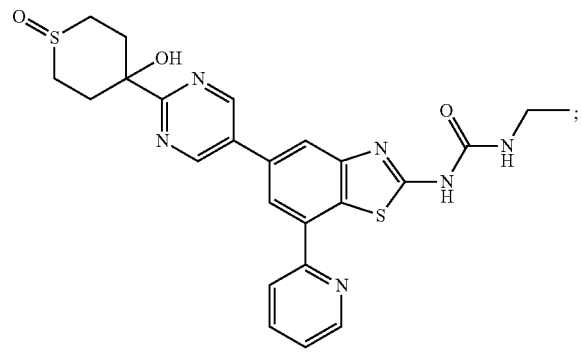
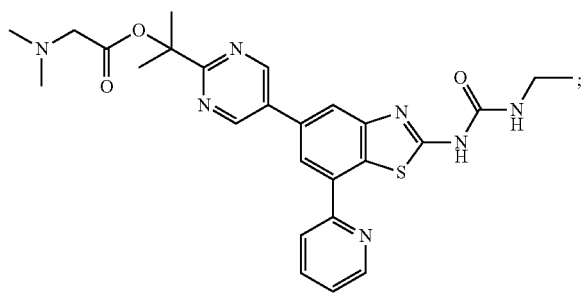
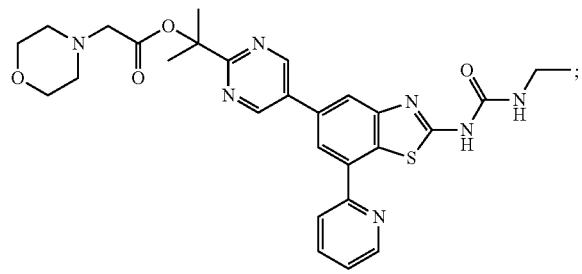
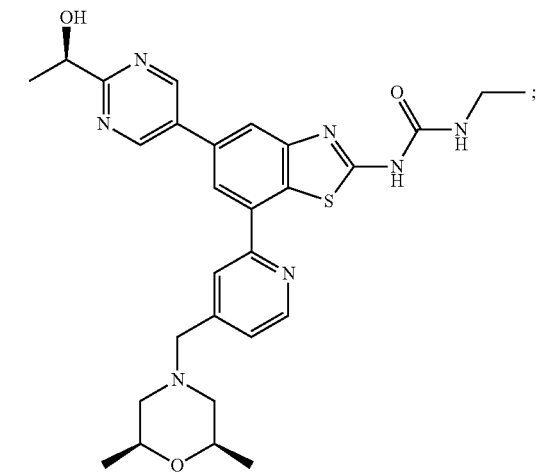
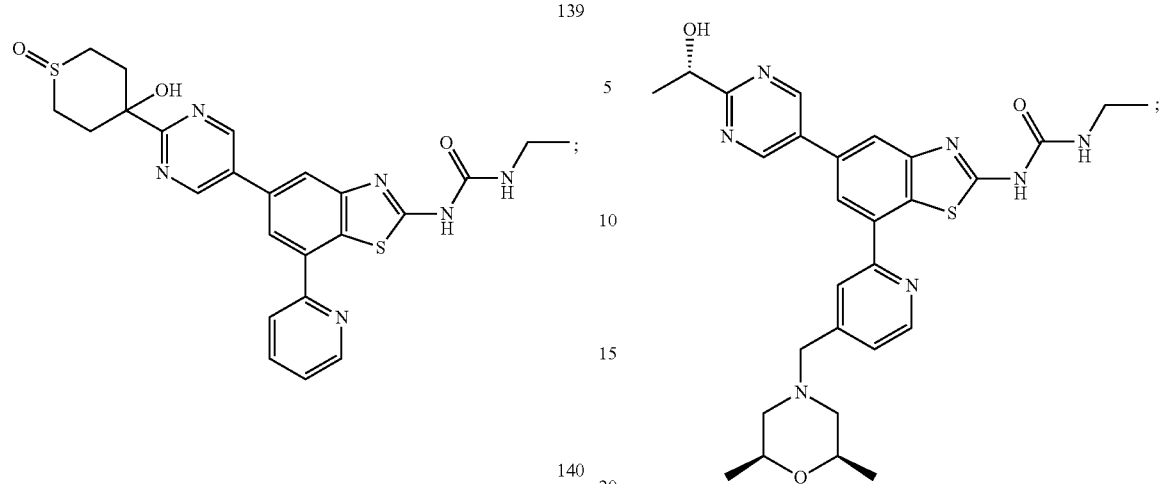

147 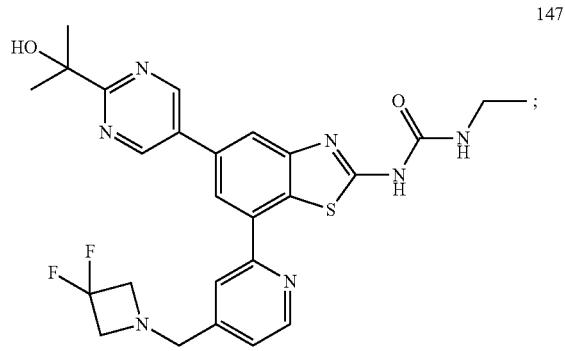
148 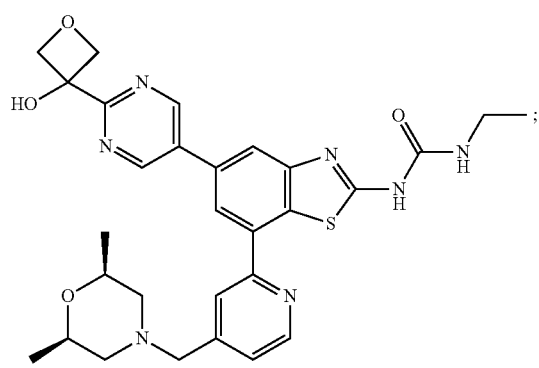
149 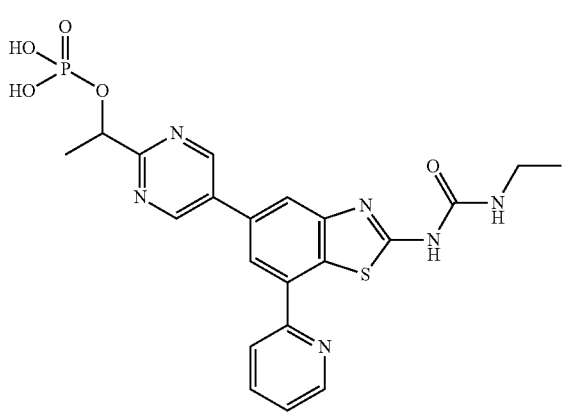
150 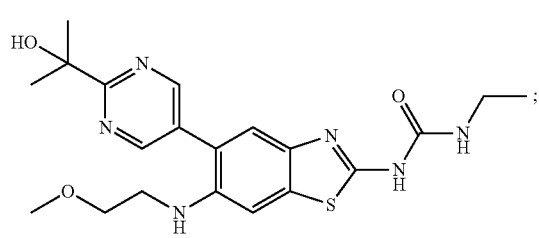
151 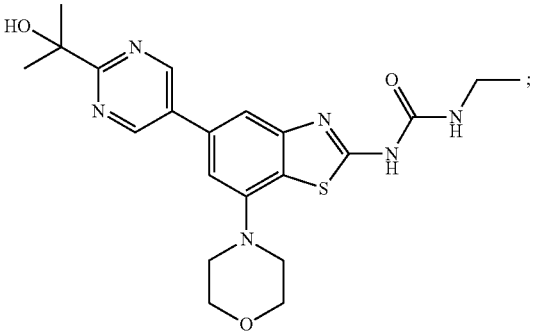
152 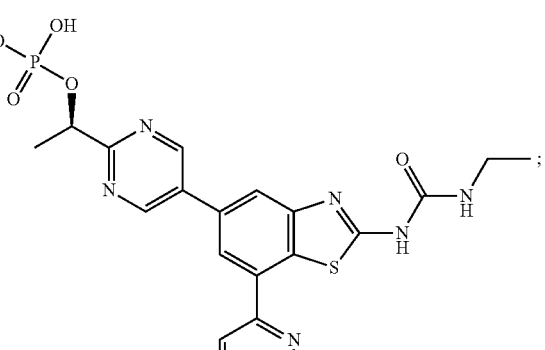
153 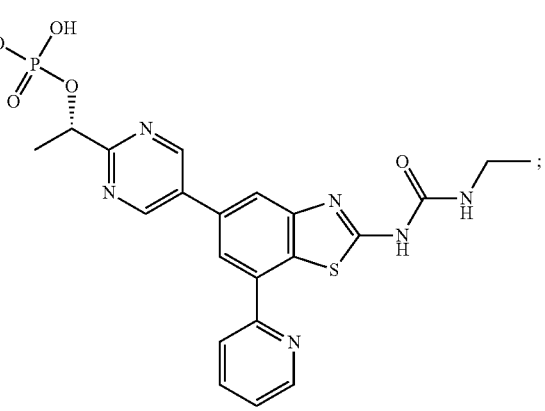
154 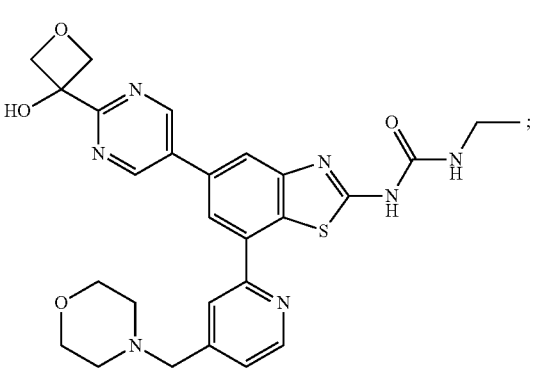

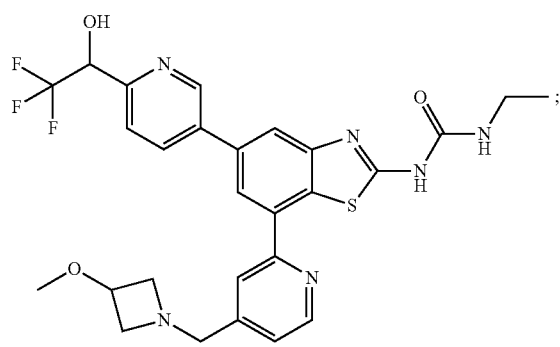
155
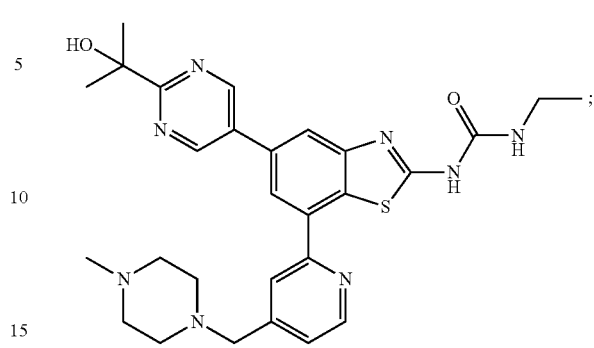
159
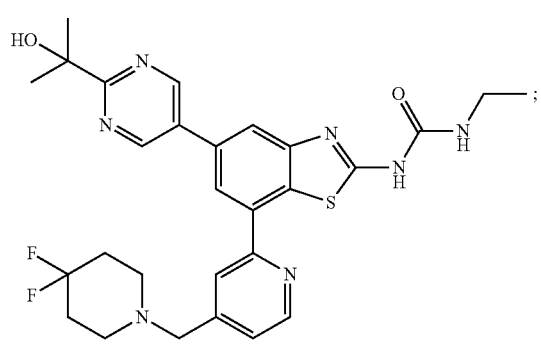
156
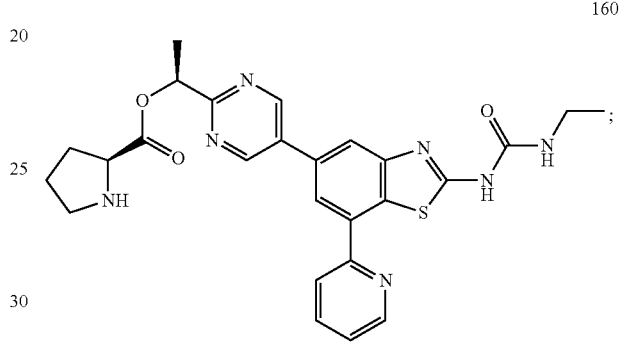
160
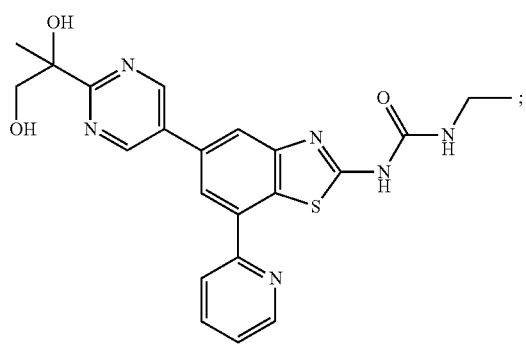
157
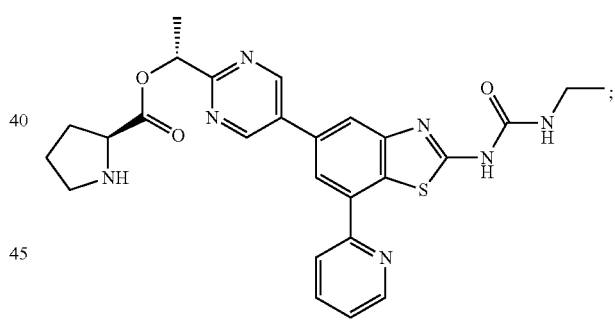
161
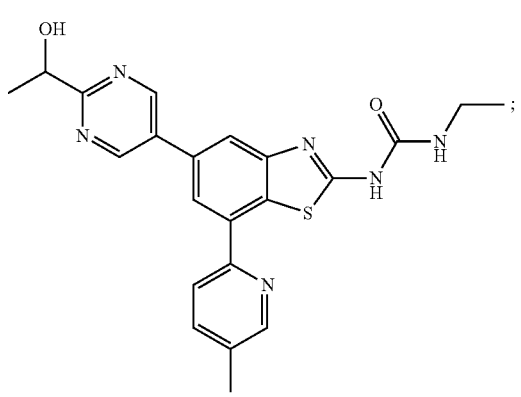
158
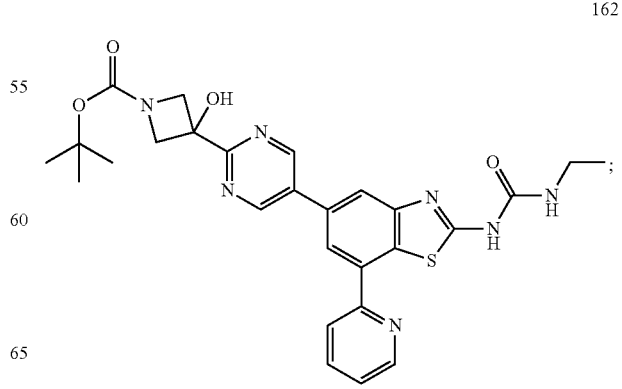
162

163
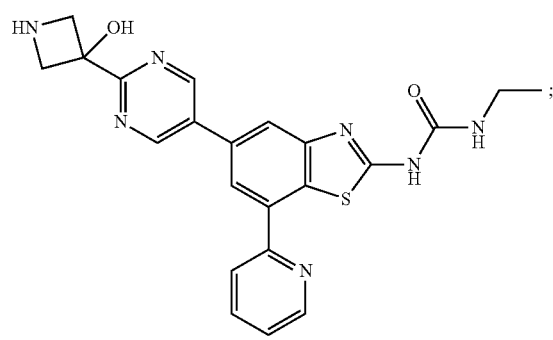
167
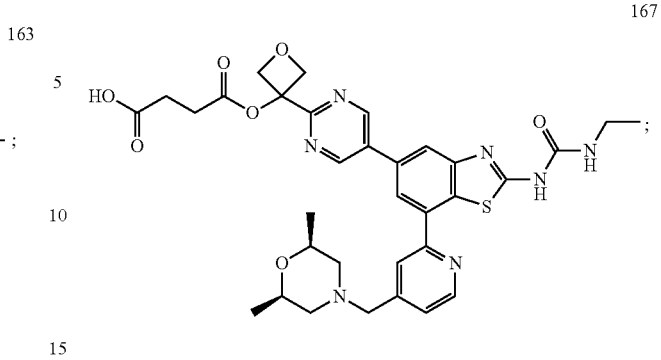
164
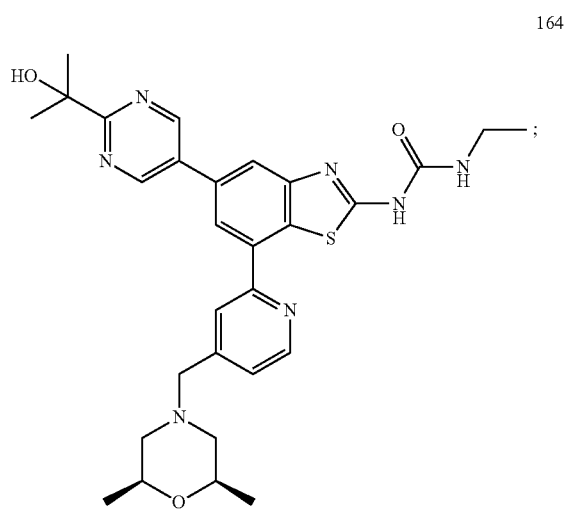
168
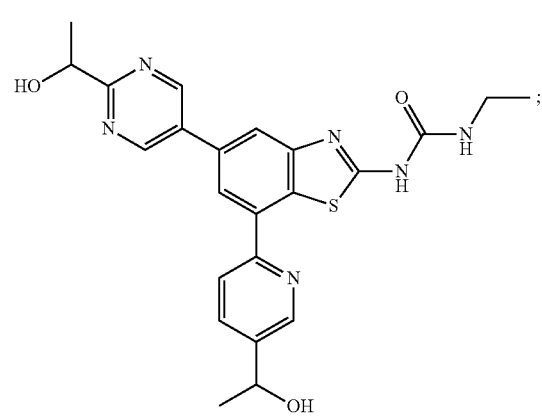
165
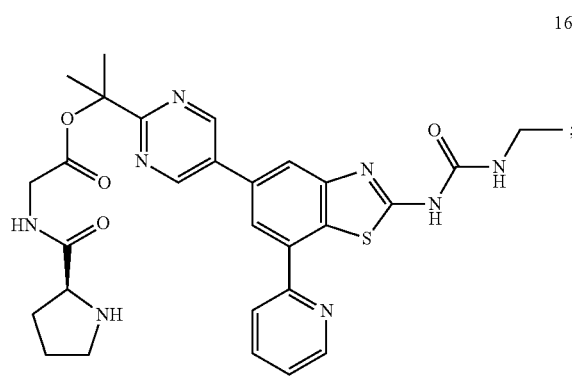
169
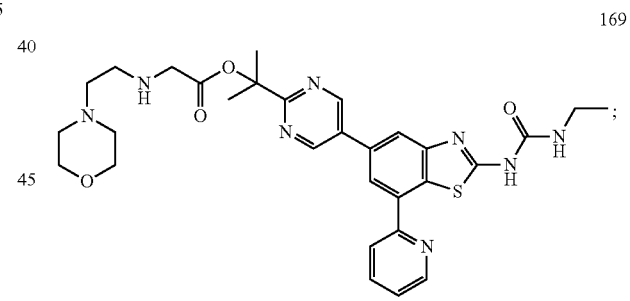
166
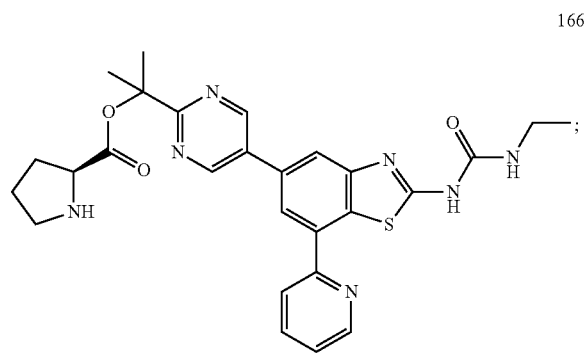
170
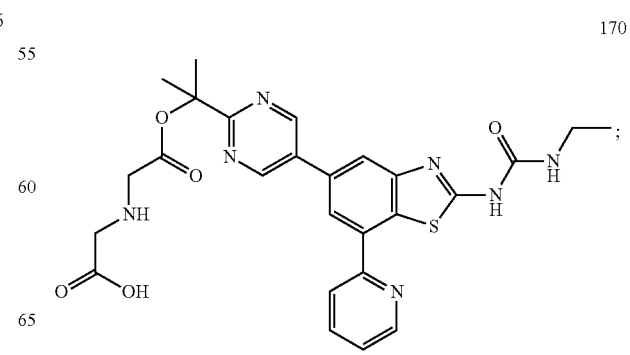

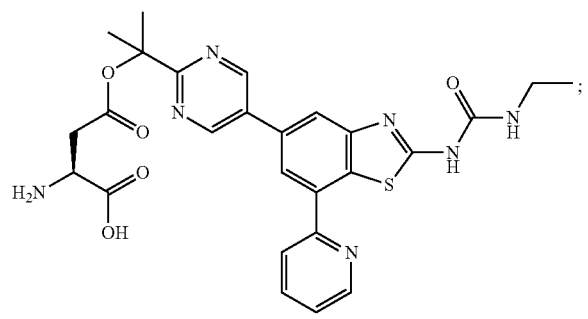
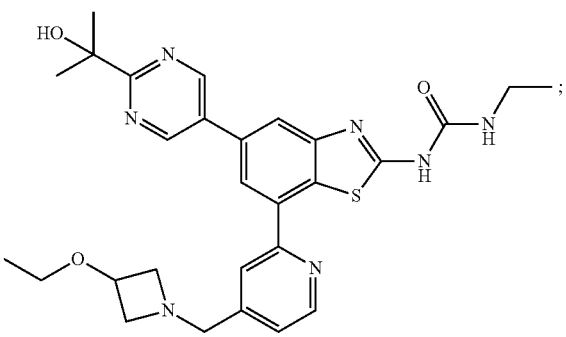

180
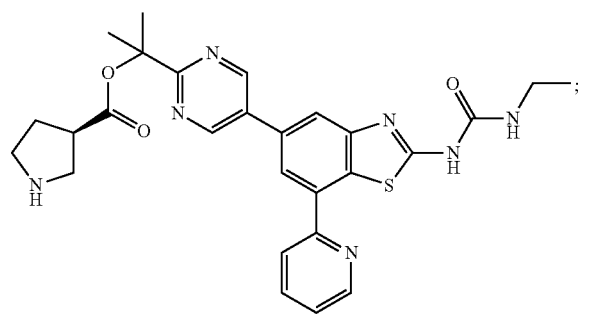
181
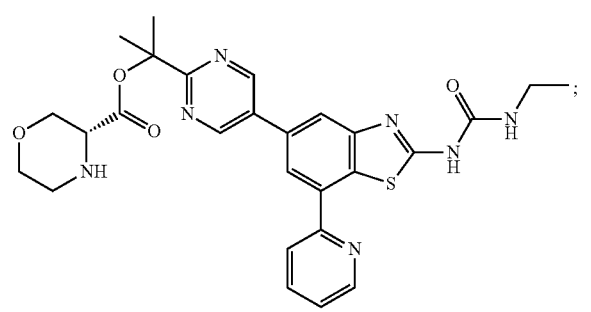
182
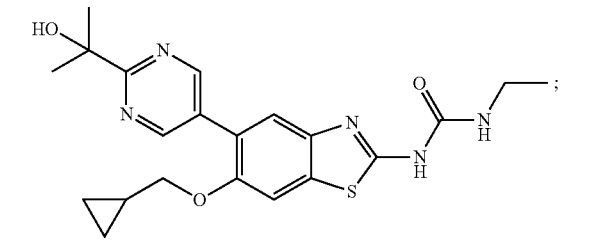
183
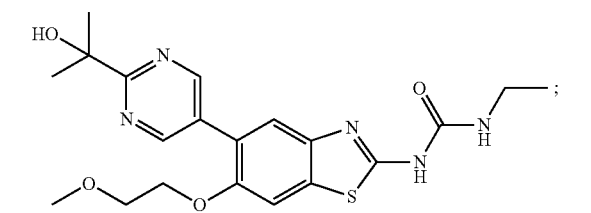
184
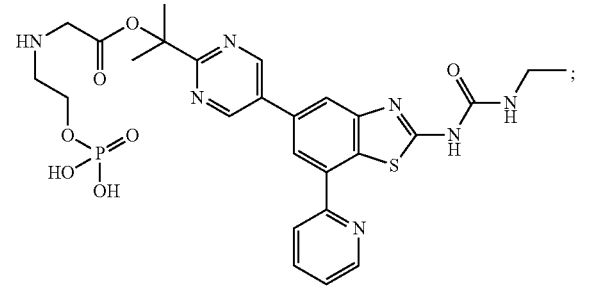
185
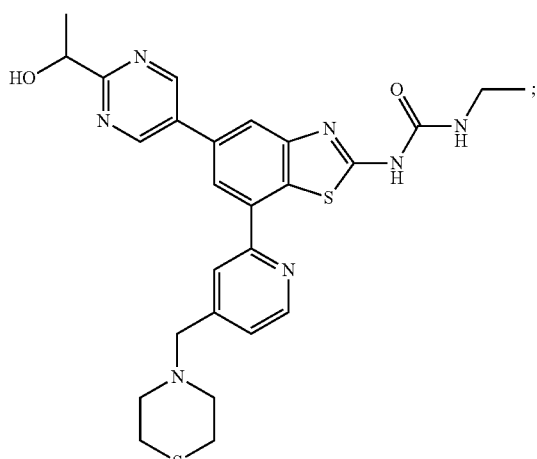
186
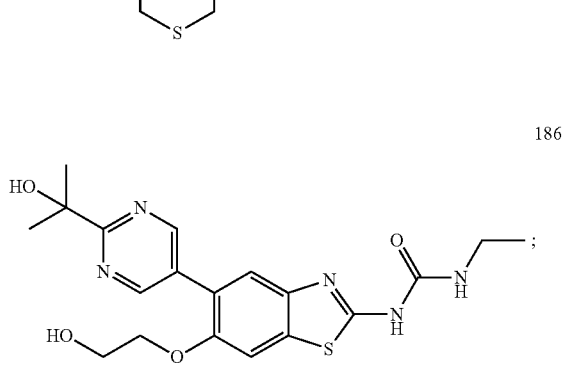
187
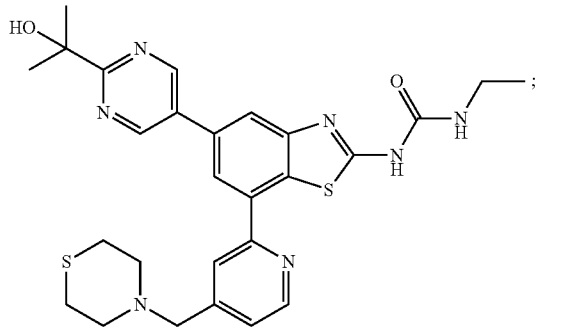
188
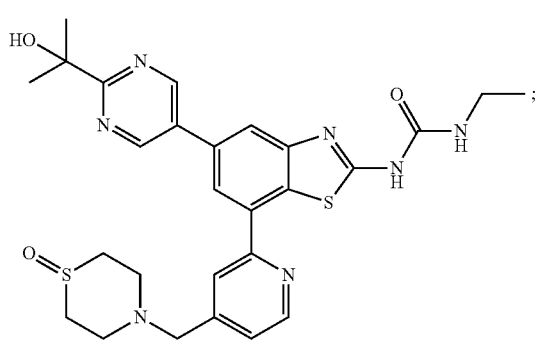

189
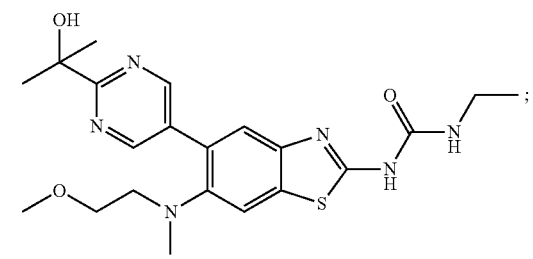
190
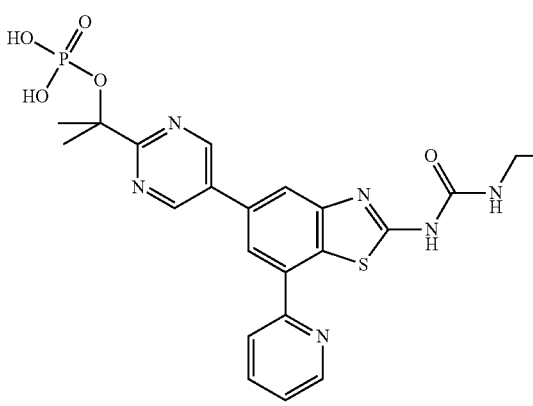
191
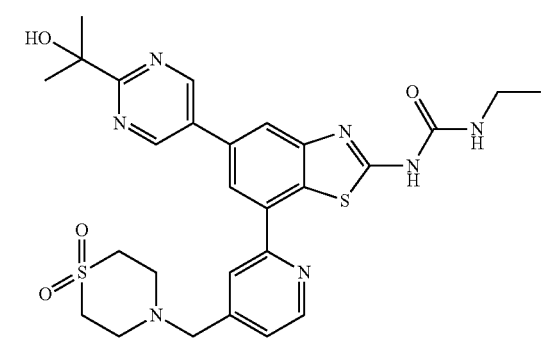
192
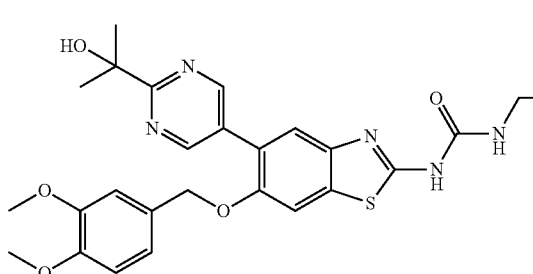
193
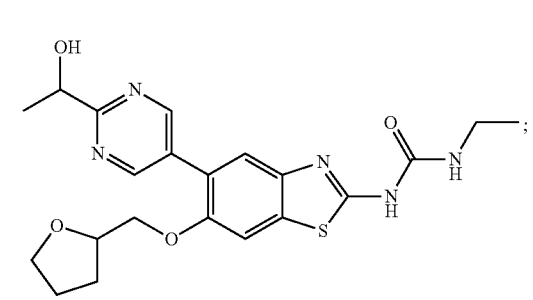
194
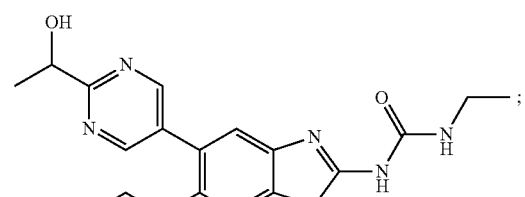
195
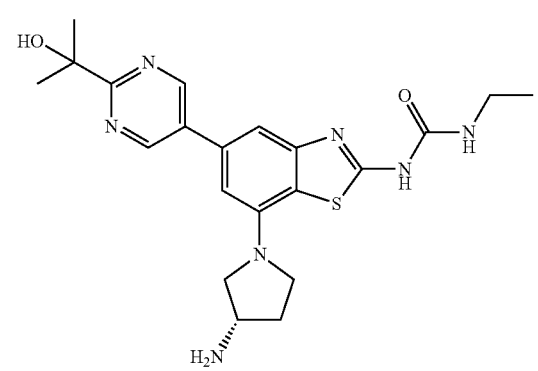
196
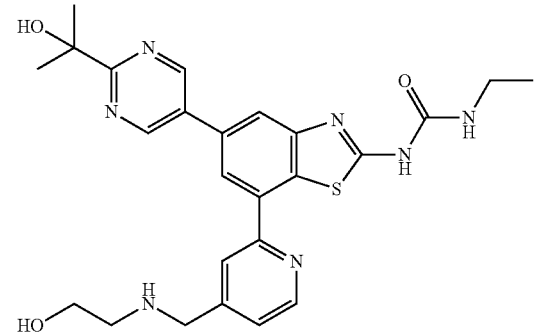
197
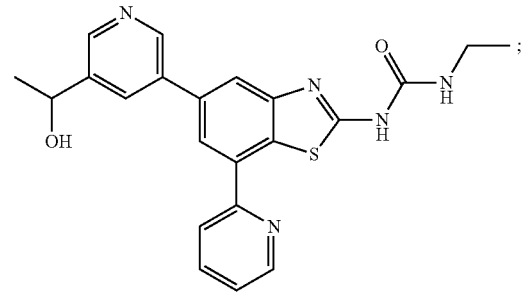
198
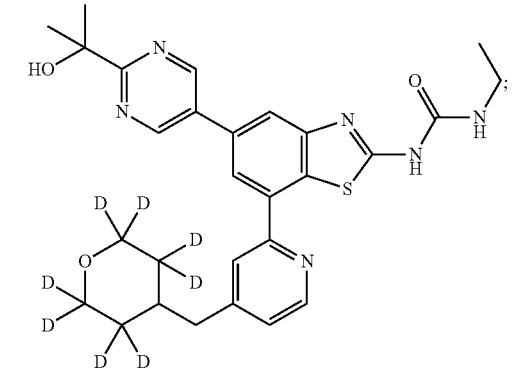

-continued

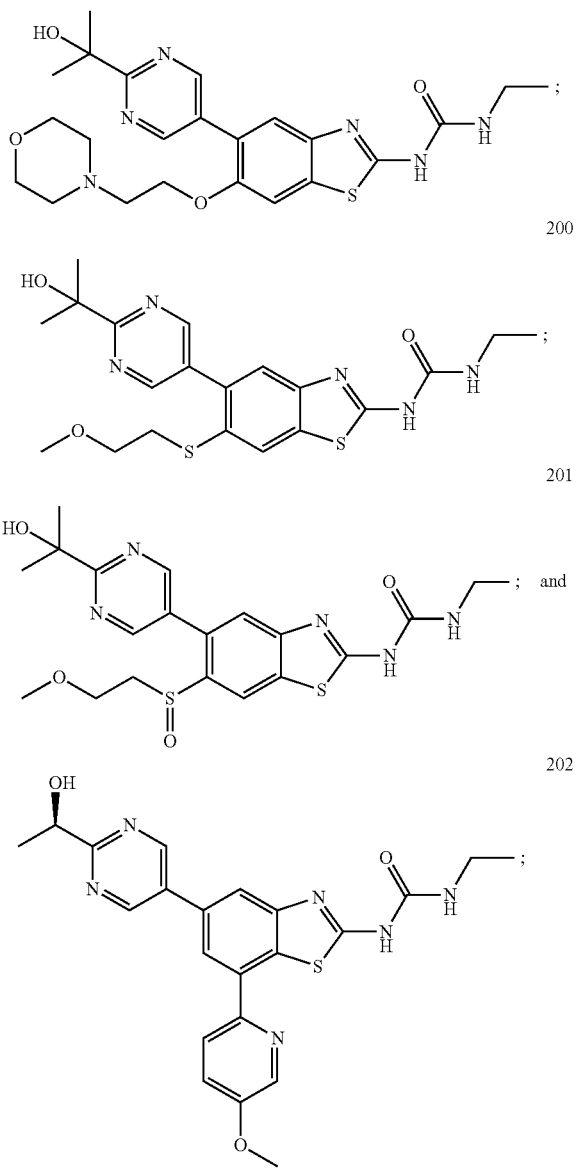

199

200

201

202 salts, racemates, diastereomers, enantiomers, esters, carbamates, phosphates, sulfates, deuterated forms and prodrugs thereof wherein compounds 1 to 202 are named as follows:
1) 1-ethyl-3-[5-[2-(1-hydroxy-1-methyl-ethyl)pyrimidin-5-yl]-7-(2-pyridyl)-1,3-benzothiazol-2-yl]urea;
2) 1-ethyl-3-[7-[4-[(3-hydroxy-3-methyl-azetidin-1-yl)methyl]-2-pyridyl]-5-[2-(1-hydroxy-1-methyl-ethyl)pyrimidin-5-yl]-1,3-benzothiazol-2-yl]urea;
3) 1-ethyl-3-[5-[2-(1-hydroxy-1-methyl-ethyl)pyrimidin-5-yl]-6-(tetrahydrofuran-2-ylmethoxy)-1,3-benzothiazol-2-yl]urea;
4) 1-ethyl-3-[6-fluoro-5-[6-[hydroxy(3-pyridyl)methyl]-3-pyridyl]-1,3-benzothiazol-2-yl]urea;
5) 1-(2-hydroxyethyl)-3-[5-[2-(1-hydroxy-1-methyl-ethyl)pyrimidin-5-yl]-7-(2-pyridyl)-1,3-benzothiazol-2-yl]urea;
6) 1-ethyl-3-[5-[5-(1-hydroxyethyl)pyrazin-2-yl]-7-(2-pyridyl)-1,3-benzothiazol-2-yl]urea;
7) 1-[5-[2-[(1S*,2R*)-1,2-dihydroxypropyl]pyrimidin-5-yl]-7-(2-pyridyl)-1,3-benzothiazol-2-yl]-3-ethyl-urea (mixture 1-[5-[2-[(1S,2R)-1,2-dihydroxypropyl]pyrimidin-5-yl]-7-(2-pyridyl)-1,3-benzothiazol-2-yl]-3-ethyl-urea; and 1-[5-[2-[(1R,2S)-1,2-dihydroxypropyl]pyrimidin-5-yl]-7-(2-pyridyl)-1,3-benzothiazol-2-yl]-3-ethyl-urea);
8) 1-[5-[2-[(3R*,4S*)-3,4-dihydroxytetrahydropyran-4-yl]pyrimidin-5-yl]-7-(2-pyridyl)-1,3-benzothiazol-2-yl]-3-ethyl-urea (mixture 1-[5-[2-[(3R,4S)-3,4-dihydroxytetrahydropyran-4-yl]pyrimidin-5-yl]-7-(2-pyridyl)-1,3-benzothiazol-2-yl]-3-ethyl-urea; and 1-[5-[2-[(3S,4R)-3,4-dihydroxytetrahydropyran-4-yl]pyrimidin-5-yl]-7-(2-pyridyl)-1,3-benzothiazol-2-yl]-3-ethyl-urea);
9) 1-ethyl-3-[5-[4-(1-hydroxyethyl)triazol-1-yl]-7-(2-pyridyl)-1,3-benzothiazol-2-yl]urea;
10) 1-ethyl-3-[5-[2-(1-hydroxy-1-methyl-ethyl)pyrimidin-5-yl]-7-pyrimidin-2-yl-1,3-benzothiazol-2-yl]urea;
11) 1-ethyl-3-[5-[4-(1-hydroxy-1-methyl-ethyl)imidazol-1-yl]-7-(2-pyridyl)-1,3-benzothiazol-2-yl]urea;
12) 1-ethyl-3-[5-[2-(1-hydroxy-1-methyl-ethyl)pyrimidin-5-yl]-7-methoxy-1,3-benzothiazol-2-yl]urea;
13) 1-ethyl-3-[5-[2-(1-hydroxy-1-methyl-ethyl)pyrimidin-5-yl]-7-(methoxymethyl)-1,3-benzothiazol-2-yl]urea;
14) 1-ethyl-3-[5-[2-(1-hydroxyethyl)pyrimidin-5-yl]-7-[(6-methyl-3-pyridyl)methoxy]-1,3-benzothiazol-2-yl]urea;
15) 1-ethyl-3-[5-[2-(1-hydroxyethyl)pyrimidin-5-yl]-7-[4-(methylsulfanylmethyl)-2-pyridyl]-1,3-benzothiazol-2-yl]urea;
16) 1-ethyl-3-[5-[2-(1-hydroxyethyl)pyrimidin-5-yl]-7-[4-(methylsulfinylmethyl)-2-pyridyl]-1,3-benzothiazol-2-yl]urea;
17) 1-ethyl-3-[5-[2-(1-hydroxyethyl)pyrimidin-5-yl]-7-(2-pyridyl)-1,3-benzothiazol-2-yl]urea;
18) 1-[5-[2-(ethylcarbamoylamino)-7-(2-pyridyl)-1,3-benzothiazol-5-yl]pyrimidin-2-yl]ethyl 4-methylpiperazine-1-carboxylate;
19) 4-[1-[5-[2-(ethylcarbamoylamino)-7-(2-pyridyl)-1,3-benzothiazol-5-yl]pyrimidin-2-yl]ethoxy]-4-oxo-butanoic acid;
20) O4-[1-[5-[2-(ethylcarbamoylamino)-7-(2-pyridyl)-1,3-benzothiazol-5-yl]pyrimidin-2-yl]-1-methyl-ethyl]O1-methyl butanedioate;
21) 4-[1-[5-[2-(ethylcarbamoylamino)-7-(2-pyridyl)-1,3-benzothiazol-5-yl]pyrimidin-2-yl]-1-methyl-ethoxy]-4-oxo-butanoic acid;
22) 1-ethyl-3-[5-[2-[(1R)-1-hydroxyethyl]pyrimidin-5-yl]-7-(2-pyridyl)-1,3-benzothiazol-2-yl]urea;
23) 1-ethyl-3-[5-[2-[(1S)-1-hydroxyethyl]pyrimidin-5-yl]-7-(2-pyridyl)-1,3-benzothiazol-2-yl]urea;
24) 1-ethyl-3-[5-[6-[hydroxy-(1-methylimidazol-2-yl)methyl]-3-pyridyl]-7-(2-pyridyl)-1,3-benzothiazol-2-yl]urea;
25) 1-ethyl-3-[5-[2-(1-hydroxy-1-methyl-ethyl)pyrimidin-5-yl]-7-[5-(morpholinomethyl)-2-pyridyl]-1,3-benzothiazol-2-yl]urea;
26) 1-ethyl-3-[5-[2-(1-hydroxy-1-methyl-ethyl)pyrimidin-5-yl]-7-[4-(pyrrolidin-1-ylmethyl)-2-pyridyl]-1,3-benzothiazol-2-yl]urea;
27) 1-ethyl-3-[5-[6-(1-hydroxy-1-methyl-ethyl)-3-pyridyl]-7-(2-pyridyl)-1,3-benzothiazol-2-yl]urea;
28) 1-ethyl-3-[5-[2-(1-hydroxy-1-methyl-ethyl)pyrimidin-5-yl]-7-[4-(morpholinomethyl)-2-pyridyl]-1,3-benzothiazol-2-yl]urea;
29) 1-ethyl-3-[5-[2-(1-hydroxy-1-methyl-ethyl)pyrimidin-5-yl]-7-[4-[(3-hydroxypyrrolidin-1-yl)methyl]-2-pyridyl]-1,3-benzothiazol-2-yl]urea;

30) 1-ethyl-3-[7-[4-[(3-hydroxyazetidin-1-yl)methyl]-2-pyridyl]-5-[2-(1-hydroxy-1-methyl-ethyl)pyrimidin-5-yl]-1,3-benzothiazol-2-yl]urea;
31) 1-ethyl-3-[5-[2-(1-hydroxy-1-methyl-ethyl)pyrimidin-5-yl]-7-[4-[(3-methoxyazetidin-1-yl)methyl]-2-pyridyl]-1,3-benzothiazol-2-yl]urea;
32) 1-ethyl-3-[5-[2-(1-hydroxy-1-methyl-ethyl)pyrimidin-5-yl]-7-[4-(2-morpholinoethoxy)-2-pyridyl]-1,3-benzothiazol-2-yl]urea;
33) 1-ethyl-3-[5-[2-(1-hydroxy-1-methyl-ethyl)pyrimidin-5-yl]-7-[4-(1-morpholinoethyl)-2-pyridyl]-1,3-benzothiazol-2-yl]urea;
34) 1-[7-[4-[(3,3-difluoropyrrolidin-1-yl)methyl]-2-pyridyl]-5-[2-(1-hydroxy-1-methyl-ethyl)pyrimidin-5-yl]-1,3-benzothiazol-2-yl]-3-ethyl-urea;
35) 1-ethyl-3-[7-[4-[[(3S)-3-fluoropyrrolidin-1-yl]methyl]-2-pyridyl]-5-[2-(1-hydroxy-1-methyl-ethyl)pyrimidin-5-yl]-1,3-benzothiazol-2-yl]urea;
36) 1-ethyl-3-[7-[4-[[(3R)-3-fluoropyrrolidin-1-yl]methyl]-2-pyridyl]-5-[2-(1-hydroxy-1-methyl-ethyl)pyrimidin-5-yl]-1,3-benzothiazol-2-yl]urea;
37) 1-[7-[4-[(3,3-difluoro-1-piperidyl)methyl]-2-pyridyl]-5-[2-(1-hydroxy-1-methyl-ethyl)pyrimidin-5-yl]-1,3-benzothiazol-2-yl]-3-ethyl-urea;
38) 1-ethyl-3-[5-[2-(1-hydroxy-1-methyl-ethyl)pyrimidin-5-yl]-7-[4-(3-morpholinopropoxy)-2-pyridyl]-1,3-benzothiazol-2-yl]urea;
39) 1-ethyl-3-[5-[2-(1-hydroxy-1-methyl-ethyl)pyrimidin-5-yl]-7-pyrazin-2-yl-1,3-benzothiazol-2-yl]urea;
40) 1-[5-[2-(1,2-dihydroxyethyl)pyrimidin-5-yl]-7-(2-pyridyl)-1,3-benzothiazol-2-yl]-3-ethyl-urea;
41) 1-[7-(dimethylaminomethyl)-6-hydroxy-5-[6-(1-hydroxy-1-methyl-ethyl)-3-pyridyl]-1,3-benzothiazol-2-yl]-3-ethyl-urea;
42) 1-ethyl-3-[5-[2-(1-hydroxy-1-methyl-ethyl)pyrimidin-5-yl]-7-[4-[[(3R)-3-methoxypyrrolidin-1-yl]methyl]-2-pyridyl]-1,3-benzothiazol-2-yl]urea;
43) 1-ethyl-3-[5-[2-(1-hydroxy-1-methyl-ethyl)pyrimidin-5-yl]-7-(6-methylpyrimidin-4-yl)-1,3-benzothiazol-2-yl]urea;
44) 1-ethyl-3-[6-hydroxy-5-[6-(1-hydroxy-1-methyl-ethyl)-3-pyridyl]-7-(morpholinomethyl)-1,3-benzothiazol-2-yl]urea;
45) 1-[6-[2-(ethylcarbamoylamino)-5-[2-(1-hydroxy-1-methyl-ethyl)pyrimidin-5-yl]-1,3-benzothiazol-7-yl]-3-pyridyl]-4-methyl-piperidine-4-carboxylic acid;
46) 2-[6-[2-(ethylcarbamoylamino)-5-[2-(1-hydroxy-1-methyl-ethyl)pyrimidin-5-yl]-1,3-benzothiazol-7-yl]-3-pyridyl]acetic acid;
47) 1-ethyl-3-[5-[2-(1-hydroxycyclohexyl)pyrimidin-5-yl]-7-(2-pyridyl)-1,3-benzothiazol-2-yl]urea;
48) 1-ethyl-3-[5-[2-(1-hydroxy-1-methyl-ethyl)thiazol-5-yl]-7-(2-pyridyl)-1,3-benzothiazol-2-yl]urea;
49) 1-ethyl-3-[5-[5-(1-hydroxy-1-methyl-ethyl)pyrazin-2-yl]-7-(2-pyridyl)-1,3-benzothiazol-2-yl]urea;
50) 1-[2-[2-(ethylcarbamoylamino)-5-[2-(1-hydroxy-1-methyl-ethyl)pyrimidin-5-yl]-1,3-benzothiazol-7-yl]-4-pyridyl]-4-methyl-piperidine-4-carboxylic acid;
51) 1-[6-[2-(ethylcarbamoylamino)-5-[2-(1-hydroxy-1-methyl-ethyl)pyrimidin-5-yl]-1,3-benzothiazol-7-yl]-2-pyridyl]-4-methyl-piperidine-4-carboxylic acid;
52) 1-[4-[2-(ethylcarbamoylamino)-5-[2-(1-hydroxy-1-methyl-ethyl)pyrimidin-5-yl]-1,3-benzothiazol-7-yl]pyrimidin-2-yl]-4-methyl-piperidine-4-carboxylic acid;
53) 1-[7-[4-[(cyclopropylamino)methyl]-2-pyridyl]-5-[2-(1-hydroxy-1-methyl-ethyl)pyrimidin-5-yl]-1,3-benzothiazol-2-yl]-3-ethyl-urea;
54) 4-[[2-[2-(ethylcarbamoylamino)-5-[2-(1-hydroxy-1-methyl-ethyl)pyrimidin-5-yl]-1,3-benzothiazol-7-yl]-4-pyridyl]amino]-1-methyl-cyclohexanecarboxylic acid;
55) 1-ethyl-3-[5-[2-(1-hydroxyethyl)pyrimidin-5-yl]-7-[4-(morpholinomethyl)-2-pyridyl]-1,3-benzothiazol-2-yl]urea;
56) 1-ethyl-3-[5-[2-(1-hydroxy-1-methyl-ethyl)pyrimidin-5-yl]-7-[5-(2-morpholinoethoxy)-2-pyridyl]-1,3-benzothiazol-2-yl]urea;
57) 1-[5-[2-(1-hydroxy-1-methyl-ethyl)pyrimidin-5-yl]-7-(2-pyridyl)-1,3-benzothiazol-2-yl]-3-propyl-urea;
58) 1-[5-[2-[cyclopropyl(hydroxy)methyl]pyrimidin-5-yl]-7-(2-pyridyl)-1,3-benzothiazol-2-yl]-3-ethyl-urea;
59) 1-ethyl-3-[5-[2-(1-hydroxypropyl)pyrimidin-5-yl]-7-(2-pyridyl)-1,3-benzothiazol-2-yl]urea;
60) 1-ethyl-3-[5-[2-(1-hydroxy-2,2-dimethyl-propyl)pyrimidin-5-yl]-7-(2-pyridyl)-1,3-benzothiazol-2-yl]urea;
61) 1-ethyl-3-[5-[2-(1-hydroxybutyl)pyrimidin-5-yl]-7-(2-pyridyl)-1,3-benzothiazol-2-yl]urea
62) [(1R)-1-[5-[2-(ethylcarbamoylamino)-7-(2-pyridyl)-1,3-benzothiazol-5-yl]pyrimidin-2-yl]ethyl](2R)-2-amino-3-methyl-butanoate;
63) [(1S)-1-[5-[2-(ethylcarbamoylamino)-7-(2-pyridyl)-1,3-benzothiazol-5-yl]pyrimidin-2-yl]ethyl](2R)-2-amino-3-methyl-butanoate;
64) 1-ethyl-3-[7-[4-[[(3S)-3-fluoropyrrolidin-1-yl]methyl]-2-pyridyl]-5-[2-(1-hydroxyethyl)pyrimidin-5-yl]-1,3-benzothiazol-2-yl]urea;
65) 1-ethyl-3-[7-[4-[(3-hydroxyazetidin-1-yl)methyl]-2-pyridyl]-5-[2-(1-hydroxyethyl)pyrimidin-5-yl]-1,3-benzothiazol-2-yl]urea;
66) 1-ethyl-3-[5-[2-(1-hydroxyethyl)pyrimidin-5-yl]-7-[4-[(3-hydroxy-3-methyl-azetidin-1-yl)methyl]-2-pyridyl]-1,3-benzothiazol-2-yl]urea;
67) 1-ethyl-3-[5-[2-(1-hydroxy-1-methyl-ethyl)pyrimidin-5-yl]-7-[4-[(3-hydroxy-3-methyl-pyrrolidin-1-yl)methyl]-2-pyridyl]-1,3-benzothiazol-2-yl]urea;
68) 1-ethyl-3-[5-[2-(1-hydroxyethyl)pyrimidin-5-yl]-7-[4-[(3-methylmorpholin-4-yl)methyl]-2-pyridyl]-1,3-benzothiazol-2-yl]urea;
69) 1-[7-[4-[[(2R,6S)-2,6-dimethylmorpholin-4-yl]methyl]-2-pyridyl]-5-[2-(1-hydroxyethyl)pyrimidin-5-yl]-1,3-benzothiazol-2-yl]-3-ethyl-urea;
70) 1-ethyl-3-[5-[2-(1-hydroxyethyl)pyrimidin-5-yl]-7-[4-[(2,2,3,3,5,5,6,6-octadeuteriomorpholin-4-yl)methyl]-2-pyridyl]-1,3-benzothiazol-2-yl]urea;
71) 1-[7-[4-[(2,5-dimethylmorpholin-4-yl)methyl]-2-pyridyl]-5-[2-(1-hydroxyethyl)pyrimidin-5-yl]-1,3-benzothiazol-2-yl]-3-ethyl-urea;
72) (2S)-1-[[2-[2-(ethylcarbamoylamino)-5-[2-(1-hydroxyethyl)pyrimidin-5-yl]-1,3-benzothiazol-7-yl]-4-pyridyl]methyl]pyrrolidine-2-carboxylic acid;
73) 1-ethyl-3-[5-[2-(1-hydroxyethyl)pyrimidin-5-yl]-7-[4-(6-oxa-2-azaspiro[3.3]heptan-2-ylmethyl)-2-pyridyl]-1,3-benzothiazol-2-yl]urea;
74) 1-[5-[2-(ethylcarbamoylamino)-7-[4-(1-hydroxy-1-methyl-ethyl)-2-pyridyl]-1,3-benzothiazol-5-yl]pyrimidin-2-yl]-4-methyl-piperidine-4-carboxylic acid;
75) 1-ethyl-3-[5-[2-(1-hydroxyethyl)pyrimidin-5-yl]-7-[4-(2-morpholinoethoxy)-2-pyridyl]-1,3-benzothiazol-2-yl]urea;
76) 1-ethyl-3-[5-[2-(1-hydroxyethyl)pyrimidin-5-yl]-7-[4-[(3-methoxyazetidin-1-yl)methyl]-2-pyridyl]-1,3-benzothiazol-2-yl]urea;
77) 1-ethyl-3-[5-[2-(1-hydroxyethyl)pyrimidin-5-yl]-7-[4-[[(3R)-3-hydroxypyrrolidin-1-yl]methyl]-2-pyridyl]-1,3-benzothiazol-2-yl]urea;

78) 1-ethyl-3-[5-[2-(1-hydroxy-1-methyl-ethyl)pyrimidin-5-yl]-7-[4-(2-methoxyethylamino)pyrimidin-2-yl]-1,3-benzothiazol-2-yl]urea;
79) 1-ethyl-3-[7-[4-(4-ethylpiperazin-1-yl)pyrimidin-2-yl]-5-[2-(1-hydroxy-1-methyl-ethyl)pyrimidin-5-yl]-1,3-benzothiazol-2-yl]urea;
80) 1-ethyl-3-[5-[2-(1-hydroxy-1-methyl-ethyl)pyrimidin-5-yl]-7-[4-(2-methoxyethoxy)-2-pyridyl]-1,3-benzothiazol-2-yl]urea;
81) 1-ethyl-3-[5-[2-(1-hydroxy-2-morpholino-ethyl)pyrimidin-5-yl]-7-(2-pyridyl)-1,3-benzothiazol-2-yl]urea;
82) 1-[5-[2-(1-hydroxy-1-methyl-ethyl)pyrimidin-5-yl]-7-(2-pyridyl)-1,3-benzothiazol-2-yl]-3-methyl-urea;
83) 1-[5-[2-(1-hydroxyethyl)pyrimidin-5-yl]-7-(2-pyridyl)-1,3-benzothiazol-2-yl]-3-methyl-urea;
84) 1-ethyl-3-[5-[2-(1-hydroxyethyl)pyrimidin-5-yl]-7-[4-[(3-hydroxy-3-methyl-pyrrolidin-1-yl)methyl]-2-pyridyl]-1,3-benzothiazol-2-yl]urea;
85) 1-ethyl-3-[7-[4-(2-hydroxyethylamino)pyrimidin-2-yl]-5-[2-(1-hydroxy-1-methyl-ethyl)pyrimidin-5-yl]-1,3-benzothiazol-2-yl]urea;
86) 1-ethyl-3-[7-[4-(3-hydroxy-3-methyl-azetidin-1-yl)pyrimidin-2-yl]-5-[2-(1-hydroxy-1-methyl-ethyl)pyrimidin-5-yl]-1,3-benzothiazol-2-yl]urea;
87) 1-[6-[2-(ethylcarbamoylamino)-5-[2-(1-hydroxy-1-methyl-ethyl)pyrimidin-5-yl]-1,3-benzothiazol-7-yl]pyrimidin-4-yl]-4-methyl-piperidine-4-carboxylic acid;
88) 1-[5-[2-(ethylcarbamoylamino)-7-[4-(1-hydroxyethyl)-2-pyridyl]-1,3-benzothiazol-5-yl]pyrimidin-2-yl]-4-methyl-piperidine-4-carboxylic acid;
89) [1-[5-[2-(ethylcarbamoylamino)-7-(2-pyridyl)-1,3-benzothiazol-5-yl]pyrimidin-2-yl]-1-methyl-ethyl]-4-methylpiperazine-1-carboxylate;
90) 1-ethyl-3-[5-[2-(1-hydroxyethyl)pyrimidin-5-yl]-7-(4-hydroxy-2-pyridyl)-1,3-benzothiazol-2-yl]urea;
91) 1-ethyl-3-[5-[2-(1-hydroxy-1-methyl-ethyl)pyrimidin-5-yl]-7-[4-(2-morpholinoethylamino)pyrimidin-2-yl]-1,3-benzothiazol-2-yl]urea;
92) 1-ethyl-3-[5-[2-(1-hydroxyethyl)pyrimidin-5-yl]-7-[4-(2-methoxyethoxy)-2-pyridyl]-1,3-benzothiazol-2-yl]urea;
93) 1-ethyl-3-[5-[2-(1-hydroxyethyl)pyrimidin-5-yl]-7-[4-(3-methoxyazetidin-1-yl)pyrimidin-2-yl]-1,3-benzothiazol-2-yl]urea;
94) 1-ethyl-3-[5-[2-(1-hydroxyethyl)pyrimidin-5-yl]-7-(4-morpholinopyrimidin-2-yl)-1,3-benzothiazol-2-yl]urea;
95) 1-ethyl-3-[5-[6-(1-hydroxyethyl)-3-pyridyl]-7-(2-pyridyl)-1,3-benzothiazol-2-yl]urea;
96) 1-ethyl-3-[7-(2-pyridyl)-5-[6-(2,2,2-trifluoro-1-hydroxy-ethyl)-3-pyridyl]-1,3-benzothiazol-2-yl]urea;
97) 1-[2-[2-(ethylcarbamoylamino)-5-[2-(1-hydroxy-1-methyl-ethyl)pyrimidin-5-yl]-1,3-benzothiazol-7-yl]pyrimidin-4-yl]-4-methyl-piperidine-4-carboxylic acid;
98) 1-ethyl-3-[5-[2-(1-ethyl-1-hydroxy-propyl)pyrimidin-5-yl]-7-(2-pyridyl)-1,3-benzothiazol-2-yl]urea;
99) 1-[5-[2-(ethylcarbamoylamino)-7-[5-(1-hydroxy-1-methyl-ethyl)-2-pyridyl]-1,3-benzothiazol-5-yl]pyrimidin-2-yl]-4-methyl-piperidine-4-carboxylic acid;
100) 1-[7-[4-(diethoxyphosphorylmethyl)-2-pyridyl]-5-[2-(1-hydroxyethyl)pyrimidin-5-yl]-1,3-benzothiazol-2-yl]-3-ethyl-urea;
101) 1-ethyl-3-[5-[2-(1-hydroxy-1-methyl-ethyl)pyrimidin-5-yl]-7-[4-(morpholinomethyl)pyrimidin-2-yl]-1,3-benzothiazol-2-yl]urea;
102) 1-ethyl-3-[5-[2-(1-hydroxy-1-methyl-ethyl)pyrimidin-5-yl]-7-[6-(morpholinomethyl)pyrazin-2-yl]-1,3-benzothiazol-2-yl]urea;
103) 1-ethyl-3-[5-[2-(1-hydroxy-1-methyl-ethyl)pyrimidin-5-yl]-7-[4-[(2-hydroxy-2-methyl-propyl)amino]pyrimidin-2-yl]-1,3-benzothiazol-2-yl]urea;
104) 1-ethyl-3-[5-[2-(1-hydroxyethyl)pyrimidin-5-yl]-7-[4-(tetrahydrofuran-2-ylmethoxy)-2-pyridyl]-1,3-benzothiazol-2-yl]urea;
105) 1-ethyl-3-[7-[4-(3-hydroxyazetidin-1-yl)pyrimidin-2-yl]-5-[2-(1-hydroxyethyl)pyrimidin-5-yl]-1,3-benzothiazol-2-yl]urea;
106) 1-ethyl-3-[7-(5-fluoro-4-morpholino-pyrimidin-2-yl)-5-[2-(1-hydroxyethyl)pyrimidin-5-yl]-1,3-benzothiazol-2-yl]urea;
107) 1-ethyl-3-[5-[2-(1-hydroxy-1-methyl-ethyl)pyrimidin-5-yl]-7-[4-[4-(2-methoxyethyl)piperazin-1-yl]pyrimidin-2-yl]-1,3-benzothiazol-2-yl]urea;
108) 1-ethyl-3-[7-[4-(morpholinomethyl)-2-pyridyl]-5-[6-(2,2,2-trifluoro-1-hydroxy-ethyl)-3-pyridyl]-1,3-benzothiazol-2-yl]urea;
109) 1-[6-[2-(ethylcarbamoylamino)-5-[2-(1-hydroxyethyl)pyrimidin-5-yl]-1,3-benzothiazol-7-yl]pyrimidin-4-yl]-4-methyl-piperidine-4-carboxylic acid;
110) 1-[2-[2-(ethylcarbamoylamino)-5-[2-(1-hydroxy-1-methyl-ethyl)pyrimidin-5-yl]-1,3-benzothiazol-7-yl]-4-pyridyl]piperidine-4-carboxylic acid;
111) 1-ethyl-3-[5-[2-(4-hydroxytetrahydropyran-4-yl)pyrimidin-2-yl]-7-(2-pyridyl)-1,3-benzothiazol-2-yl]urea;
112) 1-ethyl-3-[5-[2-(1-hydroxyethyl)pyrimidin-5-yl]-7-[4-(2-oxa-7-azaspiro[3.5]nonan-7-ylmethyl)-2-pyridyl]-1,3-benzothiazol-2-yl]urea;
113) 1-ethyl-3-[5-[2-(3-hydroxyoxetan-3-yl)pyrimidin-5-yl]-7-(2-pyridyl)-1,3-benzothiazol-2-yl]urea;
114) 1-ethyl-3-[5-[2-(1-hydroxy-1-methyl-ethyl)pyrimidin-5-yl]-7-[4-[(3-methoxy-3-methyl-azetidin-1-yl)methyl]-2-pyridyl]-1,3-benzothiazol-2-yl]urea;
115) 1-ethyl-3-[5-[2-(1-hydroxyethyl)pyrimidin-5-yl]-7-pyrimidin-2-yl-1,3-benzothiazol-2-yl]urea;
116) 1-ethyl-3-[7-[4-(2-morpholino ethoxy)-2-pyridyl]-5-[6-(2,2,2-trifluoro-1-hydroxy-ethyl)-3-pyridyl]-1,3-benzothiazol-2-yl]urea;
117) 1-[2-[2-(ethylcarbamoylamino)-5-[2-(1-hydroxyethyl)pyrimidin-5-yl]-1,3-benzothiazol-7-yl]pyrimidin-4-yl]-4-methyl-piperidine-4-carboxylic acid;
118) 1-[5-[2-[(1R*,2R*)-1,2-dihydroxypropyl]pyrimidin-5-yl]-7-(2-pyridyl)-1,3-benzothiazol-2-yl]-3-ethyl-urea (mixture 1-[5-[2-[(1R,2R)-1,2-dihydroxypropyl]pyrimidin-5-yl]-7-(2-pyridyl)-1,3-benzothiazol-2-yl]-3-ethyl-urea; and 1-[5-[2-[(1S,2S)-1,2-dihydroxypropyl]pyrimidin-5-yl]-7-(2-pyridyl)-1,3-benzothiazol-2-yl]-3-ethyl-urea);
119) 1-ethyl-3-[5-[2-(1-hydroxycyclopentyl)pyrimidin-5-yl]-7-(2-pyridyl)-1,3-benzothiazol-2-yl]urea;
120) 1-ethyl-3-[5-[2-(1-hydroxy-1-methyl-ethyl)pyrimidin-5-yl]-7-[5-(morpholinomethyl)pyrimidin-2-yl]-1,3-benzothiazol-2-yl]urea;
121) 1-ethyl-3-[5-[2-[(1R)-1-hydroxyethyl]pyrimidin-5-yl]-7-[4-(morpholinomethyl)-2-pyridyl]-1,3-benzothiazol-2-yl]urea;
122) 1-ethyl-3-[5-[2-[(1S)-1-hydroxyethyl]pyrimidin-5-yl]-7-[4-(morpholinomethyl)-2-pyridyl]-1,3-benzothiazol-2-yl]urea;
123) 4-[3-[5-[2-(ethylcarbamoylamino)-7-(2-pyridyl)-1,3-benzothiazol-5-yl]pyrimidin-2-yl]oxetan-3-yl]oxy-4-oxo-butanoic acid;
124) 4-[2-[5-[2-(ethylcarbamoylamino)-7-(2-pyridyl)-1,3-benzothiazol-5-yl]pyrimidin-2-yl]-2-hydroxy-propoxy]-4-oxo-butanoic acid;

125) 1-ethyl-3-[5-[2-(4-hydroxytetrahydropyran-4-yl)pyrimidin-5-yl]-7-[4-(morpholinomethyl)-2-pyridyl]-1,3-benzothiazol-2-yl]urea;
126) 1-[5-[2-(ethylcarbamoylamino)-7-(2-pyridyl)-1,3-benzothiazol-5-yl]pyrimidin-2-yl]ethyl 2-aminoacetate;
127) 1-ethyl-3-[5-[2-(4-hydroxytetrahydrothiopyran-4-yl)pyrimidin-5-yl]-7-(2-pyridyl)-1,3-benzothiazol-2-yl]urea;
128) 1-ethyl-3-[5-[2-(4-hydroxy-1-methyl-4-piperidyl)pyrimidin-5-yl]-7-(2-pyridyl)-1,3-benzothiazol-2-yl]urea;
129) [1-[5-[2-(ethylcarbamoylamino)-7-(2-pyridyl)-1,3-benzothiazol-5-yl]pyrimidin-2-yl]-1-methyl-ethyl]2-(2-aminoethylamino)acetate;
130) 1-[5-[2-[(1R*,2S*)-3,3-difluoro-1,2-dihydroxy-propyl]pyrimidin-5-yl]-7-(2-pyridyl)-1,3-benzothiazol-2-yl]-3-ethyl-urea (mixture 1-[5-[2-[(1R,2S)-3,3-difluoro-1,2-dihydroxy-propyl]pyrimidin-5-yl]-7-(2-pyridyl)-1,3-benzothiazol-2-yl]-3-ethyl-urea; and 1-[5-[2-[(1S,2R)-3,3-difluoro-1,2-dihydroxy-propyl]pyrimidin-5-yl]-7-(2-pyridyl)-1,3-benzothiazol-2-yl]-3-ethyl-urea);
131) 1-ethyl-3-[7-(2-pyridyl)-5-[2-[(1R*,2S*)-3,3,3-trifluoro-1,2-dihydroxy-propyl]pyrimidin-5-yl]-1,3-benzothiazol-2-yl]urea (mixture 1-ethyl-3-[7-(2-pyridyl)-5-[2-[(1R,2S)-3,3,3-trifluoro-1,2-dihydroxy-propyl]pyrimidin-5-yl]-1,3-benzothiazol-2-yl]urea; and 1-ethyl-3-[7-(2-pyridyl)-5-[2-[(1S,2R)-3,3,3-trifluoro-1,2-dihydroxy-propyl]pyrimidin-5-yl]-1,3-benzothiazol-2-yl]urea);
132) [1-[5-[2-(ethylcarbamoylamino)-7-(2-pyridyl)-1,3-benzothiazol-5-yl]pyrimidin-2-yl]-1-methyl-ethyl](2S)-2-aminopropanoate;
133) 4-[(1S)-1-[5-[2-(ethylcarbamoylamino)-7-(2-pyridyl)-1,3-benzothiazol-5-yl]pyrimidin-2-yl]ethoxy]-4-oxo-butanoic acid;
134) 4-[(1R)-1-[5-[2-(ethylcarbamoylamino)-7-(2-pyridyl)-1,3-benzothiazol-5-yl]pyrimidin-2-yl]ethoxy]-4-oxo-butanoic acid;
135) 1-[5-[2-(1,2-dihydroxy-1-methyl-ethyl)pyrimidin-5-yl]-7-[4-(morpholinomethyl)-2-pyridyl]-1,3-benzothiazol-2-yl]-3-ethyl-urea;
136) 1-[5-[2-(ethylcarbamoylamino)-7-(2-pyridyl)-1,3-benzothiazol-5-yl]pyrimidin-2-yl]ethyl 2-amino-2-methyl-propanoate;
137) 1-[5-[2-(ethylcarbamoylamino)-7-(2-pyridyl)-1,3-benzothiazol-5-yl]pyrimidin-2-yl]ethyl 3-aminopropanoate;
138) tert-butyl 4-[5-[2-(ethylcarbamoylamino)-7-(2-pyridyl)-1,3-benzothiazol-5-yl]pyrimidin-2-yl]-4-hydroxy-piperidine-1-carboxylate;
139) 1-ethyl-3-[5-[2-(4-hydroxy-1-oxo-thian-4-yl)pyrimidin-5-yl]-7-(2-pyridyl)-1,3-benzothiazol-2-yl]urea;
140) [1-[5-[2-(ethylcarbamoylamino)-7-(2-pyridyl)-1,3-benzothiazol-5-yl]pyrimidin-2-yl]-1-methyl-ethyl]2-(dimethylamino)acetate;
141) [1-[5-[2-(ethylcarbamoylamino)-7-(2-pyridyl)-1,3-benzothiazol-5-yl]pyrimidin-2-yl]-1-methyl-ethyl]2-morpholinoacetate;
142) 1-[7-[4-[[(2R,6S)-2,6-dimethylmorpholin-4-yl]methyl]-2-pyridyl]-5-[2-[(1R)-1-hydroxyethyl]pyrimidin-5-yl]-1,3-benzothiazol-2-yl]-3-ethyl-urea;
143) 1-[7-[4-[[(2R,6S)-2,6-dimethylmorpholin-4-yl]methyl]-2-pyridyl]-5-[2-[(1S)-1-hydroxyethyl]pyrimidin-5-yl]-1,3-benzothiazol-2-yl]-3-ethyl-urea;
144) [1-[5-[2-(ethylcarbamoylamino)-7-(2-pyridyl)-1,3-benzothiazol-5-yl]pyrimidin-2-yl]-1-methyl-ethyl]5-aminopentanoate;
145) [1-[5-[2-(ethylcarbamoylamino)-7-(2-pyridyl)-1,3-benzothiazol-5-yl]pyrimidin-2-yl]-1-methyl-ethyl]5-(dimethylamino)pentanoate;
146) [1-[5-[2-(ethylcarbamoylamino)-7-(2-pyridyl)-1,3-benzothiazol-5-yl]pyrimidin-2-yl]-1-methyl-ethyl]2-aminoacetate;
147) 1-[7-[4-[(3,3-difluoroazetidin-1-yl)methyl]-2-pyridyl]-5-[2-(1-hydroxy-1-methyl-ethyl)pyrimidin-5-yl]-1,3-benzothiazol-2-yl]-3-ethyl-urea;
148) 1-[7-[4-[[(2R,6S)-2,6-dimethylmorpholin-4-yl]methyl]-2-pyridyl]-5-[2-(3-hydroxyoxetan-3-yl)pyrimidin-5-yl]-1,3-benzothiazol-2-yl]-3-ethyl-urea;
149) 1-[5-[2-(ethylcarbamoylamino)-7-(2-pyridyl)-1,3-benzothiazol-5-yl]pyrimidin-2-yl]ethyl dihydrogen phosphate;
150) 1-ethyl-3-[5-[2-(1-hydroxy-1-methyl-ethyl)pyrimidin-5-yl]-6-(2-methoxyethylamino)-1,3-benzothiazol-2-yl]urea;
151) 1-ethyl-3-[5-[2-(1-hydroxy-1-methyl-ethyl)pyrimidin-5-yl]-7-morpholino-1,3-benzothiazol-2-yl]urea;
152) [(1R)-1-[5-[2-(ethylcarbamoylamino)-7-(2-pyridyl)-1,3-benzothiazol-5-yl]pyrimidin-2-yl]ethyl]dihydrogen phosphate;
153) [(1S)-1-[5-[2-(ethylcarbamoylamino)-7-(2-pyridyl)-1,3-benzothiazol-5-yl]pyrimidin-2-yl]ethyl]dihydrogen phosphate;
154) 1-ethyl-3-[5-[2-(3-hydroxyoxetan-3-yl)pyrimidin-5-yl]-7-[4-(morpholinomethyl)-2-pyridyl]-1,3-benzothiazol-2-yl]urea;
155) 1-ethyl-3-[7-[4-[(3-methoxyazetidin-1-yl)methyl]-2-pyridyl]-5-[6-[2,2,2-trifluoro-1-hydroxy-ethyl]-3-pyridyl]-1,3-benzothiazol-2-yl]urea;
156) 1-[7-[4-[(4,4-difluoro-1-piperidyl)methyl]-2-pyridyl]-5-[2-(1-hydroxy-1-methyl-ethyl)pyrimidin-5-yl]-1,3-benzothiazol-2-yl]-3-ethyl-urea;
157) 1-[5-[2-[1,2-dihydroxy-1-methyl-ethyl]pyrimidin-5-yl]-7-(2-pyridyl)-1,3-benzothiazol-2-yl]-3-ethyl-urea;
158) 1-ethyl-3-[5-[2-[1-hydroxyethyl]pyrimidin-5-yl]-7-(5-methyl-2-pyridyl)-1,3-benzothiazol-2-yl]urea;
159) 1-ethyl-3-[5-[2-(1-hydroxy-1-methyl-ethyl)pyrimidin-5-yl]-7-[4-[(4-methylpiperazin-1-yl)methyl]-2-pyridyl]-1,3-benzothiazol-2-yl]urea;
160) [(1S)-1-[5-[2-(ethylcarbamoylamino)-7-(2-pyridyl)-1,3-benzothiazol-5-yl]pyrimidin-2-yl]ethyl](2S)-pyrrolidine-2-carboxylate;
161) [(1R)-1-[5-[2-(ethylcarbamoylamino)-7-(2-pyridyl)-1,3-benzothiazol-5-yl]pyrimidin-2-yl]ethyl](2S)-pyrrolidine-2-carboxylate;
162) tert-butyl 3-[5-[2-(ethylcarbamoylamino)-7-(2-pyridyl)-1,3-benzothiazol-5-yl]pyrimidin-2-yl]-3-hydroxy-azetidine-1-carboxylate;
163) 1-ethyl-3-[5-[2-(3-hydroxyazetidin-3-yl)pyrimidin-5-yl]-7-(2-pyridyl)-1,3-benzothiazol-2-yl]urea;
164) 1-[7-[4-[[(2R,6S)-2,6-dimethylmorpholin-4-yl]methyl]-2-pyridyl]-5-[2-(1-hydroxy-1-methyl-ethyl)pyrimidin-5-yl]-1,3-benzothiazol-2-yl]-3-ethyl-urea;
165) [1-[5-[2-(ethylcarbamoylamino)-7-(2-pyridyl)-1,3-benzothiazol-5-yl]pyrimidin-2-yl]-1-methyl-ethyl]2-[[(2S)-pyrrolidine-2-carbonyl]amino]acetate;
166) [1-[5-[2-(ethylcarbamoylamino)-7-(2-pyridyl)-1,3-benzothiazol-5-yl]pyrimidin-2-yl]-1-methyl-ethyl](2S)-pyrrolidine-2-carboxylate;
167) 4-[3-[5-[7-[4-[[(2R,6S)-2,6-dimethylmorpholin-4-yl]methyl]-2-pyridyl]-2-(ethylcarbamoylamino)-1,3-benzothiazol-5-yl]pyrimidin-2-yl]oxetan-3-yl]oxy-4-oxo-butanoic acid;

168) 1-ethyl-3-[7-[5-(1-hydroxyethyl)-2-pyridyl]-5-[2-(1-hydroxyethyl)pyrimidin-5-yl]-1,3-benzothiazol-2-yl]urea;
169) [1-[5-[2-(ethylcarbamoylamino)-7-(2-pyridyl)-1,3-benzothiazol-5-yl]pyrimidin-2-yl]-1-methyl-ethyl]2-(2-morpholinoethylamino)acetate;
170) 2-[[2-[1-[5-[2-(ethylcarbamoylamino)-7-(2-pyridyl)-1,3-benzothiazol-5-yl]pyrimidin-2-yl]-1-methyl-ethoxy]-2-oxo-ethyl]amino]acetic acid;
171) (2S)-2-amino-4-[1-[5-[2-(ethylcarbamoylamino)-7-(2-pyridyl)-1,3-benzothiazol-5-yl]pyrimidin-2-yl]-1-methyl-ethoxy]-4-oxo-butanoic acid;
172) [1-[5-[2-(ethylcarbamoylamino)-7-(2-pyridyl)-1,3-benzothiazol-5-yl]pyrimidin-2-yl]-1-methyl-ethyl]-4-aminobutanoate;
173) 1-ethyl-3-[5-[2-(4-hydroxy-1,1-dioxo-thian-4-yl)pyrimidin-5-yl]-7-(2-pyridyl)-1,3-benzothiazol-2-yl]urea;
174) 1-ethyl-3-[5-[2-(4-hydroxy-4-piperidyl)pyrimidin-5-yl]-7-(2-pyridyl)-1,3-benzothiazol-2-yl]urea;
175) 1-[7-[4-[(3-ethoxyazetidin-1-yl)methyl]-2-pyridyl]-5-[2-(1-hydroxy-1-methyl-ethyl)pyrimidin-5-yl]-1,3-benzothiazol-2-yl]-3-ethyl-urea;
176) 1-ethyl-3-[5-[2-(1-hydroxy-1-methyl-ethyl)pyrimidin-5-yl]-6-methoxy-1,3-benzothiazol-2-yl]urea;
177) 1-ethyl-3-[6-fluoro-5-[2-(1-hydroxy-1-methyl-ethyl)pyrimidin-5-yl]-1,3-benzothiazol-2-yl]urea;
178) 1-ethyl-3-[7-(3-fluoro-4-methoxy-2-pyridyl)-5-[2-[1-hydroxyethyl]pyrimidin-5-yl]-1,3-benzothiazol-2-yl]urea;
179) 3-[[2-[1-[5-[2-(ethylcarbamoylamino)-7-(2-pyridyl)-1,3-benzothiazol-5-yl]pyrimidin-2-yl]-1-methyl-ethoxy]-2-oxo-ethyl]amino]propanoic acid;
180) [1-[5-[2-(ethylcarbamoylamino)-7-(2-pyridyl)-1,3-benzothiazol-5-yl]pyrimidin-2-yl]-1-methyl-ethyl](3R)-pyrrolidine-3-carboxylate;
181) [1-[5-[2-(ethylcarbamoylamino)-7-(2-pyridyl)-1,3-benzothiazol-5-yl]pyrimidin-2-yl]-1-methyl-ethyl](3R)-morpholine-3-carboxylate;
182) 1-[6-(cyclopropylmethoxy)-5-[2-(1-hydroxy-1-methyl-ethyl)pyrimidin-5-yl]-1,3-benzothiazol-2-yl]-3-ethyl-urea;
183) 1-ethyl-3-[5-[2-(1-hydroxy-1-methyl-ethyl)pyrimidin-5-yl]-6-(2-methoxyethoxy)-1,3-benzothiazol-2-yl]urea;
184) [1-[5-[2-(ethylcarbamoylamino)-7-(2-pyridyl)-1,3-benzothiazol-5-yl]pyrimidin-2-yl]-1-methyl-ethyl]2-(2-phosphonooxyethylamino)acetate;
185) 1-ethyl-3-[5-[2-[1-hydroxyethyl]pyrimidin-5-yl]-7-[4-(thiomorpholinomethyl)-2-pyridyl]-1,3-benzothiazol-2-yl]urea;
186) 1-ethyl-3-[6-(2-hydroxyethoxy)-5-[2-(1-hydroxy-1-methyl-ethyl)pyrimidin-5-yl]-1,3-benzothiazol-2-yl]urea;
187) 1-ethyl-3-[5-[2-(1-hydroxy-1-methyl-ethyl)pyrimidin-5-yl]-7-[4-(thiomorpholinomethyl)-2-pyridyl]-1,3-benzothiazol-2-yl]urea;
188) 1-ethyl-3-[5-[2-(1-hydroxy-1-methyl-ethyl)pyrimidin-5-yl]-7-[4-[(1-oxo-1,4-thiazinan-4-yl)methyl]-2-pyridyl]-1,3-benzothiazol-2-yl]urea;
189) 1-ethyl-3-[5-[2-(1-hydroxy-1-methyl-ethyl)pyrimidin-5-yl]-6-[2-methoxyethyl(methyl)amino]-1,3-benzothiazol-2-yl]urea;
190) [1-[5-[2-(ethylcarbamoylamino)-7-(2-pyridyl)-1,3-benzothiazol-5-yl]pyrimidin-2-yl]-1-methyl-ethyl]dihydrogen phosphate;
191) 1-[7-[4-[(1,1-dioxo-1,4-thiazinan-4-yl)methyl]-2-pyridyl]-5-[2-(1-hydroxy-1-methyl-ethyl)pyrimidin-5-yl]-1,3-benzothiazol-2-yl]-3-ethyl-urea;
192) 1-[6-[(3,4-dimethoxyphenyl)methoxy]-5-[2-(1-hydroxy-1-methyl-ethyl)pyrimidin-5-yl]-1,3-benzothiazol-2-yl]-3-ethyl-urea;
193) 1-ethyl-3-[5-[2-[1-hydroxyethyl]pyrimidin-5-yl]-6-(tetrahydrofuran-2-ylmethoxy)-1,3-benzothiazol-2-yl]urea;
194) 1-ethyl-3-[5-[2-[1-hydroxyethyl]pyrimidin-5-yl]-6-morpholino-1,3-benzothiazol-2-yl]urea;
195) 1-[7-[(3S)-3-aminopyrrolidin-1-yl]-5-[2-(1-hydroxy-1-methyl-ethyl)pyrimidin-5-yl]-1,3-benzothiazol-2-yl]-3-ethyl-urea;
196) 1-ethyl-3-[7-[4-[(2-hydroxyethylamino)methyl]-2-pyridyl]-5-[2-(1-hydroxy-1-methyl-ethyl)pyrimidin-5-yl]-1,3-benzothiazol-2-yl]urea;
197) 1-ethyl-3-[5-[5-(1-hydroxyethyl)-3-pyridyl]-7-(2-pyridyl)-1,3-benzothiazol-2-yl]urea;
198) 1-ethyl-3-[5-[2-(1-hydroxy-1-methyl-ethyl)pyrimidin-5-yl]-7-[4-[(2,2,3,3,5,5,6,6-octadeuteriomorpholin-4-yl)methyl]-2-pyridyl]-1,3-benzothiazol-2-yl]urea;
199) 1-ethyl-3-[5-[2-(1-hydroxy-1-methyl-ethyl)pyrimidin-5-yl]-6-(2-morpholinoethoxy)-1,3-benzothiazol-2-yl]urea;
200) 1-ethyl-3-[5-[2-(1-hydroxy-1-methyl-ethyl)pyrimidin-5-yl]-6-(2-methoxyethylsulfanyl)-1,3-benzothiazol-2-yl]urea;
201) 1-ethyl-3-[5-[2-(1-hydroxy-1-methyl-ethyl)pyrimidin-5-yl]-6-(2-methoxyethylsulfinyl)-1,3-benzothiazol-2-yl]urea; and
202) 1-ethyl-3-[5-[2-[(1R)-1-hydroxyethyl]pyrimidin-5-yl]-7-(5-methoxy-2-pyridyl)-1,3-benzothiazol-2-yl]urea.

In a further particular embodiment, esters preferably ester prodrugs of these compounds and their salts, racemates, diastereomers, enantiomers and deuterated forms thereof are preferred. In yet another further particular embodiment, phosphates, preferably phosphate prodrugs of these compounds and their salts, racemates, diastereomers, enantiomers and deuterated forms thereof are preferred.

Accordingly, in one embodiment the compound is an ester or phosphate selected from the group consisting of any one of compounds 18, 19, 20, 21, 62, 63, 123, 126, 129, 132, 133, 134, 136, 137, 140, 141, 144,145, 146, 149, 152, 153, 160, 161, 165, 166, 167, 169, 170, 171, 172, 179, 180, 181, 184 and 190, their salts, racemates, diastereomers, enantiomers and deuterated forms thereof.

The salts of the compound of Formula (I) are preferably pharmaceutically acceptable, but it will be appreciated that non-pharmaceutically acceptable salts also fall within the scope of the present invention, since these are useful as intermediates in the preparation of pharmaceutically acceptable salts.

Suitable pharmaceutically acceptable salts include, but are not limited to, salts of pharmaceutically acceptable inorganic acids such as hydrochloric, sulfuric, phosphoric, nitric, carbonic, boric, sulfamic, and hydrobromic acids, or salts of pharmaceutically acceptable organic acids such as acetic, propionic, butyric, tartaric, maleic, malonic, hydroxymaleic, fumaric, malic, citric, lactic, mucic, gluconic, benzoic, succinic, oxalic, phenylacetic, methanesulphonic, toluenesulphonic, benzenesulphonic, ethane-1,2-disulfonic, salicylic, sulphanilic, aspartic, glutamic, gentisic, edetic, stearic, palmitic, pamoic, oleic, lauric, pantothenic, tannic, ascorbic and valeric acids.

Base salts include, but are not limited to, those formed with pharmaceutically acceptable cations, such as sodium, potassium, lithium, calcium, magnesium, zinc, ammonium, alkylammonium such as salts formed from triethylamine, alkoxyammonium such as those formed with ethanolamine and salts formed from ethylenediamine, choline or amino acids such as arginine, lysine or histidine. General information on types of pharmaceutically acceptable salts and their formation is known to those skilled in the art and is as described in general texts such as "*Handbook of Pharmaceutical salts*" P. H. Stahl, C. G. Wermuth, 1$^{st}$ edition, 2002, Wiley-VCH.

Basic nitrogen-containing groups may be quarternized with such agents as lower alkyl halide, such as methyl, ethyl, propyl, and butyl chlorides, bromides and iodides; dialkyl sulfates like dimethyl and diethyl sulfate; and others such as alkylphosphonates or phosphoramidates.

Hydroxyl groups may be esterified with groups including lower alkyl carboxylic acids, such as acetic acid and 2,2-dimethylpropionic acid, or sulfonated with groups including alkyl sulfonic acids, such as methyl sulfonic acid or phosphorylated with groups including alkylphosphonic acids, such as methylenephosphonic acid, or directly attached to phosphonate esters, phosphinate esters, or phosphate esters.

It will be recognised that the compounds of formula I may possess asymmetric centres and are therefore capable of existing in more than one stereoisomeric form. The invention thus also relates to compounds in substantially pure isomeric form at one or more asymmetric centres e.g., greater than about 90% ee, such as about 95% or 97% ee or greater than 99% ee, as well as mixtures, including racemic mixtures, thereof.

Such isomers may be prepared by asymmetric synthesis, for example using chiral intermediates, or by chiral resolution.

This invention also encompasses prodrugs of compounds of Formula (I). Compounds of Formula (I) having free amino, amido, hydroxy or carboxylic groups can be converted into prodrugs.

Particularly preferred are prodrugs of hydroxyl groups such as carbamates, phoshphates, sulfates and ester groups including those derived from amino acids and dipeptides and moieties designed to release the parent via hydrolysis or internal cyclisation of the prodrug moiety.

Compositions

There is also provided a composition comprising a compound of Formula (I) its salts, isomers, racemates, diastereomers, enantiomers and prodrugs thereof.

Preferably, the composition further comprises a pharmaceutically acceptable carrier, diluent or excipient.

The compositions of the present invention may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

Pharmaceutical formulations include those for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier or diluent, may thus be placed into the form of pharmaceutical compositions and unit dosages thereof, and in such form may be employed as solids, such as tablets or filled capsules, or liquids as solutions, suspensions, emulsions, elixirs or capsules filled with the same, all for oral use, in the form of suppositories for rectal administration; or in the form of sterile injectable solutions for parenteral (including subcutaneous) use.

In one embodiment the compositions of the present invention are formulated for oral administration and/or intravenous (IV) administration.

In another embodiment the compositions of the present invention may be administered in combination with or additionally comprise another antibacterial agent. Suitable antibacterial agents will be familiar to those in the art and may include penicillins, cephalosporins, carbapenems, monobactams, beta-lactams, glycopetides, aminoglycosides, tetracyclines, macrolides, ketolides, quinolones, fluoroquinolones, oxazolidinones, coumarins, cyclothialidines, vancomycin and derivatives thereof.

Methods of Treatment

The present invention provides a method for the treatment of a bacterial infection comprising administration of a compound of Formula (I) or a pharmaceutically acceptable salt thereof to a subject suffering from said infection.

The compounds of the present invention may be administered by any suitable means, for example, orally, parenterally, such as by subcutaneous, intravenous, intramuscular, or intracisternal injection or infusion techniques (e.g., as sterile injectable aqueous or non-aqueous solutions or suspensions).

The present invention also provides compound of Formula (I) or a pharmaceutically acceptable salt thereof for use in the treatment of a bacterial infection.

The term "effective amount" means the amount of the subject composition that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In the treatment or prevention of bacterial infections, an appropriate dosage level will generally be about 0.01 to 500 mg per kg patient body weight per day which can be administered in single or multiple doses. For oral administration, the compositions are preferably provided in the form of tablets containing 1.0 to 1000 milligrams of the active ingredient.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, caprine, equine, canine, feline, rodent or murine species can be treated. However, the method can also be practiced in other species, such as avian species (e.g., chickens).

The subjects treated in the above method are mammals, including, but not limited to, cows, sheep, goats, horses, dogs, cats, guinea pigs, rats or other bovine, ovine, caprine, equine, canine, feline, rodent or murine species, and preferably a human being, male or female.

Methods of Preparation

Generally, the compounds of the invention may be prepared by coupling an intermediate of formula (i-a) with a precursor of formula (ii-a):

(i-a)

(ii-a)

or alternatively coupling an intermediate of formula (i-b) with a precursor of formula (ii-b):

(i-b)

(ii-b)

under the conditions described including suitable variations or alternatives thereof in the methods and examples which follow. Formation of compounds of the invention as their salts, racemates, enantiomers, esters, carbamates, phosphates, sulfates, deuterated forms and prodrugs thereof is also described.

General Method A

Compounds of the invention may be prepared under Suzuki coupling conditions familiar to those skilled in the art. Suitable conditions include (i) coupling a precursor comprising a boronic acid or a boronate ester thereof with an intermediate comprising a halo (particularly Cl, Br and I) or triflate (or vice versa); (ii) in the presence of a base, such as cesium carbonate or potassium carbonate; (iii) a palladium catalyst, such as $Pd(dppf)Cl_2$ or $Pd(PPh_3)_2Cl_2$; and (iv) an organic solvent, such as dioxane or DMF.

General Method B

Compounds of the invention may be prepared by reduction of a keto moiety to a secondary alcohol under reduction conditions. Suitable conditions include (i) a reducing agent such as $NaBH_4$; and (ii) an organic solvent, such as THF.

General Method C

Compounds of the invention comprising a diol moiety may be prepared by oxidation of an alkene moiety under oxidation conditions. Suitable conditions include (i) an oxidizing reagent such as $OsO_4$; and (ii) an organic solvent, such as pyridine.

General Method D

Compounds of the invention comprising a diol moiety may be prepared under epoxide ring opening conditions familiar to those in the art.

General Method E

Compounds of the invention may be prepared by alkylation of an aldehyde moiety to a secondary alcohol via organometallic addition. Suitable conditions include (i) a Grignard reagent such as halo(alkyl)magnesium; and (ii) an organic solvent, such as $Et_2O$.

General Method F

Compounds of the invention may be prepared under Stille coupling conditions familiar to those in the art. Suitable conditions include (i) coupling a precursor comprising a halo (particularly Cl, Br and I) with an intermediate comprising a stannylated moiety such as tributyltin (or vice versa); (ii) in the presence of palladium catalyst, such as $Pd(PPh_3)_4$; and (iii) an organic solvent, such as DMF.

General Method G

Compounds of the invention may be prepared under Chan-Lam coupling conditions familiar to those in the art. Suitable conditions include (i) coupling a precursor containing an N—H moiety with an intermediate comprising a boronic acid (or vice versa); (ii) in the presence of a copper reagent such as $Cu(OAc)_2 \cdot H_2O$ in an oxygen atmosphere.

General Method H

Compounds of the invention containing prodrug forms of the secondary or tertiary alcohol moieties may be formed under suitable conditions familiar to those in the art. Prodrug forms include carbamates, phosphates and esters including those derived from amino acids and dipeptides and suitable conditions to form them are described in the examples which follow.

General Method I

Compounds of the invention may be prepared under Buchwald-Hartwig coupling conditions familiar to those in the art. Suitable conditions include (i) coupling a precursor comprising of a halo with an intermediate comprising of a N—H moiety (or vice versa); (ii) in the presence of a palladium catalyst, such as $Pd_2(dba)_3$; (iii) a suitable ligand, such as Xantphos; (iv) a suitable base such as $Cs_2CO_3$; and (v) an organic solvent, such as 1,4-dioxane.

Salt Formation Method(s)

Salts of the compounds of the invention may be formed using conditions familiar to those in the art, for example, as follows.

General Salt Formation Conditions

The free base material is dissolved or suspended in an organic solvent, organic solvent mixture or organic solvent water mixture (for example; DCM, THF, THF/MeOH, EtOH) and a solution/suspension of the acid in the same organic solvent or organic solvent mixture in molar equivalents of 1 or greater than 1 is added. The acid may also be added neat. The salt product may precipitate at room temperature or alternatively the addition may be done at a higher temperature with subsequent cooling to enable precipitation of the salt product. An antisolvent (for example; hexanes, n-heptane, Isopropyl acetate) may be added after the addition of acid to enable precipitation of the salt product which is collected by vacuum filtration and washed with an appropriate organic solvent.

Example Hydrochloride Salts

Hydrochloride salts can be made, for example, by suspending the compound in a suitable solvent, such as acetonitrile, and adding aqueous 2M hydrochloric acid solution. Dilution of the mixture with water and then removal of the solvent gives the hydrochloride salt of the compound.

Example Methanesulphonic Acid Salts

Methanesulphonic acid salts can be made, for example, by suspending the compound in a suitable solvent, such as acetonitrile, and adding 1 equivalent of methanesulphonic acid in water. Removal of the solvent gives the methanesulphonic acid salt of the compound.

Chiral Separation Method(s) and Synthesis

Compounds of the invention may be separated into their diastereoisomers or enantiomers under chiral HPLC conditions familiar to those in the art. Alternatively, chiral precursor moieties may be resolved from their racemates via derivatization with a chiral auxiliary, such as a blocked amino acid, e.g., Boc-valine, separated by fractional crystallization of diastereomers from a suitable solvent, such as heptane, and reconstitution of the enantiomeric precursors through cleavage of the auxiliary, such as base-mediated cleavage on resin or in solution. Mitsonobu-type inversion of enantiomerically enriched mixtures of chiral alcohols can also be accomplished by coupling the alcohol with the chiral auxiliary, such as an amino acid, e.g. Boc-valine, in the presence of trialkylated phosphines, such as triphenylphosphine, and dialkylazodicarboxylates, and fractionally crystallizing the enriched diastereomeric mixture as above.

Protecting Groups

During the reactions a number of the moieties may need to be protected. Suitable protecting groups are well known in industry and have been described in many references such as Protecting Groups in Organic Synthesis, Greene T W, Wiley-Interscience, New York, 1981. It will be understood that in addition to protecting groups such as hydroxyl and amino groups during the course of reaction, the urea moiety may require protection under any of the reactions conditions described herein, for example, as a 5-methyl-1,3,5-triazinan-2-one.

Functional Group Interconversions

Further, it will be understood that compounds of the invention produced under any of the reaction conditions described herein may undergo further functionalisation under suitable conditions familiar to those in the art. That is, the skilled person will appreciate that a wide diversity of compounds may be provided by functional group interconversions of hydroxyls and carboxylates including but not limited to halogens, ethers, ketones, carboxylic acids, esters, carbonates, amines, amides, ureas, carbamates, sulfates, sulfonamides, phosphates, heterocycles, heteroaryls, optionally substituted alkyl chain extensions and so on.

EXAMPLES

Those skilled in the art will appreciate that the invention described herein is susceptible to variations and modifications other than those specifically described.

The invention will now be described without limitation by reference to the examples which follow.

The abbreviations used in the Examples are as follows unless indicated otherwise.

ABBREVIATIONS

Ac: acetyl
ACN: acetonitrile
cfus: colony forming units
DCM: dichloromethane
DIPEA: N,N-diisopropylethylamine
DMAP: N,N-dimethylpyridin-4-amine
DMF: N, N-dimethylformamide
DMSO: dimethylsulfoxide
EtOAc: ethyl acetate
$Et_2O$: diethyl ether
EtOH: ethanol
g: gram(s)
h: hour(s)
$H_2O$: Water
HPLC: high performance liquid chromatography
IPA: propan-2-ol
kg: kilogram(s)
L: liter(s)
LCMS: liquid chromatography coupled mass spectrometry
LDA: lithium diisopropylamide
M: molar
mg: milligram(s)
min: minute(s)
mL: milliliter(s)
MeOH: methanol
mol: mole(s)
mmol: millimole(s)
MS: mass spectrometry
NBS: N-bromosuccinimide
NMP: 1-methylpyrrolidin-2-one
NMR: nuclear magnetic resonance
$Pd(dppf)Cl_2$: [1,1'-Bis(diphenylphosphino)ferrocene]dichloropalladium(II), DCM adduct
$Pd_2(dba)_3$ Tris(dibenzylideneacetone)dipalladium(0)
$Pd(PPh_3)_4$ Tetrakis(triphenylphosphine)palladium(0)
RT: room temperature
THF: tetrahydrofuran
TLC: thin-layer chromatography Compound Synthesis $^1$H NMR spectra were recorded on either a Brüker Avance DRX 400, AC 200 or AM 300 spectrometer. Spectra were recorded in deuterated solvents (CDCl$_3$, MeOD, DMSO-d$_6$, CD$_3$CN, or Acetone-d$_6$) using the residual solvent peak as a reference. Chemical shifts are reported on the δ scale in parts per million (ppm) using the following conventions to assign the multiplicity: s (singlet), d (doublet), t (triplet), q (quartet), p (pentet), m (multiplet) and prefixed br (broad). Mass spectra (ESI) were recorded on either a Micromass Platform QMS or Thermo Finnigan LCQ Advantage spectrometer. Flash chromatography was performed on 40-63 μm silica gel 60 (Merck No. 9385). Automated flash chromatography was performed either on a Combi-Flash™ purification system using Combi-Flash™ silica gel columns or on a Biotage SP4 purification system using either GraceResolv™ silica gel cartridges, Grace Reveleris™ C-18 reverse phase silica gel cartridges or Biotage SNAP™ C-18 reverse phase silica gel cartridges. Preparative HPLC was carried out using either a Gilson 322 pump with a Gilson 215 liquid handler and a HP1100 PDA detector or an Agilent 1200 Series mass detected preparative LCMS using a Varian XRs C-18 100×21.2 mm column. Unless otherwise specified, the HPLC systems employed Phenomenex C8(2) columns using either acetonitrile or acetonitrile containing 0.06% TFA in water, water containing 0.1% TFA or water containing 0.1% formic acid.

Example(s) of Intermediates

[2-(ethylcarbamoyl amino)-7-(2-pyridyl)-1,3-benzothiazol-5-yl]boronic acid (Intermediate 1)

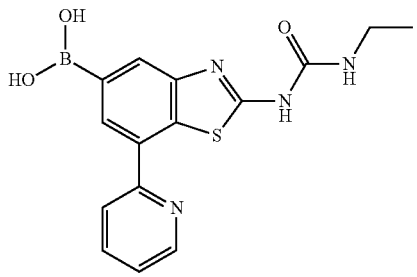 [SMILES: CCNC(=O)Nc1nc2cc(B(O)O)cc(-c3ccccn3)c2s1]

$^1$H-NMR (DMSO-d$_6$, 400 MHz): δ 1.10 (t, J=7.20 Hz, 3H), 3.20 (m, 2H), 6.84 (br s, 1H), 7.41 (m, 1H), 8.01 (m, 1H), 8.12 (s, 1H), 8.25 (m, 3H), 8.40 (s, 1H), 8.79 (d, J=4.0 Hz, 1H) and 10.57 (br s, 1H). MS: 343.25 [M+H]$^+$.

2-amino-3-bromo-5-nitro-phenol (i)

To a stirred solution of 2-amino-5-nitro-phenol (500 g, 3.24 mol) in ACN (12 L) was added bromine (290 mL, 5.63 mol) drop wise over a period of 30 min. The mixture was stirred at 30-35° C. for 1 h, then the solvent was evaporated to dryness. Hexane (2 L) was added and the mixture evaporated to dryness. Hexane (5 L) was added and the mixture stirred for 1 h and filtered. The solid (1102 g) was washed with hexane (2 L). The residue was added to ice-cold H$_2$O (2.5 L) followed by the addition of a saturated solution of sodium thiosulfate (2.5 L) and extraction with EtOAc (2×10 L). The combined organic layers were washed with brine, dried (Na$_2$SO$_4$), filtered and concentrated at 40-45° C. in vacuo to obtain i (643 g, 85%).

3-bromo-5-nitro-phenol (ii)

To a cooled solution (−10° C.) of i (643 g, 2.76 mol) in EtOH (13 L) was added conc. H$_2$SO$_4$ (515 mL, 9.97 mol) over a period of 35 min at −10 to −2° C. The mixture was allowed to warm to RT and then heated to 50-55° C. followed by the portion-wise addition of NaNO$_2$ (671 g, 9.72 mol) over 30 min and the mixture heated at reflux for 3 h. The mixture was concentrated to 3 L and cooled to 0° C. followed by the addition of H$_2$O (5 L) and extraction with EtOAc (3×6 L). The combined organic layers were washed with brine, dried (Na$_2$SO$_4$), filtered and concentrated in vacuo. The residue was treated with 25% ether-hexane mixture (6 L) and stirred for 1 h, filtered and the solid and washed with hexane (3 L) to obtain ii (505 g, 84%).

1-benzyloxy-3-bromo-5-nitro-benzene (iii)

To a solution of ii (770 g, 3.53 mol) in acetone (10 L) was added K$_2$CO$_3$ (2.45 kg, 17.75 mol) at RT followed by benzyl bromide (632 mL, 5.32 mol) over a period of 30 min. The mixture was stirred for 15 min and then heated at reflux for 3 h. The mixture was filtered through celite and the acetone was distilled off. The residue was purified over silica eluting with EtOAc:hexane (5:95) to obtain iii (551 g, 51%).

3-benzyloxy-5-bromo-aniline (iv)

To a solution of iii (551 g, 1.78 mol) in THF (11 L) was added SnCl$_2$.2H$_2$O (2.17 kg, 9.62 mol) at RT. The mixture was refluxed for 3 h. The mixture was cooled to 0-5° C. and basified with saturated NaHCO$_3$ solution and extracted with EtOAc (4×5 L). The combined organic layer were washed with brine, dried (Na$_2$SO$_4$), filtered and concentration in vacuo gave iv (480 g, 97%).

N-[(3-benzyloxy-5-bromophenyl)carbamothioyl] benzamide (v)

To a solution of iv (480 g, 1.73 mol) in acetone (10 L) was added benzoylisothiocyanate (280 mL, 2.08 mol) at RT and the mixture stirred for 45 min. The acetone was distilled off and hexane (2 L) added and the mixture concentrated to dryness. To the residue was added hexane (4 L) and the mixture heated to 40° C. for 30 min The solid was collected by filtration and washed with hexane (2×2 L) to obtain v (648 g, 85%).

3-benzyloxy-5-bromo-phenyl)thiourea (vi

To a solution of v (648 g, 1.47 mol) in THF (12 L) was added NaOH solution (300 g, 7.5 mol in 3 L H$_2$O) at RT. The mixture was heated at 70° C. overnight. The THF layer was decanted off and the aqueous layer was extracted with EtOAc (3×2 L). The combined organic layers were washed with brine, dried (Na$_2$SO$_4$), filtered and concentrated in vacuo. The residue was treated with mixture of Et$_2$O and hexane (5:95, 3.0 L), filtered, washed with hexane and dried under high vacuum to obtain vi (387 g, 78%).

5-benzyloxy-7-bromo-1,3-benzothiazol-2-amine (vii)

To an ice-cold suspension of vi (372 g, 1.10 mol) in ACN (6 L) was added dropwise a solution of bromine (65 mL 1.26 mol in 50 mL ACN) over a period of 30 min. The mixture was stirred for 30 min at 0-5° C. and then slowly allowed to warm to RT and stirred for 1 h. The solid was filtered off and washed with hexane (2×3 L). The solid residue was taken in ice H₂O, basified with aq. NH₃ (pH 10-12) and stirred for 30 min at 5-10° C. The resulting solid was filtered off and washed with H₂O and dried under high vacuum to obtain vii (216 g, 59%). $^1$H-NMR (DMSO-$d_6$, 400 MHz): δ 5.12 (s, 2H), 6.92 (d, J=2.40 Hz, 1H), 6.98 (d, J=2.0 Hz, 1H), 7.30-7.45 (m, 5H) and 7.69 (br s, 2H). MS: 334.79 [M+H]⁺.

1-(5-benzyloxy-7-bromo-1,3-benzothiazol-2-yl)-3-ethyl-urea (viii)

To a suspension of vii (216 g, 0.64 mol) in 1,4-dioxane (4 L) was added ethylisocyanate (380 mL, 4.81 mol). The mixture was heated up to 80-85° C. overnight. The solvent was distilled off and the residue was co-evaporated with hexane. The residue was treated with H₂O at 78-80° C. for 3-5 h. The resulting solid was filtered off and washed with hot H₂O, dried under high vacuum to obtain viii (196 g, 75%). $^1$H-NMR (DMSO-$d_6$, 400 MHz): δ 1.08 (t, J=7.20 Hz, 3H), 3.18 (q, J=6.80 Hz, 2H), 5.17 (s, 2H), 6.71 (br s, 1H), 7.15 (d, J=2.0 Hz, 1H), 7.26 (br s, 1H), 7.31-7.47 (m, 5H) and 10.82 (br s, 1H). MS: 405.90 [M+H]⁺.

1-[5-benzyloxy-7-(2-pyridyl)-1,3-benzothiazol-2-yl]-3-ethyl-urea (ix)

To a stirred solution of viii (110 g, 0.27 mol) in DMF (1.1 L) was added 2-tributylstannyl pyridine (298 g, 0.81 mol). The resulting solution was purged with N₂ for 15-20 min followed by addition of Pd(PPh₃)₄ (25.41 g, 0.022 mol). The resulting reaction mixture was heated to 100° C. under N₂ atmosphere for 15-16 h. The reaction was cooled to 40-45° C. and filtered through celite. The celite was washed with DMF (500 mL) and hot EtOAc (1.50 L) and the combined filtrate concentrated at 60-70° C. in vacuo. The residue was purified through silica (20% EtOAc-Hexanes to 100% EtOAc) to obtain ix (76 g, 70%). $^1$H-NMR (DMSO-$d_6$, 400 MHz): δ 1.08 (t, J=7.20 Hz, 3H), 3.19 (q, J=6.80 Hz, 2H), 5.26 (s, 2H), 6.84 (br s, 1H), 7.32-7.43 (m, 5H), 7.51 (d, J=7.20 Hz, 2H), 7.69 (d, J=2.0 Hz, 1H), 7.95 (m, 1H), 8.25 (m, 1H), 8.78 (m, 1H) and 10.46 (br s, 1H). MS: 405.30 [M+H]⁺.

1-ethyl-3-[5-hydroxy-7-(2-pyridyl)-1,3-benzothiazol-2-yl]urea (x)

To a stirred solution of ix (76 g, 0.187 mol) in DCM (1.7 L) was added methane sulfonic acid (270 mL, 4.17 mol) dropwise over 30 min. The mixture was stirred at RT for 3 h. The reaction was concentrated in vacuo. EtOAc (1 L) was added to the residue and this solution was poured carefully onto the crushed ice. The pH of the solution was modified to 8-9 by addition of saturated NaHCO₃ solution followed by extraction with EtOAc (3×5 L). The combined organics were washed with H₂O, brine, dried (Na₂SO₄), filtered and concentrated in vacuo. The residue was stirred in Et₂O (1.0 L) for 1 h at RT and then filtered to obtain x (57.0 g, 97%). $^1$H-NMR (DMSO-$d_6$, 400 MHz): δ 1.08 (t, J=7.20 Hz, 3H), 3.20 (m, 2H), 6.86 (br s, 1H), 7.0 (s, 1H), 7.46 (s, 2H), 7.96 (m, 1H), 8.10 (m, 1H), 8.76 (m, 1H), 9.59 (br s, 1H) and 10.41 (br s, 1H). MS: 315.06 [M+H]⁺.

[2-(ethylcarbamoylamino)-7-(2-pyridyl)-1,3-benzothiazol-5-yl]trifluoromethanesulfonate (xi)

To a stirred solution of x (57 g, 0.181 mol) in DMF (1.7 L) was added N-phenylbis(trifluoromethane sulphonimide) (80.74 g, 0.226 mol) and DIPEA (28 g, 0.217 mol). The mixture was stirred at RT for 3 h. The reaction was concentrated at 60-70° C. in vacuo. Et₂O was added to the residue and evaporated to dryness. The residue thus obtained was stirred with Et₂O (1.5 L) for 1 h and then filtered to obtain xi (55.0 g, 68%). $^1$H-NMR (DMSO-$d_6$, 400 MHz): δ 1.11 (t, J=7.20 Hz, 3H), 3.20 (m, 2H), 6.81 (br s, 1H), 7.50 (m, 1H), 7.78 (d, J=2.0 Hz, 1H), 8.01 (m, 1H), 8.12 (d, J=2.40 Hz, 1H), 8.35 (m, 1H), 8.84 (m, 1H) and 10.77 (br s, 1H). MS: 446.98 [M+H]⁺.

[2-(ethylcarbamoylamino)-7-(2-pyridyl)-1,3-benzothiazol-5-yl]boronic acid (Intermediate 1)

To a stirred solution of xi (25 g, 56.1 mmol) in DMSO (250 mL) at RT was added bis(neopentylglycolato)diboron (25.2 g, 112 mmol) and KOAc (16.5 g, 168 mmol). The resulting reaction mixture was de-gassed by purging N₂ for 15-20 min followed by addition of Pd(dppf)Cl₂ (6.8 g, 8.4 mmol). The mixture was purged with N₂ for 15-20 min and then heated to 80° C. for 90 min. The reaction was poured onto saturated NH₄Cl solution (1 L). The resulting precipitate was filtered and dried under vacuum. The solid cake was taken in 2M NaOH (200 mL) and stirred for 45 min at RT. The solution was filtered and the filtrate was acidified up to pH 5-6 and the resulting solid collected by filtration to give Intermediate 1 (17 g, 88%).

The following intermediate(s) were similarly prepared:

[2-(Ethylcarbamoyl amino)-7-[4-(morpholinomethyl)-2-pyridyl]-1,3-benzothiazol-5-yl]boronic acid (Intermediate 2)

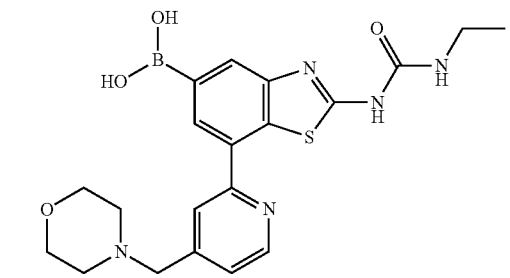 [SMILES: CCNC(=O)Nc1nc2cc(B(O)O)cc(-c3cc(CN4CCOCC4)ccn3)c2s1]

MS: 413.13 [M+H]⁺.

Prepared in analogous manner to Intermediate 1 with the exception that the addition of the C7-substituent to 1-(5-benzyloxy-7-bromo-1,3-benzothiazol-2-yl)-3-ethyl-urea was performed under Suzuki coupling conditions instead of Stille coupling conditions as follows:

1-[5-benzyloxy-7-[4-(morpholinomethyl)-2-pyridyl]-1,3-benzothiazol-2-yl]-3-ethyl-urea (i)

A mixture of 1-(5-benzyloxy-7-bromo-1,3-benzothiazol-2-yl)-3-ethyl-urea (27.7 g, 68.3 mmol), 2-(5,5-dimethyl-1,3,2-dioxaborinan-2-yl)-5,5-dimethyl-1,3,2-dioxaborinane (18.2 g, 80.7 mmol) and potassium acetate (12.2 g, 124 mmol) was suspended in DMSO (120 mL). The mixture was degassed for 15 min with a stream of N₂. Pd(dppf)Cl₂ (5.07 g, 6.21 mmol) was added and the mixture heated for 6 h at 85° C., then cooled to RT. A solution of Precursor 10 (13.2 g, 62.1 mmol) in DMSO (20 mL) was added, followed by Cs₂CO₃ (30.3 g, 93.1 mmol) and H₂O (30 mL). The mixture was degassed for 10 min under a stream of N$_2$. Pd(PPh$_3$)$_2$Cl$_2$ (4.36 g, 6.21 mmol) was added and the mixture heated at 85° C. overnight. The solution was cooled and diluted with water (400 mL), stirred vigorously until a solid formed and the supernatant discarded. The solids were suspended in EtOAc/DCM (300 mL) and filtered through a short plug of silica gel, eluting with 5-10% MeOH/DCM. The solution was then concentrated, dissolved in DCM (500 mL) and stirred with 3M HCl (150 mL) for 2 days at RT. The precipitate was collected by filtration, washing with DCM and H$_2$O. The resulting solid material was suspended in EtOAc/DCM (200 mL), sonicated and the solid collected by filtration to obtain i (25.5 g). MS: 504.17 [M+H]$^+$.

1-(7-bromo-5-iodo-1,3-benzothiazol-2-yl)-3-ethyl-urea (Intermediate 3)

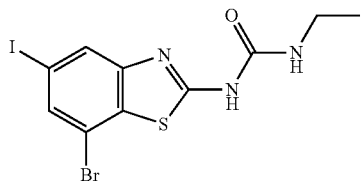 [SMILES: CCNC(=O)Nc1nc2cc(I)cc(Br)c2s1]

$^1$H NMR (DMSO-d$_6$, 400 MHz): δ 1.08 (t, J=7.20 Hz, 3H), 3.20 (q, J=6.80, 2H), 6.73 (br s, 1H), 7.72 (s, 1H), 7.96 (s, 1H) and 11.07 (br s, 1H). MS: 426.0 [M+H]$^+$.

2-bromo-4,6-dinitroaniline (i)

To a stirred mixture of H$_2$O (3.75 L) and acetic acid (375 mL) at RT was added 2,4-dinitroaniline (500 g, 2.73 mol) followed by drop wise addition of bromine (210 mL, 4.09 mol) over 30 min. The reaction mixture was stirred at RT for 15 min and then heated to 100° C. for 2 h. The reaction was cooled to RT and poured onto ice-cold H$_2$O (5-6 L) and basified (pH 8-10) with aqueous ammonia. The solid was filtered, washed with cold H$_2$O and dried under vacuum. This solid was washed with n-pentane to obtain i (600 g, 84%).

1,2-dibromo-3,5-dinitrobenzene (ii)

To a stirred solution of i (600 g, 2.28 mol) in ACN (5 L) at RT was added tert-butylnitrite (680 mL, 5.7 mol) and cupric bromide (767 g, 3.43 mol). The mixture was heated to 70° C. for 1 h under N$_2$. The reaction was cooled to RT, acidified with 1M HCl solution, H$_2$O (4 L) added and extracted with EtOAc (3×4 L). The combined organics were dried (Na$_2$SO$_4$), filtered and concentrated in vacuo to obtain ii (723 g, 97%). $^1$H NMR (CDCl$_3$, 400 MHz): δ 8.48 (d, J=2.40 Hz, 1H) and 8.68 (d, J=2.40 Hz, 1H).

2-bromo-4,6-dinitro-phenyl)thiocyanate (iii

To a stirred solution of ii (723 g, 2.22 mol) in MeOH (7.5 L) at RT was added potassium thiocyanate (431 g, 4.44 mol) and the mixture stirred under N$_2$ for 16 h. The reaction was filtered and washed with MeOH. The filtrate was concentrated in vacuo. The residue was purified over silica (2-6% EtOAc-hexane) to obtain iii (549 g, 81%).

7-bromobenzothiazole-2,5-diamine (iv)

To a stirred mixture of EtOH (8.37 L) and H$_2$O (8.37 L) at RT was added iii (549 g, 1.81 mol) followed by addition of Fe powder (2.02 kg, 36.11 mol) and drop wise addition of HCl (12M, 527 mL) over 30 min. The mixture was stirred at RT for 20 min and then heated to 80° C. for 45 min. The reaction was cooled to RT, basified to pH 8-10 by addition of aqueous ammonia solution. The solution was passed through celite, washed with EtOAc and the combined filtrate evaporated in vacuo. H$_2$O (8 L) was added and extracted with EtOAc (2×4 L). The combined organics were washed with brine, dried (Na$_2$SO$_4$), filtered and concentrated in vacuo to obtain iv (412 g, 93%). $^1$H NMR (DMSO-d$_6$, 400 MHz): δ 5.16 (br s, 2H), 6.50 (d, J=2.0 Hz, 1H), 6.53 (d, J=1.60 Hz, 1H) and 7.44 (br s, 2H). MS: 243.86 [M+H]$^+$.

7-bromo-5-iodobenzothiazol-2-amine (v)

To THF (6 L) at −78° C. under N$_2$ was added BF$_3$-etherate (50% assay, 708 mL, 2.81 mol) followed by a slow addition of a solution of iv (275 g, 1.02 mol) in THF (500 mL) over 20 min. Tert-butyl nitrite (548 L, 4.61 mol) was then added to the solution at −78° C. and the mixture was stirred at the same temperature for 40 min and then warmed to −5-0° C. Et$_2$O was added (at −5-0° C.) and the mixture stirred for 20 min. The solid was filtered and taken in acetone at 0° C. followed by sequential addition of KI (510 g, 3.07 mol) and iodine (519 g, 2.04 mol) and the mixture stirred at 0° C. for 30 min. The reaction was quenched with saturated solution of sodium metabisulfite and extracted with EtOAc (3×5 L). The combined organics were dried (Na$_2$SO$_4$), filtered and concentrated in vacuo at 45° C. The residue was purified over basic alumina (30-35% EtOAc-hexane) to obtain v (235 g, 65%). $^1$H NMR (DMSO-d$_6$, 400 MHz): δ 7.50 (d, J=1.20 Hz, 1H), 7.63 (d, J=1.20 Hz, 1H) and 7.91 (br s, 2H). MS: 354.90 [M+H]$^+$.

1-(7-bromo-5-iodobenzothiazol-2-yl)-3-ethylurea (Intermediate 3)

To a stirred solution of vi (250 g, 0.70 mol) in 1,4-dioxane at RT was added ethylisocyanate (278 mL, 3.52 mol). The mixture was heated to 80° C. for 10-12 h under N$_2$. The solvent was evaporated, n-hexane added and the mixture concentrated to dryness. The residue was stirred in hot H$_2$O (2 L) at 60-65° C. for 30-40 min and then filtered. The residue was then treated with a mixture of Et$_2$O and n-pentane and filtered to obtain Intermediate 3 (264 g, 88%).

1-[7-Bromo-5-[2-(1-hydroxy-1-methyl-ethyl)pyrimidin-5-yl]-1,3-benzothiazol-2-yl]-3-ethyl-5-methyl-1,3,5-triazinan-2-one (Intermediate 4)

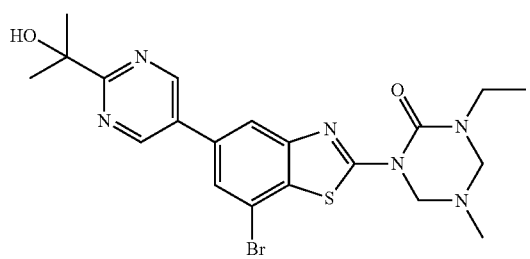 [SMILES: CCN1CN(C)CN(c2nc3cc(-c4cnc(C(C)(C)O)nc4)cc(Br)c3s2)C1=O]

$^1$HNMR (DMSO-d$_6$ 400 MHz): δ 9.20 (s, 2H), 8.13 (s, 1H), 7.91 (s, 1H), 5.14 (m, 3H), 4.39 (s, 2H), 3.36 (q, J=7.20 Hz, 2H), 2.54 (s, 3H), 1.53 (s, 6H) and 1.12 (t, J=7.20 Hz, 3H).

2-(5-bromopyrimidin-2-yl)propan-2-ol) (i)

To an ice-cold solution of methyl 5-bromopyrimidine-2-carboxylate (10 g, 46.1 mmol) in $Et_2O$ (200 mL) was added drop wise methyl magnesium bromide (3.0 M in $Et_2O$, 61.4 mL, 184 mmol) over 30 min. The reaction mixture was slowly warmed up to RT and continued to stir for 2 h. The mixture was quenched with saturated $NH_4Cl$ solution at 0° C. and the organic layer separated from the biphasic solution. The aqueous layer was re-extracted with EtOAc (2×250 mL). The combined organic layers were washed with brine solution, dried over $Na_2SO_4$, filtered and evaporated in vacuo. The crude residue was purified over silica eluting with 20% EtOAc:hexane to obtain i (6.0 g, 62%). 1HNMR (DMSO-d6, 400 MHz): δ 8.97 (s, 2H), 5.15 (s, 1H) and 1.47 (s, 6H).

2-(5-(4,4,5,5-tetramethyl-1,3,2-dioxaborolan-2-yl)pyrimidin-2-yl)propan-2-ol (ii)

To the solution of i (6.0 g, 27.6 mmol) in 1,4-dioxane (60 mL) was added bis(pinacolato)diboron (8.42 g, 33.2 mmol) and KOAc (4.06 g, 41.5 mmol). The reaction mass was degassed by purging $N_2$ for 15 min. $Pd_2(dba)_3$ (1.43 g, 1.4 mmol) and tricyclohexylphosphine (0.93 g, 3.31 mmol) was added to the reaction mixture that was degassed for 10 min. The resulting reaction mixture was heated at 80° C. for 2 h. The mixture was cooled to RT and filtered through a celite bed. The filtrate was concentrated in vacuo to obtain ii (5.11 g, 70%). MS: 265.13 $[M+H]^+$.

1-(7-bromo-5-(2-(2-hydroxypropan-2-yl)pyrimidin-5-yl)benzo[d]thiazol-2-yl)-3-ethyl-5-methyl-1,3,5-triazinan-2-one (Intermediate 4)

To a solution of Intermediate 3 (7.50 g, 15.48 mmol) and ii (5.11 g, 19.36 mmol) in 1,4-dioxane:MeOH (75:50 mL) was added potassium phosphate (6.15 g, 29.03 mmol) at RT. The resulting mixture was degassed for 15-20 min by purging $N_2$ followed by the addition of $Pd(PPh_3)_4$ (2.23 g, 1.93 mmol). The reaction mixture was again degassed for another 15-20 min and then heated up to 80° C. for 2 h. The mixture was cooled to RT and passed through celite bed and washed with EtOAc. The filtrate was evaporated in vacuo and the residue purified over silica eluting with 3% MeOH:DCM to obtain Intermediate 4 (7.50 g, 97%).

The following intermediate(s) were similarly prepared.

1-[7-bromo-5-[2-(1-hydroxy-1-methyl-ethyl)pyrimidin-5-yl]-1,3-benzothiazol-2-yl]-3-ethyl-urea (Intermediate 5)

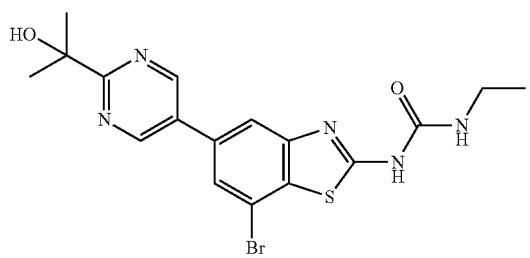 [SMILES: CCNC(=O)Nc1nc2cc(-c3cnc(C(C)(C)O)nc3)cc(Br)c2s1]

MS: 437.91 $[M+H]^+$.

1-(5-Bromo-6-methoxy-1,3-benzothiazol-2-yl)-3-ethyl-urea (Intermediate 6)

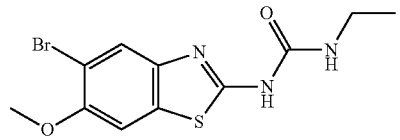 [SMILES: CCNC(=O)Nc1nc2cc(Br)c(OC)cc2s1]

MS: 329.94 & 331.91 $[M+H]^+$.

1-Ethyl-3-(6-methoxy-1,3-benzothiazol-2-yl)urea(i)

6-methoxy-1,3-benzothiazol-2-amine (5.0 g, 27.7 mmol) was dissolved in anhydrous DMSO (20 mL) and triethylamine (15.5 mL, 111 mmol) followed by ethyl isocyanate (4.39 mL, 55.5 mmol) were added. The mixture was stirred at RT under $N_2$ for 4 h then quenched with $H_2O$ (~200 mL) and stirred for 1 h. The resulting white solid was collected by filtration and rinsed with $H_2O$ and then with acetone (100 mL) and the filtrate collected separately to the aqueous filtrate. The filtrate was concentrated to dryness in vacuo and combined with the solid collected by filtration to obtain i (6.27 g, 90%).
MS: 251.96 $[M+H]^+$.

1-(5-Bromo-6-methoxy-1,3-benzothiazol-2-yl)-3-ethyl-urea (Intermediate 6)

Compound i (1.10 g, 4.38 mmol) was suspended in DCM (50 mL) and MeOH (5 mL) and bromine (0.34 mL, 6.60 mmol) added. The mixture was stirred at RT for 1.5 h then concentrated to dryness in vacuo to give Intermediate 6 (2.17 g).

Ethyl 1-[5-[7-bromo-2-(ethylcarbamoylamino)-1,3-benzothiazol-5-yl]pyrimidin-2-yl]-4-methyl-piperidine-4-carboxylate (Intermediate 7)

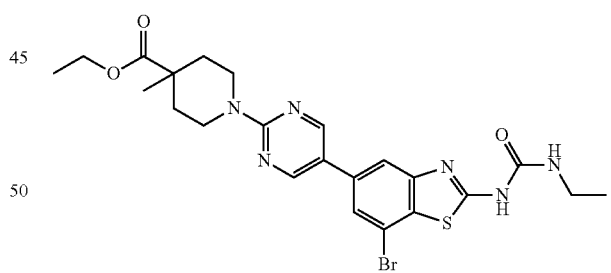

$^1H$ NMR (DMSO-$d_6$ 400 MHz): δ 1.09 (t, J=7.20 Hz, 3H), 1.20 (m, 6H), 1.45 (m, 2H), 2.03 (m, 2H), 3.16 (m, 2H), 3.30 (q, J=7.20, 2H), 4.12 (q, J=6.80 Hz, 2H), 4.25 (m, 2H), 6.75 (br s, 1H), 7.69 (s, 1H), 7.86 (s, 1H); 8.75 (s, 2H) and 10.91 (br s, 1H). MS: 547.11 $[M+H]^+$.

O1-tert-butyl O4-ethyl 4-methylpiperidine-1,4-dicarboxylate (i)

A solution of O1-tert-butyl O4-ethyl piperidine-1,4-dicarboxylate (1.5 g, 5.84 mmol) in THF (25 mL) was cooled to −78° C. followed by dropwise addition of LDA (1.80 M in THF, 6.5 mL, 11.68 mmol) at −78° C. The resulting mixture was stirred at −78° C. for 45 min followed by addition of methyl iodide (1.2 mL, 17.52 mmol). The temperature was slowly raised up to RT and left at RT for 6 h. The reaction was cooled to 0° C. and quenched by the dropwise addition of saturated NH₄Cl solution (50 mL). The reaction was extracted with EtOAc (3×100 mL). The combined organics were washed with brine, dried (Na₂SO₄), filtered and concentrated in vacuo. Purification by chromatography on silica eluting with 2% EtOAc in hexane gave i (1.0 g, 65%).

Ethyl 4-methylpiperidine-4-carboxylate hydrochloride (ii)

To an ice-cold solution of i (1 g, 3.68 mmol) in 1,4-dioxane (10 mL) was added HCl-1,4-dioxane (4.0 M, 15 mL) solution and stirred at RT for 30 min. The solvent was evaporated to obtain ii (0.90 g). MS: 172.16 [M+H]⁺.

Ethyl 1-(5-bromopyrimidin-2-yl)-4-methylpiperidine-4-carboxylate (iii)

To a solution of ii (0.9 g, 4.35 mmol) in EtOH (10 mL) was added DIPEA (2.30 mL, 13 mmol) at RT and the mixture stirred at RT for 10 min followed by addition of 5-bromo-2-chloropyrimidine (0.7 g, 3.6 mmol). The mixture was heated at 70° C. for 1 h. The solvent was evaporated and the crude residue purified by chromatography on silica eluting with 1.5% EtOAc:hexane to obtain iii (0.90 g, 75%). ¹H NMR (DMSO-d₆, 400 MHz): δ 1.17 (s, 3H), 1.21 (t, J=7.20 Hz, 3H) 1.40 (m, 2H), 2.00 (m, 2H), 3.24 (m, 2H), 4.11 (m, 2H), 4.15 (q, J=7.20 Hz, 2H), 8.43 (s, 2H). MS: 328.08 [M+H]⁺.

Ethyl 4-methyl-1-(5-(4,4,5,5-tetramethyl-1,3,2-dioxaborolan-2-yl)pyrimidin-2-yl)piperidine-4-carboxylate (iv)

To the solution of iii (25 g, 76.2 mmol) in 1,4-dioxane (250 mL) was added potassium acetate (22.4 g, 228.6 mmol) and bis(pinacolato)diboron (38.7 g, 152.4 mmol). The mixture was degassed for 15-20 min by purging with N₂ followed by the addition of Pd₂(dba)₃ (4.0 g, 3.80 mmol) and tricyclohexyl phosphine (2.55 gm, 9.12 mmol). The mixture was again degassed for another 15-20 min and then heated up to 80° C. for 3 h. The mixture was cooled to RT and diluted with 500 mL of EtOAc and passed through a celite bed. The filtrate was evaporated to obtain iv (20 g, 70%). MS: 376.30 [M+H]⁺.

Ethyl 1-(5-(7-bromo-2-(3-ethylureido)benzothiazol-5-yl)pyrimidin-2-yl)-4-methylpiperidine-4-carboxylate (Intermediate 7)

To a solution of Intermediate 3 (22.7 g, 53.2 mmol) and iv (20 g, 53.2 mmol) in 1,4-dioxane:MeOH (300:180 mL) was added potassium phosphate (17 g, 79 mmol) at RT. The resulting mixture was degassed for 15-20 min by purging N₂ followed by the addition of Pd(PPh₃)₄ (6.1 g, 5.32 mmol). The reaction mixture was again degassed for another 15-20 min and then heated up to 80° C. for 5 h. The reaction mixture was cooled to RT, diluted with EtOAc (500 mL) and passed through celite bed. The filtrate was evaporated and the crude residue was purified by chromatography on silica eluting with 1.5% MeOH:DCM to obtain Intermediate 7 (12 g, 41%).

1-(7-bromo-5-iodobenzo[d]thiazol-2-yl)-3-ethyl-5-methyl-1,3,5-triazinan-2-one (Intermediate 8)

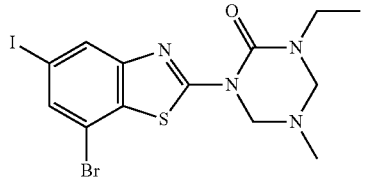 [SMILES: CCN1CN(C)CN(c2nc3cc(I)cc(Br)c3s2)C1=O]

¹H-NMR (DMSO-d₆, 400 MHz): δ 1.11 (t, J=7.20 Hz, 3H), 2.50 (s, 3H), 3.35 (m, 2H), 4.37 (s, 2H), 5.07 (s, 2H), 7.48 (s, 1H), 8.01 (s, 1H).

To a solution of Intermediate 3 (50 g, 117.37 mmol) in MeOH (1 L) was added formaldehyde (37% aq solution, 95 mL), methylamine (2M solution in THF, 587 mL, 1.17 mol) and N-methylmorpholine (130 mL, 1.17 mmol). The resulting solution was stirred at 75° C. for 5-6 h. The MeOH was evaporated in vacuo. Then ice-cold H₂O, was added and the mixture stirred for 30 min and then filtered. The residue was washed with cold H₂O followed by n-hexane and EtOAc. The residue was dried under high vacuum to give Intermediate 8 (56 g, quantitative).

1-Ethyl-3-[7-hydroxy-5-[2-(1-hydroxy-1-methylethyl)pyrimidin-5-yl]-1,3-benzothiazol-2-yl]-5-methyl-1,3,5-triazinan-2-one (Intermediate 9)

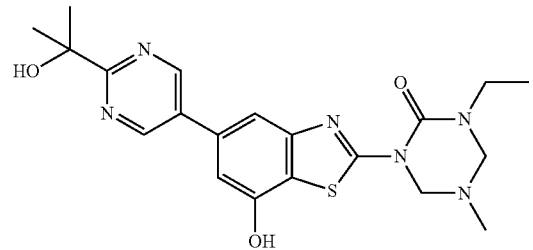 [SMILES: CCN1CN(C)CN(c2nc3cc(-c4cnc(C(C)(C)O)nc4)cc(O)c3s2)C1=O]

¹H NMR (400 MHz, CDCl₃) δ 9.68 (s, 1H), 8.83 (s, 2H), 7.34 (s, 1H), 6.82 (s, 1H), 5.07 (s, 2H), 4.63 (s, 1H), 4.21 (s, 2H), 3.37 (q, J=7.0 Hz, 2H), 2.55 (s, 3H), 1.52 (s, 6H), 1.13-1.08 (m, 4H). MS: 429 [M+H]⁺.

[2-(3-ethyl-5-methyl-2-oxo-1,3,5-triazinan-1-yl)-5-[2-(1-hydroxy-1-methyl-ethyl)pyrimidin-5-yl]-1,3-benzothiazol-7-yl]boronic acid (i)

A mixture of Intermediate 4 (500 mg), potassium acetate (300 mg), bis(neopentyl glycolato)diboron (460 mg) and Pd(dppf)₂Cl₂ (70 mg) in toluene (10 mL) was degassed (×3) under vacuum then heated at 130° C. for 90 min. The mixture was cooled and filtered through Celite. The filtrate was concentrated to give i (465 mg). MS: 457.02 [M+H]⁺.

1-ethyl-3-[7-hydroxy-5-[2-(1-hydroxy-1-methylethyl)pyrimidin-5-yl]-1,3-benzothiazol-2-yl]-5-methyl-1,3,5-triazinan-2-one (Intermediate 9)

A solution of Compound ii (465 mg) in acetone (5 mL) was chilled to 0° C. then treated dropwise with a solution of oxone (940 mg) in sat NaHCO₃ (35 mL). The reaction was stirred at RT overnight, then oxone (100 mg) in sat NaHCO$_3$ (5 mL) was added. The mixture was neutralised with 1M HCl and extracted with 4:1 DCM:IPA (3×30 mL). The organic extract was washed with brine (2.0 mL) then concentrated. The residue was suspended in 5% MeOH:DCM and purified by chromatography on silica eluting with 0-10% MeOH:DCM to give Intermediate 9 (240 mg).

The following intermediate(s) were similarly prepared.

1-ethyl-3-[7-hydroxy-5-[2-(1-hydroxyethyl)pyrimidin-5-yl]-1,3-benzothiazol-2-yl]-5-methyl-1,3,5-triazinan-2-one (Intermediate 10)

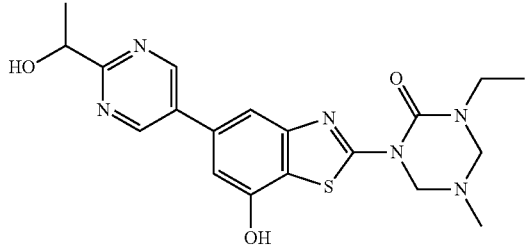 [SMILES: CCN1CN(C)CN(c2nc3cc(-c4cnc(C(C)O)nc4)cc(O)c3s2)C1=O]

MS: 415.1 [M+H]$^+$.

1-[5-bromo-7-(dimethylaminomethyl)-6-hydroxy-1,3-benzothiazol-2-yl]-3-ethyl-urea (Intermediate 11)

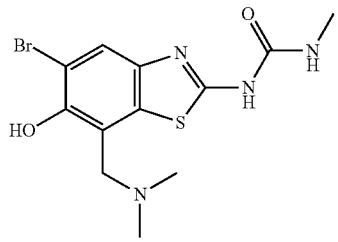 [SMILES: CNC(=O)Nc1nc2cc(Br)c(O)c(CN(C)C)c2s1]

MS 372.89 & 374.87 [M+H]$^+$.

Preparation of 1-(5-bromo-6-hydroxy-1,3-benzothiazol-2-yl)-3-ethyl-urea (i)

Intermediate 6 (1.30 g, 3.94 mmol) was suspended in hydrogen bromide solution (6.82 mL, 47% aq., 59.1 mmol) and the resulting suspension warmed to 110° C. Hydrogen bromide solution (14 mL, 47% aq., 121.3 mmol) was added portion-wise over the course of the reaction. After 47 h, the reaction mixture was cooled to RT then in ice and the pH adjusted with sodium hydroxide solution (1 M, aq.) to pH 8. The mixture was filtered and the resulting solid washed with H$_2$O and ACN. The solid was sucked dry to give i (1.01 g, 81%). MS 315.87 & 317.84 [M+H]$^+$.

1-[5-bromo-7-(dimethylaminomethyl)-6-hydroxy-1,3-benzothiazol-2-yl]-3-ethyl-urea (Intermediate 11)

To a mixture of i (209 mg, 0.66 mmol) in DMF (2 mL) was added triethylamine (0.14 mL, 0.99 mmol) followed by N,N-dimethylmethyleneiminium chloride (147 mg, 0.79 mmol) were added. The mixture was stirred at RT. After 4.25 h, more N,N-dimethylmethyleneiminium chloride (~10 mg) was added and stirring continued. After 6 h, the solvent was evaporated with a stream of N$_2$. The residue was suspended in DCM (~10 mL) and filtered through a PTFE filter. The solid was washed with DCM (~15 ml) and the filtrate concentrated in vacuo to give an oil. The oil was purified by chromatography, on silica eluting with 0-5% MeOH in DCM to give Intermediate 11 (176 mg, 71%).

1-[5-bromo-6-hydroxy-7-(morpholinomethyl)-1,3-benzothiazol-2-yl]-3-ethyl-urea (Intermediate 12)

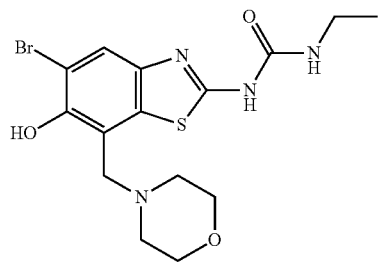 [SMILES: CCNC(=O)Nc1nc2cc(Br)c(O)c(CN3CCOCC3)c2s1]

MS 414.93 & 416.91 [M+H]$^+$.

Paraformaldehyde (29 mg, 0.05 mmol) was suspended in anhydrous DMF (2 mL) under argon and morpholine (0.08 mL, 0.95 mmol) added. The mixture was stirred at RT for 10 min then Intermediate 6 (200 mg, 0.63 mmol) added. The mixture was stirred at RT overnight, heated to 90° C. for 2 h then cooled to RT. The mixture was diluted with H$_2$O and a precipitate formed. EtOAc was added but the precipitate remained insoluble. The suspension was filtered through a PTFE filter and the solid rinsed with H$_2$O and EtOAc. The biphasic filtrate was extracted into EtOAc (4×20 mL). The combined organic layers were washed with H$_2$O (3×50 mL), dried (Na$_2$SO$_4$) and concentrated in vacuo. The material was purified by chromatography, on silica eluting with 0-10% MeOH in DCM to give Intermediate 12 (28 mg, 11%).

1-(5-Bromo-6-fluoro-benzothiazol-2-yl)-3-ethyl-urea (Intermediate 13)

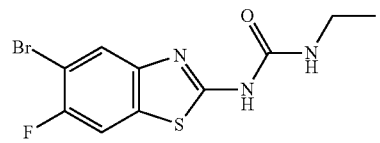

$^1$H-NMR (400 MHz, DMSO-d$_6$): δ 1.08 (t, J=6.80 Hz, 3H), 3.17 (m, 2H), 6.69 (br s, 1H), 7.92 (d, J=6.40 Hz, 1H), 8.0 (d, J=8.40 Hz, 1H) and 10.86 (br s, 1H).

1-Benzoyl-3-(5-bromo-2,4-difluoro-phenyl)-thiourea (i)

To a solution of 5-bromo-2,4-difluoro-aniline (1.0 g, 4.81 mmol) in acetone (25.0 mL) was added drop wise benzoyl isothiocyanate (0.71 mL, 5.29 mmol) and the mixture stirred at RT for 30 min. The solvent was evaporated and the residue washed with hexane and Et$_2$O to get i (1.70 g). $^1$H-NMR (400 MHz, CDCl$_3$): δ 7.02-7.06 (m, 1H), 7.56 (t, J=8.0 Hz, 2H), 7.68 (t, J=7.60 Hz, 1H), 7.91 (d, J=7.60 Hz, 2H), 8.67 (t, J=7.60 Hz, 1H), 9.15 (br s, 1H) and 12.65 (br s, 1H).

5-Bromo-2,4-difluoro-phenyl)-thiourea (ii)

To a solution of i (1.70 g, 4.60 mmol) in THF (35.0 mL) was added a solution of NaOH (0.97 g, 24.25 mmol) in H$_2$O (13.0 mL). The mixture was stirred at 70° C. for 15 h. The THF was evaporated, H$_2$O added and the mixture extracted with EtOAc (3×50 mL). The combined organics were washed with brine and concentrated to obtain ii (1.0 g, 83%). MS 267.03 (M+H)$^+$.

5-Bromo-6-fluoro-benzothiazol-2-ylamine (iii)

To a solution of ii (0.75 g, 2.80 mmol) in NMP (5.0 mL) was added NaH (0.17 g, 4.21 mmol, 60% dispersion in oil) portion wise. The mixture was heated at 130° C. for 2 h. and then poured onto crushed ice and extracted with EtOAc (3×50 mL). The combined organics were evaporated. Purification by chromatography on silica eluting with 12% EtOAc-Hexane gave iii (0.36 g, 52%). $^1$H-NMR (400 MHz, DMSO-d$_6$): δ 7.57 (d, J=6.40 Hz, 1H), 7.66 (br s, 2H) and 7.79 (d, 8.80 Hz, 1H).

1-(5-Bromo-6-fluoro-benzothiazol-2-yl)-3-ethyl-urea (Intermediate 13)

To a solution of iii (0.36 g, 1.45 mmol) in 1,4-dioxane (25.0 mL) was added ethyl isocyanate (0.69 mL, 8.74 mmol) and the mixture heated at 80° C. for 15 h. The solvent was evaporated and the residue stirred with H$_2$O at 60° C. for 5 h. The solution was filtered and washed with Et$_2$O to obtain Intermediate 13 (0.30 g, 69%).

Example(s) of Precursor(s)

| | | |
|---|---|---|
| 2-(5-Bromopyridin-2-yl)propan-2-ol (Precursor 1) | [structure] | $^1$H NMR (CDCl$_3$, 400 MHz): δ 8.8 (s, 2H), 4.3 (s, 1H), 1.6 (s, 6H). MS: 218.78 [M + H]$^+$. |

Ethyl 5-bromopyrimidine-2-carboxylate (500 mg) was placed in Et$_2$O (10 mL) and the mixture cooled to 0° C. Methyl magnesium bromide (3M in Et$_2$O) (1.32 mL) was added dropwise, the reaction allowed to warm to RT and stirred for 30 min. The reaction was quenched by the addition of Na$_2$CO$_3$ solution (sat. aq. 2 mL), diluted with H$_2$O (50 mL) and extracted with EtOAc (2×50 mL). The combined organics were dried (MgSO$_4$) and concentrated in vacuo. Purification by chromatography on silica, eluting with a gradient of 0-100% EtOAc in hexane gave Precursor 1 (256 mg).

The following precursor(s) were similarly prepared.

(Precursor 2)

MS: 216 & 218 [M + H]$^+$.
2-(2-bromo-4-pyridyl)propan-2-ol (Precursor 3)

MS: 270 [M + H]$^+$.
5-Bromo-2-(1-methylimidazol-2-yl)pyridine

A flask containing 5-bromo-2-iodo-pyridine (500 mg) in THF (2.5 mL) was cooled to −5° C. Isopropyl magnesium chloride (2M in THF) (0.92 mL) was added slowly and the reaction stirred for 50 min. 1-Methylimidazole-2-carbaldehyde (288 mg) was added and the mixture stirred for 3 h. The mixture was cooled to 0° C. and 2M HCl added until the pH ~7, then H$_2$O (2 mL) and toluene (10 mL) were added and the organic layer collected and concentrated. This was partitioned between EtOAc and H$_2$O and the organic layer dried (MgSO$_4$) and concentrated. The residue was crystallised from EtOAc to give Precursor 3 (150 mg).

(Precursor 4)

MS: 204.8 [M + H]$^+$
1-(5-Bromopyrimidin-2-yl)ethanol

5-Bromo-2-iodo-pyrimidine (1 g) was dissolved in THF (15 mL) and chloro(methyl)magnesium (3M in Et$_2$O, 2.34 mL) was added at −78° C., then the mixture was stirred at −78° C. for 30 min. Acetaldehyde (0.60 mL) was added dropwise to the resulting solution and the reaction was allowed to stir whilst warming to 0° C. over 30 min. MeOH was added and the mixture concentrated in vacuo. The resultant solid was dissolved in DCM/IPA (5:1; 80 mL) and washed with brine (50 mL). Purification by chromatography on silica, eluting with 0-20% EtOAc in heptane gave Precursor 4 (244 mg).

The following precursor(s) were similarly prepared.

(Precursor 5)

MS: 332.9 & 334.9, 1:1 [M + H]$^+$
1-(5-bromopyrimidin-2-yl)-2-[tert-butyl(dimethyl)silyl]oxy-ethanol (Precursor 6)

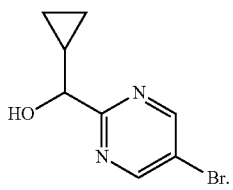

MS: 228.8 [M + H]+
(5-bromopyrimidin-2-yl)-
cyclopropyl methanol (Precursor 7)

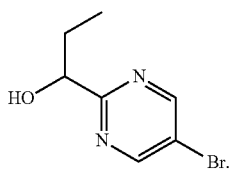

MS: 216.9 [M + H]+
1-(5-bromopyrimidin-2-yl)
propan-1-ol (Precursor 8)

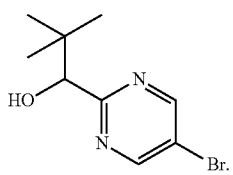

MS: 244.9 [M + H]+
1-(5-bromopyrimidin-2-yl)-
2,2-dimethyl-propan-1-ol (Precursor 9)

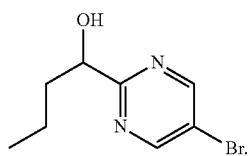

MS: 230.9 [M + H]+
1-(5-bromopyrimidin-2-yl)-
butan-1-ol (Precursor 10)

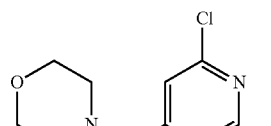

2-Chloro-4-morpholinomethylpyridine

To a solution of 2-chloro-4-(chloromethyl)pyridine (10 g) in THF (200 mL) was added morpholine (5.94 mL) and $K_2CO_3$ (18.8 g). The mixture was stirred at RT for 3 days. The reaction was filtered, the solids washed with EtOAc, and the filtrate concentrated. This material was purified on a plug of silica (0-50% EtOAc/DCM) to give Precursor 10 (6.87 g).

| Ethyl 1-(2-chloro-4-pyridyl)-4-methyl-piperidin-4-carboxylate (Precursor 11) | 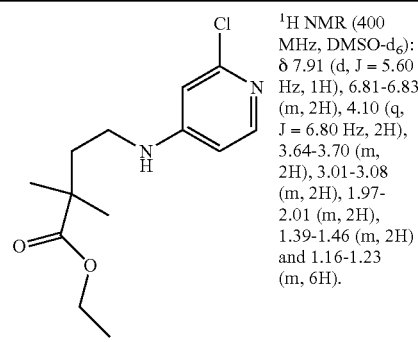 | 1H NMR (400 MHz, DMSO-d6): δ 7.91 (d, J = 5.60 Hz, 1H), 6.81-6.83 (m, 2H), 4.10 (q, J = 6.80 Hz, 2H), 3.64-3.70 (m, 2H), 3.01-3.08 (m, 2H), 1.97-2.01 (m, 2H), 1.39-1.46 (m, 2H) and 1.16-1.23 (m, 6H). |
|---|---|---|

To a solution of 4-bromo-2-chloro-pyridine (2.0 g, 10.39 mmol) in EtOH (25 mL) was added DIPEA (5.50 mL, 31.17 mmol) followed by ethyl 4-methylpiperidine-4-carboxylate hydrochloride (2.60 g, 12.50 mmol). The resulting reaction mixture was heated up to 85° C. for 16 h. The solvent was evaporated and the residue purified over silica eluting with 20% EtOAc-hexanes to give Precursor 11 (1.80 g, 75%).

The following precursor(s) were similarly prepared.

| ethyl 1-(6-bromo-2-pyridyl)-4-methyl-piperidine-4-carboxylate (Precursor 12) | 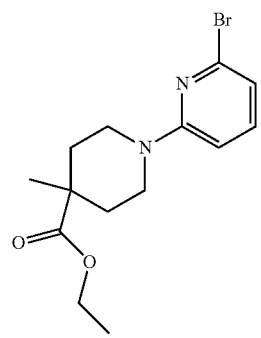 [SMILES: CCOC(=O)C1(C)CCN(c2cccc(Br)n2)CC1] | MS: 327.0 [M + H]+. 1H NMR (400 MHz, CDCl3): δ 7.22 (s, 1H), 6.70 (d, J = 7.60 Hz, 1H), 6.51 (d, J = 8.40 Hz, 1H), 4.16 (q, J = 6.80 Hz, 2H), 3.88-3.94 (m, 2H), 3.07-3.14 (m, 2H), 2.15-2.18 (m, 2H), 1.43-1.50 (m, 2H) and 1.22-1.28 (m, 6H). |
|---|---|---|

-continued

| ethyl 1-(6-chloro-3-pyridyl)-4-methyl-piperidine-4-carboxylate (Precursor 13) | 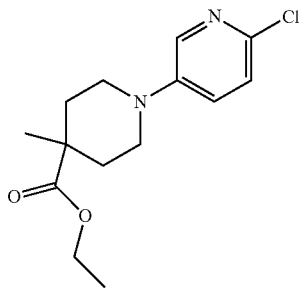 [SMILES: CCOC(=O)C1(C)CCN(c2ccc(Cl)nc2)CC1] | MS 283.11 [M + H]+. 1H NMR (400 MHz, DMSO-d6): δ 8.14 (d, J = 2.40 Hz, 1H), 7.63 (dd, J = 2.40 and 9.20 Hz, 1H), 6.81 (d, J = 9.20 Hz, 1H), 4.10 (q, J = 7.20 Hz, 2H), 3.84-3.89 (m, 2H), 3.05-3.12 (m, 2H), 1.96-2.0 (m, 2H), 1.36-1.43 (m, 2H) and 1.16-1.20 (m, 6H). |
| --- | --- | --- |
| ethyl 1-(4-chloropyrimidin-2-yl)-4-methyl-piperidine-4-carboxylate (Precursor 14) | 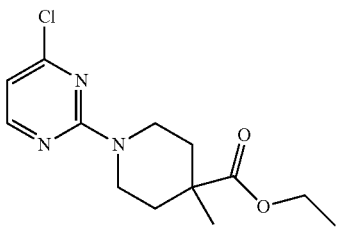 [SMILES: CCOC(=O)C1(C)CCN(c2nccc(Cl)n2)CC1] | MS 284.19 [M + H]+. 1H NMR (400 MHz, CDCl3): δ 8.0 (d, J = 6.40 Hz, 1H), 6.37 (d, J = 6.40 Hz, 1H), 4.20 (q, J = 6.80 Hz, 2H), 4.11 (m, 2H), 3.13-3.20 (m, 2H), 2.19-2.22 (m, 2H), 1.40-1.48 (m, 2H) and 1.24-1.29 (m, 6H). |
| ethyl 1-(2-chloropyrimidin-4-yl)-4-methyl-piperidine-4-carboxylate (Precursor 15) | 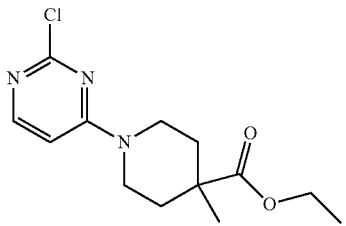 [SMILES: CCOC(=O)C1(C)CCN(c2ccnc(Cl)n2)CC1] | MS 284.05 [M + H]+. 1H NMR (400 MHz, DMSO-d6): δ 8.05 (d, J = 6.0 Hz, 1H), 6.85 (d, J = 5.60 Hz, 1H), 4.13 (q, J = 7.20 Hz, 2H), 3.99 (m, 2H), 3.15-3.21 (m, 2H), 1.98-2.02 (m, 2H), 1.38-1.45 (m, 2H) and 1.17-1.22 (m, 6H). |
| ethyl 1-(6-chloropyrimidin-4-yl)-4-methyl-piperidine-4-carboxylate (Precursor 16) | 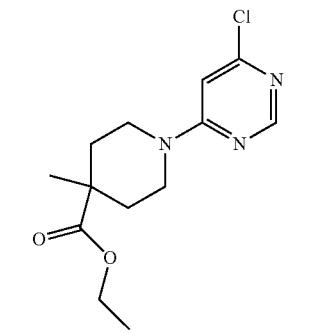 [SMILES: CCOC(=O)C1(C)CCN(c2cc(Cl)ncn2)CC1] | MS 284.09 [M + H]+. 1H NMR (400 MHz, DMSO-d6): δ 8.30 (s, 1H), 6.96 (s, 1H), 4.13 (m, 2H), 4.05 (m, 2H), 3.15-3.22 (m, 2H), 1.97-2.01 (m, 2H), 1.37-1.47 (m, 2H) and 1.15-1.21 (m, 6H). |
| ethyl 1-(2-chloro-4-pyridyl)piperidine-4-carboxylate (Precursor 17) | 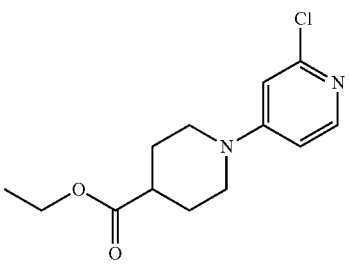 [SMILES: CCOC(=O)C1CCN(c2ccnc(Cl)c2)CC1] | MS [M + H]+. 1H NMR (400 MHz, DMSO-d6): δ 7.92 (d, J = 5.60 Hz, 1H), 6.82-6.84 (m, 2H), 4.07 (q, J = 7.20 Hz, 2H), 3.85-3.89 (m, 2H), 2.96-3.02 (m, 2H), 2.60-2.66 (m, 1H), 1.84-1.87 (m, 2H), 1.48-1.57 (m, 2H) and 1.17 (t, J = 7.20 Hz, 3H). |
| 2-chloro-N-(2-morpholinoethyl)pyrimidin-4-amine (Precursor 18) | 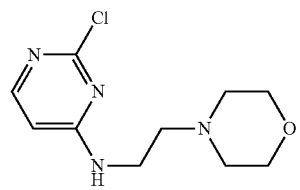 [SMILES: Clc1nccc(NCCN2CCOCC2)n1] | MS 243.11 [M + H]+. 1H NMR (400 MHz, DMSO-d6): δ 7.87 (m, 2H), 6.48 (d, J = 5.60 Hz, 1H), 3.57 (m, 4H), 3.39 (m, 2H), 2.45 (m, 6H), |

| | | |
|---|---|---|
| 2-chloro-N-(2-methoxyethyl)pyrimidin-4-amine (Precursor 19) | 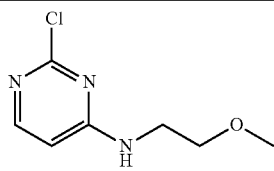 | MS 188.01 [M + H]⁺. ¹H NMR (CDCl₃, 400 MHz): δ 7.99 (d, J = 5.60 Hz, 1H), 6.26 (d, J = 5.60 Hz, 1H), 5.47 (br s, 1H), 3.55 (br. s, 4H) and 3.37 (s, 3H). |
| 1-(2-chloropyrimidin-4-yl)azetidin-3-ol (Precursor 20) | 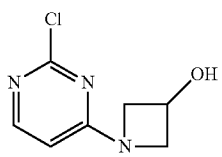 [SMILES: OC1CN(c2ccnc(Cl)n2)C1] | MS 185.98 [M + H]⁺. ¹H NMR (400 MHz, DMSO-d₆): δ 8.04 (d, J = 6.0 Hz, 1H), 6.37 (d, J = 6.0 Hz, 1H), 5.86 (m, 1H), 4.60 (m, 1H), 4.27 (m, 2H) and 3.79 (m, 2H). |
| 2-chloro-4-(3-methoxyazetidin-1-yl)pyrimidine (Precursor 21) | 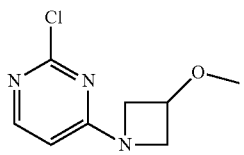 | MS 200.04 [M + H]⁺. ¹H NMR (CDCl₃, 400 MHz): δ 8.00 (d, J = 4.80 Hz, 1H), 6.08 (d, J = 6.0 Hz, 1H), 4.28-4.36 (m, 3H), 4.0 (m, 2H) and 3.33 (s, 3H). |
| 1-(2-chloropyrimidin-4-yl)-3-methyl-azetidin-3-ol(Precursor 22) | 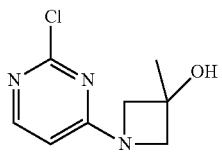 | MS 200.06 [M + H]⁺. ¹H NMR (CDCl₃, 400 MHz): δ 7.96 (d, J = 5.20 Hz, 1H), 6.05 (d, J = 5.60 Hz, 1H), 4.04 (br s, 4H) and 1.61 (s, 3H). |
| 4-(2-chloropyrimidin-4-yl)morpholine (Precursor 23) | 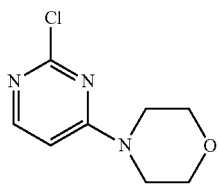 [SMILES: Clc1nccc(N2CCOCC2)n1] | MS 200.06 [M + H]⁺. ¹H NMR (CDCl₃, 400 MHz): δ 8.08 (d, J = 6.0 Hz, 1H), 6.39 (d, J = 6.0 Hz, 1H), 3.78 (m, 4H) and 3.64 (m, 4H). |
| 2-chloro-4-(4-ethylpiperazin-1-yl)pyrimidine (Precursor 24) | 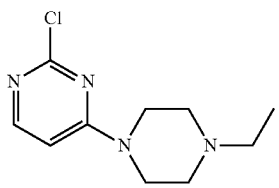 | ¹H NMR (CDCl₃, 400 MHz): δ 8.02 (d, J = 6.0 Hz, 1H), 6.38 (d, J = 5.60 Hz, 1H), 3.67 (m, 4H), 2.52 (m, 4H), 2.48 (q, J = 7.20 Hz, 2H) and 1.12 (t, J = 7.20 Hz, 3H). |
| 2-chloro-4-[4-(2-methoxyethyl)piperazin-1-yl]pyrimidine (Precursor 25) | 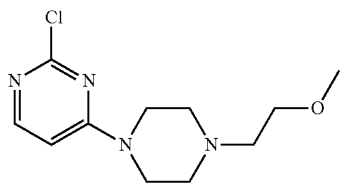 [SMILES: COCCN1CCN(c2ccnc(Cl)n2)CC1] | ¹H NMR (CDCl₃, 400 MHz): δ 8.03 (d, J = 6.40 Hz, 1H), 6.38 (d, J = 6.0 Hz, 1H), 3.7 (m, 4H), 3.60 (t, J = 5.20 Hz, 2H), 3.29 (s, 3H), 2.64 (t, J = 5.20 Hz, 2H) and 2.60 (m, 4H). |
| 4-(2-chloro-5-fluoro-pyrimidin-4-yl)morpholine (Precursor 26) | 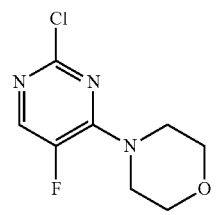 [SMILES: Fc1cnc(Cl)nc1N1CCOCC1] | MS 218.0 [M + H]⁺. ¹H NMR (CDCl₃, 400 MHz): δ 7.95 (d, J = 6.0 Hz, 1H) and 3.74-3.81 (m, 8H). |
| ethyl 4-[(2-chloro-4-pyridyl)amino]-1-methyl-cyclohexanecarboxylate (Precursor 27) | 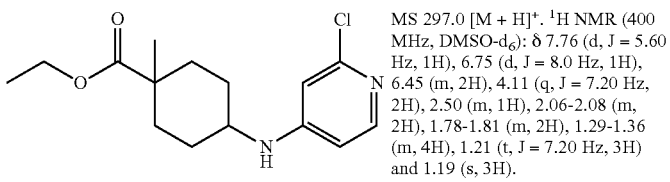 | MS 297.0 [M + H]⁺. ¹H NMR (400 MHz, DMSO-d₆): δ 7.76 (d, J = 5.60 Hz, 1H), 6.75 (d, J = 8.0 Hz, 1H), 6.45 (m, 2H), 4.11 (q, J = 7.20 Hz, 2H), 2.50 (m, 1H), 2.06-2.08 (m, 2H), 1.78-1.81 (m, 2H), 1.29-1.36 (m, 4H), 1.21 (t, J = 7.20 Hz, 3H) and 1.19 (s, 3H). |

| | | |
|---|---|---|
| 1-[(2-bromo-4-pyridyl)methyl]-3-methyl-pyrrolidin-3-ol (Precursor 28) | 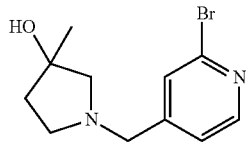 | MS 271.97 [M + H]⁺. ¹H NMR (400 MHz, DMSO-d₆): δ 8.29-8.31 (d, J = 4.80 Hz, 1H), 7.57 (s, 1H), 7.37-7.38 (d, J = 4.40 Hz, 1H), 4.58 (s, 1H), 3.64 (s, 2H), 2.64-2.68 (m, 2H), 2.42-2.44 (m, 2H), 1.72-1.75 (m, 2H) and 1.23 (s, 3H) |
| 1-[(2-bromo-4-pyridyl)methyl]-3-methyl-azetidin-3-ol (Precursor 29) | 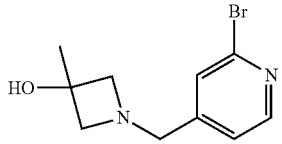 | ¹H NMR (400 MHz, DMSO-d₆): δ 8.29 (d, J = 5.20 Hz, 1H), 7.50 (s, 1H), 7.32 (d, J = 4.8 Hz, 1H), 5.21 (s, 1H), 3.61 (s, 2H), 3.33 (s, 2H), 2.90 (d, J = 6.40 Hz, 2H) and 1.36 (s, 3H). |
| 1-[(2-bromo-4-pyidyl)methyl]azetidin-3-ol (Precursor 30) | 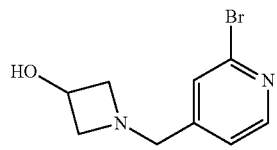 | MS 243.07 [M + H]⁺. ¹H NMR (400 MHz, DMSO-d₆): δ 8.28 (d, J = 4.80 Hz, 1H), 7.50 (s, 1H), 7.31 (d, J = 5.20 Hz, 1H), 5.35 (d, 1H), 4.17-4.25 (m, 1H), 3.59 (s, 2H), 3.48-3.54 (m, 2H) and 2.77-2.81 (t, J = 6.80 Hz, 2H). |
| 2-bromo-4-[(3,3-difluoropyridin-1-yl)methyl]pyridine (Precursor 31) | 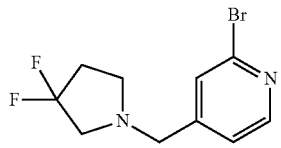 | MS 277.07 [M + H]⁺. ¹H NMR (400 MHz, DMSO-d₆): δ 8.34 (d, J = 5.20 Hz, 1H), 7.57 (s, 1H), 7.39 (d, J = 5.20 Hz, 1H), 3.67 (s, 2H) 2.90 (m, 2H), 2.72 (m, 2H) and 2.27 (m, 2H). |
| (3R)-1-[(2-bromo-4-pyridyl)methyl] pyrrolidin-3-ol (Precursor 32) | 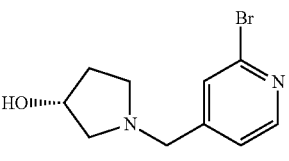 [SMILES: O[C@@H]1CCN(Cc2ccnc(Br)c2)C1] | MS 257.05 [M + H]⁺. ¹H NMR (400 MHz, DMSO-d₆): δ 8.30 (d, J = 5.20 Hz, 1H), 7.56 (s, 1H), 7.37 (d, J = 4.80 Hz, 1H), 5.75 (s, 1H), 4.72 (d, J = 4.40 Hz, 1H), 3.55-3.65 (m, 2H), 2.61-2.68 (m, 2H), and 2.38-2.50 (m, 1H), 2.31-2.38 (m, 1H), 1.95-2.04 (m, 1H) and 1.52-1.59 (m, 1H). |
| 4-[(6-chloro-3-pyridyl)methyl] morpholine (Precursor 33) | 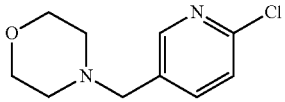 [SMILES: Clc1ccc(CN2CCOCC2)cn1] | MS 213.04 [M + H]⁺. |
| N-[(2-bromo-4-pyridyl)methyl] cyclopropanamine (Precursor 34) | 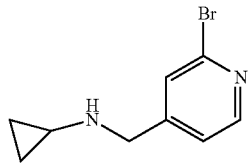 [SMILES: Brc1cc(CNC2CC2)ccn1] | MS 227.05 [M + H]⁺. |
| 4-[(2-bromo-4-pyridyl) methyl]-3-methyl-morpholine (Precursor 35) | 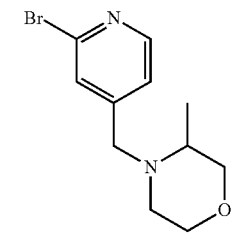 | MS 271.10 [M + H]⁺. |
| (2R,6S)-4-[(2-bromo-4-pyridyl)methyl]-2,6-dimethyl-morpholine (Precursor 36) | 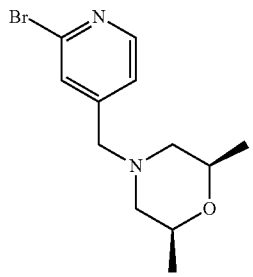 [SMILES: C[C@@H]1CN(Cc2ccnc(Br)c2)C[C@H](C)O1] | MS 285.07 [M + H]⁺. |

-continued

| | | |
|---|---|---|
| 4-[(2-bromo-4-pyridyl)methyl]-2,2,3,3,5,5,6,6-octadeuterio-morpholine (Precursor 37) | 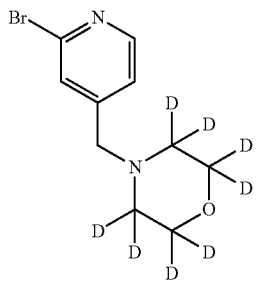 [SMILES: [2H]C1([2H])OC([2H])([2H])C([2H])([2H])N(Cc2ccnc(Br)c2)C1([2H])[2H]] | MS 265.17 [M + H]$^+$. |
| 4-[(2-bromo-4-pyridyl)methyl]-2,5-dimethyl-morpholine (Precursor 38) | 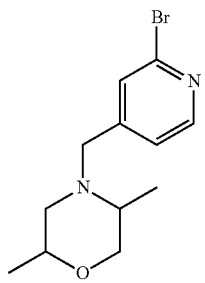 [SMILES: CC1CN(Cc2ccnc(Br)c2)C(C)CO1] | MS 285.12 [M + H]$^+$. |
| methyl (2S)-1-[(2-chloro-4-pyridyl)methyl] pyrrolidine-2-carboxylate (Precursor 39) | 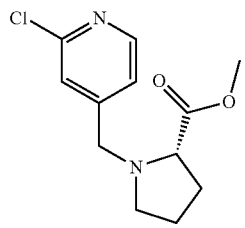 [SMILES: COC(=O)[C@@H]1CCCN1Cc1ccnc(Cl)c1] | MS 255.06 [M + H]$^+$. |
| 2-[(2-bromo-4-pyridyl) methyl]-6-oxa-2-azaspiro[3.3]heptane (Precursor 40) | 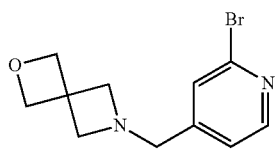 [SMILES: Brc1cc(CN2CC3(COC3)C2)ccn1] | MS 269.07 [M + H]$^+$. |
| 2-bromo-4-(methylsulfanylmethyl) pyridine (Precursor 41) | 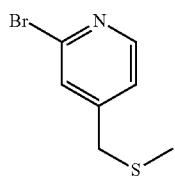 | MS 220.0 [M + H]$^+$. |
| 7-[(2-bromo-4-pyridyl) methyl]-2-oxa-7-azaspiro[3.5]nonane (Precursor 42) | 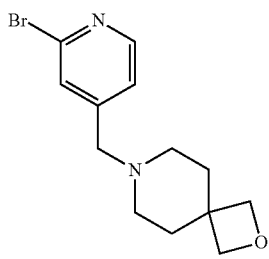 [SMILES: Brc1cc(CN2CCC3(CC2)COC3)ccn1] | MS 297.16 [M + H]$^+$. |

(Precursor 43)

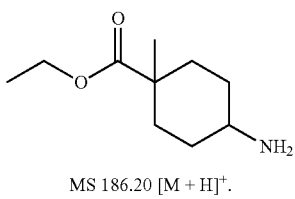

MS 186.20 [M + H]⁺.
Ethyl 4-amino-1-methylcyclohexanecarboxylate

Ethyl 4-aminocyclohexanecarboxylate (i)

To an ice-cold solution of 4-aminocyclohexanecarboxylic acid (5.0 g, 34.92 mmol) in EtOH (20 mL) was added thionyl chloride (7.60 mL, 104.76 mmol). The mixture was heated at 80° C. for 3 h. The solvent was evaporated in vacuo to obtain i (7.23 g). $^1$H NMR (400 MHz, DMSO-$d_6$): δ 4.19 (q, J=7.20 Hz, 2H), 3.71 (m, 1H), 2.71 (m, 1H), 2.06 (m, 2H), 1.90 (m, 2H), 1.69 (m, 2H), 1.55 (m, 2H), and 1.25 (t, J=7.20 Hz, 3H).

Ethyl 4-(1,3-dioxoisoindolin-2-yl)cyclohexanecarboxylate) (ii)

A solution of i (0.50 g, 2.92 mmol) in toluene (10 mL) was added Et₃N (1.02 mL, 7.30 mmol) and phthalic anhydride (0.56 g, 3.80 mmol). The mixture was refluxed for 8 h using a dean-stark apparatus for removal of H₂O. The solvent was evaporated in vacuo, H₂O (50 mL) added and the mixture stirred for 30 min at RT. The solid material thus obtained was collected by filtration and dried to obtain ii (0.30 g, 34%). $^1$H NMR (400 MHz, DMSO-$d_6$): δ 7.84 (s, 4H), 4.19 (q, J=7.20 Hz, 2H), 3.71 (m, 1H), 2.71 (m, 1H), 2.06 (m, 2H), 1.90 (m, 2H), 1.69 (m, 2H), 1.60 (m, 2H), and 1.23 (t, J=7.20 Hz, 3H).

Ethyl 4-(1,3-dioxoisoindolin-2-yl)-1-methylcyclohexanecarboxylate (iii)

A solution of ii (0.30 g, 1.0 mmol) in THF (10 mL) was cooled to −78° C. followed by dropwise addition of LDA (1.60 M in THF, 1.88 mL, 3.0 mmol) at −78° C. The mixture was stirred at −78° C. for 30 min followed by addition of methyl iodide (0.311 mL, 5.0 mmol) at −78° C. The temperature of the reaction mass was slowly raised up to RT and left to stir overnight. The reaction was cooled to 0° C. and quenched by dropwise addition of saturated NH₄Cl solution (30 mL). The reaction was extracted with EtOAc (3×50 mL). The combined organics were washed with brine, dried (Na₂SO₄), filtered and concentrated in vacuo to obtain iii (0.30 g, 97%). MS 316.12 [M+H]⁺.

Ethyl 4-amino-1-methylcyclohexanecarboxylate (Precursor 43)

To an ice-cold solution of iii (0.30 g, 0.95 mmol) in EtOH (20 mL) was added hydrazine hydrate (0.115 mL, 2.38 mmol) and the resulting reaction mixture was heated at 80° C. for 3 h. The solvent was evaporated in vacuo, H₂O (20 mL) added and extracted with EtOAc (3×50 mL). The organics were washed with brine, dried (Na₂SO₄), filtered and concentrated in vacuo to give Precursor 43 (0.18 g).

| | | |
|---|---|---|
| (S)-2-bromo-4-((3-fluoropyrrolidin-1-yl)methyl)pyridine (Precursor 44) | 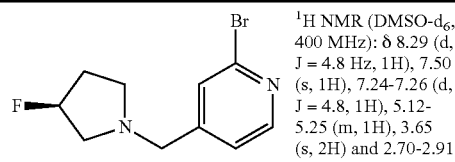 | $^1$H NMR (DMSO-$d_6$, 400 MHz): δ 8.29 (d, J = 4.8 Hz, 1H), 7.50 (s, 1H), 7.24-7.26 (d, J = 4.8, 1H), 5.12-5.25 (m, 1H), 3.65 (s, 2H) and 2.70-2.91 (m, 3H), 2.45-2.51 (m, 1H), and 2.03-2.25 (m, 2H). MS 259.05 [M + H]⁺. |

2-Bromopyridin-4-yl)methanol (i

To a solution of 2-bromopyridine-4-carbaldehyde (20 g, 107.52 mmol) in MeOH (150 mL) was added portion wise sodium borohydride (12.0 g, 322.56 mmol) at 0° C. under inert atmosphere. The mixture was stirred at RT for 1 h. Saturated NH₄Cl solution was added followed by extraction with EtOAc (3×200 mL). The combined organic layers were dried (Na₂SO₄) and evaporated in vacuo to obtain i (18.0 g, 90%). $^1$H NMR (DMSO-$d_6$, 400 MHz): δ 8.30 (d, J=4.8 Hz, 1H), 7.54 (s, 1H), 7.35 (d, J=4.8 Hz, 1H), 5.55 (t, J=6.0 Hz, 1H) and 4.53-4.54 (d, J=5.6 Hz, 2H).

2-Bromo-4-(bromomethyl)pyridine) (ii)

To the solution of i (18 g, 95.74 mmol) in toluene (180 mL) was added dropwise phosphorous tribromide (13.4 mL, 143.62 mmol) at 0° C. under inert atmosphere. The mixture was heated at 100° C. for 30 min. The reaction was cooled at 0° C. and NaHCO₃ solution added followed by extraction with EtOAc (2×500 mL). The combined organic layer were dried (Na₂SO₄) and evaporated in vacuo. The residue was purified over silica eluting with 15% EtOAc:Hexane to obtain ii (12.0 g, 50%). $^1$H NMR (CDCl₃, 400 MHz): δ 8.35 (d, J=4.8 Hz, 1H), 7.51 (s, 1H), 7.26 (d, J=6.0 Hz, 1H) and 4.34 (s, 2H). MS 251.80 [M+H]⁺.

S)-2-Bromo-4-((3-fluoropyrrolidin-1-yl)methyl)pyridine (Precursor 44

To an ice-cold solution of ii (3.0 g, 11.95 mmol) in DMSO (10 mL) was added KOH (1.0 g, 17.92 mmol) followed by the addition of (S)-3-fluoropyrrolidine hydrochloride (2.2 g, 17.92 mmol) under inert atmosphere. The mixture was stirred at 0° C. to RT for 20 min. The mixture was diluted with ice cold H₂O followed by extraction with EtOAc (3×150 mL). The combined organic layers were washed with brine, dried (Na₂SO₄) and evaporated in vacuo to give Precursor 44 (3.0 g, 96%).

The following precursor(s) were similarly prepared.

| | | |
|---|---|---|
| 2-bromo-4-[(3-methoxyazetidin-1-yl)methyl]pyridine (Precursor 45) | 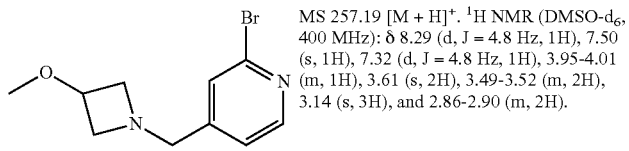 | MS 257.19 [M + H]⁺. ¹H NMR (DMSO-d₆, 400 MHz): δ 8.29 (d, J = 4.8 Hz, 1H), 7.50 (s, 1H), 7.32 (d, J = 4.8 Hz, 1H), 3.95-4.01 (m, 1H), 3.61 (s, 2H), 3.49-3.52 (m, 2H), 3.14 (s, 3H), and 2.86-2.90 (m, 2H). |
| 2-bromo-4-[(3,3-difluoro-1-piperidyl)methyl]pyridine (Precursor 46) | 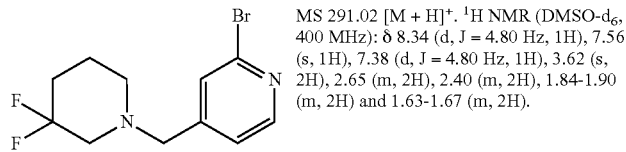 | MS 291.02 [M + H]⁺. ¹H NMR (DMSO-d₆, 400 MHz): δ 8.34 (d, J = 4.80 Hz, 1H), 7.56 (s, 1H), 7.38 (d, J = 4.80 Hz, 1H), 3.62 (s, 2H), 2.65 (m, 2H), 2.40 (m, 2H), 1.84-1.90 (m, 2H) and 1.63-1.67 (m, 2H). |
| 4-[(2-bromo-4-pyridyl)methyl]morpholine (Precursor 47) | 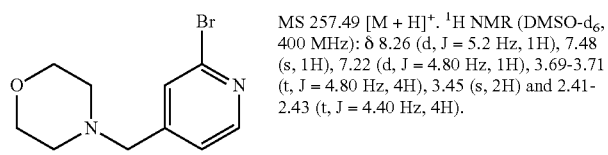 | MS 257.49 [M + H]⁺. ¹H NMR (DMSO-d₆, 400 MHz): δ 8.26 (d, J = 5.2 Hz, 1H), 7.48 (s, 1H), 7.22 (d, J = 4.80 Hz, 1H), 3.69-3.71 (t, J = 4.80 Hz, 4H), 3.45 (s, 2H) and 2.41-2.43 (t, J = 4.40 Hz, 4H). |
| 2-bromo-4-(pyrrolidin-1-ylmethyl)pyridine (Precursor 48) | 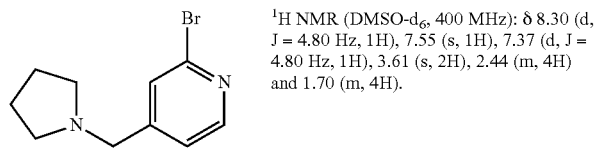 | ¹H NMR (DMSO-d₆, 400 MHz): δ 8.30 (d, J = 4.80 Hz, 1H), 7.55 (s, 1H), 7.37 (d, J = 4.80 Hz, 1H), 3.61 (s, 2H), 2.44 (m, 4H) and 1.70 (m, 4H). |
| 2-bromo-4-[(3,3-difluoroazetidin-1-yl)methyl]pyridine (Precursor 49) | 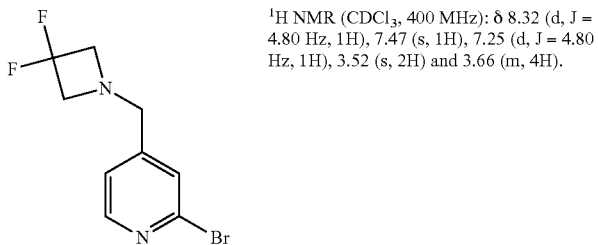 | ¹H NMR (CDCl₃, 400 MHz): δ 8.32 (d, J = 4.80 Hz, 1H), 7.47 (s, 1H), 7.25 (d, J = 4.80 Hz, 1H), 3.52 (s, 2H) and 3.66 (m, 4H). |

To an ice-cold solution of 2-bromoisonicotinaldehyde (0.40 g, 2.15 mmol) in THF (5 mL) was added 3,3-difluoroazetidine hydrochloride (0.41 g, 3.12 mmol) and N-methyl morpholine (catalytic). The reaction was stirred at 0° C. for 15 min followed by the portion wise addition of sodium cyano borohydride (0.41 g, 6.45 mmol). The mixture was stirred at RT for 16 h. H₂O (50 mL) was added followed by extraction with EtOAc (3×100 mL). The combined organics were washed with brine, dried (Na₂SO₄), filtered and concentrated in vacuo. Purification by chromatography on silica (30% EtOAc-Hexane) gave Precursor 49 (0.18 g, 32%).

| | | |
|---|---|---|
| 4-((6-bromo-pyrazin-2-yl)methyl)morpholine (Precursor 50) | 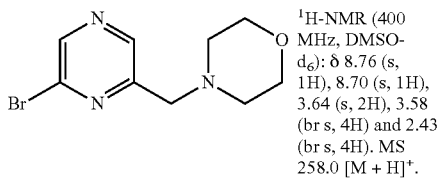 | ¹H-NMR (400 MHz, DMSO-d₆): δ 8.76 (s, 1H), 8.70 (s, 1H), 3.64 (s, 2H), 3.58 (br s, 4H) and 2.43 (br s, 4H). MS 258.0 [M + H]⁺. |

2-bromo-6-(bromomethyl)pyrazine (i)

To a solution of 2-bromo-6-methyl-pyrazine (3.0 g, 17.31 mmol) in CCl₄ (25 mL) was added NBS (4.60 g, 26.01 mmol) and AIBN (0.248 g, 1.734 mmol) at RT. The mixture was stirred at 55° C. for 48 h. H₂O was added followed by extraction with EtOAc (3×100 mL). The combined organics were washed with brine, dried (Na₂SO₄) and concentrated in vacuo. The residue was purified over silica eluting with 5% EtOAc:Hexane to obtain i (1.40 g, 32%). ¹H NMR (CDCl₃, 400 MHz): δ 8.64 (s, 1H), 8.62 (s, 1H) and 4.50 (s, 2H).

4((6-bromopyrazin-2-yl)methyl)morpholine (Precursor 50)

To an ice-cold solution of i (1.29 g, 4.81 mmol) in ACN (30 mL) was added morpholine (0.46 g, 5.28 mmol) and the mixture stirred at 0° C. for 45 min. H₂O was added and the mixture extracted with EtOAc (3×50 mL). The combined organics were washed with brine, dried (Na₂SO₄), and concentrated in vacuo. The residue was purified over silica eluting with 90% EtOAc:Hexane to obtain Precursor 50 (0.6 g, 50%).

The following precursor(s) were similarly prepared.

| | | |
|---|---|---|
| 4-[(2-chloropyrimidin-5-yl)methyl]morpholine (Precursor 51) | 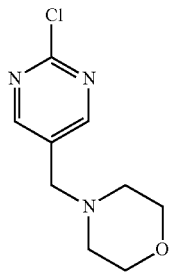 [SMILES: Clc1ncc(CN2CCOCC2)cn1] | MS 214.10 [M + H]⁺.<br>$^1$H NMR (CDCl$_3$, 400 MHz): δ 8.61 (s, 2H) 3.72 (br s, 4H), 3.52 (s, 2H) and 2.48 (br s, 4H). MS [M + H]⁺. |
| 3-Methylpyrrolidin-3-ol hydrochloride (Precursor 52) | 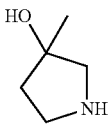 | $^1$H-NMR (400 MHz, DMSO-d$_6$): δ 4.71 (s, 1H), 3.33-3.46 (m, 2H), 1.72-1.74 (m, 2H) and 1.41 (s, 2H), 1.38 (s, 9H) and 1.28 (s, 3H). MS 202.28 [M + H]⁺. | tert-Butyl 3-hydroxy-3-methylpyrrolidine-1-carboxylate (i)

To an ice-cold solution of tert-butyl 3-oxopyrrolidine-1-carboxylate (1.0 g, 5.40 mmol) in Et$_2$O (20 mL) was added methylmagnesium bromide (3.50 mL, 10.80 mmoL) drop wise under an inert atmosphere. The mixture was stirred at RT for 1 h, then quenched with NH$_4$Cl solution followed by extraction with EtOAc (3×100 mL). The combined organic layers were washed with brine, dried (Na$_2$SO$_4$), filtered and concentrated in vacuo. Trituration with n-pentane gave i (1.0 g, 92%). 3-Methylpyrrolidin-3-ol hydrochloride (Precursor 52): To a solution of 4M HCl in 1,4-dioxane (10 mL) at 0° C. was added i (0.850 g, 4.22 mmol) and the mixture stirred for 2 h at RT. The solvent was removed in vacuo and trituration with Et$_2$O gave Precursor 52 (0.490 g). MS 102.15 [M+H]⁺.

| | | |
|---|---|---|
| 2-bromo-4-((3-methoxy-3-methylazetidin-1-yl)methyl)pyridine (Precursor 54) |  | MS 271.05 [M + H]⁺. |

To an ice-cold solution of Precursor 29 (0.75 g, 2.92 mmol) in DMF (15 mL) was added NaH (60% dispersion in mineral oil, 0.175 g, 4.38 mmol) portion wise. The mixture was stirred at 0° C. for 10 min followed by drop wise addition of methyl iodide (0.27 mL, 4.38 mmol). The reaction mixture was left to stir at 0° C. for 30 min. H$_2$O (10 mL) was added, followed by extraction with EtOAc (3×50 mL). The combined organics were washed with H$_2$O, brine, dried (Na$_2$SO$_4$) and concentrated in vacuo. The residue was purified over silica eluting with 40% EtOAc:Hexane to obtain Precursor 54 (0.24 g, 30%).

The following precursor(s) were similarly prepared.

(Precursor 55)

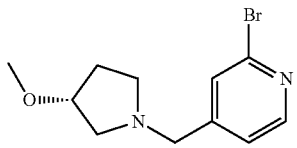

MS 271.0 [M + H]⁺.
2-bromo-4-[[(3R)-3-methoxypyrrolidin-1-yl]methyl]pyridine (Precursor 56)

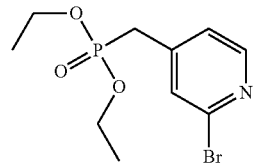

MS 309.98 [M + H]⁺.
2-bromo-4-(diethoxyphosphorylmethyl)pyridine 2-bromo-4-(bromomethyl)pyridine (2.3912 mmol; 600 mg and triethylphosphite (2.6 mmol; 440 mg) were suspended in ACN (5 mL) in a sealed microwave tube and heated at 100° C. in a microwave for 1 h. The mixture was concentrated in vacuo to give Precursor 56 (700 mg, 95%).

| | | |
|---|---|---|
| 4-(2-((2-chloropyridin-4-yl)oxy)ethyl)morpholine (Precursor 57) | 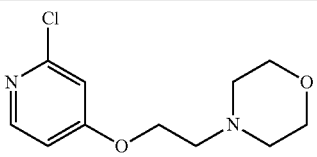 [SMILES: Clc1cc(OCCN2CCOCC2)ccn1] | $^1$H-NMR (400 MHz, DMSO-d$_6$): δ 8.18 (d, J = 6.0 Hz, 1H), 7.12 (d, J = 2.0 Hz, 1H), 6.99-7.01 (m, 1H), 4.19-4.22 (t, J = 5.60 Hz, 2H), 3.55-3.57 (t, J = 4.80 Hz, 4H), 2.61 (t, J = 6.40 Hz, 2H) and 2.45-2.50 (m, 4H). MS 243.09 [M + H]⁺. |

The following precursor(s) were similarly prepared.

| | | |
|---|---|---|
| 3-methyl-azetidin-3-ol hydrochloride (Precursor 53) | 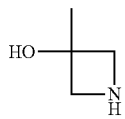 | $^1$H NMR (400 MHz, DMSO-d$_6$): δ 3.81-3.83 (m, 2H), 3.69-3.72 (m, 3H), 2.83 (br s, 1H) and 1.42 (s, 3H). |

To an ice-cold solution of 2-chloropyridin-4-ol (1.0 g, 7.72 mmol) and 4-(2-chloroethyl)morpholine hydrochloride (1.16 g, 7.72 mmol) in DMF (10 mL) was added K$_2$CO$_3$ (3.20 g, 23.16 mmol). The mixture was stirred at RT for 16 h. H$_2$O (20 mL) was added followed by extraction with EtOAc (3×100 mL). The combined organic layer were washed with brine, dried (Na$_2$SO$_4$) and evaporated in vacuo. The residue was purified on silica eluting with 5% MeOH:DCM to obtain Precursor 57 (0.60 g, 33%).

The following precursor(s) were similarly prepared.

| | | |
|---|---|---|
| 4-[3-[(2-chloro-4-pyridyl)oxy]propyl]morpholine (Precursor 58) | 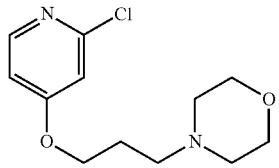 [SMILES: Clc1cc(OCCCN2CCOCC2)ccn1] | 1H-NMR (400 MHz, DMSO-$d_6$): δ 8.18 (d, J = 6.0 Hz, 1H), 7.10 (d, J = 2.0 Hz, 1H), 6.98-7.10 (dd, J = 2.0 Hz and 5.60 Hz respectively, 1H), 4.13 (t, J = 6.40 Hz, 2H), 3.55-3.57 (t, J = 4.80 Hz, 4H), 2.34-2.40 (m, 6H) and 1.83-1.90 (m, 2H). |
| 2-chloro-4-(tetrahydrofuran-2-ylmethoxy)pyridine (Precursor 59) | 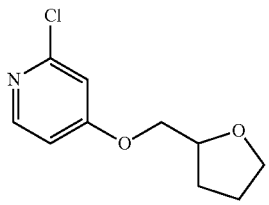 [SMILES: Clc1cc(OCC2CCCO2)ccn1] | MS 214.08 [M + H]$^+$. |
| 2-chloro-4-(2-methoxyethoxy)pyridine (Precursor 60) | 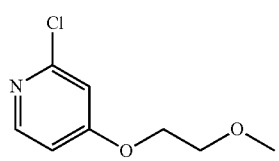 | 1H NMR (CDCl$_3$, 400 MHz): δ 8.18 (d, J = 5.60 Hz, 1H), 6.88 (s, 1H), 6.79 (d, J = 5.60 Hz, 1H), 4.17 (m, 2H), 3.76 (m, 2H) and 2.43 (s, 3H). |
| 4-[2-[(6-chloro-3-pyridyl)oxy]ethyl]morpholine (Precursor 61) | 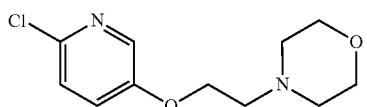 | MS 243.11 [M + H]$^+$. |
| 2-((2-chloropyrimidin-4-yl)amino)ethanol: (Precursor 62) | 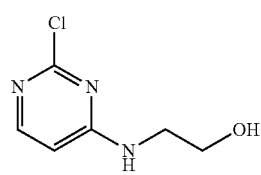 [SMILES: OCCNc1ccnc(Cl)n1] | $^1$H NMR (400 MHz, DMSO-$d_6$): δ 7.96 (br. s, 1H), 7.87 (d, J = 5.60 Hz, 1H), 6.48 (d, J = 5.60 Hz, 1H), 4.81 (m, 1H) and 3.52 (m, 4H). MS 174.01 [M + H]$^+$. |

A solution of 2-chloro-N-(2-methoxyethyl)pyrimidin-4-amine (1.0 g, 5.34 mmol) in DCM (10 mL) was cooled to −10° C. followed by drop wise addition of BBr$_3$ (0.70 mL, 8.02 mmol). The mixture was stirred at RT for 3 h. NaHCO$_3$ solution (5 mL) was added followed by extraction with DCM (2×50 mL). The combined organics were washed with H$_2$O, brine, dried (Na$_2$SO$_4$) and evaporated in vacuo. The residue was purified on silica eluting with 80% EtOAc:Hexane to obtain Precursor 62 as a white solid (0.35 g, 38%).

| | | |
|---|---|---|
| 4-(1-(2-chloropyridin-4-yl)ethyl)morpholine (Precursor 63) | 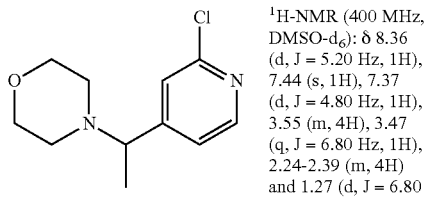 | $^1$H-NMR (400 MHz, DMSO-$d_6$): δ 8.36 (d, J = 5.20 Hz, 1H), 7.44 (s, 1H), 7.37 (d, J = 4.80 Hz, 1H), 3.55 (m, 4H), 3.47 (q, J = 6.80 Hz, 1H), 2.24-2.39 (m, 4H) and 1.27 (d, J = 6.80 Hz, 3H). |

1-(2-chloropyridin-4-yl)ethanol (i)

To an ice-cold solution of 1-(2-chloro-4-pyridyl)ethanone (1.0 g, 6.42 mmol) in MeOH was added NaBH$_4$ (0.73 g, 19.21 mmol) and the solution stirred at RT for 30 min. The reaction was then quenched with saturated NH$_4$Cl solution followed by extraction with EtOAc (3×100 mL). The combined organic layers were washed with brine, dried (Na$_2$SO$_4$) and evaporated in vacuo to obtain i (0.61 g, 60%). MS 158.10 [M+H]$^+$.

1-(2-chloropyridin-4-yl)ethyl methanesulfonate (ii)

To an ice-cold solution of i (0.25 g, 1.58 mmol) in DCM (10 mL) was added Et$_3$N (0.43 mL, 3.16 mmol) and the resulting solution was stirred for 15 min at the same temperature followed by addition of methanesulfonyl chloride (0.18 mL, 2.37 mmol). The mixture was stirred at RT for 4 h. The reaction was quenched with H$_2$O and extracted with EtOAc (3×100 mL). The combined organic layers were washed with brine, dried (Na$_2$SO$_4$) and evaporated in vacuo to obtain ii (0.30 g, 80%). MS 236.38 [M+H]$^+$.

4-(1-(2-chloropyridin-4-yl)ethyl)morpholine (Precursor 63)

To an ice-cold solution of ii (0.30 g, 1.33 mmol) in DMSO (5 mL) was added powdered KOH (0.11 g, 1.99 mmol). The mixture was stirred at 0° C. for 15 min followed by addition of morpholine (0.23 g, 2.66 mmol) and the mixture then stirred at RT for 16 h. Ice-cold H$_2$O was added to the reaction mass followed by extraction with EtOAc (3×100 mL). The combined organic layer were washed with brine, dried (Na$_2$SO$_4$) and evaporated in vacuo to obtain Precursor 63 (0.28 g, 93%).

| 1-(5-bromopyridin-2-yl)ethanol (Precursor 64) | 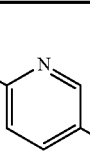 | $^1$H NMR (DMSO-$d_6$, 400 MHz): δ 8.59 (m, 1H), 8.03 (d, J = 8.40 Hz, 1H), 7.49 (d, J = 8.40 Hz, 1H), 5.50 (d, J = 4.40 Hz, 1H), 4.69 (m, 1H), 1.34 (d, J = 6.40 Hz, 3H). |
|---|---|---|

To an ice-cold solution of 5-bromopyridine-2-carbaldehyde (1.0 g, 5.37 mmol) in THF (10.0 mL) was added methyl magnesium bromide (3.44 mL, 6.88 mmol, 2M in Et$_2$O). The resulting reaction mixture was stirred at RT for 16 h. H$_2$O (100 mL) was added followed by extraction with EtOAc (3×100 mL). The combined organics were washed with brine, dried (Na$_2$SO$_4$), filtered and concentrated in vacuo. The residue was purified over silica (50% EtOAc-hexanes) to obtain Precursor 64 (0.80 g, 74%).

The following precursor(s) were similarly prepared.

| 1-(2-bromo-4-pyridyl)ethanol (Precursor 65) | 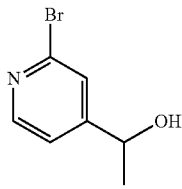 | MS 202 [M + H]$^+$. |
|---|---|---|
| 1-(5-bromo-pyridin-2-yl)-2,2,2-trifluoroethanol (Precursor 66) | 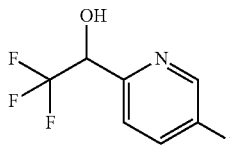 | $^1$H NMR (DMSO-$d_6$, 400 MHz): δ 8.73 (m, 1H), 8.17 (dd, J = 2.0 and 8.40 Hz, 1H), 7.60 (d, J = 8.40 Hz, 1H), 7.16 (d, J = 6.0 Hz, 1H) and 5.15 (m, 1H). MS 255.88 [M + H]$^+$. |

To an ice-cold solution of 5-bromopyridine-2-carbaldehyde (0.5 g, 2.69 mmol) in THF (10 mL) was added trimethyl (trifluoromethyl)silane (0.57 g, 4.03 mmol) followed by TBAF (6.73 mL, 6.73 mmol, 1.0 M THF). The mixture was stirred at RT for 16 h. H$_2$O (100 mL) was added followed by extraction with EtOAc (3×50 mL). The combined organics were washed with brine, dried (Na$_2$SO$_4$) and concentrated in vacuo The residue was purified over silica (20% EtOAc-hexanes) to obtain Precursor 66 (0.61 g, 89%).

(Precursor 67)

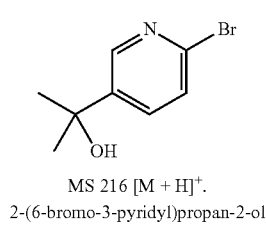

MS 216 [M + H]$^+$.
2-(6-bromo-3-pyridyl)propan-2-ol

To a solution of 1-(6-bromo-3-pyridyl)ethanone (500 mg, 2.68 mmol) in THF (20 mL) to 0° C. was added methyl magnesium bromide (3 M in diethylether, 1.2 mL, 3.7 mmol) dropwise and the mixture allowed to warm to RT and stirred for 60 min. The mixture was re-cooled to 0° C. and NaHCO$_3$ solution (100 mL) added. The mixture was extracted with EtOAc (100 mL). The organic layer was separated and the aqueous layer extracted with a further portion of EtOAc (100 mL). The organic layers were combined, dried (MgSO$_4$) and concentrated in vacuo. Purification by chromatography, on silica eluting with 0-5% methanol in DCM, followed by further chromatography, on silica eluting with 0-50% EtOAc in n-heptane, gave Precursor 67.

(Precursor 68)

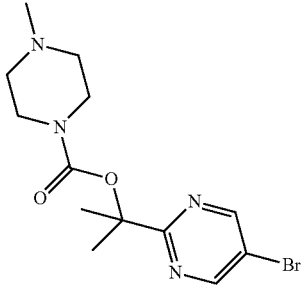

MS 344.87 & 342.87 [M + H]$^+$.
2-(5-bromopyrimidin-2-yl)propan-2-yl 4-methylpiperazine-1-carboxylate 2-(5-bromopyrimidin-2-yl)propan-2-yl 4-nitrophenyl carbonate (i)

Sodium hydride (110 mg, 2.8 mmol) was added to a solution of Precursor 1 in THF (10 ml) at 0° C. and stirred for 1 h. To this mixture was added 4-nitrophenyl carbonochloridate (560 mg, 2.8 mmol) portionwise and the solution was stirred at 0° C. for 1 h. EtOAc (3 ml) and H$_2$O were added, the organic layer separated, dried and concentrated to give i (900 mg).

2-(5-bromopyrimidin-2-yl)propan-2-yl 4-methylpiperazine-1-carboxylate (Precursor 68)

1-methylpiperazine (1.05 g, 10.47 mmol) was added to a solution of i (1 g, 2.1 mmol) in DMF (10 mL) and stirred at RT for 18 h. The mixture was concentrated in vacuo and the residue partitioned between EtOAc (20 mL) and H$_2$O (10 mL), the organic layer was separated and washed with further H$_2$O (2×5 mL), dried (MgSO$_4$), filtered and concentrated in vacuo. Purification by chromatography on silica, eluting with 0-10% MeOH/DCM gave Precursor 68 (144 mg, 20%).

(Precursor 69)

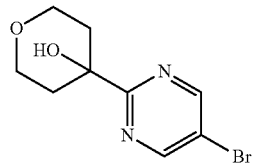

MS 258.92 & 260.88 [M + H]$^+$.
4-(5-bromopyrimidin-2-yl)tetrahydro-2H-pyran-4-ol 5-Bromo-2-iodo-pyrimidine (1.14 g, 4 mmol) in toluene (4 mL) was added dropwise to a solution of n-BuLi (2.76 mL 1.52 M) in toluene (8 mL) at −78° C. After stirring at −78° C. for 1 h, and tetrahydro-4H-pyran-4-one (1.6 g, 1.5 mL, 16 mmol) which had been dried over 3 Å molecular sieves for >30 mins, was added in one portion with vigorous stirring. The reaction allowed to warm to RT and stirred for 3 h. The reaction was quenched with NH₄Cl (10 mL), and extracted with EtOAc (4×20 mL). The organic layers were combined, dried (Na₂SO₄), concentrated in vacuo. The residue was purified by flash chromatography (10%-45% EtOAc in heptane) to give Precursor 69 (535 mg, 53%).

The following precursor(s) were similarly prepared.

(Precursor 70)

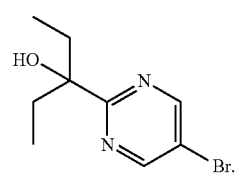

MS 244.86 [M + H]⁺
3-(5-bromopyrimidin-2-yl)
pentan-3-ol (Precursor 71)

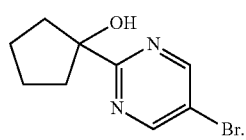

MS 242.88 [M + H]⁺
1-(5-bromopyrimidin-2-yl)
cyclopentanol (Precursor 72)

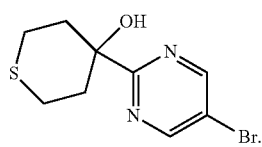

MS 276.91 [M + H]⁺
4-(5-bromopyrimidin-2-yl)
tetrahydrothiopyran-4-ol (Precursor 73)

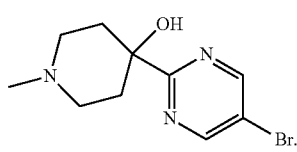

MS 270.02 [M + H]⁺
4-(5-bromopyrimidin-2-yl)-
1-methyl-piperidin-4-ol (Precursor 74)

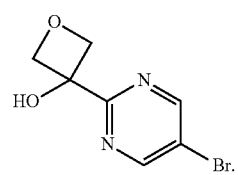

MS 230.96 & 232.94
[M + H]⁺
3-(5-bromopyrimidin-2-yl)
oxetan-3-ol (Precursor 75)

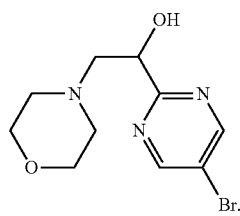

MS 288.05 & 290.01 [M + H]⁺
1-(5-bromopyrimidin-2-yl)-
2-morpholino-ethanol

5-bromo-2-vinyl-pyrimidine (i)

5-Bromo-2-iodo-pyrimidine (2.15 g, 7.55 mmol), 4,4,5,5-tetramethyl-2-vinyl-1,3,2-dioxaborolane (1.60 mL, 9.43 mmol) and PdCl₂(dppf). (300 mg, 0.40 mmol) were dissolved in 1,4-dioxane (15 mL). A solution of Cs₂CO₃ (4.91 g, 15.1 mmol) in H₂O (5 mL) was added and the mixture heated at 80° C. for 30 min. The reaction mixture was diluted with EtOAc (100 mL), washed with H₂O, brine and separated. The organic fraction was dried and concentrated in vacuo. Purification by chromatography on silica, eluting with 5-25% EtOAc/heptane gave i (1.10 g, 79%). MS 185.11 & 187.09 [M+H]⁺.

5-bromo-2-(oxiran-2-yl)pyrimidine (ii)

Acetic acid (680 μL, 11.9 mmol) and i (1.1 g, 5.95 mmol) were dissolved in 1,4-dioxane (30 mL) and H₂O (80 mL). The solution was cooled to 0° C. and NBS (1.27 g, 7.13 mmol) added portion-wise. The reaction was allowed to warm to RT, then 2M NaOH (50 mL) was added and stirring was continued for 16 h. The reaction was diluted with H₂O and extracted with EtOAc. The organic fraction was washed with brine and dried (Na₂SO₄). Purification by chromatography on silica, eluting with 10-50% EtOAc/heptane gave ii (140 mg, 12%). MS 200.92 & 202.91 [M+H]⁺.

1-(5-bromopyrimidin-2-yl)-2-morpholino-ethanol (Precursor 75)

A solution of ii (140 mg, 0.70 mmol) in morpholine (2.0 mL) was heated at 120° C. under microwave irradiation for 1 h. Concentration to dryness under a stream of N₂ afforded Precursor 75.

(Precursor 76)

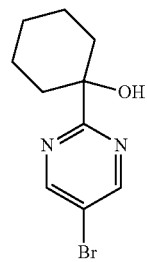

MS 257.0 & 259.0; 1:1 [M + H]⁺.
1-(5-bromopyrimidin-2-yl)cyclohexanol

Methyl 5-bromopyrimidine-2-carboxylate (250 mg; 1.15 mmol) was dissolved in anhydrous THF (10 mL) and cooled to 0° C. Pentamethylenebis(magnesium bromide) (0.5 M in THF 3.0 mL, 1.3 mmol) was introduced drop-wise and the mixture stirred for 15 min. The reaction was quenched with MeOH (0.5 mL), partitioned with EtOAc (100 mL), washed with $H_2O$ (100 mL), dried ($MgSO_4$) and concentrated in vacuo. Purification by chromatography on silica, eluting with 0-100%, EtOAc in n-heptane gave Precursor 76 (7%).

It will be understood that esters of any of the preceding Precursor(s) may be formed as illustrated by the following example(s).

(Precursor 77)

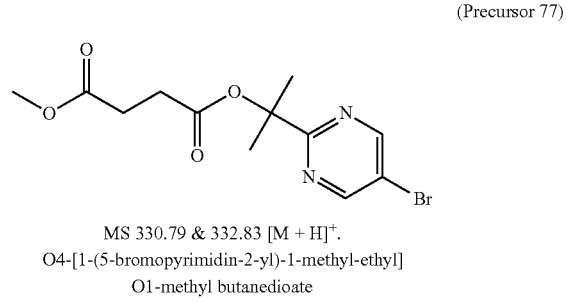 [SMILES: COC(=O)CCC(=O)OC(C)(C)c1ncc(Br)cn1]

MS 330.79 & 332.83 $[M + H]^+$.
O4-[1-(5-bromopyrimidin-2-yl)-1-methyl-ethyl]
O1-methyl butanedioate Precursor 1 (8.0 g, 36.9 mmol) was dissolved in anhydrous DMF (80 mL) under argon and cooled in an ice bath. Sodium hydride (1.62 g, 60% in mineral oil, 40.5 mmol) was added portion-wise and the reaction stirred for 10 min. Methyl 4-chloro-4-oxobutyrate (13.6 mL, 111 mmol) was added and the mixture warmed to RT. More methyl 4-chloro-4-oxobutyrate (4.50 mL, 36.9 mmol) was added after 18 h and stirring continued. Further methyl 4-chloro-4-oxobutyrate (4.50 mL, 36.9 mmol) was added after 25.5 h and stirring continued. The mixture was quenched with $H_2O$ after 45 h, then cooled in an ice bath and basified to pH 9 with $NaHCO_3$ (sat., aq.) solution. The mixture was extracted into EtOAc (4×200 mL). The combined organic phases were washed with $H_2O$ and brine, dried ($Na_2SO_4$) and concentrated to dryness in vacuo to give an oil. The mixture was purified by chromatography, Biotage SP4, 120 g Si cartridge, 0-20% EtOAc in cyclohexane to give Precursor 77, 8.02 g (66%).

(Precursor 78)

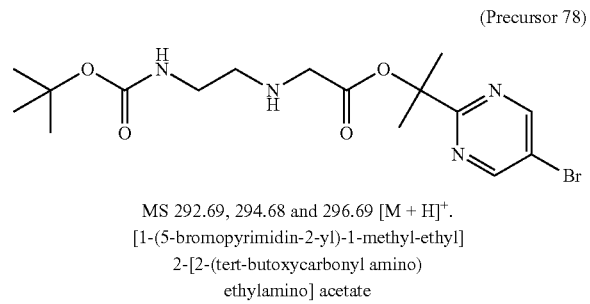 [SMILES: CC(C)(C)OC(=O)NCCNCC(=O)OC(C)(C)c1ncc(Br)cn1]

MS 292.69, 294.68 and 296.69 $[M + H]^+$.
[1-(5-bromopyrimidin-2-yl)-1-methyl-ethyl]
2-[2-(tert-butoxycarbonyl amino)
ethylamino] acetate

[1-(5-bromopyrimidin-2-yl)-1-methyl-ethyl]2-chloroacetate (i)

Precursor 1 (1.03 g, 4.75 mmol) was dissolved in anhydrous DMF (15 mL) under argon. Sodium hydride (209 mg, 60% in mineral oil, 5.22 mmol) was added and the mixture stirred for 15 min. Chloroacetyl chloride (1.13 mL, 14.2 mmol) was added and the mixture stirred at RT. After 18 h, chloroacetyl chloride (1.13 mL, 14.2 mmol) was added and stirring continued. The mixture was quenched with $H_2O$ after 42 h and extracted into EtOAc (4×50 mL). The combined organic phases were washed with $H_2O$ and brine, dried ($Na_2SO_4$) and concentrated to dryness in vacuo. Purification by chromatography on silica, eluting with 0-20% EtOAc in n-heptane gave i (930 mg, 67%).

[1-(5-bromopyrimidin-2-yl)-1-methyl-ethyl]2-[2-(tert-butoxycarbonylamino)ethylamino]acetate (Precursor 78)

DMAP (4 mg, 0.03 mmol) and i (97 mg, 0.33 mmol) were dissolved in anhydrous THF (5 mL) under argon and DIPEA (0.09 mL, 0.50 mmol) and N-Boc-ethylenediamine (0.06 mL, 0.40 mmol) added. The mixture was stirred at RT for 1 h then warmed to 50° C. for 17 h. More DIPEA (0.09 mL, 0.50 mmol), DMAP (4 mg, 0.03 mmol) and N-Boc-ethylenediamine (0.06 mL, 0.40 mmol) were added and the temperature raised to 60° C. After 30 h, the mixture was cooled to RT, quenched with $H_2O$ and extracted into EtOAc (4×10 mL). The combined organic phase was washed with brine, dried ($Na_2SO_4$) and concentrated to dryness in vacuo to give Precursor 78 (191 mg). MS 416.97 and 418.95 $[M+H]^+$.

(Precursor 79)

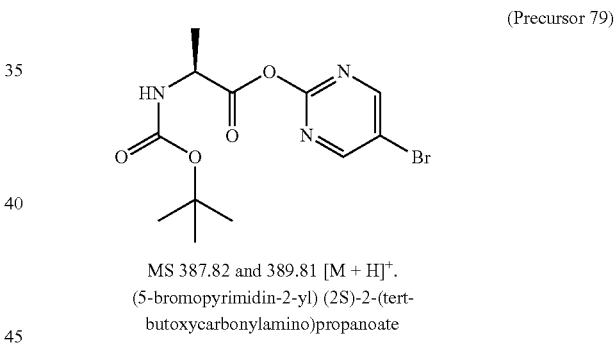

MS 387.82 and 389.81 $[M + H]^+$.
(5-bromopyrimidin-2-yl) (2S)-2-(tert-butoxycarbonylamino)propanoate (2S)-2-(tert-Butoxycarbonylamino)propanoic acid (95 mg, 0.50 mmol), Precursor 1 (109 mg, 0.50 mmol) and DMAP (61 mg, 0.50 mmol) were dissolved in THF (2 mL). DCC (104 mg, 0.50 mmol) was added last and the reaction was stirred at RT under argon for 16 h. Additional (2S)-2-(tert-butoxycarbonylamino)propanoic acid (95 mg, 0.50 mmol), DMAP (61 mg, 0.50 mmol) and DCC (104 mg, 0.50 mmol) were added and the reaction stirred at RT for 16 h. The reaction was filtered and washed with THF and the filtrate concentrated in vacuo. Purification by chromatography on silica, eluting with 10-50% EtOAc/heptane, followed by purification by chromatography on silica, eluting with 0-10% MeOH/DCM gave Precursor 79 (148 mg, 76%). It will be understood that boronic acid and esters thereof e.g. boronates such as 4,4,5,5-tetramethyl-1,3,2-dioxaborolan-2-yl and 5,5-dimethyl-1,3,2-dioxaborinan-2-yl, of any of the preceding Precursor(s) may be formed as illustrated by the following example(s).

(Precursor 80)

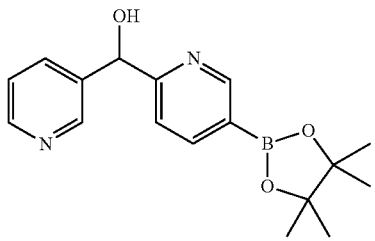

MS 313.18 [M + H]+.
3-pyridyl-[5-(4,4,5,5-tetramethyl-1,3,2-dioxaborolan-2-yl)-2-pyridyl]methanol 5-Bromopyridin-2-yl)(pyridin-3-yl)methanone (i A solution of 3-bromopyridine (2.50 g, 15.82 mmol) in THF (25.0 mL) was cooled to −78° C. followed by drop wise addition of n-BuLi (1.60 M in hexane, 11.90 mL, 18.98 mmol). The mixture was stirred at −78° C. for 30 min followed by addition of methyl 5-bromopicolinate (4.10 g, 18.98 mmol) dissolved in minimum amount of THF at −78° C. The temperature of the reaction was slowly raised up to RT and then stirred overnight. The reaction was then cooled to 0° C. and saturated NH4Cl solution (50 mL) added followed by extraction with EtOAc (3×100 mL). The combined organics were washed with brine, dried (Na2SO4), filtered and concentrated in vacuo. The residue was purified over silica eluting with 25% EtOAc-hexanes to obtain i (2.50 g, 60%). MS 263.09 [M+H]+.

5-Bromopyridin-2-yl)(pyridin-3-yl)methanol (ii

To an ice-cold solution of i (2.50 g, 9.50 mmol) in MeOH (25.0 mL) was added sodium borohydride (1.05 g, 28.50 mmol) portion wise. The resulting mixture was stirred at RT for 30 min, then H2O (50 mL) was added followed by extraction with EtOAc (3×100 mL). The combined organic layers were dried (Na2SO4), filtered and evaporated in vacuo to obtain ii (1.75 g, 70%). MS 265.11 (M+H)+.

3-pyridyl-[5-(4,4,5,5-tetramethyl-1,3,2-dioxaborolan-2-yl)-2-pyridyl]methanol (Precursor 80)

To the solution of ii (0.50 g, 1.89 mmol) in 1,4-dioxane (10 mL) was added bis(pinacolato)diboron (0.53 g, 2.08 mmol) and KOAc (0.28 g, 2.84 mmol). The reaction was degassed by purging N2 for 15 min followed by addition of Pd2(dba)3 (O) (0.10 g, 0.10 mmol) and tricyclohexylphosphine (0.06 g, 0.23 mmol). The reaction was degassed for 10 min and heated up to 80° C. for 2 h. The resulting mixture was cooled to RT and filtered through a celite bed. The filtrate was concentrated in vacuo to obtain Precursor 80 (0.41 g, 70%).

(Precursor 81)

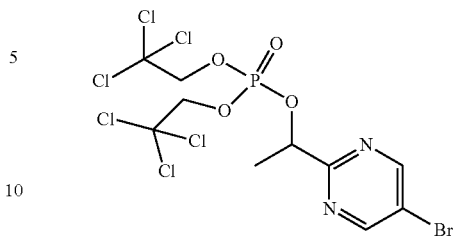

MS: 546.74 [M + H]+.
1-(5-bromopyrimidin-2-yl)ethyl bis(2,2,2-trichloroethyl) phosphate N,N-dimethylpyridin-4-amine (120 mg) was added to a solution of bis(2,2,2-trichloroethyl)phosphorochloridate (450 mg) and Precursor 4 (200 mg) in THF (10 mL) and the mixture heated at 70° C. for 1 h. The mixture was cooled to RT and filtered. The filtrate was concentrated in vacuo and purified by chromatography on silica, eluting with 40% EtOAc/n-heptane-80%% EtOAc/n-heptane to give Precursor 81 (300 mg, 56%).

It will be understood that any of the preceding Precursor(s) having a chiral alcohol may be synthesised from an enantiomeric resolving agent and/or separated into their respective enantiomers by suitable chiral separation methods known to those in the art such as chiral HPLC as illustrated by the following example(s).

1S)-1-(5-bromopyrimidin-2-yl)ethanol (Precursor 82) and (1R)-1-(5-bromopyrimidin-2-yl)ethanol (Precursor 83

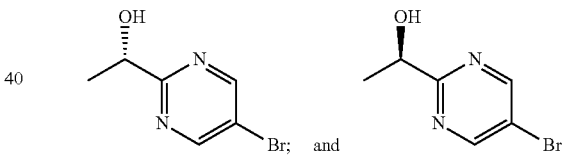

1H NMR (400 MHz, CDCl3): δ 8.78 (s, 2H); 4.92 (dq, J=5.6, 6.8 Hz, 1H); 3.80 (1H, d, J=5.6 Hz); 1.55 (t, J=6.8 Hz, 3H).

1-(5-bromopyrimidin-2-yl)ethyl(2R)-2-(tert-butoxycarbonylamino)-3-methyl-butanoate (i)

A mixture of Precursor 4 (27.8 g, 137 mmol), Boc-D-valine (32.7 g, 151 mmol) and DMAP (10.0 g, 82.2 mmol) was dissolved in THF (200 mL). The mixture was cooled in an ice bath. A solution of DCC (31.1 g, 151 mmol) in THF (50 mL) was added. After 10 min, the cooling bath was removed. The mixture was stirred overnight, filtered, the DCU precipitate was washed with several portions of EtOAc, and the combined filtrates were concentrated. The residue was then eluted through a plug of silica (20% EtOAc/heptane) to give i (64.7 g).

[(1S)-1-(5-bromopyrimidin-2-yl)ethyl](2R)-2-(tert-butoxycarbonylamino)-3-methyl-butanoate (ii)

i (64.7 g) was crystallised from hot heptane. The solids obtained were collected by filtration and recrystallised from hot heptane, yielding ii (15.4 g).

1S)-1-(5-bromopyrimidin-2-yl)ethanol (Precursor 82

Amberlite® basic ion exchange resin and ii (15.4 g, 38.3 mmol) were stirred in MeOH (50 mL) overnight at RT. The suspension was filtered through a pad of silica using 1:1 MeOH/DCM and the filtrate concentrated in vacuo. Crystallisation from hot heptane gave Precursor 82 (5.85 g). (1S)-1-(5-bromopyrimidin-2-yl)ethanol (Precursor 83) was similarly prepared using Boc-L-valine. Mitsunobu inversion of one enantiomer to the desired enantiomer may also be employed.

Chiral HPLC was used to demonstrate the chiral purity of the enantiomers (Column: Chirapak IC, 0.46 cm×25 cm; 20 min isocratic gradent; 5:95 EtOH:n-hexane+0.1% diethylamine) retention time=14.65 min/17.53 min.

Alternatively, Precursor 82 (S-enantiomer) may be synthesized as follows.

(47 g) was added and the mixture stirred for 1 hour. The solvent was removed and the residue dissolved in methanol (100 mL) and ammonia (7M in methanol) (150 mL) added over ~10 mins cooling the reaction mixture in a cold water bath. Once the addition was complete the reaction was allowed to warm to room temperature. The resulting suspension was concentrated to a thick mixture, diluted with ethyl acetate and filtered through celite. The filtrate was cooled to ~10° C. and HCl (4M in dioxane) (100 mL) added dropwise. After stirring for 90 mins, the mixture was filtered to collect the white precipitate (washing with ethyl acetate and then dried in a vacuum oven at 40° C. to give (2S)-2-hydroxypropanamidine hydrochloride hydrochloride salt as a white solid (12 g, 43%). $^1$H NMR (CDCl$_3$) δ 8.8 (m, 4H), 6.26 (s, 1H), 4.43 (q, J=6.7 Hz, 1H), 1.35 (d, J=6.7 Hz, 3H).

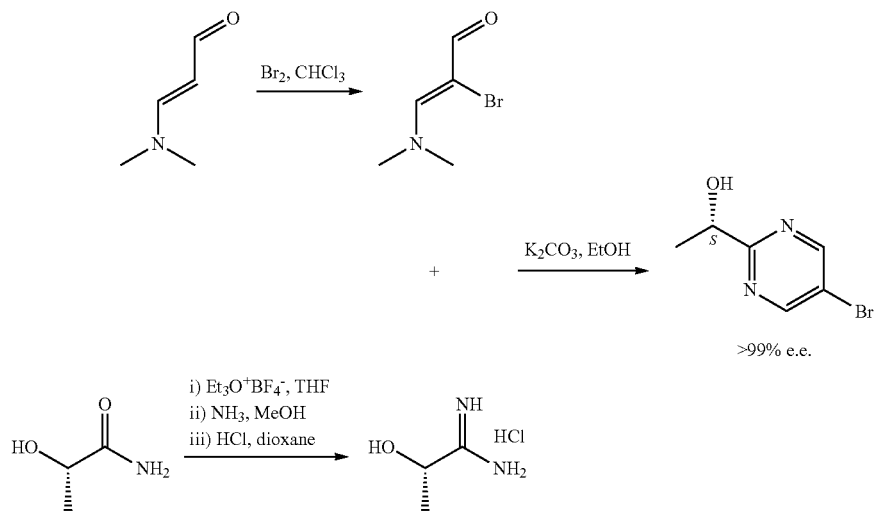

(Z)-2-bromo-3-(dimethylamino)prop-2-enal (1S)-1-(5-bromopyrimidin-2-yl)ethanol (3-(Dimethylamino)acrolein (25 g) was dissolved in chloroform (250 mL), and the mixture cooled in an ice/water bath. bromine (40 g; 13 mL) was added dropwise and once the addition was complete, the reaction was allowed to warm to room temperature and stirred for 1 hour. The reaction was diluted with DCM (150 mL) and quenched by the addition of aq. sat Na$_2$SO$_5$ solution (50 mL) and aq. sat. NaHCO$_3$ solution (250 mL). The organic layer was collected and dried (MgSO$_4$) and the solvent removed in vacuo. Once the material had solidified, it was suspended in ethyl acetate:heptane (1:1-100 mL) and the resulting solid material collected by filtration. Washing with ethyl acetate:heptane and air drying gave (Z)-2-bromo-3-(dimethylamino)prop-2-enal as a fawn coloured solid (25 g, 75%). $^1$H NMR (CDCl$_3$) δ 8.85 (s, 1H), 7.2 (s, 1H), 3.36 (s, 6H).

(2S)-2-hydroxypropanamidine hydrochloride hydrochloride salt (2S)-2-hydroxypropanamide (20 g) was placed in a flask with THF (100 mL) and triethyloxonium tetrafluoroborate (Z)-2-bromo-3-(dimethylamino)prop-2-enal (11.5 g), potassium carbonate (13.4 g), ethanol (200 mL) and 2-hydroxy-2-methyl-propanamidine hydrochloride (12.1 g) were placed in a flask and the mixture heated at 85° C. overnight. The reaction mixture was cooled and the mixture filtered, washed with ethanol and the combined filtrates concentrated in vacuo with silica gel. This residue was purified by chromatography on silica, eluting with 0-50% ethyl acetate in heptane to give (1S)-1-(5-bromopyrimidin-2-yl)ethanol as a white solid (2.1 g, 16%). $^1$H NMR (CDCl$_3$) δ 8.83 (s, 2H), 4.98 (m, 1H), 3.8 (m, 1H), 1.6 (d, J=6.6 Hz, 3H). Chiral HPLC: Column. Chirapak IC, 0.46 cm×25 cm; 20 min isocratic gradent; 5:95 EtOH:n-hexane+0.1% diethylamine) retention time=14.08 min. (racemic mixture: ~14.5 min: S isomer; ~17.5 min: R isomer).

Precursor 83 (R-enantiomer) may be formed using R-lactamide.

Once formed, Precursor 82 or Precursor 83 may be coupled to an Intermediate core then optionally subjected to Mitsunobu inversion conditions to obtain the other enantiomeric form, if desired.

Example(s) of General Method A

1-Ethyl-3-(5-(2-(2-hydroxypropan-2-yl)pyrimidin-5-yl)-7-(pyridin-2-yl)benzo[d]thiazol-2-yl)urea (1)

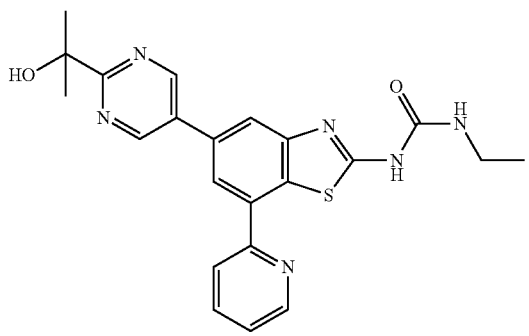 [SMILES: CCNC(=O)Nc1nc2cc(-c3cnc(C(C)(C)O)nc3)cc(-c3ccccn3)c2s1]

$^1$H NMR (400 MHz, CDCl$_3$) δ 9.05 (s, 2H), 8.77 (d, J=4.1 Hz, 1H), 8.03 (d, J=8.1 Hz, 1H), 7.93 (t, J=8.7 Hz, 1H), 7.91-7.77 (m, 2H), 7.35-7.29 (m, 1H), 3.44-3.31 (m, 3H), 1.66 (s, 6H), 1.32-1.15 (m, 4H). MS: 435.1 [M+H]$^+$.

Precursor 1 (50 mg) was placed in a flask with Intermediate 1 (100 mg), Cs$_2$CO$_3$ (67 mg), Pd(dppf)Cl$_2$ (16 mg), DMF (3 mL) and H$_2$O (0.5 mL) and the mixture heated at 85° C. for 16 h. The mixture was cooled to RT and partitioned between H$_2$O (50 mL) and EtOAc (50 mL). The organic layer was collected and the aqueous layer extracted with EtOAc (2×50 mL). The combined organic layers were dried (MgSO$_4$) and the solvent removed in vacuo. Purification by chromatography on silica, eluting with a gradient of 0-10% MeOH in DCM gave Compound 1 (12 mg).

The following compound(s) were similarly prepared noting that alternative catalysts, bases, solvents and reaction times may be employed and the urea may require protection as a 5-methyl-1,3,5-triazinan-2-one.

1-Ethyl-3-(7-(4-((3-hydroxy-3-methylazetidin-1-yl)methyl)pyridin-2-yl)-5-(2-(2-hydroxypropan-2-yl)pyrimidin-5-yl)benzo[d]thiazol-2-yl)urea (2)

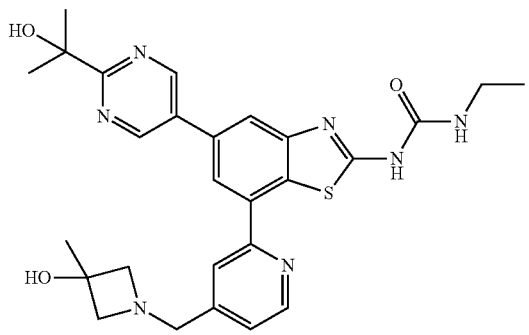 [SMILES: CCNC(=O)Nc1nc2cc(-c3cnc(C(C)(C)O)nc3)cc(-c3cc(CN4CC(C)(O)C4)ccn3)c2s1]

$^1$H NMR (DMSO-d$_6$): δ 10.61 (br s, 1H), 9.33 (s, 2H), 8.72 (d, J=5.20 Hz, 1H), 8.34 (m, 2H), 8.12 (s, 1H), 7.36 (m, 1H), 6.84 (m, 1H), 5.21 (s, 1H), 5.15 (s, 1H), 3.74 (s, 2H), 3.17-3.26 (m, 4H), 2.97-2.99 (m, 2H), 1.57 (s, 6H), 1.38 (s, 3H) and 1.09 (t, J=7.20 Hz, 3H). MS: 534.32 [M+H]$^+$.

1-(7-(5,5-dimethyl-1,3,2-dioxaborinan-2-yl)-5-(2-(2-hydroxypropan-2-yl)pyrimidin-5-yl)benzo[d]thiazol-2-yl)-3-ethyl-5-methyl-1,3,5-triazinan-2-one (i)

To a solution of Intermediate 4 (0.25 g, 0.51 mmol) in toluene (10 mL) was added bis(neopentylglycolato)diboron (0.23 g, 1.01 mmol) and potassium acetate (0.15 g, 1.53 mmol). The reaction mass was degassed by purging N$_2$ for 15 min followed by addition of Pd(dppf)Cl$_2$ (0.041 g, 0.091 mmol). The mixture was degassed for 10-15 min and then heated at 130° C. for 30 min. The mixture was cooled to RT and filtered through celite. The filtrate was concentrated in vacuo to obtain i (0.21 g, 80% crude).

MS: 455.20 [M−H]$^+$, (MS of corresponding boronic acid observed).

1-Ethyl-3-(7-(4-((3-hydroxy-3-methylazetidin-1-yl)methyl)pyridin-2-yl)-5-(2-(2-hydroxypropan-2-yl)pyrimidin-5-yl)benzo[d]thiazol-2-yl)-5-methyl-1,3,5-triazinan-2-one (ii)

To a solution of i (0.427 g, 0.81 mmol) in 1,4-dioxane-H$_2$O (9:1, 10 mL) was added Precursor 29 (0.231 g, 0.90 mmol) and Cs$_2$CO$_3$ (0.791 g, 2.43 mmol). The reaction mixture was degassed by purging N$_2$ for 15 min followed by addition of Pd(dppf)Cl$_2$ (0.066 g, 0.08 mmol). The mixture was heated in a microwave at 110° C. for 30 min. The mixture was diluted with H$_2$O and extracted with EtOAc (2×50 mL). The combined organics were washed with brine, dried (Na$_2$SO$_4$) and concentrated in vacuo. The residue was purified over silica eluting with 7% MeOH:DCM to obtain ii (0.303 g, 63%).
$^1$H-NMR (400 MHz, DMSO-d6): δ 9.34 (s, 2H), 8.75 (d, J=4.40 Hz, 1H), 8.38 (m, 2H), 8.20 (s, 1H), 7.37 (m, 1H), 5.23 (br s, 1H), 5.15 (s, 3H), 4.38 (s, 2H), 3.75 (br s, 2H), 3.38 (m, 2H), 3.26 (m, 2H), 2.94 (m, 2H), 2.55 (s, 3H), 1.57 (s, 6H), 1.38 (s, 3H), and 1.12 (t, J=7.20 Hz, 3H). MS: 589.31 [M+H]$^+$.

1-ethyl-3-(7-(4-((3-hydroxy-3-methylazetidin-1-yl)methyl)pyridin-2-yl)-5-(2-(2-hydroxypropan-2-yl)pyrimidin-5-yl)benzo[d]thiazol-2-yl)urea (2)

An ice-cold solution of ii (0.25 g, 0.42 mmol) in MeOH-DCM (0.50 and 10 mL respectively) was purged with HCl (g) for 10 min and the mixture stirred at RT for 16 h. The solvent was evaporated and the residue triturated with a mixture of MeOH and Et$_2$O to obtain Compound 2 (0.225 g, 90%).

1-Ethyl-3-[5-[2-(1-hydroxy-1-methyl-ethyl)pyrimidin-5-yl]-6-(tetrahydrofuran-2-ylmethoxy)-1,3-benzothiazol-2-yl]urea (3)

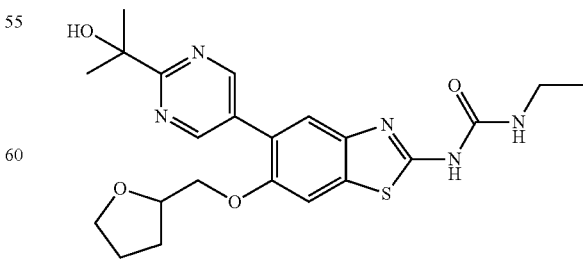

$^1$HNMR (DMSO-d$_6$, 400 MHz): δ 10.63 (br s, 1H), 9.00 (s, 2H), 7.72 (m, 2H), 6.68 (m, 1H), 5.12 (s, 1H), 4.21 (m, 1H), 4.06 (m, 2H), 3.68 (m, 2H), 3.18 (m, 2H), 1.94 (m, 1H), 1.71 (m, 2H), 1.65 (m, 1H), 1.61 (s, 6H) and 1.22 (t, J=6.8 Hz, 3H). LCMS: 458.20 [M+H]+.

2-((2-Bromo-4-nitrophenoxy)methyl)tetrahydrofuran (i)

To an ice cold solution of 2-bromo-1-fluoro-4-nitro-benzene (5.0 g, 22.72 mmol) in DMSO (40 mL) was added NaOH (1.36 g, 34.09 mmol) and (tetrahydrofuran-2-yl)methanol (3.47 g, 34.09 mmol) at 0° C. The mixture was stirred at RT for 1 h, then poured into H$_2$O (50 mL), the pH adjusted ~7 with 1M HCl and extracted with EtOAc (2×250 mL). The combined organics were washed with H$_2$O, brine, dried (Na$_2$SO$_4$), filtered and concentrated in vacuo to obtain i (6.50 g, 95%). $^1$HNMR (CDCl$_3$, 400 MHz): δ 8.46 (d, J=2.40 Hz, 1H), 8.20 (dd, J=2.40 and 9.20 Hz respectively, 1H), 6.98 (d, J=9.20 Hz, 1H), 4.36 (m, 1H), 4.16 (m, 2H) 3.97 (m, 1H) 3.86 (m, 1H) 2.07 (m 2H) and 1.95 (m, 2H).

3-Bromo-4-((tetrahydrofuran-2-yl)methoxy)aniline (ii)

To the solution of i (5.5 g, 18.2 mmol) in THF (30 mL) was added stannous chloride dihydrate (12.3 g, 54.6 mmol) at RT. The mixture was stirred at 60° C. for 5 h. The mixture was poured into saturated sodium bicarbonate solution (100 mL) and extracted with EtOAc (2×500 mL). The combined organics were washed with H$_2$O, brine, dried (Na$_2$SO$_4$) and concentrated in vacuo. The crude residue was purified over silica (50% EtOAc:Hexanes) to obtain ii (4.0 g, 82%). MS: 272.0 [M+H]+.

5-bromo-6-((tetrahydrofuran-2-yl)methoxy)benzo[d]thiazol-2-amine (iii)

To a solution of ii (3.0 g, 11.62 mmol) in acetic acid (50 mL) was added ammonium thiocynate (4.18 g, 55.11 mmol) at RT. The resulting mixture was stirred at RT for 15 min followed by the addition of bromine (0.68 mL, 13.22 mmol) in acetic acid (5 mL). The mixture was stirred at RT for 5 h. The pH was adjusted to >7 with ammonia solution followed by extraction with EtOAc (2×200 mL). The combined organics were washed with H$_2$O, brine solution, dried (Na$_2$SO$_4$) and concentrated in vacuo. The residue was purified over silica (60% EtOAc-Hexanes) to obtain iii (1.0 g, 26%). $^1$HNMR (DMSO-d$_6$, 400 MHz): δ 7.50 (s, 1H), 7.49 (s, 1H), 7.43 (br s, 2H), 4.18 (m, 1H), 3.96 (m, 2H), 3.80 (m, 1H), 3.69 (m, 1H), 1.96 (m, 2H) and 1.78 (m, 2H). MS: 329.0 [M+H]+.

1-(5-Bromo-6-((tetrahydrofuran-2-yl)methoxy)benzo[d]thiazol-2-yl)-3-ethylurea (iv)

To a solution of iii (1.0 g, 3.03 mmol) in 1,4-dioxane (10 mL) was added ethyl isocynate (1.23 mL, 15.19 mmol) at RT. The mixture was stirred at 80° C. for 5 h. The reaction mixture was evaporated in vacuo, H$_2$O (50 mL) added to and the mixture stirred at 70° C. for 4 h. The residue was filtered and dried under vacuum to obtain iv (1.0 g, 83%). $^1$HNMR (DMSO-d$_6$, 400 MHz): δ 10.69 (br s, 1H), 7.80 (s, 1H), 7.68 (s, 1H), 6.65 (m, 1H), 4.21 (m, 1H), 4.04 (m, 2H), 3.83 (m, 1H), 3.70 (m, 1H), 3.16 (m, 2H), 2.0 (m, 2H), 1.82 (m, 2H) and 1.09 (t, J=7.20 Hz, 3H). MS: 400 [M+H]+.

1-Ethyl-3-(5-(2-(2-hydroxypropan-2-yl)pyrimidin-5-yl)-6-((tetrahydrofuran-2-yl)methoxy)benzo[d]thiazol-2-yl)urea (3)

To a solution of iv (0.303 g, 0.75 mmol) and the 4,4,5,5-tetramethyl-1,3,2-dioxaborolon-2-yl) ester of Precursor 1 (0.20 g, 0.75 mmol) in 1,4-dioxane:MeOH (5:3, 8.0 mL) was added potassium phosphate (0.24 g, 1.13 mmol) at RT. The mixture was degassed for 15-20 min by purging N$_2$ followed by the addition of Pd(dppf)Cl$_2$ (0.062 g, 0.075 mmol). The mixture was degassed for 15-20 min and heated at 80° C. for 5 h. The reaction mixture was cooled to RT, diluted with EtOAc (500 ml) and filtered through celite. The filtrate was evaporated in vacuo and the crude residue was purified over silica (5% MeOH-DCM) to obtain Compound 3 (0.15 g, 43%).

1-Ethyl-3-[5-[2-(1-hydroxy-1-methyl-ethyl)pyrimidin-5-yl]-6-(2-methoxyethylamino)-1,3-benzothiazol-2-yl]urea (150)

Compound 150 was similarly prepared to Compound 3, starting from 1-[5-bromo-6-(2-methoxyethylamino)-1,3-benzothiazol-2-yl]-3-ethyl-urea and 2-methoxyethanamine

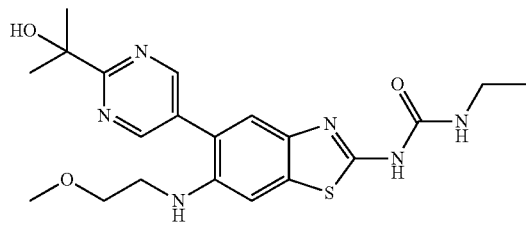 [SMILES: CCNC(=O)Nc1nc2cc(-c3cnc(C(C)(C)O)nc3)c(NCCOC)cc2s1]

$^1$H NMR (400 MHz, DMSO-d$_6$): δ 10.46 (br s, 1H), 8.85 (s, 2H), 7.34 (s, 1H), 7.23 (s, 1H), 6.65 (m, 1H), 5.13 (br s, 1H), 4.87 (m, 1H), 3.48 (m, 2H), 3.17-3.24 (m, 7H), 1.55 (s, 6H), and 1.08 (m, 3H). MS 431.16 [M+H]+

1-Ethyl-3-(6-fluoro-5-(6-(hydroxy(pyridin-3-yl)methyl)pyridin-3-yl)benzo[d]thiazol-2-yl)urea (4)

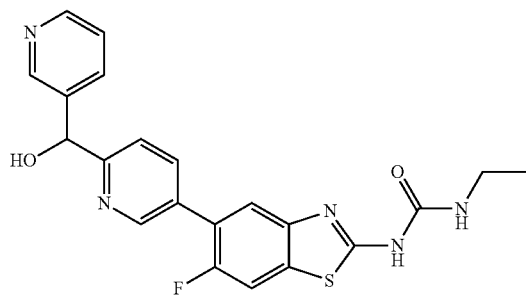 [SMILES: CCNC(=O)Nc1nc2cc(-c3ccc(C(O)c4cccnc4)nc3)c(F)cc2s1]

$^1$H NMR (400 MHz; DMSO-d$_6$): δ 8.67 (m, 2H), 8.45 (d, J=3.60 Hz, 1H), 8.05 (m, 1H), 7.95 (m, 1H), 7.73-7.81 (m, 3H), 7.35 (m, 1H), 6.74 (m, 1H), 6.36 (d, J=4.0 Hz, 1H), 5.85 (d, J=4.0 Hz, 1H), 3.38 (m, 1H), 3.21 (m, 2H) and 1.08 (t, J=7.20 Hz, 3H). MS: 424.31 [M+H]+

To a solution of Precursor 80 (0.2 g, 0.6 mmol) in 1,4-dioxane (5 mL) and MeOH (3 mL) was added Intermediate 13 (0.2 g, 0.6 mmol) and potassium phosphate (0.2 g, 0.96 mmol). The reaction mass was degassed by purging N$_2$ for 15 min followed by addition of Pd(dppf)Cl$_2$ (0.05 g, 0.06 mmol). The mixture was degassed for 10 min and heated at 80° C. for 4 h. The solvent was evaporated, H$_2$O (50 mL) added and the mixture extracted with EtOAc (4×50 mL). The combined organics were washed with brine, dried (Na$_2$SO$_4$) and concentrated in vacuo. The residue was purified over silica eluting with 2.50% MeOH in DCM to obtain Compound 4 (0.02 g, 10%).

1-(2-Hydroxyethyl)-3-(5-(2-(2-hydroxypropan-2-yl)pyrimidin-5-yl)-7-(pyridin-2-yl)benzo[d]thiazol-2-yl)urea (5)

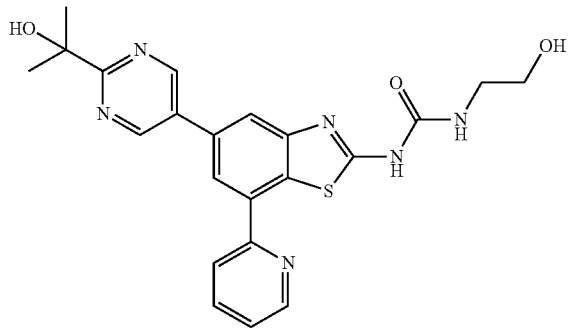 [SMILES: CC(C)(O)c1ncc(-c2cc(-c3ccccn3)c3sc(NC(=O)NCCO)nc3c2)cn1]

$^1$H NMR (400 MHz; CD$_3$OD) δ=9.14 (s, 2H), 8.70 (d, J=4.3 Hz, 1H), 8.20 (d, J=8.0 Hz, 1H), 8.10 (s, 1H), 7.97-7.82 (m, 2H), 7.42-7.25 (m, 1H), 3.75 (t, J=5.5 Hz, 2H), 3.46 (t, J=5.5 Hz, 2H), 1.69 (s, 6H). MS: 451.08 [M+H]$^+$

[2-amino-7-(2-pyridyl)-1,3-benzothiazol-5-yl]trifluoromethanesulfonate (i)

[2-(ethylcarbamoylamino)-7-(2-pyridyl)-1,3-benzothiazol-5-yl]trifluoromethanesulfonate (1.34 g, 3.0 mmol) was dissolved in DMSO (10 mL) and stirred at 160° C. for 16 h. The mixture was diluted with EtOAc, washed with H$_2$O, brine. The organic fraction was concentrated in vacuo to afford i (1.01 g, 90%). MS: 375.96 [M+H]$^+$.

[2-(2-hydroxyethylcarbamoylamino)-7-(2-pyridyl)-1,3-benzothiazol-5-yl]trifluoromethanesulfonate (ii)

Compound i (445 mg, 1.18 mmol) was dissolved in DMF (7 mL) and solution of CDI (577 mg, 3.56 mmol) in DMF (3 mL) was added drop-wise at 0° C. with stirring under argon. The mixture was warmed to RT and stirred for 16 h. A solution of ethanolamine (710 μL, 11.85 mmol) in DMF (2 mL) was then added and the mixture stirred at RT for 4 h. The mixture was diluted with EtOAc, washed with H$_2$O, brine. The organic fraction was dried (Na$_2$SO$_4$) and concentrated in vacuo. The residue was washed with MeOH and Et$_2$O to afford ii (253 mg, 46%). MS: 463.00 [M+H]$^+$.

2-[5-(4,4,5,5-tetramethyl-1,3,2-dioxaborolan-2-yl)pyrimidin-2-yl]propan-2-ol (iii)

Precursor 1 (140 mg, 0.645 mmol), bispinacolatodiboron (197 mg, 0.774 mmol) and potassium acetate (95 mg, 0.967 mmol) were suspended in anhydrous 1,4-dioxane (5 mL). Tricyclohexylphosphine (23 mg, 0.081 mmol) and Pd$_2$(dba)$_3$ (30 mg, 0.032 mmol) were added and the mixture degassed/purged with argon (×3). The reaction mixture was stirred at 100° C. under microwave irradiation for 1 h. The reaction was cooled to RT, filtered and washed with 1,4-dioxane (5 mL) to give iii. MS: 182.96 [M+H]$^+$ (boronic acid).

1-(2-hydroxyethyl)-3-(5-(2-(2-hydroxypropan-2-yl)pyrimidin-5-yl)-7-(pyridin-2-yl)benzo[d]thiazol-2-yl)urea (5)

To a solution of iii (165 mg, 0.626 mmol) in 1,4-dioxane (12 mL) was added ii (193 mg, 0.417 mmol) and PdCl$_2$(dppf) (34 mg, 0.042 mmol). A solution of Cs$_2$CO$_3$ (410 mg, 1.30 mmol) in H$_2$O (3 mL) was added, the reaction vessel sealed, then evacuated/purged with argon (×3). The mixture was then heated under microwave irradiation at 100° C. for 30 min. LCMS analysis indicated complete conversion. The mixture was diluted with EtOAc (100 mL), washed with H$_2$O, brine, then separated and dried (Na$_2$SO$_4$). The organic fraction was concentrated in vacuo. Purification by chromatography on silica, eluting with 0-10% MeOH/EtOAc followed by additional chromatography on silica, eluting with 0-10% MeOH/DCM afforded Compound 5 (9 mg, 5%).

Example(s) of General Method B

1-Ethyl-3-[5-[5-(1-hydroxyethyl)pyrazin-2-yl]-7-(2-pyridyl)-1,3-benzothiazol-2-yl]urea (6)

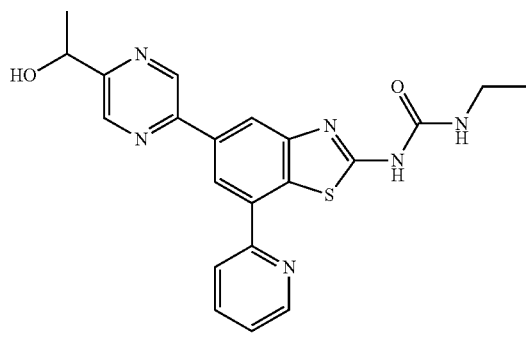 [SMILES: CCNC(=O)Nc1nc2cc(-c3cnc(C(C)O)cn3)cc(-c3ccccn3)c2s1]

$^1$H NMR (400 MHz; d$_6$-DMSO): δ==10.70 (bs, 1H), 9.43 (d, J=1.5 Hz, 1H), 8.96-8.78 (m, 2H), 8.71 (d, J=1.5 Hz, 1H), 8.47 (t, J=5.3 Hz, 2H), 8.14-7.94 (m, 1H), 7.49 (ddd, J=7.5, 4.9, 0.9 Hz, 1H), 6.88 (bt, J=5.4 Hz, 1H), 5.65 (d, J=4.7 Hz, 1H), 5.00-4.84 (m, 1H), 3.29-3.15 (m, 2H), 1.50 (d, J=6.6 Hz, 3H), 1.14 (t, J=7.2 Hz, 3H). MS: 421.08 [M+H]$^+$.

1-[5-(5-acetylpyrazin-2-yl)-7-(2-pyridyl)-1,3-benzothiazol-2-yl]-3-ethyl-urea (i)

Intermediate 1 (171 mg, 0.5 mmol), 1-(5-chloropyrazin-2-yl)ethanone (94 mg, 0.60 mmol) and PdCl$_2$(dppf) (41 mg, 0.05 mmol) were suspended in 1,4-dioxane (8 mL). A solution of Cs$_2$CO$_3$ (488 mg, 1.50 mmol) in H$_2$O (2 mL) was added. The mixture was then heated under microwave irradiation at 100° C. for 30 min. The mixture was filtered, washed with H$_2$O, EtOH, MeOH and Et$_2$O to afford i (172 mg, 82%). MS: 419.06 [M+H]$^+$.

1-ethyl-3-(5-(5-(1-hydroxyethyl)pyrazin-2-yl)-7-(pyridin-2-yl)benzo[d]thiazol-2-yl)urea (6)

To a suspension of i (63 mg, 0.15 mmol) in THF (5 mL) was added a solution of NaBH$_4$ (29 mg, 0.75 mmol) in H$_2$O (1 mL) and the mixture stirred at RT for 30 min. The reaction was diluted with EtOAc (50 mL) and washed with H$_2$O and brine. The organic fraction was dried (Na$_2$SO$_4$) and concentrated in vacuo to afford Compound 6 (62 mg, 98%).

Example(s) of General Method C

1-[5-[2-[(1S*,2R*)-1,2-dihydroxypropyl]pyrimidin-5-yl]-7-(2-pyridyl)-1,3-benzothiazol-2-yl]-3-ethyl-urea (7)

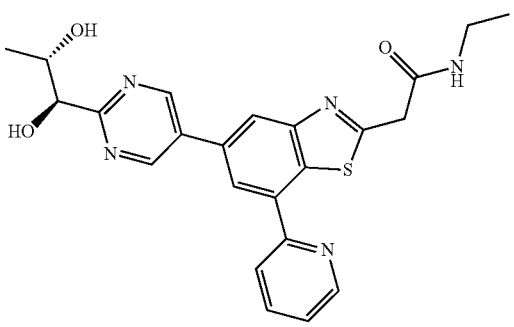 [SMILES: CCNC(=O)Cc1nc2cc(-c3cnc([C@@H](O)[C@H](C)O)nc3)cc(-c3ccccn3)c2s1]

$^1$H NMR (400 MHz, CDCl$_3$) δ 9.14 (s, 2H), 8.70 (s, 1H), 8.14-7.90 (m, 2H), 7.82 (t, J=7.3 Hz, 1H), 7.75 (s, 1H), 7.30 (d, J=10.5 Hz, 1H), 4.55 (s, 1H), 4.14 (d, J=7.2 Hz, 1H), 3.23 (s, 2H), 1.42 (d, J=3.9 Hz, 3H), 1.26 (t, J=7.1 Hz, 3H). MS: 451.1 [M+H]$^+$.

5-bromopyrimidin-2-yl)methanol (i

An solution of NaBH$_4$ (510 mg, 2.70 mmol) in H$_2$O (10 mL) was introduced drop-wise to a solution of methyl 5-bromopyrimidine-2-carboxylate (3.05 g, 14.1 mmol) in THF (100 mL) at 0° C. The mixture was allowed to warm slowly to RT overnight. The majority of the THF was evaporated, and the resulting residue was diluted with EtOAc (200 mL). The organic fraction was washed with brine (200 mL), dried (MgSO$_4$) and purified over silica, eluting with 0-60% EtOAc: n-heptane) to afford i (510 mg, 19%). MS: 189.0 & 191.0; 1:1 [M+H]$^+$.

5-bromo-2-(bromomethyl)pyrimidine (ii)

Methanesulfonyl chloride (0.31 mL, 4.0 mmol) was added to a stirred suspension of i (510 mg, 2.7 mmol) and triethylamine (820 μL, 5.9 mmol) in THF (30 mL) at 0° C. for 10 min. The solution was treated with LiBr (1.2 g, 13 mmol) in THF (25 mL) and allowed to stir, whilst warming to RT over 1 h. The majority of the reaction solvent was removed in vacuo, and the mixture diluted with EtOAc (200 mL). The organic fraction was sequentially washed with sat. aq. NH$_4$Cl (2×100 mL), brine (1×100 mL) and dried (MgSO$_4$) to afford ii (663 mg, 98%). MS: 251.0, 253.0 & 254.8; 1:2:1 [M+H]$^+$.

5-bromo-2-(diethoxyphosphorylmethyl)pyrimidine (iii)

Compound 1i (663 mg, 2.63 mmol) was dissolved in 10 mL of ACN and triethylphosphite (0.92 mL, 5.26 mmol) added. The reaction was heated in a microwave for 1 h at 100° C. The reaction was concentrated in vacuo affording iii (813 mg, 100%) MS: 308.9 & 310.9; 1:1 [M+H]$^+$.

1-[5-[2-(diethoxyphosphorylmethyl)pyrimidin-5-yl]-7-(2-pyridyl)-1,3-benzothiazol-2-yl]-3-ethyl-urea (iv)

Intermediate 1 (860 mg, 2.5 mmol), iii (813 mg, 2.63 mmol), Cs$_2$CO$_3$ (2.57 g, 7.90 mmol) and Pd(PPh$_3$)$_2$Cl$_2$ (90 mg, 0.10 mmol) were dissolved in 1-4-dioxane:H$_2$O (10:1; 10 mL) and degassed with a stream of N$_2$ for 10 min. The reaction was sealed under an atmosphere of N$_2$ and heated at 100° C. for 1 h in a microwave reactor. The mixture was concentrated in vacuo, purified over silica (gradient elution: 0-10% DCM-MeOH) and triturated from acetone affording iv (410 mg, 29%). MS: 527.1 [M+H]$^+$.

1-ethyl-3-[5-[2-[(E)-prop-1-enyl]pyrimidin-5-yl]-7-(2-pyridyl)-1,3-benzothiazol-2-yl]urea (v)

Sodium methoxide (0.5 M MeOH solution; 0.9 mL, 0.43 mmol) was added drop-wise to a suspension of iv (104 mg, 0.198 mmol) in THF (10 mL). Acetaldehyde (40 μL, 0.69 mmol) was introduced and the mixture stirred for 90 min. The reaction was diluted with EtOAc (60 mL), washed with sat. NaHCO$_3$(aq) (60 mL). The organic fraction was dried (MgSO$_4$), concentrated in vacuo, and purified over silica (gradient elution: 0-10%, DCM-MeOH) affording v (79 mg, 96%). MS: 417.1 [M+H]$^+$.

1-[5-[2-[(1S*,2R*)-1,2-dihydroxypropyl]pyrimidin-5-yl]-7-(2-pyridyl)-1,3-benzothiazol-2-yl]-3-ethyl-urea (7)

Osmium tetroxide (10 mg; 60 μmol) was added to a solution of v (230 mg, 600 μmol), N-methylmorpholine N-oxide (160 mg; 1.40 mmol) and pyridine (20 μL) in THF-Me$_2$CO (5:1; 90 mL). The reaction was quenched with sat. Na$_2$S$_2$O$_5$ (aq) (20 mL), extracted with EtOAc (150 mL), washed with brine (75 mL). dried (MgSO$_4$) and concentrated in vacuo. Purification over silica (gradient elution: 0-10%, DCM-MeOH) afforded Compound 7 (93 mg, 38%).

Example(s) of General Method D 1-(5-(2-(3,4-dihydroxytetrahydro-2H-pyran-4-yl)pyrimidin-5-yl)-7-(pyridin-2-yl)benzo[d]thiazol-2-yl)-3-ethylurea (8)

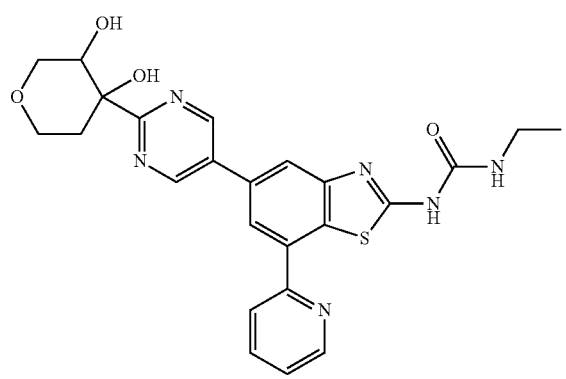 [SMILES: CCNC(=O)Nc1nc2cc(-c3cnc(C4(O)CCOCC4O)nc3)cc(-c3ccccn3)c2s1]

$^1$H NMR (400 MHz, DMSO-d$_6$) δ 10.62 (s, 1H), 9.34 (s, 2H), 8.83 (dd, J=4.8, 0.8 Hz, 1H), 8.53 (d, J=8.3 Hz, 1H), 8.40 (d, J=1.4 Hz, 1H), 8.15 (d, J=0.9 Hz, 1H), 8.02 (td, J=7.9, 1.8 Hz, 1H), 7.53-7.41 (m, 1H), 6.94-6.77 (m, 1H), 5.41 (s, 1H), 4.76 (t, J=7.5 Hz, 1H), 3.93 (d, J=11.0 Hz, 2H), 3.82-3.70 (m, 2H), 3.69-3.62 (m, 1H), 3.28-3.15 (m, 2H), 2.69-2.55 (m, 1H), 1.81 (d, J=13.8 Hz, 1H), 1.12 (t, J=7.2 Hz, 3H). MS: 493.1, [M+H]$^+$.

5-bromo-2-(3,6-dihydro-2H-pyran-4-yl)pyrimidine (i)

5-bromo-2-iodo-pyrimidine (250 mg; 0.88 mmol) and 2-(3,6-dihydro-2H-pyran-4-yl)-4,4,5,5-tetramethyl-1,3,2-dioxaborolane (196 mg, 0.92 mmol) were dissolved in 1,4-dioxane-H$_2$O (10:1; 10 mL) and degassed with a stream of N$_2$ for 10 min. Pd(Ph$_3$)$_2$Cl$_2$ (30 mg, 0.04 mmol) was introduced and the reaction sealed and heated in a microwave reactor for 30 min at 80° C. The reaction was concentrated in vacuo, re-dissolved in DCM, filtered and purified over silica (gradient elution, 0-50% EtOAc-n-heptane) yielding i (105 mg, 50%). MS: 241.1 & 243.0; 1:1 [M+H]$^+$.

5-bromo-2-(3,7-dioxabicyclo[4.1.0]heptan-6-yl)pyrimidine (ii)

Compound i (105 mg; 0.436 mmol) was dissolved in DCM (15 mL) and cooled to 0° C., then solid 3-chlorobenzenecarboperoxoic acid (280 mg, 1.14 mmol) was added and the mixture stirred overnight. The mixture was quenched with 1M Na$_2$S$_2$O$_3$ (aq) (5 mL), washed with sat. NaHCO$_3$ (aq) (3×30 mL) followed by brine (1×30 mL). The organic fraction was dried (MgSO$_4$). Purification by chromatography on silica eluting with 0-50% EtOAc-n-heptane gave ii (20 mg, 18%). MS: 256.9 & 258.8; 1:1 [M+H]$^+$.

1-[5-[2-(3,7-dioxabicyclo[4.1.0]heptan-6-yl)pyrimidin-5-yl]-7-(2-pyridyl)-1,3-benzothiazol-2-yl]-3-ethyl-urea (iii)

Intermediate 1 (29 mg, 0.085 mmol), ii (20 mg, 78 mmol), Cs$_2$CO$_3$ (55 mg 0.17 mmol) and Pd(Ph$_3$)$_2$Cl$_2$ (3 mg, 4 mmol) were dissolved in 1,4-dioxane:H$_2$O (10:1, 10 mL). The mixture was degassed with a stream of N$_2$ for 10 min, then heated in a microwave reactor at 80° C. for 1 h. The reaction was concentrated in vacuo, re-dissolved in a minimum quantity of DCM and purified by chromatography on silica (0-10% DCM-MeOH) yielding iii (23 mg 57%). MS: 475.0, [M+H]$^+$.

1-(5-(2-(3,4-dihydroxytetrahydro-2H-pyran-4-yl)pyrimidin-5-yl)-7-(pyridin-2-yl)benzo[d]thiazol-2-yl)-3-ethylurea (8)

Compound iii (20 mg; 0.042 mmol) was dissolved in THF-H$_2$O (10:1, 11 mL). Conc. sulfuric acid (20 µL) and p-toluenesulphonic acid (0.7 mg, 4 mmol) were added and the mixture stirred at RT. The mixture was concentrated in vacuo and purified over silica (0-100% 0.1% FA (aq)-MeCN) yielding Compound 8 (8.8 mg, 42%).

Example(s) of General Method E

1-Ethyl-3-[5-[4-(1-hydroxyethyl)triazol-1-yl]-7-(2-pyridyl)-1,3-benzothiazol-2-yl]urea (9)

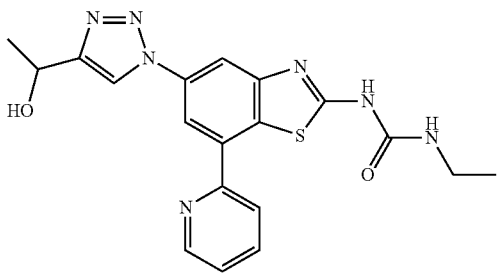 [SMILES: CCNC(=O)Nc1nc2cc(-n3cc(C(C)O)nn3)cc(-c3ccccn3)c2s1]

$^1$H NMR (400 MHz, DMSO-d$_6$) δ 10.97 (br s, 1H), 8.91 (s, 1H), 8.84 (d, J=3.9 Hz, 1H), 8.46 (d, J=8.2 Hz, 1H), 8.41 (s, 1H), 8.16 (s, 1H), 8.03 (td, J=7.9, 1.8 Hz, 1H), 7.49 (dd, J=7.2, 5.2 Hz, 1H), 7.02 (br s, 1H), 5.41 (d, J=4.8 Hz, 1H), 5.00-4.92 (m, 1H), 3.26-3.15 (m, 2H), 1.52 (d, J=6.5 Hz, 3H), 1.11 (t, J=7.2 Hz, 3H). MS: 410.0 [M+H]$^+$.

1-(5-azido-7-bromo-1,3-benzothiazol-2-yl)-3-ethyl-lurea (i)

Intermediate 3 (3.0 g, 7.04 mmol), sodium azide (930 mg, 14.08 mmol), sodium L-ascorbic acid (350 mg, 1.8 mmol) and CuI (120 mg; 0.63 mmol) were suspended in a mixture of DMSO (100 mL) and H$_2$O (24 mL). N,N'-dimethylethane-1,2-diamine (100 mg, 1.1 mmol) was added and the suspension heated at 100° C. overnight, H$_2$O was added and the resultant solid collected by filtration. This was rinsed with H$_2$O and dried in vacuo to give i (1.68 g). MS: 342.9 [M+H]$^+$.

1-{7-bromo-5-[4-(diethoxymethyl)-1H-1,2,3-triazol-1-yl]-1,3-benzothiazol-2-yl}-3-ethyl-5-methyl-1,3,5-triazinan-2-one (ii)

Compound i (1.68 g, 4.89 mmol) was suspended in MeOH (65 mL) and formaldehyde (37 wt % in H$_2$O, 7.94 g, 97.9 mmol) then methylamine (2 M in MeOH, 24.5 mL, 49 mmol) added. The suspension was heated to 80° C. for 5 h. H$_2$O was added and the mixture extracted with EtOAc and then DCM. The organic layers were dried (Na$_2$SO$_4$), filtrated and concentrated in vacuo to give a residue that contained 1-(5-azido-7-bromo-1,3-benzothiazol-2-yl)-3-ethyl-5-methyl-1,3,5-triazinan-2-one (1.31 g). A part of this mixture (827 mg; 2.09 mmol) was suspended in DMF (36 mL), cooled down at 0° C. and then treated with 3,3-diethoxyprop-1-yne (535 mg, 4.17 mmol), DIPEA (320 mg, 2.5 mmol) and CuI (70 mg; 0.37 mmol). The ice bath was removed and the reaction let to stir overnight at RT. The mixture was freeze-dried and the residue purified by chromatography on silica (0-5% MeOH gradient in DCM) to give a residue that was triturated with EtOAc affording ii (354 mg, 13%) $^1$H NMR (400 MHz, DMSO-d$_6$) δ 8.90 (s, 1H), 8.26 (d, J=1.8 Hz, 1H), 8.10 (d, J=1.8 Hz, 1H), 5.75 (s, 1H), 5.13 (s, 2H), 4.40 (s, 2H), 3.63 (qq, J=9.6, 7.1 Hz, 4H), 3.38 (q, J=7.1 Hz, 2H), 2.55 (s, 3H), 1.18 (t, J=7.1 Hz, 6H), 1.13 (t, J=7.1 Hz, 3H).

1-{5-[4-(diethoxymethyl)-1H-1,2,3-triazol-1-yl]-7-(pyridin-2-yl)-1,3-benzothiazol-2-yl}-3-ethyl-5-methyl-1,3,5-triazinan-2-one (iii)

Compound 1i (415 mg, 0.79 mmol) was suspended in DMF (5 mL) and tributyl(2-pyridyl)stannane (250 mg, 1.68 mmol) added. The mixture was degassed by freeze-drying the reaction vessel under vacuo and back filling with argon. CuI (30 mg, 0.2 mmol) and Pd(PPh$_3$)$_2$Cl$_2$ (1:2) (60 mg, 0.08 mmol) were added. The mixture was degassed with argon and heated at 110° C. overnight. The mixture was filtered through celite, washing with DMF. The filtrate was freeze-dried to give a residue that was purified by chromatography on silica (0-100% EtOAc gradient in heptane) to give iii (250 mg, 60%). $^1$H NMR (400 MHz, DMSO-d$_6$) δ 9.06 (br s, 1H), 8.85 (ddd, J=4.8, 1.7, 0.9 Hz, 1H), 8.53 (d, J=2.0 Hz, 1H), 8.52-8.49 (m, 1H), 8.30 (d, J=2.0 Hz, 1H), 8.06-8.01 (m, 1H), 7.49 (ddd, J=7.5, 4.9, 0.9 Hz, 1H), 5.79 (s, 1H), 5.16 (s, 2H), 4.39 (s, 2H), 3.72-3.59 (m, 4H), 3.40 (q, J=7.1 Hz, 2H), 2.56 (s, 3H), 1.20 (t, J=7.1 Hz, 6H), 1.14 (t, J=7.1 Hz, 3H). MS: 523.0 [M+H]$^+$.

1-Ethyl-3-[5-(4-formyl-1H-1,2,3-triazol-1-yl)-7-(pyridin-2-yl)-1,3-benzothiazol-2-yl]urea (iv)

Compound iii (250 mg, 0.48 mmol) was suspended in 1M HCl solution (9 mL) and the mixture heated at 70° C. overnight. The mixture was concentrated in vacuo to give iv (213 mg, quantitative). MS: 394.0 [M+H]$^+$.

1-ethyl-3-{5-[4-(1-hydroxyethyl)-1H-1,2,3-triazol-1-yl]-7-(pyridin-2-yl)-1,3-benzothiazol-2-yl}urea (9)

To a suspension of iv (40 mg, 0.1 mmol) in THF (0.7 mL) was added bromo(methyl)magnesium 3M in Et$_2$O (0.250 mL, 0.1 mmol) and the mixture heated at 40° C. for 1 h. NH$_4$Cl (sat. aq.) was added and the mixture extracted with DCM:IPA (5:1). The organic layers were washed with brine and then concentrated in vacuo to give a crude product that was purified by reverse phase SP4 (ACN gradient in H$_2$O) affording Compound 9 (1.9 mg, 4%).

Example(s) of General Method F

1-Ethyl-3-(5-(2-(2-hydroxypropan-2-(pyrimidin-5-yl)-7-(pyrimidin-2-yl)benzo[d]thiazol-2-yl)urea (10)

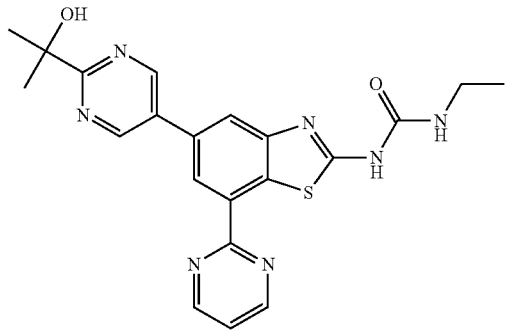 [SMILES: CCNC(=O)Nc1nc2cc(-c3cnc(C(C)(C)O)nc3)cc(-c3ncccn3)c2s1]

$^1$H NMR (DMSO-d$_6$): δ 10.72 (br s, 1H), 9.24 (s, 2H), 9.08 (d, J=4.80 Hz, 2H), 8.70 (s, 1H), 8.23 (s, 1H), 7.57 (t, J=4.80 Hz, 1H), 6.82 (m, 1H), 5.17 (s, 1H), 3.22 (m, 2H), 1.56 (s, 6H) and 1.12 (t, J=7.20 Hz, 3H). MS: 436.15 [M+H]$^+$.

A solution of Intermediate 5 (0.30 g, 0.68 mmol) and 2-(tributylstannyl)pyrimidine (0.253 g, 0.68 mmol) in DMF (10 mL) was degassed by purging with N$_2$ for 15 min followed by addition of Pd(PPh$_3$)$_4$ (0.078 g, 0.06 mmol). The mixture was degassed by purging with N$_2$ for 10 min and then heated to 80° C. for 16 h. Ice-cold H$_2$O was added to the reaction followed by extraction with EtOAc (3×100 mL). The combined organics were washed with brine, dried (Na$_2$SO$_4$), filtered and concentrated in vacuo. The residue was purified over silica (2.50% MeOH-DCM) to give Compound 10 (0.015 g, 5%).

Example(s) of General Method G

1-ethyl-3-(5-(4-(2-hydroxypropan-2-yl)-1H-imidazol-1-yl)-7-(pyridin-2-yl)benzo[d]thiazol-2-yl)urea (11)

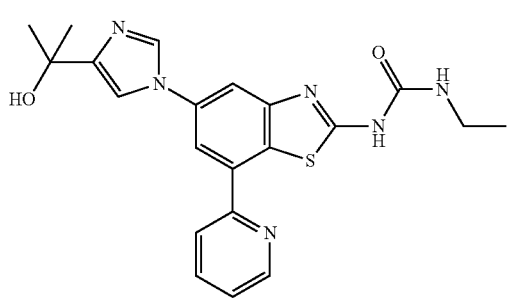 [SMILES: CCNC(=O)Nc1nc2cc(-n3cnc(C(C)(C)O)c3)cc(-c3ccccn3)c2s1]

$^1$H NMR (400 MHz, MeOD) δ 8.73 (d, J=4.8Hz, 1H), 8.22 (d, J=8.2 Hz, 1H), 8.20 (d, J=1.4 Hz, 1H), 8.01 (d, J=2.0 Hz, 1H), 7.92 (td, J=7.9, 1.8 Hz, 1H), 7.77 (d, J=2.0 Hz, 1H), 7.55 (d, J=1.4 Hz, 1H), 7.37 (dd, J=7.5, 4.9 Hz, 1H), 3.37-3.32 (m, 2H), 1.62 (s, 6H), 1.23 (t, J=7.2 Hz, 3H). MS: 422.99 [M+H]$^+$.

2-(1H-imidazol-4-yl)propan-2-ol (i)

Methyl 1H-imidazole-4-carboxylate (430 mg) was heated at reflux in HMDS (1 mL) for 30 min and the excess HMDS then distilled off. The residue was placed under vacuum then flushed twice with N$_2$ before dissolving in THF. The solution was cooled to 0° C., and MeMgBr (4.5 mL; 3M) added dropwise at 0° C. and the mixture warmed to RT overnight. The mixture was quenched with 1 mL sat. NH$_4$Cl then diluted with 2-3 mL H$_2$O. The mixture was concentrated in vacuo to an aqueous emulsion which was applied to a 12 g C18 reverse phase column. Elution with 100% ACN gave a residue that was further purified by chromatography on silica eluting with MeOH/DCM to afford i (280 mg).

1-ethyl-3-(5-(4-(2-hydroxypropan-2-yl)-1H-imidazol-1-yl)-7-(pyridin-2-yl)benzo[d]thiazol-2-yl)urea (11)

Compound i (74 mg) and Intermediate 1 (100 mg) were suspended in pyridine with 4 Å mol. sieves. The mixture was degassed and flushed with oxygen and Cu(OAc)$_2$.H$_2$O added. The mixture was again degassed and flushed with oxygen then left stirring at 80° C. for 280 min. The reaction was quenched by adding NH$_4$Cl sat. and diluted with EtOAc and H$_2$O. The mixture was extracted with EtOAc and the organics combined, dried (Na$_2$SO$_4$) and evaporated to dryness. Purification by chromatography on silica, eluting with DCM/MeOH (0-10%) followed by reverse phase chromatography on a C18 column eluting with ACN/H$_2$O afforded Compound 11 (7.5 mg).

Example(s) of Further Functionalisation

Alkylation of a Hydroxyl Group

1-Ethyl-3-(5-(2-(2-hydroxypropan-2-yl)pyrimidin-5-yl)-7-methoxybenzo[d]thiazol-2-yl)urea (12)

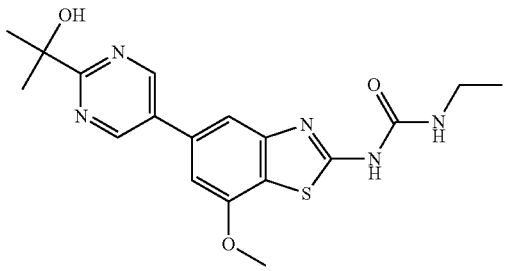 [SMILES: CCNC(=O)Nc1nc2cc(-c3cnc(C(C)(C)O)nc3)cc(OC)c2s1]

$^1$H NMR (400 MHz, Acetone-d$_6$) δ 9.22 (d, J=2.7 Hz, 2H), 7.65 (s, 1H), 7.22 (s, 1H), 4.11 (s, 3H), 3.44-3.26 (m, 2H), 1.60 (s, 6H), 1.19 (t, J=7.2 Hz, 3H). MS: 388.03 [M+H]$^+$.

A solution of Intermediate 9 (240 mg) and Cs$_2$CO$_3$ (220 mg) in anhydrous DMF (10 mL) was chilled to 0° C. then treated with iodomethane (83.5 mg). The reaction was allowed to warm to RT over 90 min then quenched with H$_2$O. The mixture was concentrated under vacuum and the resulting residue suspended in DCM & minimal MeOH for purification by chromatography on silica (0-5% MeOH:DCM). The residue was suspended in THF (10 mL) and treated with 1M HCl (10 mL). The reaction was stirred at RT for 90 min then neutralised with NaHCO$_3$ solution. The mixture was diluted with EtOAc (15 mL) and a white solid formed between the aqueous and organic layers. The solid was collected by filtration and dried under vacuum with heating at 50° C. to give Compound 12 (83 mg).

Ether Formation from a Halo Moiety Via an Aldehyde

1-Ethyl-3-(5-(2-(2-hydroxypropan-2-yl)pyrimidin-5-yl)-7-(methoxymethyl)benzo[d]thiazol-2-yl)urea (13)

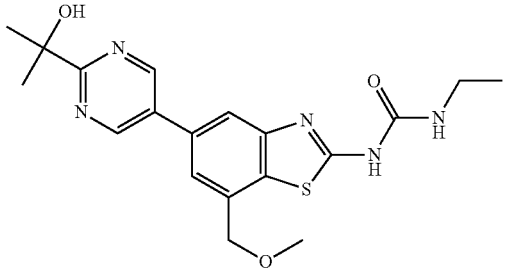 [SMILES: CCNC(=O)Nc1nc2cc(-c3cnc(C(C)(C)O)nc3)cc(COC)c2s1]

$^1$H NMR (400 MHz, CDCl$_3$) δ 9.13 (s, 2H), 7.95 (s, 1H), 7.23 (s, 1H), 4.67 (s, 2H), 3.48 (dd, J=12.1, 6.3 Hz, 2H), 3.44 (s, 3H), 1.63 (s, 6H), 1.33-1.21 (m, 3H). MS 402.04 [M+H]$^+$.

2-(3-ethyl-5-methyl-2-oxo-1,3,5-triazinan-1-yl)-5-[2-(1-hydroxy-1-methyl-ethyl)pyrimidin-5-yl]-1,3-benzothiazole-7-carbaldehyde (i)

A solution of Intermediate 4 (200 mg, 0.41 mmol) in THF (10 mL) was chilled to −80° C. under N$_2$ then treated with nBuLi (0.89 mL, 1.22 mmol). After 1 min DMF (0.06 mL, 0.81 mmol) was added and the reaction allowed to warm to RT over 30 min. The reaction was diluted with NaHCO$_3$ (20 mL) then extracted with EtOAc (2×15 mL). The organic extract was dried (MgSO$_4$), filtered and concentrated. The residue was suspended in DCM then purified by chromatography on silica eluting with (0-5% MeOH:DCM) to give i (38.5 mg, 22%). MS 441.01 [M+H]$^+$.

1-Ethyl-3-(5-(2-(2-hydroxypropan-2-yl)pyrimidin-5-yl)-7-(methoxymethyl)benzo[d]thiazol-2-yl)urea A solution of i (23 mg, 0.05 mmol) in MeOH (2 mL) was treated with H$_2$SO$_4$ (20 mL, 0.38 mmol) then stirred at RT for 90 min. The reaction was neutralised with NaHCO$_3$, then extracted with EtOAc (2×10 mL). The organic extract was dried (MgSO$_4$), filtered and concentrated. The crude material was suspended in DCM (2 mL) and treated with triethylsilane (50 μL, 0.31 mmol) and BF$_3$OEt$_2$ (25 μL, 0.20 mmol). The reaction was stirred at RT for 30 min, quenched with MeOH (2 mL) and stirred for 1 h. The mixture was diluted with EtOAc (5 mL) and washed with NaHCO$_3$ (5 mL) and H$_2$O (5 mL). The organic extract was dried (MgSO$_4$), filtered and concentrated. The material was suspended in MeCN:MeOH and purified by reverse phase chromatography (5-40-50-100% MeCN:H$_2$O+0.1% FA) to give Compound 13 (7.3 mg, 21%).

1-ethyl-3-(5-(2-(1-hydroxyethyl)pyrimidin-5-yl)-7-((6-methylpyridin-3-yl)methoxy)benzo[d]thiazol-2-yl)urea (14)

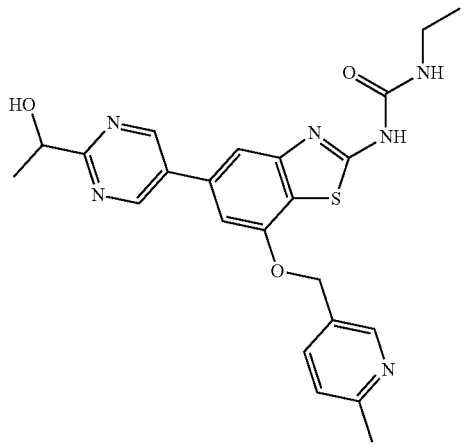 [SMILES: CCNC(=O)Nc1nc2cc(-c3cnc(C(C)O)nc3)cc(OCc3ccc(C)nc3)c2s1]

$^1$H NMR (400 MHz, D$_2$O) δ 8.60 (s, 2H), 8.29 (s, 1H), 8.15 (d, J=7.0 Hz, 1H), 7.77 (d, J=8.3 Hz, 1H), 6.91 (s, 1H), 6.38 (s, 1H), 3.03-2.90 (m, 2H), 2.75 (s, 3H), 1.45 (t, J=10.7 Hz, 3H), 1.00 (dt, J=14.1, 7.1 Hz, 3H). MS: 465.1 [M+H]$^+$.

1-ethyl-3-[5-[2-(1-hydroxyethyl)pyrimidin-5-yl]-7-[(6-methyl-3-pyridyl)methoxy]-1,3-benzothiazol-2-yl]-5-methyl-1,3,5-triazinan-2-one (i)

Methanesulfonyl chloride; (120 μL; 1.50 mmol) was introduced drop-wise to a solution of (6-methyl-3-pyridyl)methanol (100 mg; 0.812 mmol) and triethylamine (0.32 mL; 2.25 mmol) in anhydrous DCM (6 mL) at 0° C. and stirring was continued for 30 min at 0° C. The mixture was quenched with MeOH (2 mL), concentrated in vacuo and purified on silica (gradient elution, 50-100%, n-heptane-EtOAc) affording 6-methyl-3-pyridyl)methyl methanesulfonate (95 mg, 58%).

In a separate flask, Intermediate 10 (45 mg, 0.11 mmol) and K₂CO₃ (68 mg, 0.49 mmol) were dissolved in DMF (10 mL), and solution of (6-methyl-3-pyridyl)methyl methanesulfonate (95 mg, 0.47 mmol) in DMF (3 mL) was added at RT. The reaction was heated to 45° C. for 3 h. Concentrating the reaction mixture to ⅓ of its original volume and diluting with EtOAc (100 mL), washing with H₂O (100 mL), followed by brine (100 mL), and back extracting the aqueous phase with DCM:IPA (5:1, 100 mL) followed by purification by chromatography on silica eluting with 0-10%, DCM in MeOH gave i (30 mg, 53%).

1-ethyl-3-(5-(2-(1-hydroxyethyl)pyrimidin-5-yl)-7-((((6-methylpyridin-3-yl)methoxy)benzo[d]thiazol-2-yl)urea (14)

Compound i (30 mg; 58 μmol) was suspended in THF (3 mL) and concentrated HCl (1 mL) was introduced and heated to 45° C. for 1.5 h. The reaction was concentrated in vacuo, and purified by reverse phase chromatography, gradient elution, 25-80%, 0.1% FA (aq) in ACN) and lyophilized in the presence of 1M HCl (ca. 3 mL) to give Compound 14 (23 mg, 79%).

Sulfone Formation from a Thioether

1-Ethyl-3-[5-[2-(1-hydroxyethyl)pyrimidin-5-yl]-7-[4-(methylsulfanylmethyl)-2-pyridyl]-1,3-benzothiazol-2-yl]urea (15); and 1-ethyl-3-[5-[2-(1-hydroxyethyl)pyrimidin-5-yl]-7-[4-(methylsulfinylmethyl)-2-pyridyl]-1,3-benzothiazol-2-yl]urea (16)

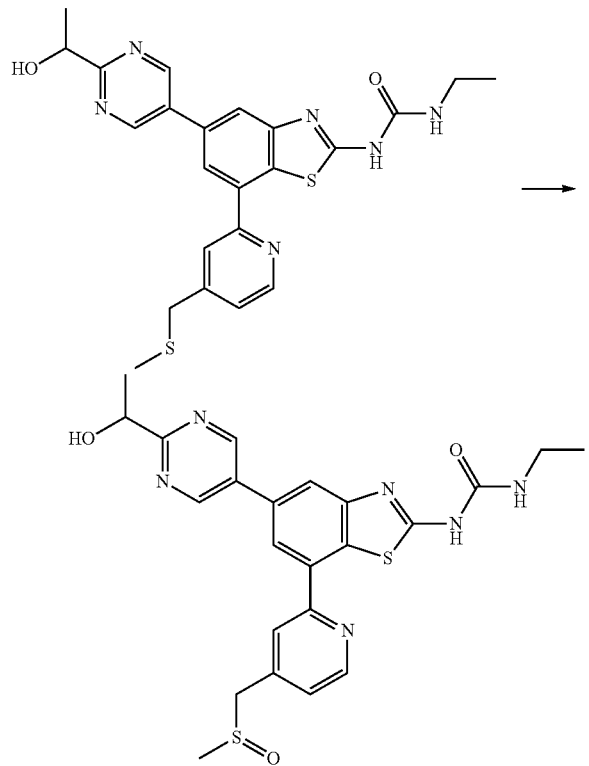

A solution of oxone (45 mg, 0.073 mmol) in H₂O (0.5 mL) was added to a solution of Compound 15 (70 mg, 0.146 mmol) in DMF (4.5 mL) at RT and stirred for 1 h. The mixture was diluted with EtOAc (50 mL) and washed with H₂O. The aqueous fraction was saturated with NaCl and re-extracted with EtOAc (3×50 mL). The combined organic layers were dried (Na₂SO₄) and concentrated in vacuo. The residue was purified by chromatography on silica, eluting with 0-30% MeOH/EtOAc to afford Compound 16 (15 mg, 21%). MS: 496.97 [M+H]⁺; ¹H NMR (400 MHz; d₆-DMSO): δ=10.79 (bs, 1H), 9.36 (s, 2H), 8.87 (d, J=4.9 Hz, 1H), 8.52 (s, 1H), 8.39 (d, J=1.5 Hz, 1H), 8.20 (d, J=1.5 Hz, 1H), 7.47 (dd, J=5.1, 1.2 Hz, 1H), 7.03 (bd, J=5.2 Hz, 1H), 5.35 (d, J=5.5 Hz, 1H), 4.94 (p, J=6.5 Hz, 1H), 4.36 (d, J=12.5 Hz, 1H), 4.25-4.07 (m, 1H), 3.28 (dd, J=7.1, 5.7 Hz, 2H), 2.64 (s, 3H), 1.54 (d, J=6.6 Hz, 3H), 1.18 (t, J=7.2 Hz, 3H).

Example(s) of General Method H

1-Ethyl-3-[5-[2-(1-hydroxyethyl)pyrimidin-5-yl]-7-(2-pyridyl)-1,3-benzothiazol-2-yl]urea (17); and 1-(5-(2-(3-ethylureido)-7-(pyridin-2-yl)benzo[d]thiazol-5-yl)pyrimidin-2-yl)ethyl 4-methylpiperazine-1-carboxylate (18)

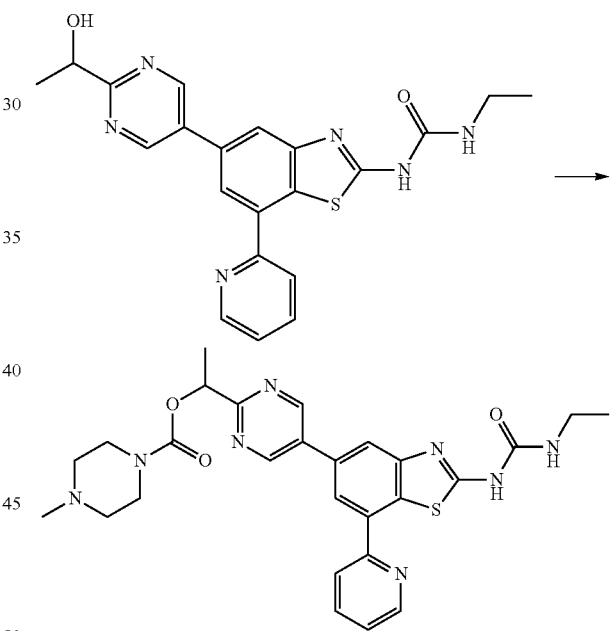

Compound 17, similarly prepared to Compound 1, (0.2378 mmol; 100 mg) was dissolved in DMF (1 mL) and di(imidazol-1-yl)methanone (0.26 mmol; 42 mg) added and stirred at RT for 18 h. 1-Methylpiperazine (0.29 mmol; 29 mg) was added and the mixture stirred at RT for 18 h. The mixture was concentrated in vacuo and the residue was purified by chromatography on silica eluting with 0-12% MeOH/DCM followed by reverse phase chromatography to give Compound 18 (12 mg) as the formate salt. ¹H NMR (400 MHz, DMSO-d₆) δ 10.69 (s, 1H), 9.39 (s, 2H), 8.84 (d, J=4.0 Hz, 1H), 8.55 (d, J=8.2 Hz, 1H), 8.42 (d, J=1.4 Hz, 1H), 8.18 (d, J=1.1 Hz, 1H), 8.03 (td, J=7.9, 1.7 Hz, 1H), 7.48 (dd, J=7.1, 5.1 Hz, 1H), 6.92 (t, J=5.2 Hz, 1H), 4.54 (d, J=12.9 Hz, 1H), 4.36 (d, J=12.9 Hz, 1H), 3.27-3.18 (m, 2H), 2.77 (s, 3H), 1.14 (t, J=7.2 Hz, 3H). MS 453.01 [M+H]⁺.

4-[1-[5-[2-(ethylcarbamoylamino)-7-(2-pyridyl)-1,3-benzothiazol-5-yl]pyrimidin-2-yl]ethoxy]-4-oxo-butanoic acid (19)

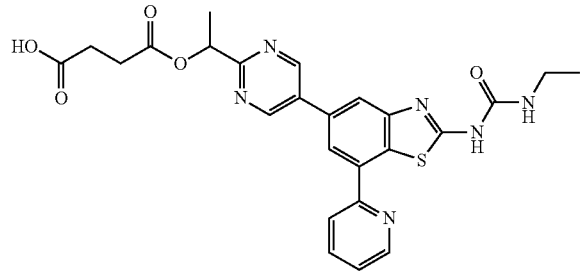 [SMILES: CCNC(=O)Nc1nc2cc(-c3cnc(C(C)OC(=O)CCC(=O)O)nc3)cc(-c3ccccn3)c2s1]

$^1$H NMR (400 MHz, CDCl$_3$) δ 8.90 (s, 2H), 8.70-8.63 (m, 1H), 7.91 (d, J=8.1 Hz, 1H), 7.83-7.67 (m, 3H), 7.20-7.13 (m, 1H), 5.83 (q, J=6.8 Hz, 1H), 3.30-3.13 (m, 2H), 2.63 (dd, J=6.8, 2.1 Hz, 2H), 2.52 (dd, J=6.5, 2.9 Hz, 2H), 1.57 (d, J=6.8 Hz, 3H), 1.09 (t, J=7.3 Hz, 2H). MS 521.09 [M+H]$^+$.

A solution of Compound 17 (250 mg) was treated with DIPEA (230 mg), DMAP (40 mg) and succinic anhydride (150 mg) then stirred at 50° C. for 6 h. Then DIPEA (300 µL) and succinic anhydride (100 mg) were added and the reaction stirred overnight. The mixture was diluted with H$_2$O (30 mL) and washed with EtOAc (3×15 mL). The aqueous extract was concentrated to give a crude brown gum. Purification by chromatography on silica eluting with 0-5% MeOH in DCM gave a solid that was suspended in hot MeOH, left to cool to RT and the resulting solid collected by filtration and dried under vacuum to give Compound 19.

O4-[1-[5-[2-(Ethylcarbamoylamino)-7-(2-pyridyl)-1,3-benzothiazol-5-yl]pyrimidin-2-yl]-1-methyl-ethyl] O1-methyl butanedioate (20); and 4-((2-(5-(2-(3-ethylureido)-7-(pyridin-2-yl)benzo[d]thiazol-5-yl)pyrimidin-2-yl)propan-2-yl)oxy)-4-oxobutanoic acid (21)

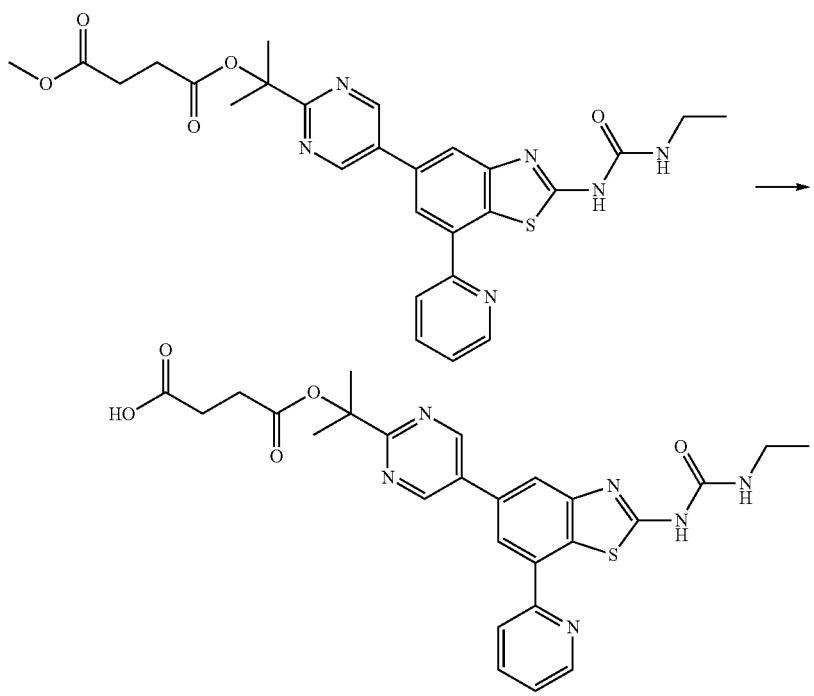

Compound 20, similarly prepared to Compound 1, (179 mg, 0.33 mmol) was dissolved in MeOH (18 mL) and NaOH (0.65 mL, 1 M, aq) added. The solution was stirred at RT, then further NaOH (0.65 mL, 1 M, aq) was added after 1.5 h and 3.5 h. H$_2$O (0.5 mL) was added after 7 h. The solution was stirred at RT overnight. After 23 h, the mixture was acidified to pH 4.5 with HCl (1 M, aq) and the solution concentrated to dryness in vacuo, azeotroping with ACN (3×20 mL). The solid was purified by chromatography on silica, eluting with 0-5% MeOH in DCM, followed by further chromatography on silica eluting with 0-50% MeOH in EtOAc and further chromatography on silica eluting with 0-5% MeOH in DCM to give Compound 21 (47 mg, 27%). $^1$H NMR (400 MHz, MeOD): δ 9.14 (s, 2H), 8.77 (ddd, J=4.3, 1.7, 0.8 Hz, 1H), 8.29 (d, J=7.8 Hz, 1H), 8.19 (d, J=1.5 Hz, 1H), 7.99 (d, J=1.5 Hz, 1H), 7.96 (dt, J=7.8 and 1.7 Hz, 1H), 7.40 (ddd, J=7.4, 4.3, 0.8 Hz, 1H), 3.37 (q, J=7.2 Hz, 2H), 2.71 (m, 2H), 2.60 (m, 2H), 1.87 (s, 6H), 1.27 (t, J=7.2 Hz, 3H). MS: 535.05 [M+H]$^+$.

Example(s) of General Method I 1-ethyl-3-[5-[2-(1-hydroxy-1-methyl-ethyl)pyrimidin-5-yl]-7-morpholino-1,3-benzothiazol-2-yl]urea (151)

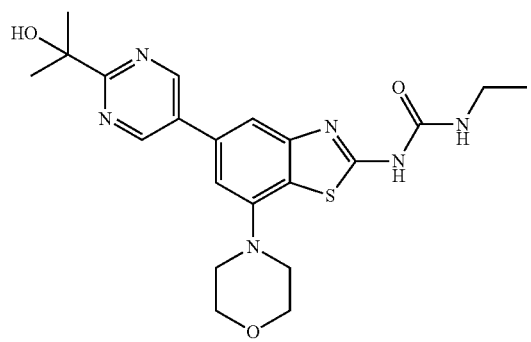 [SMILES: CCNC(=O)Nc1nc2cc(-c3cnc(C(C)(C)O)nc3)cc(N3CCOCC3)c2s1]

$^1$H NMR (400 MHz; DMSO-d$_6$): δ 10.75 (br s, 1H), 9.16 (s, 2H), 7.72 (s, 1H), 7.16 (s, 1H), 6.73 (m, 1H), 5.11 (s, 1H), 3.86 (m, 4H), 3.17-3.26 (m, 6H), 1.54 (s, 6H) and 1.09 (t, J=7.20 Hz, 3H). MS: 443.28 [M+H]$^+$ 1-ethyl-3-[5-[2-(1-hydroxy-1-methyl-ethyl)pyrimidin-5-yl]-7-morpholino-1,3-benzothiazol-2-yl]-5-methyl-1,3,5-triazinan-2-one (i)

To a solution of Intermediate 4 (0.25 g, 0.51 mmol) in 1,4-dioxane (10 mL) was added morpholine (0.066 g, 0.77 mmol) followed by Cs$_2$CO$_3$ (0.25 g, 0.77 mmol). The resulting solution was purged with nitrogen for 30 min followed by addition of Pd$_2$(dba)$_3$ (0.026 g, 0.025 mmol) and Xantphos (0.035 g, 0.061 mmol). The reaction mixture was again purged with nitrogen for 15 min and then heated up to 80° C. overnight. After the completion of reaction (TLC monitoring), the reaction was cooled to RT, filtered through celite bed, washed the celite bed with EtOAc and concentrated the combined filtrate under reduced pressure. The crude residue was then purified over silica gel (100-200 M, 3% MeOH-DCM) to obtain i as off-white solid (0.07 g, 28%). $^1$H-NMR (DMSO-d$_6$, 400 MHz): δ 9.18 (s, 2H), 7.79 (s, 1H), 7.19 (s, 1H), 5.12 (s, 3H), 4.37 (s, 2H), 3.80-3.83 (m, 4H), 3.35-3.38 (m, 2H), 3.21-3.23 (m, 4H), 2.54 (s, 3H), 1.54 (s, 6H) and 1.08 (t, J=6.80 Hz, 3H).

1-Ethyl-3-[5-[2-(1-hydroxy-1-methyl-ethyl)pyrimidin-5-yl]-7-morpholino-1,3-benzothiazol-2-yl]urea (151)

To an ice-cold solution of i (0.065 g, 0.13 mmol) in THF (3 mL) was added 6N—HCl (2 mL). The mixture was stirred at RT for 4 h. After completion of reaction (TLC monitoring), the mixture was poured into saturated NaHCO$_3$ solution followed by extraction with EtOAc (2×50 mL). The combined organics were washed with brine, dried over Na$_2$SO$_4$, filtered and concentrated under reduced pressure. The residue obtained was triturated with MeOH-Et$_2$O to afford Compound 151 as a white solid (0.035 g, 61%).

Example(s) of Chiral Separation and Synthesis (R)-1-ethyl-3-(5-(2-(1-hydroxyethyl)pyrimidin-5-yl)-7-(pyridin-2-yl)benzo[d]thiazol-2-yl)urea (22) & (S)-1-ethyl-3-(5-(2-(1-hydroxyethyl)pyrimidin-5-yl)-7-(pyridin-2-yl)benzo[d]thiazol-2-yl)urea (23)

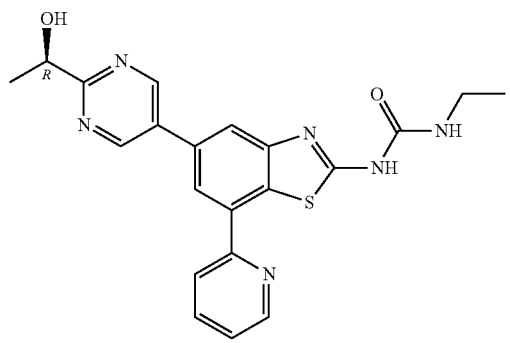

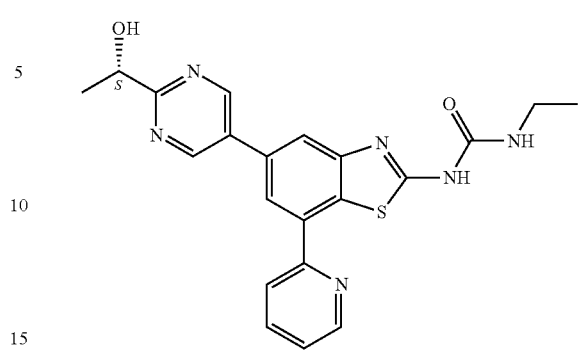

The (R) and (S) enantiomers of Compound 17 were separated by chiral prep-HPLC:

Column: Chiralpak IC (250×20 mm) 5 n

Mobile phase: 100% MeOH

Sampling details: 25 mg in a mix of 0.5 mL TFA and 0.5 mL of MeOH

Flow rate: 18 mL/min.

Run time: 20 min.

Retention Time 9.3 min; 14.7 min.

[(1R)-1-[5-[2-(ethylcarbamoylamino)-7-(2-pyridyl)-1,3-benzothiazol-5-yl]pyrimidin-2-yl]ethyl]dihydrogen phosphate (152); & [(1S)-1-[5-[2-(ethylcarbamoylamino)-7-(2-pyridyl)-1,3-benzothiazol-5-yl]pyrimidin-2-yl]ethyl]dihydrogen phosphate (153)

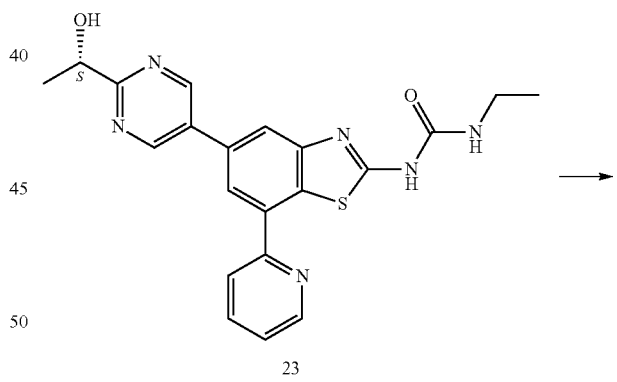

23

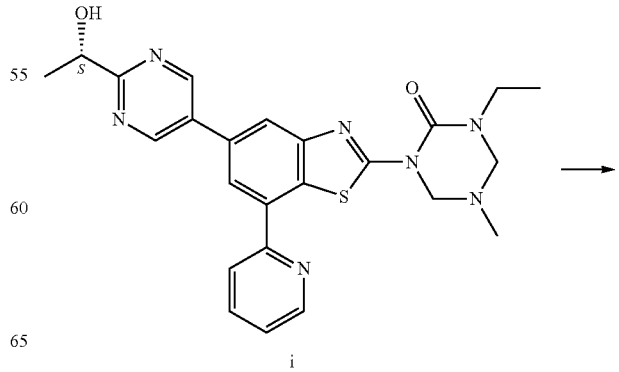

i

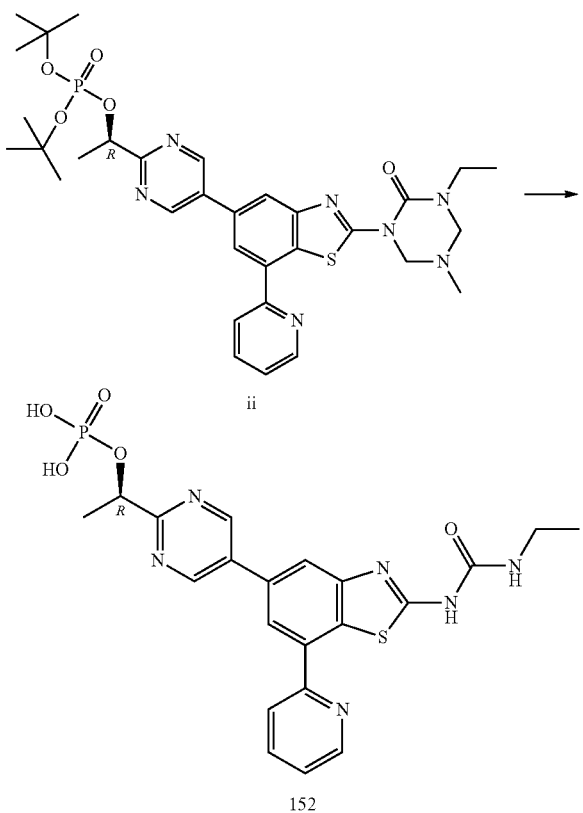

1-ethyl-3-[5-[2-[(1S)-1-hydroxyethyl]pyrimidin-5-yl]-7-(2-pyridyl)-1,3-benzothiazol-2-yl]-5-methyl-1,3,5-triazinan-2-one (i)

Compound 23 (12.67 g, 30.13 mmol) was suspended in MeOH (150 mL). Formaldehyde (48.9 mL, 0.603 mol, as a 37% aqueous solution) was added, along with N-methylmorpholine (33.1 mL, 0.301 mol) and methylamine (151 mL of a 2M THF solution). The white suspension was heated at 70° C. overnight. TLC showed almost complete conversion to product after 19 hrs and the solution was cooled to room temperature then concentrated to ~33% volume under reduced pressure and partitioned between $H_2O$ (150 mL) and EtOAc (300 mL). Heat was applied to the biphasic mixture to help solubilize the product. The organic layer was washed with brine, filtered through $MgSO_4$, and concentrated to dryness under reduced pressure. The solid was swished in EtOAc (100 mL), filtered, washed with EtOAc and heptane, and dried to give i as a white solid (11.97 g, 76%). MS: 475.93 [M+H]$^+$.

Di-tert-butyl[(1R)-1-[5-[2-(3-ethyl-5-methyl-2-oxo-1,3,5-triazinan-1-yl)-7-(2-pyridyl)-1,3-benzothiazol-5-yl]pyrimidin-2-yl]ethyl]phosphate (ii)

Preparation of di-tert-butyl hydrogen phosphate: Potassium di-tert-butyl phosphate (45 g) was dissolved in water (160 mL). Hydrochloric acid (1M, aq) was added until the pH was ~3. The resultant precipitate was collected by filtration, washed with water, and dried under vacuum overnight to give di-tert-butyl phosphonic acid as a white solid. Then, to a suspension of i (18.68 g, 39.28 mmol), triphenylphosphine (17.51 g, 66.78 mmol), and di-tert-butyl hydrogen phosphate (10.73 g, 51.06 mmol) in THF and triphenylphosphine were suspended in anhydrous THF (200 mL). A solution of DIAD (13.5 g, 66.78 mmol) in THF (20 mL) was added dropwise. The mixture was stirred at room temperature and monitored by LCMS to completion then was concentrated under reduced pressure. $Et_2O$ (300 mL) was added and the mixture sonicated, resulting in a bright white solid, which was filtered, washed with $Et_2O$ (100 mL) and air dried. The filtrate also contained some product. After concentration to 150 mL the filtrate was chilled in ice, yielding more solid material. The solids were collected, redissolved in DCM, and plugged (50-100% EtOAc/DCM to remove Mitsonobu by-products then 10% MeOH/DCM to elute the desired product. After concentrating the relevant fraction to a white solid, this material was recrystallized from DCM/ether/heptane, filtered, washed with heptane, and dried overnight to give ii as a white solid (17.09 g, 64%). $^1$H NMR (400 MHz) δ 9.41 (s, 2H); 8.83 (d, J=4.4 Hz, 1H); 8.53 (d, J=8 Hz, 1H); 8.43 (d, J=1.2 Hz, 1H); 8.21 (d, J=1.2 Hz, 1H); 8.01 (dt, J=8, 1.6 Hz, 1H); 7.46 (dd, J=7.2, 4.8 Hz); 5.43 (m, 1H); 5.16 (s, 2H); 4.38 (s, 2H); 3.39 (q, J=7.2 Hz, 2H); 3.32 (br s, 2H); 2.55 (s, 3H); 1.64 (d, J=6.8 Hz, 3H); 1.38 (s, 9H); 1.36 (s, 9H); 1.14 (t, J=7.2 Hz). MS: 667.78 (M+H)$^+$. Chiral HPLC: Column. Chirapak IC, 0.46 cm×25 cm; 25 min isocratic gradient 100% MeOH retention time=17.12 min.

[(1R)-1-[5-[2-(ethylcarbamoylamino)-7-(2-pyridyl)-1,3-benzothiazol-5-yl]pyrimidin-2-yl]ethyl]dihydrogen phosphate (152)

A solution of ii (17.0 g, 25.46 mmol) in anhydrous THF (300 mL) was treated with 4 M HCl in dioxane (63.6 mL, 10 eq.). A precipitate formed immediately upon addition of acid and the reaction monitored to completion by LCMS. $H_2O$ (50 mL) was added and the solution concentrated to remove approx. 150 mL of THF, at which point a flocculent precipitate began to form. The mixture was stirred at room temperature overnight, yielding a white precipitate which was filtered, washed several times with water, followed by MeOH and $Et_2O$, then dried at 50° C. for 6 hours to give Compound 152 as a white solid (12.0 g, 95%). MS: 501.07 [M+H]$^+$. $^1$H NMR (400 MHz, DMSO-d$_6$): δ 10.7 (br s 1H), 9.35 (s, 2H), 8.85-8.81 (m, 1H), 8.53 (d, J=8.3 Hz, 1H), 8.39 (d, J=1.6 Hz, 1H), 8.15 (d, J=1.6 Hz, 1H), 8.05-7.99 (m, 1H), 7.49-7.44 (m, 1H), 6.93 (t, J=5.5 Hz, 1H), 5.48-5.39 (m, 1H), 3.27-3.17 (m, 2H), 1.63 (d, J=6.6 Hz, 3H), 1.12 (t, J=7.2 Hz, 3H). Compound 153 may be similarly prepared, starting from Compound 22.

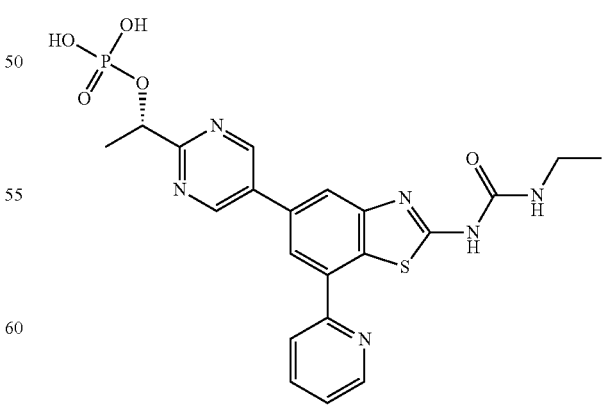

$^1$H NMR (400 MHz, DMSO-d$_6$): δ 10.6 (br s, 1H), 9.35 (s, 2H), 8.85-8.81 (m, 1H), 8.53 (d, J=8.3 Hz, 1H), 8.39 (d, J=1.6 Hz, 1H), 8.15 (d, J=1.6 Hz, 1H), 8.05-7.99 (m, 1H), 7.56-7.31

(m, 1H), 6.89 (t, J=5.5 Hz, 1H), 5.47-5.38 (m, 1H), 3.26-3.18 (m, 2H), 1.63 (d, J=6.6 Hz, 3H), 1.12 (t, J=7.2 Hz, 3H). MS: 501.05 [M+H]$^+$.

The following compounds were similarly prepared with reference to the general method(s) and/or examples previously described.

TABLE 1

Compounds and characterisation data

| No. | Observed LCMS [M + H]$^+$ | $^1$H NMR |
|---|---|---|
| 24 | 486 | (DMSO-d$_6$): δ 10.62 (s, 1H), 9.0 (s, 1H), 8.8 (d, 1H), 8.5 (d, 1H), 8.4 (d, 1H), 8.35 (s, 1H), 8.05 (m, 2H), 7.8 (s, 1H), 7.5 (m, 1H), 7.1 (s, 1H), 6.9 (s, 1H), 6.8 (s, 1H), 6.3 (d, 1H), 6.0 (d, 1H), 3.7 (s, 3H), 3.25 (m, 2H), 1.15 (t, 3H) |
| 25 | 534.15 | (CDCl$_3$): δ 9.22 (s, 2H), 8.66 (s, 1H), 8.13 (s, 1H), 7.89 (s, 1H), 7.82 (d, J = 8.2 Hz, 1H), 7.77 (s, 1H), 3.84-3.67 (m, 4H), 3.58 (s, 2H), 3.41 (s, 2H), 2.51 (s, 4H), 1.61 (s, 6H), 1.31-1.26 (m, 3H). |
| 26 | 518.17 | (CDCl$_3$) δ 9.18 (s, 2H), 8.66 (d, J = 4.7 Hz, 1H), 8.46 (s, 1H), 8.16 (s, 1H), 8.02 (s, 1H), 7.93 (s, 1H), 3.92 (s, 2H), 3.51-3.36 (m, 2H), 2.80 (s, 4H), 1.92 (s, 4H), 1.63 (s, 6H), 1.35-1.22 (m, 3H). |
| 27 | 434.05 | (CDCl$_3$) δ 8.91 (d, J = 1.6 Hz, 1H), 8.59 (d, J = 4.5 Hz, 1H), 8.12-7.98 (m, 4H), 7.82 (t, J = 7.6 Hz, 1H), 7.42 (d, J = 8.2 Hz, 1H), 7.21 (dd, J = 7.2, 5.0 Hz, 1H), 3.56-3.43 (m, 2H), 1.59 (s, 6H), 1.32 (t, J = 7.2 Hz, 3H). |
| 28 | 534.18 | (DMSO-d$_6$) δ 10.63 (br s, 1H); 9.35 (s, 2H); 8.77 (d, J = 5 Hz, 1H); 8.44 (1H, s); 8.39 (1H, s); 8.15 (1H, s); 7.47 (d, J = 5 Hz, 1H); 6.90 (br s, 1H); 5.15 (s, 1H); 3.66 (s, 2H); 3.63 (s, 4H); 3.23 (m, 2H); 2.46 (s, 4H); 1.59 (s, 6H); 1.14 (t, J = 7 Hz, 3H).<br>Methano sulphonate salt form: $^1$H NMR (400 MHz; D$_2$O): δ = 8.70 (s, 2H), 8.25 (s, 1H), 7.83 (s, 1H), 7.34 (s, 1H), 7.17 (s, 2H), 4.28 (s, 2H), 4.00 (s, 4H), 3.33 (s, 4H), 3.21-3.02 (m, 2H), 2.83 (s, 3H), 1.66 (s, 6H), 1.12 (t, J = 7.2 Hz, 3H). MS: 534.19 [M + H]$^+$<br>HCl salt form: $^1$H NMR (400 MHz; DMSO-d$_6$): δ = 12.24 (bs, 1H), 9.45 (s, 2H), 9.11 (s, 1H), 8.92 (d, J = 5.0 Hz, 1H), 8.55 (d, J = 1.5 Hz, 1H), 8.22 (d, J = 1.5 Hz, 1H), 7.66 (dd, J = 5.0, 0.9 Hz, 1H), 7.20 (bs, 1H), 4.54 (s, 2H), 3.96 (s, 4H), 3.46-3.29 (m, 2H), 3.29-3.09 (m, 4H), 1.59 (s, 6H), 1.14 (t, J = 7.2 Hz, 3H). MS: 534.18 [M + H]$^+$ |
| 29 | 534.3 | (DMSO-d$_6$) δ 10.80 (br s, 1H), 9.32 (s, 2H), 8.75 (d, J = 4.80 Hz, 1H), 8.42 (s, 1H), 8.37 (s, 1H), 8.12 (s, 1H), 7.42 (d, J = 4.80 Hz, 1H), 7.05 (m, 1H), 5.16 (br s, 1H), 4.74 (br s, 1H), 4.22 (br s, 1H), 3.67-3.78 (m, 2H), 3.38 (m, 2H), 3.17-3.24 (m, 2H), 2.73-2.75 (m, 1H), 2.63-2.67 (m, 1H), 2.37-2.40 (m, 1H), 2.01-2.06 (m, 1H), 1.56 (s, 6H) and 1.11 (t, J = 7.20 Hz, 3H). |
| 30 | 520.25 | (DMSO-d$_6$) δ 10.67 (br s, 1H), 9.33 (s, 2H), 8.73 (d, J = 4.80 Hz, 1H), 8.36 (br s, 2H), 8.12 (s, 1H), 7.35 (d, J = 4.80 Hz, 1H), 6.92 (m, 1H), 5.35 (d, J = 6.40 Hz, 1H), 5.15 (s, 1H), 4.21-4.26 (m, 1H), 3.71 (s, 2H), 3.58 (t, J = 6.40 Hz, 2H), 3.21 (m, 2H), 2.85 (t, J = 6.40 Hz, 2H), 1.57 (s, 6H) and 1.11 (t, J = 7.20 Hz, 3H). |
| 31 | 534.28 | (DMSO-d$_6$) δ 10.62 (br s, 1H), 9.35 (s, 2H), 8.73 (d, J = 4.80 Hz, 1H), 8.38 (m, 2H), 8.13 (s, 1H), 7.35 (d, J = 4.80 Hz, 1H), 6.86 (m, 1H), 5.15 (s, 1H), 4.0-4.03 (m, 1H), 3.74 (s, 2H), 3.57 (t, J = 6.40 Hz, 2H), 3.21 (m, 2H), 3.15 (s, 3H), 2.93 (m, 2H), 1.57 (s, 6H) and 1.11 (t, J = 7.20 Hz, 3H). |
| 32 | 564.3 | (DMSO-d$_6$) δ 10.62 (br s, 1H), 9.33 (s, 2H), 8.61 (d, J = 5.60 Hz, 1H), 8.40 (s, 1H), 8.12 (s, 1H), 8.03 (s, 1H), 7.05 (m, 1H), 6.90 (m, 1H), 5.15 (s, 1H), 4.34 (t, J = 5.60 Hz, 2H), 3.57-3.59 (m, 4H), 3.31-3.36 (m, 4H), 3.19-3.22 (m, 2H), 2.76 (t, J = 5.60 Hz, 2H), 1.57 (s, 6H) and 1.11 (t, J = 7.20 Hz, 3H). |
| 33 | 548.31 | (DMSO-d$_6$) δ 10.61 (br s, 1H), 9.33 (s, 2H), 8.76 (d, J = 4.80 Hz, 1H), 8.39 (s, 2H), 8.13 (s, 1H), 7.42 (m, 1H), 6.85 (m, 1H), 5.15 (s, 1H), 3.53-3.58 (m, 5H), 3.18-3.25 (m, 2H), 2.50 (m, 2H), 2.32 (m, 2H), 1.57 (s, 6H), 1.38 (d, J = 6.80 Hz, 3H), and 1.11 (t, J = 7.20 Hz, 3H). |
| 34 | 554.25 | (DMSO-d$_6$) δ 10.63 (br s, 1H), 9.33 (s, 2H), 8.76 (d, J = 4.80 Hz, 1H), 8.43 (s, 1H), 8.38 (s, 1H), 8.14 (s, 1H), 7.43 (m, 1H), 6.86 (m, 1H), 5.16 (s, 1H), 3.79 (s, 2H), 3.18-3.24 (m, 2H), 2.92-2.99 (m, 2H), 2.78 (t, J = 6.80 Hz, 2H), 2.23-2.34 (m, 2H), 1.57 (s, 6H) and 1.11 (t, J = 7.20 Hz, 3H). |
| 35 | 536.28 | (DMSO-d$_6$) δ 10.63 (br s, 1H), 9.32 (s, 2H), 8.75 (d, J = 4.80 Hz, 1H), 8.50 (s, 1H), 8.38 (s, 1H), 8.13 (s, 1H), 7.42 (d, J = 4.80 Hz, 1H), 6.86 (t, J = 5.20 Hz, 1H), 5.15 (m, 2H), 3.78 (s, 2H), 3.18-3.33 (m, 2H), 2.80-2.89 (m, 2H), 2.66-2.68 (m, 1H), 2.39-2.50 (m, 1H), 2.12-2.19 (m, 1H), 1.89-1.98 (m, 1H), 1.56 (s, 6H) and 1.11 (t, J = 7.20 Hz, 3H). |
| 36 | 536.26 | (DMSO-d$_6$) δ 10.62 (br s, 1H), 9.32 (s, 2H), 8.75 (d, J = 4.80 Hz, 1H), 8.43 (s, 1H), 8.38 (s, 1H), 8.13 (s, 1H), 7.43 (d, J = 4.80 Hz, 1H), 6.86 (t, J = 5.20 Hz, 1H), 5.15 (m, 2H), 3.78 (s, 2H), 3.19-3.23 (m, 2H), 2.80-2.89 (m, 2H), 2.64-2.76 (m, 1H), 2.41-2.45 (m, 1H), 2.11-2.21 (m, 1H), 1.85-1.96 (m, 1H), 1.56 (s, 6H) and 1.11 (t, J = 7.20 Hz, 3H). |
| 37 | 568.3 | (DMSO-d$_6$) δ 10.64 (br s, 1H), 9.32 (s, 2H), 8.77 (d, J = 5.20 Hz, 1H), 8.41 (s, 1H), 8.36 (s, 1H), 8.14 (s, 1H), 7.36-7.42 (m, 1H), 6.88 (m, 1H), 5.16 (s, 1H), 3.76 (s, 2H), 3.12-3.25 (m, 4H), 2.72 (t, J = 11.20 Hz, 2H), 1.86-1.93 (m, 2H), 1.69 (m, 2H), 1.57 (s, 6H) and 1.11 (t, J = 7.20 Hz, 3H). |

TABLE 1-continued

Compounds and characterisation data

| No. | Observed LCMS [M + H]+ | 1H NMR |
|---|---|---|
| 38 | 578.31 | (DMSO-d6) δ 10.60 (br s, 1H), 9.33 (s, 2H), 8.61 (d, J = 5.60 Hz, 1H), 8.38 (s, 1H), 8.12 (s, 1H), 8.01 (s, 1H), 7.04 (m, 1H), 6.86 (m, 1H), 5.15 (s, 1H), 4.26 (t, J = 6.0 Hz, 2H), 3.57 (m, 4H), 3.17-3.24 (m, 2H), 2.44-2.46 (m, 2H), 2.37 (br s, 4H), 1.91-1.98 (m, 2H), 1.56 (s, 6H) and 1.11 (t, J = 7.20 Hz, 3H). |
| 39 | 436.19 | (DMSO-d6) δ 10.78 (br s, 1H), 9.81 (s, 1H), 9.36 (s, 2H), 8.89 (s, 1H), 8.71 (s, 1H), 8.56 (s, 1H), 8.22 (s, 1H), 6.92 (m, 1H), 5.16 (s, 1H), 3.21 (m, 2H), 1.57 (s, 6H) and 1.11 (t, J = 7.20 Hz, 3H) |
| 40 | 437 | (CDCl3) δ 9.04 (s, 2H), 8.79-8.71 (m, 1H), 8.04-7.76 (m, 4H), 7.31-7.26 (m, 3H), 4.94 (t, J = 4.5 Hz, 1H), 4.02 (ddd, J = 25.6, 11.5, 4.5 Hz, 2H), 3.34 (dd, J = 3.3, 1.6 Hz, 2H), 1.22 (t, J = 7.3 Hz, 3H). |
| 41 | 429.98 | (CDCl3) δ 8.87 (1 H, d, J = 1.8 Hz), 8.13 (1 H, dd, J = 8.2 and 1.8 Hz), 7.74 (1 H, s), 7.46 (1 H, d, J = 8.2 Hz), 3.87 (2 H, s), 3.46 (2 H, m), 2.44 (6 H, s), 1.64 (6 H, s), 1.30 (3 H, t, J = 7.2 Hz). |
| 42 | 548.34 | (DMSO-d6) δ 9.32 (s, 2H), 8.75 (d, J = 5.20 Hz, 1H), 8.42 (s, 1H), 8.37 (s, 1H), 8.12 (s, 1H), 7.41 (d, J = 4.80 Hz, 1H), 6.90 (m, 1H), 5.15 (s, 1H), 3.90 (m, 1H), 3.77 (s, 2H), 3.21 (m, 3H), 3.15 (s, 3H), 2.72-2.76 (m, 1H), 2.59-2.65 (m, 1H), 2.54 (m, 1H), 1.97-2.04 (m, 1H), 1.57-1.72 (m, 1H), 1.57 (s, 6H) and 1.11 (t, J = 7.20 Hz, 3H). |
| 43 | 450.24 | (DMSO-d6) δ 10.70 (br s, 1H), 9.34 (s, 2H), 9.27 (s, 1H), 8.55 (m, 2H), 8.25 (s, 1H), 6.83 (m, 1H), 5.16 (s, 1H), 3.21 (m, 2H), 2.60 (s, 3H), 1.57 (s, 6H) and 1.11 (t, J = 7.20 Hz, 3H) |
| 44 | 471.96 | (CDCl3) δ 10.8 (1 H, br s), 8.91 (1 H, d, J = 1.9 Hz), 8.11 (1 H, dd, J = 8.2 and 1.9 Hz), 7.78 (1 H, s), 7.48 (1 H, dd, J = 8.2 and 0.6 Hz), 4.98 (1 H, br s), 3.92 (2 H, s), 3.80 (4 H, br s), 3.47 (2 H, m), 2.70 (4 H, br s), 1.65 (6 H, s), 1.30 (3 H, t, J = 7.3 Hz). |
| 45 | 574.20 [M − H]− | (DMSO-d6) δ 12.43 (br s, 1H), 10.82 (br s, 1H), 9.24 (s, 2H), 8.54 (s, 1H), 7.94-8.0 (m, 1H), 7.66 (s, 1H), 7.03 (m, 1H), 6.77 (m, 1H), 5.14 (br s, 1H), 4.01-4.04 (m, 2H), 3.15-3.25 (m, 4H), 2.0-2.04 (m, 2H), 1.55 (s, 6H), 1.40-1.45 (m, 2H), 1.19 (s, 3H) and 1.09 (t, J = 7.20 Hz, 3H). |
| 46 | 493.21 | (DMSO-d6) δ 10.74 (br s, 1H), 9.32 (s, 2H), 8.69 (s, 1H), 8.45 (d, J = 8.40 Hz, 1H), 8.36 (s, 1H), 8.12 (s, 1H), 7.89 (d, J = 8.40 Hz, 1H), 7.02 (m, 1H), 5.15 (s, 1H), 3.74 (s, 2H), 3.20-3.23 (m, 2H), 1.56 (s, 6H) and 1.11 (t, J = 7.20 Hz, 3H). |
| 47 | 475.1 | (CDCl3) δ 10.25 (s, 1H), 9.26 (s, 2H), 8.64 (dd, J = 4.6, 0.7 Hz, 1H), 7.77-7.60 (m, 3H), 7.54 (d, J = 17.3 Hz, 2H), 7.21-7.08 (m, 2H), 3.11 (dd, J = 18.7, 11.4 Hz, 2H), 1.64-1.50 (m, 2H), 1.48-1.29 (m, 4H), 1.26 (t, J = 7.3 Hz, 4H), 0.97 (t, J = 7.1 Hz, 3H). |
| 48 | 440.03 | (CDCl3) δ 8.79 (d, J = 4.3 Hz, 1H), 8.04 (d, J = 8.1 Hz, 1H), 8.00 (s, 1H), 7.96 (d, J = 1.0 Hz, 1H), 7.89 (s, 1H), 7.86 (dd, J = 7.9, 1.7 Hz, 1H), 7.33 (dd, J = 6.8, 5.0 Hz, 1H), 3.44-3.37 (m, 3H), 1.78 (s, 6H), 1.32 (t, J = 7.3 Hz, 3H). |
| 49 | 435.12 | (DMSO-d6) δ 10.68 (s, 1H), 9.44-9.33 (m, 1H), 9.08-8.97 (m, 1H), 8.85 (ddd, J = 4.8, 1.7, 0.9 Hz, 1H), 8.70 (d, J = 1.5 Hz, 1H), 8.52-8.38 (m, 2H), 8.09-7.97 (m, 1H), 7.49 (ddd, J = 7.5, 4.9, 0.9 Hz, 1H), 6.87 (t, J = 5.4 Hz, 1H), 3.29-3.13 (m, 2H), 1.56 (s, 6H), 1.14 (dd, J = 9.3, 5.0 Hz, 3H). |
| 50 | 576.32 | (DMSO-d6) δ 10.88 (br s, 1H), 9.32 (s, 2H), 8.34 (d, J = 5.60 Hz, 1H), 8.31 (s, 1H), 8.06 (s, 1H), 7.71 (br s, 1H), 7.28 (br s, 1H), 6.89 (m, 1H), 5.15 (br s, 1H), 3.84-3.87 (m, 2H), 3.14-3.34 (m, 4H), 2.07-2.10 (m, 2H), 1.56 (s, 6H), 1.34-1.44 (m, 2H), 1.15 (s, 3H) and 1.11 (t, J = 7.20 Hz, 3H) |
| 51 | 576.34 | (DMSO-d6) δ 12.40 (br s, 1H), 10.67 (br s, 1H), 9.29 (s, 2H), 8.21 (s, 1H), 8.07 (s, 1H), 7.67-7.71 (m, 1H), 7.62-7.64 (m, 1H), 6.93 (m, 1H), 6.89 (m, 1H), 5.13 (s, 1H), 4.14-4.17 (m, 2H), 3.38 (m, 2H), 3.21-3.24 (m, 2H), 2.07-2.11 (m, 2H), 1.56 (s, 6H), 1.45-1.50 (m, 2H), 1.19 (s, 3H) and 1.12 (t, J = 7.20 Hz, 3H). |
| 52 | 577.38 | (DMSO-d6) δ 12.50 (br s, 1H), 10.66 (br s, 1H), 9.22 (s, 2H), 8.61 (s, 1H), 8.42 (d, J = 6.0 Hz, 1H), 8.15 (s, 1H), 6.86-6.88 (m, 2H), 5.14 (s, 1H), 4.26-4.32 (m, 2H), 3.38 (m, 2H), 3.21-3.24 (m, 2H), 2.08-2.11 (m, 2H), 1.56 (s, 6H), 1.44-1.49 (m, 2H), 1.20 (s, 3H) and 1.14 (t, J = 7.20 Hz, 3H) |
| 53 | 504.11 | (CDCl3) δ 9.16 (s, 2H), 8.64 (s, 1H), 8.00 (s, 2H), 7.84 (s, 1H), 7.24 (d, J = 3.2 Hz, 1H), 4.02 (s, 2H), 3.64-3.19 (m, 2H), 2.29 (s, 1H), 1.62 (s, 6H), 1.28 (dd, J = 14.6, 7.4 Hz, 4H), 0.56 (d, J = 5.5 Hz, 3H). |
| 54 | 590.34 | (DMSO-d6) δ 12.20 (br s, 1H), 10.55 (br s, 1H), 9.28 (s, 2H), 8.20 (d, J = 6.0 Hz, 1H), 8.06-8.11 (m, 2H), 7.36 (s, 1H), 6.89 (m, 1H), 6.55 (m, 1H), 5.15 (s, 1H), 3.50-3.52 (m, 2H), 3.15-3.24 (m, 2H), 2.50 (m, 1H), 2.03-2.10 (m, 2H), 1.86-1.94 (m, 2H), 1.56 (s, 6H), 1.29-1.38 (m, 2H) and 1.09-1.13 (m, 6H). |
| 55 | 520.25 | (DMSO-d6) δ 10.70 (br s, 1H), 9.32 (s, 2H), 8.75 (d, J = 4.40 Hz, 1H), 8.37-8.42 (m, 2H), 8.12 (s, 1H), 7.43 (d, J = 4.40 Hz, 1H), 6.87 (m, 1H), 5.30 (d, J = 5.20 Hz, 1H), 4.86 (m, 1H), 3.61-3.70 (m, 6H), 3.19 (m, 2H), 2.43-2.45 (m, 4H), 1.47 (d, J = 6.40 Hz, 3H) and 1.11 (t, J = 7.20 Hz, 3H). |
| 56 | 564.31 | (DMSO-d6) δ 10.60 (br s, 1H), 9.31 (s, 2H), 8.52 (s, 1H), 8.45 (d, J = 8.80 Hz, 1H), 8.29 (s, 1H), 8.07 (s, 1H), 7.62 (m, 1H), 6.86 (m, 1H), 5.15 (s, |

TABLE 1-continued

Compounds and characterisation data

| No. | Observed LCMS [M + H]+ | $^1$H NMR |
|---|---|---|
| | | 1H), 4.30 (t, J = 5.60 Hz, 2H), 3.59 (br s, 4H), 3.21 (m, 2H), 2.75 (t, J = 5.60 Hz, 2H), 2.45-2.50 (m, 4H), 1.56 (s, 6H) and 1.09 (t, J = 7.20 Hz, 3H). |
| 57 | 449.11 | (DMSO-d$_6$) δ = 10.58 (bs, 1H), 9.35 (s, 2H), 8.84 (ddd, J = 4.8, 1.7, 0.9 Hz, 1H), 8.54 (d, J = 8.3 Hz, 1H), 8.41 (d, J = 1.6 Hz, 1H), 8.16 (d, J = 1.3 Hz, 1H), 8.10-7.98 (m, 1H), 7.48 (ddd, J = 7.5, 4.9, 0.9 Hz, 1H), 6.92 (bt, J = 5.5 Hz, 1H), 5.15 (s, 1H), 3.18 (dd, J = 13.0, 6.7 Hz, 2H), 1.59 (s, 6H), 1.53 (dd, J = 14.2, 7.3 Hz, 2H), 0.93 (t, J = 7.4 Hz, 3H). |
| 58 | 447.1 | (DMSO-d$_6$) δ 10.61 (s, 1H), 9.32 (s, 2H), 8.83 (d, J = 4.0 Hz, 1H), 8.53 (d, J = 8.2 Hz, 1H), 8.40 (d, J = 1.1 Hz, 1H), 8.14 (s, 1H), 8.02 (td, J = 8.1, 1.7 Hz, 1H), 7.46 (dd, J = 7.0, 5.2 Hz, 1H), 6.86 (d, J = 5.3 Hz, 1H), 5.28 (d, J = 6.0 Hz, 1H), 3.38 (dd, J = 14.0, 7.0 Hz, 2H), 1.42-1.28 (m, 1H), 1.12 (t, J = 7.0 Hz, 3H), 0.54-0.46 (m, 2H), 0.46-0.33 (m, 2H). |
| 59 | 435.1 | (DMSO-d$_6$) δ 10.62 (s, 1H), 9.32 (s, 2H), 8.90-8.76 (m, 1H), 8.53 (d, J = 8.3 Hz, 1H), 8.39 (d, J = 1.5 Hz, 1H), 8.14 (d, J = 1.2 Hz, 1H), 8.02 (td, J = 7.8, 1.8 Hz, 1H), 7.46 (ddd, J = 7.5, 4.9, 0.8 Hz, 1H), 6.87 (t, J = 5.3 Hz, 1H), 5.21 (d, J = 5.9 Hz, 1H), 4.63 (dt, J = 11.7, 5.8 Hz, 1H), 3.27-3.16 (m, 2H), 1.98-1.73 (m, 2H), 1.18-1.06 (m, 3H), 0.90 (t, J = 7.4 Hz, 3H). |
| 60 | 463.1 | (DMSO-d$_6$) δ 10.62 (s, 1H), 9.33 (s, 2H), 8.83 (ddd, J = 4.8, 1.7, 0.8 Hz, 1H), 8.54 (d, J = 8.3 Hz, 1H), 8.40 (d, J = 1.6 Hz, 1H), 8.14 (d, J = 1.2 Hz, 1H), 8.08-7.95 (m, 1H), 7.46 (ddd, J = 7.5, 4.9, 0.9 Hz, 1H), 6.86 (t, J = 5.5 Hz, 1H), 5.02 (d, J = 6.7 Hz, 1H), 4.44 (d, J = 6.8 Hz, 1H), 3.26-3.18 (m, 2H), 1.12 (t, J = 7.2 Hz, 3H), 0.95 (s, 9H). |
| 69 | 548.18 | (DMSO-d$_6$) δ = 10.64 (s, 1H), 9.34 (s, 2H), 8.77 (d, J = 5.3 Hz, 1H), 8.43 (s, 1H), 8.38 (d, J = 1.6 Hz, 1H), 8.14 (d, J = 1.4 Hz, 1H), 7.44 (dd, J = 5.0, 1.0 Hz, 1H), 6.90 (t, J = 5.4 Hz, 1H), 5.30 (d, J = 5.6 Hz, 1H), 4.97-4.83 (m, 1H), 3.70-3.57 (m, 4H), 3.28-3.17 (m, 2H), 2.75 (d, J = 10.2 Hz, 2H), 1.75 (t, J = 10.7 Hz, 2H), 1.51 (d, J = 6.6 Hz, 3H), 1.14 (t, J = 7.2 Hz, 3H), 1.05 (d, J = 6.3 Hz, 6H). |
| 70 | 528.18 | (DMSO-d$_6$) δ = 10.64 (bs, 1H), 9.34 (s, 2H), 8.84-8.71 (m, 1H), 8.43 (s, 1H), 8.38 (d, J = 1.6 Hz, 1H), 8.14 (d, J = 1.4 Hz, 1H), 7.45 (dd, J = 5.1, 1.2 Hz, 1H), 6.90 (bt, J = 5.4 Hz, 1H), 5.30 (d, J = 5.6 Hz, 1H), 4.99-4.82 (m, 1H), 3.66 (s, 2H), 3.24 (tt, J = 12.9, 6.5 Hz, 2H), 1.51 (d, J = 6.6 Hz, 3H), 1.14 (t, J = 7.2 Hz, 3H). |
| 71 | 548.19 | (DMSO-d$_6$) δ = 10.64 (bs, 1H), 9.33 (s, 2H), 8.77 (d, J = 5.0 Hz, 1H), 8.43 (d, J = 13.5 Hz, 1H), 8.37 (s, 1H), 8.14 (d, J = 1.1 Hz, 1H), 7.55-7.40 (m, 1H), 6.90 (bt, J = 5.3 Hz, 1H), 5.30 (d, J = 5.6 Hz, 1H), 4.97-4.81 (m, 1H), 4.18 (d, J = 14.5 Hz, 0.5H), 3.77 (d, J = 14.5 Hz, 0.5H), 3.73-3.50 (m, 3H), 3.28-3.17 (m, 3H), 2.86-2.76 (m, 0.5H), 2.72-2.59 (m, 0.5H), 2.45-2.29 (m, 1.5H), 1.86 (dd, J = 11.4, 10.3 Hz, 0.5H), 1.51 (d, J = 6.6 Hz, 3H), 1.14 (t, J = 7.2 Hz, 3H), 1.10-0.95 (m, 6H). |
| 72 | 548.06 | (DMSO-d$_6$) δ 9.32 (s, 2H), 8.80-8.75 (m, 1H), 8.44 (brs, 1H), 8.34 (d, J = 1.6 Hz, 1H), 8.13 (d, J = 1.5 Hz, 1H), 7.48 (d, J = 5.1 Hz, 1H), 7.08 (t, J = 5.1 Hz, 1H), 4.89 (q, J = 6.6 Hz, 1H), 4.13 (d, J = 14.1 Hz, 1H), 3.83 (d, J = 14.2 Hz, 1H), 3.28-3.20 (m, 5H), 3.11-2.98 (m, 2H), 2.14 (ddd, J = 16.5, 12.3, 8.2 Hz, 2H), 1.97-1.85 (m, 2H), 1.85-1.74 (m, 3H), 1.13 (dd, J = 9.4, 5.0 Hz, 3H). |
| 73 | 532.15 | (DMSO-d$_6$) δ 10.63 (s, 1H), 9.34 (s, 2H), 8.75 (d, J = 5.5 Hz, 1H), 8.49-8.27 (m, 2H), 8.14 (d, J = 1.5 Hz, 1H), 7.36 (d, J = 5.5 Hz, 1H), 6.88 (t, J = 5.5 Hz, 1H), 5.30 (d, J = 5.6 Hz, 1H), 4.99-4.83 (m, 1H), 4.64 (s, 4H), 3.68 (s, 2H), 3.41 (s, 4H), 3.23 (dd, J = 7.2, 5.8 Hz, 2H), 1.51 (d, J = 6.6 Hz, 3H), 1.14 (t, J = 7.2 Hz, 3H). |
| 74 | 576.19 | (Acetone-d$_6$) δ 8.79 (s, 2H), 8.75 (dd, J = 5.2, 0.7 Hz, 1H), 8.49 (s, 1H), 8.22 (d, J = 1.6 Hz, 1H), 7.89 (d, J = 1.6 Hz, 1H), 7.58 (dd, J = 5.2, 1.6 Hz, 1H), 7.17 (s, 1H), 4.50-4.42 (m, 2H), 3.44-3.32 (m, 4H), 2.20-2.12 (m, 2H), 1.62 (s, 6H), 1.53-1.44 (m, 2H), 1.29 (s, 3H), 1.21 (t, J = 7.2 Hz, 3H). |
| 75 | 548.12 [M − H]− | (DMSO-d$_6$) δ 10.96 (br s, 1H), 10.73 (br s, 1H), 9.32 (s, 2H), 8.68 (d, J = 5.60 Hz, 1H), 8.35 (s, 1H), 8.15 (s, 1H), 7.93 (s, 1H), 7.13 (d, J = 5.60 Hz, 1H), 7.00 (br s, 1H), 4.87 (m, 1H), 4.69 (m, 2H), 3.81 (m, 3H), 3.64 (m, 2H), 3.54-3.57 (m, 2H), 3.19-3.24 (m, 5H), 1.47 (t, J = 6.40 Hz, 3H) and 1.11 (t, J = 7.20 Hz, 3H). |
| 76 | 518.09 [M − H]− | (DMSO-d$_6$) δ 10.62 (br s, 1H), 9.32 (s, 2H), 8.73 (d, J = 4.40 Hz, 1H), 8.37-8.39 (m, 2H), 8.13 (s, 1H), 7.36 (d, J = 4.40 Hz, 1H), 6.85 (m, 1H), 5.30 (d, J = 5.60 Hz, 1H), 4.86-4.91 (m, 1H), 4.02 (m, 1H), 3.76 (br s, 2H), 3.59 (m, 2H), 3.21 (m, 2H), 3.15 (s, 3H), 2.95 (m, 2H), 1.48 (d, J = 6.40 Hz, 3H) and 1.09 (t, J = 7.20 Hz, 3H). |
| 77 | 518.11 [M − H]− | (DMSO-d$_6$) δ 10.63 (br s, 1H), 9.32 (s, 2H), 8.74 (d, J = 4.80 Hz, 1H), 8.42 (s, 1H), 8.37 (s, 1H), 8.12 (s, 1H), 7.41 (d, J = 4.80 Hz, 1H), 6.88 (m, 1H), 5.30 (d, J = 5.20 Hz, 1H), 4.85-4.89 (m, 1H), 4.74 (d, J = 4.40 Hz, 1H), 4.22 (m, 1H), 3.68-3.72 (m, 2H), 3.38 (m, 1H), 3.20-3.23 (m, 2H), 2.67-2.72 (m, 2H), 2.38-2.41 (m, 1H), 1.98-2.05 (m, 1H), 1.55-1.61 (m, 1H), 1.47 (d, J = 6.80 Hz, 3H) and 1.09 (t, J = 7.20 Hz, 3H). |
| 78 | 509.1 | (DMSO-d$_6$) δ 10.63 (br s, 1H), 9.21 (s, 2H), 8.61 (s, 1H), 8.26 (d, J = 5.20 Hz, 1H), 8.20 (s, 1H), 7.82 (m, 1H), 6.84 (m, 1H), 6.55 (d, J = 5.60 Hz, |

TABLE 1-continued

Compounds and characterisation data

| No. | Observed LCMS [M + H]+ | 1H NMR |
|---|---|---|
| | | 1H), 5.17 (s, 1H), 3.78 (m, 2H), 3.63 (m, 2H), 3.38 (s, 3H), 3.20 (m, 2H), 1.55 (s, 6H) and 1.11 (t, J = 7.20 Hz, 3H) |
| 79 | 548.19 | (DMSO-$d_6$ + $D_2O$): δ 9.32 (s, 2H), 8.68 (s, 1H), 8.56 (d, J = 6.80 Hz, 1H), 8.30 (s, 1H), 7.18 (d, J = 6.80 Hz, 1H), 3.67 (m, 4H), 3.18-3.22 (m, 6H), 2.34 (m, 2H), 1.55 (s, 6H), 1.29 (t, J = 7.20 Hz, 3H) and 1.09 (t, J = 7.20 Hz, 3H) |
| 80 | 509.16 | (DMSO-$d_6$ + $D_2O$): δ 9.31 (s, 2H), 8.65 (d, J = 5.20 Hz, 1H), 8.21-8.24 (m, 1H), 8.15 (s, 1H), 7.96 (s, 1H), 7.23 (m, 1H), 4.36-4.45 (m, 2H), 3.74 (m, 2H), 3.36 (s, 3H), 3.14-3.18 (m, 2H), 1.55 (s, 6H) and 1.10 (t, J = 7.20 Hz, 3H). |
| 81 | 506.12 | (DMSO-$d_6$) δ 10.63 (bs, 1H), 9.35 (s, 2H), 8.85 (dd, J = 4.8, 0.8 Hz, 1H), 8.55 (d, J = 8.3 Hz, 1H), 8.42 (d, J = 1.5 Hz, 1H), 8.16 (d, J = 1.4 Hz, 1H), 8.04 (td, J = 7.9, 1.8 Hz, 1H), 7.56-7.41 (m, 1H), 6.88 (bs, 1H), 5.33 (d, J = 5.8 Hz, 1H), 4.93 (dd, J = 12.8, 5.7 Hz, 1H), 3.55 (t, J = 4.6 Hz, 4H), 3.29-3.18 (m, 2H), 2.88 (dd, J = 12.6, 5.5 Hz, 1H), 2.79-2.69 (m, 1H), 2.59-2.53 (m, 2H), 2.50-2.42 (m, 2H), 1.14 (t, J = 7.2 Hz, 3H). |
| 82 | 421.06 | (DMSO-$d_6$) δ 10.97 (bs, 1H), 9.34 (s, 2H), 8.85 (ddd, J = 4.8, 1.7, 0.9 Hz, 1H), 8.54 (d, J = 8.3 Hz, 1H), 8.40 (d, J = 1.6 Hz, 1H), 8.15 (d, J = 1.6 Hz, 1H), 8.08-7.97 (m, 1H), 7.48 (ddd, J = 7.5, 4.9, 0.9 Hz, 1H), 7.06 (bd, J = 4.3 Hz, 1H), 5.15 (s, 1H), 2.77 (d, J = 4.6 Hz, 3H), 1.59 (s, 6H). |
| 83 | 407.07 | (DMSO-$d_6$) δ 10.75 (bs, 1H), 9.34 (s, 2H), 8.91-8.79 (m, 1H), 8.54 (d, J = 8.3 Hz, 1H), 8.40 (d, J = 1.5 Hz, 1H), 8.15 (s, 1H), 8.09-7.95 (m, 1H), 7.48 (ddd, J = 7.5, 4.9, 0.8 Hz, 1H), 6.80 (d, J = 3.7 Hz, 1H), 5.30 (d, J = 5.6 Hz, 1H), 4.99-4.78 (m, 1H), 2.78 (d, J = 4.5 Hz, 3H), 1.50 (d, J = 6.6 Hz, 3H). |
| 84 | 534.13 | (DMSO-$d_6$) δ 10.66 (br s, 1H), 9.32 (s, 2H), 8.74 (d, J = 4.80 Hz, 1H), 8.43 (br s, 1H), 8.37 (s, 1H), 8.13 (s, 1H), 7.44 (m, 1H), 6.92 (m, 1H), 5.30 (d, J = 5.20 Hz, 1H), 4.86 (m, 1H), 4.62 (br s, 1H), 3.76 (br s, 2H), 3.33 (m, 2H), 3.20 (m, 2H), 2.59-2.75 (m, 2H), 1.76 (m, 2H), 1.47 (d, J = 6.40 Hz, 3H), 1.25 (s, 3H) and 1.09 (t, J = 6.80 Hz, 3H). |
| 85 | 495.19 | (DMSO-$d_6$) δ 10.64 (br s, 1H), 9.21 (s, 2H), 8.61 (s, 1H), 8.24 (m, 1H), 8.15 (s, 1H), 7.76 (m, 1H), 6.86 (m, 1H), 6.54 (d, J = 6.0 Hz, 1H), 5.15 (s, 1H), 4.74 (m, 1H), 3.29 (m, 4H), 3.21 (m, 2H), 1.56 (s, 6H) and 1.11 (t, J = 7.20 Hz, 3H) |
| 86 | 521.26 | (DMSO-$d_6$) δ 10.62 (br s, 1H), 9.21 (s, 2H), 8.61 (s, 1H), 8.40 (d, J = 6.0 Hz, 1H), 8.19 (s, 1H), 6.91 (br s, 1H), 6.43 (d, J = 6.0 Hz, 1H), 5.84 (s, 1H), 5.15 (s, 1H), 4.10 (br s, 4H), 3.21 (m, 2H), 1.56 (s, 6H), 1.49 (s, 3H) and 1.12 (t, J = 7.20 Hz, 3H) |
| 87 | 575.23 [M − H]− | (DMSO-$d_6$) δ 12.54 (br s, 1H), 10.72 (br s, 1H), 9.33 (s, 2H), 8.71 (s, 1H), 8.43 (s, 1H), 8.15 (s, 1H), 7.69 (s, 1H), 6.99 (m, 1H), 5.15 (br s, 1H), 4.26-4.28 (m, 2H), 3.38 (m, 2H), 3.20 (m, 2H), 2.04-2.11 (m, 2H), 1.57 (s, 6H), 1.40-1.45 (m, 2H), 1.22 (s, 3H) and 1.11 (t, J = 7.20 Hz, 3H) |
| 88 | 562.18 | (Acetone-$d_6$) δ 8.80 (s, 2H), 8.76 (dd, J = 5.0, 0.6 Hz, 1H), 8.40 (s, 1H), 8.22 (d, J = 1.6 Hz, 1H), 7.90 (d, J = 1.6 Hz, 1H), 7.47 (dd, J = 5.1, 0.9 Hz, 1H), 5.02 (q, J = 6.5 Hz, 1H), 4.50-4.42 (m, 2H), 3.43-3.33 (m, 4H), 2.19-2.13 (m, 2H), 1.54-1.44 (m, 5H), 1.29 (s, 3H), 1.21 (t, J = 7.2 Hz, 3H). |
| 89 | 560.9 | ($CDCl_3$) δ 9.84 (br s, 1H), 9.06 (s, 2H), 8.56 (d, J = 4.2 Hz, 1H), 7.91 (dd, J = 11.7, 4.5 Hz, 2H), 7.83-7.67 (m, 2H), 7.55 (d, J = 12.7 Hz, 1H), 7.15 (dd, J = 7.1, 5.0 Hz, 1H), 3.72 (m, 2H), 3.59-3.40 (m, 4H), 2.47 (s, 4H), 2.36 (s, 3H), 1.90 (s, 6H), 1.31 (t, J = 7.2 Hz, 3H). |
| 90 | 435.16 [M − H]− | (DMSO-$d_6$) δ 10.85 (br s, 1H), 10.61 (br s, 1H), 9.30 (s, 2H), 8.50 (m, 1H), 8.34 (s, 1H), 8.09 (s, 1H), 7.80 (s, 1H), 6.87 (m, 2H), 5.31 (d, J = 5.60 Hz, 1H), 4.88 (m, 1H), 3.21 (m, 2H), 1.47 (d, J = 6.40 Hz, 3H) and 1.11 (t, J = 7.20 Hz, 3H) |
| 91 | 564.24 | (DMSO-$d_6$ + $D_2O$): δ 9.25 (s, 2H), 8.55 (s, 1H), 8.24 (s, 2H), 6.80 (s, 1H), 4.09 (s, 2H), 3.91 (br s, 2H), 3.76 (br s, 2H), 3.58 (br s, 4H), 3.16-3.24 (m, 4H), 1.54 (s, 6H) and 1.08 (t, J = 7.20 Hz, 3H) |
| 92 | 495.27 | (DMSO-$d_6$) δ 10.59 (br s, 1H), 9.33 (s, 2H), 8.61 (m, 1H), 8.40 (s, 1H), 8.12 (s, 1H), 8.05 (s, 1H), 7.05 (d, J = 5.20 Hz, 1H), 6.86 (m, 1H), 5.30 (d, J = 5.20 Hz, 1H), 4.87 (m, 1H), 4.36 (m, 2H), 3.73 (m, 2H), 3.33 (s, 3H), 3.21 (m, 2H), 1.49 (d, J = 6.40 Hz, 3H) and 1.11 (t, J = 7.20 Hz, 3H). |
| 93 | 507.17 | (DMSO-$d_6$) δ 10.62 (br s, 1H), 9.20 (s, 2H), 8.60 (s, 1H), 8.42 (d, J = 6.0 Hz, 1H), 8.16 (s, 1H), 6.85 (m, 1H), 6.44 (d, J = 5.60 Hz, 1H), 5.33 (d, J = 5.60 Hz, 1H), 4.86 (t, J = 6.40 Hz, 1H), 4.45 (m, 3H), 4.04 (br s, 2H), 3.30 (s, 3H), 3.22 (m, 2H), 1.48 (d, J = 6.40 Hz, 3H) and 1.11 (t, J = 7.20 Hz, 3H) |
| 94 | 507.27 | (DMSO-$d_6$) δ 10.65 (br s, 1H), 9.22 (s, 2H), 8.61 (s, 1H), 8.48 (d, J = 6.0 Hz, 1H), 8.16 (s, 1H), 6.85-6.88 (m, 2H), 5.31 (d, J = 5.60 Hz, 1H), 4.88 (m, 1H), 3.75-3.81 (m, 8H), 3.22 (m, 2H), 1.48 (d, J = 6.80 Hz, 3H) and 1.11 (t, J = 7.20 Hz, 3H) |
| 95 | 420.28 | (DMSO-$d_6$) δ 10.61 (br s, 1H), 8.99 (s, 1H), 8.81 (m, 1H), 8.51 (d, J = 8.0 Hz, 1H), 8.30 (m, 2H), 7.98-8.02 (m, 2H), 7.62 (m, 1H), 7.45 (m, 1H), 6.86 (m, 1H), 5.45 (d, J = 4.40 Hz, 1H), 4.81 (q, J = 5.60 Hz, 1H), 3.21 (m, 2H), 1.43 (d, J = 6.40 Hz, 3H) and 1.11 (t, J = 7.20 Hz, 3H) |

TABLE 1-continued

Compounds and characterisation data

| No. | Observed LCMS [M + H]+ | 1H NMR |
|---|---|---|
| 96 | 474.2 | (DMSO-d6) δ 10.63 (br s, 1H), 9.11 (s, 1H), 8.83 (m, 1H), 8.53 (d, J = 8.0 Hz, 1H), 8.42 (m, 1H), 8.35 (s, 1H), 8.07 (s, 1H), 8.0 (m, 1H), 7.75 (d, J = 8.0 Hz, 1H), 7.44 (m, 1H), 7.10 (m, 1H), 6.85 (br s, 1H), 5.22 (m, 1H), 3.21 (m, 2H) and 1.11 (t, J = 6.8 Hz, 3H) |
| 97 | 577.37 | (DMSO-d6) δ 12.53 (br s, 1H), 10.67 (br s, 1H), 9.23 (s, 2H), 8.62 (s, 1H), 8.42 (br s, 1H), 8.16 (s, 1H), 6.88 (m, 2H), 5.16 (br s, 1H), 4.32 (m, 2H), 3.37 (m, 2H), 3.22 (m, 2H), 2.07-2.11 (m, 2H), 1.56 (s, 6H), 1.44-1.49 (m, 2H), 1.20 (s, 3H) and 1.12 (t, J = 7.20 Hz, 3H) |
| 98 | 463.11 | (DMSO-d6) δ 10.64 (br s, 1H), 9.37 (s, 2H), 8.83 (br d, J = 3.9 Hz, 1H), 8.54 (d, J = 8.3 Hz, 1H), 8.42 (d, J = 1.5 Hz, 1H), 8.16 (s, 1H), 8.02 (td, J = 7.9, 1.8 Hz, 1H), 7.46 (dd, J = 7.1, 5.2 Hz, 1H), 6.85 (t, J = 5.4 Hz, 1H), 4.89 (s, 1H), |
| 99 | 576.22 | (Acetone-d6) δ 8.79 (s, 2H), 8.75 (dd, J = 5.2, 0.7 Hz, 1H), 8.49 (s, 1H), 8.22 (d, J = 1.6 Hz, 1H), 7.89 (d, J = 1.6 Hz, 1H), 7.58 (dd, J = 5.2, 1.6 Hz, 1H), 4.46 (dt, J = 13.8, 4.2 Hz, 2H), 3.43-3.33 (m, 4H), 2.20-2.13 (m, 2H), 1.62 (s, 6H), 1.53-1.44 (m, 2H), 1.29 (s, 3H), 1.21 (t, J = 7.2 Hz, 3H). |
| 100 | 571.08 | (DMSO-d6) δ 10.62 (s, 1H), 9.39 (s, 2H), 8.92-8.76 (m, 1H), 8.55 (d, J = 8.3 Hz, 1H), 8.42 (d, J = 1.5 Hz, 1H), 8.17 (d, J = 1.1 Hz, 1H), 8.04 (td, J = 7.8, 1.8 Hz, 1H), 7.48 (ddd, J = 7.4, 4.9, 0.8 Hz, 1H), 6.87 (t, J = 5.4 Hz, 1H), 5.30 (s, 1H), 3.84 (td, J = 11.0, 2.2 Hz, 2H), 3.79-3.69 (m, 2H), 3.29-3.18 (m, 2H), 2.33-2.21 (m, 2H), 1.78 (d, J = 12.1 Hz, 2H), 1.14 (t, J = 7.2 Hz, 3H). |
| 101 | 535.21 | (DMSO-d6) δ 11.51 (br s, 1H), 10.96 (br s, 1H), 9.37 (s, 2H), 9.17 (d, J = 4.80 Hz, 1H), 8.97 (s, 1H), 8.30 (s, 1H), 7.74 (d, J = 4.80 Hz, 1H), 7.14 (m, 1H), 4.75 (s, 2H), 4.00 (br s, 4H), 3.62-3.64 (m, 2H), 3.35 (br s, 2H), 3.21 (m, 2H), 1.57 (s, 6H) and 1.11 (t, J = 7.20 Hz, 3H). |
| 102 | 535.22 | (DMSO-d6 + D2O): δ 9.77 (s, 1H), 9.34 (s, 2H), 8.88 (s, 1H), 8.53 (s, 1H), 8.21 (s, 1H), 4.68 (s, 2H), 4.03 (br s, 2H), 3.85 (br s, 2H), 3.60 (br s, 2H), 3.49 (br s, 2H), 3.20 (m, 2H), 1.55 (s, 6H) and 1.09 (t, J = 7.20 Hz, 3H) |
| 103 | 523.24 | (DMSO-d6) δ 10.64 (br s, 1H), 9.21 (s, 2H), 8.62 (s, 1H), 8.24 (d, J = 5.60 Hz, 1H), 8.14 (s, 1H), 7.57 (m, 1H), 6.81 (m, 1H), 6.65 (d, J = 6.0 Hz, 1H), 5.17 (s, 1H), 4.53 (s, 1H), 3.67 (d, J = 5.20 Hz, 1H), 3.36 (m, 1H), 3.20 (m, 2H), 1.55 (s, 6H), 1.23 (s, 6H) and 1.11 (t, J = 7.20 Hz, 3H) |
| 104 | 521.2 | (DMSO-d6) δ 10.64 (br s, 1H), 9.33 (s, 2H), 8.60 (d, J = 5.60 Hz, 1H), 8.38 (s, 1H), 8.12 (s, 1H), 8.03 (s, 1H), 7.05 (m, 1H), 6.95 (m, 1H), 4.84-4.89 (m, 1H), 4.18-4.24 (m, 3H), 3.79-3.84 (m, 2H), 3.67-3.73 (m, 1H), 3.19-3.27 (m, 2H), 2.01-2.13 (m, 1H), 1.85-1.93 (m, 2H), 1.70-1.73 (m, 1H), 1.49 (d, J = 6.40 Hz, 3H) and 1.11 (t, J = 7.20 Hz, 3H). |
| 105 | 493.15 | (DMSO-d6) δ 10.61 (br s, 1H), 9.20 (s, 2H), 8.61 (s, 1H), 8.40 (d, J = 6.0 Hz, 1H), 8.16 (s, 1H), 6.83 (m, 1H), 6.42 (d, J = 6.0 Hz, 1H), 5.90 (d, J = 6.80 Hz, 1H), 5.32 (d, J = 5.60 Hz, 1H), 4.88 (m, 1H), 4.70 (m, 1H), 4.52 (br s, 2H), 4.09 (br s, 2H), 3.21 (m, 2H), 1.48 (d, J = 6.40 Hz, 3H) and 1.11 (t, J = 7.20 Hz, 3H) |
| 106 | 525.22 | (DMSO-d6) δ 10.67 (br s, 1H), 9.21 (s, 2H), 8.52-8.54 (m, 2H), 8.16 (s, 1H), 6.82 (m, 1H), 5.30 (d, J = 5.60 Hz, 1H), 4.86 (m, 1H), 3.86 (m, 4H), 3.80 (m, 4H), 3.20 (m, 2H), 1.48 (d, J = 6.40 Hz, 3H) and 1.11 (t, J = 7.20 Hz, 3H) |
| 107 | 578.28 | (DMSO-d6 + D2O): δ 9.29 (s, 2H), 8.59 (s, 1H), 8.52 (d, J = 6.40 Hz, 1H), 8.22 (s, 1H), 7.06 (d, J = 6.80 Hz, 1H), 3.56-3.79 (m, 8H), 3.37 (m, 2H), 3.33 (s, 3H), 3.21 (m, 2H), 2.50 (m, 2H), 1.54 (s, 6H) and 1.09 (t, J = 7.20 Hz, 3H) |
| 108 | 573.21 | (DMSO-d6) δ 10.62 (br s, 1H), 9.11 (s, 1H), 8.76 (d, J = 4.80 Hz, 1H), 8.41 (m, 2H), 8.33 (s, 1H), 8.06 (s, 1H), 7.76 (d, J = 8.0 Hz, 1H), 7.44 (m, 1H), 7.10 (m, 1H), 6.85 (m, 1H), 5.22 (m, 1H), 3.64 (s, 2H), 3.61 (m, 4H), 3.21 (m, 2H), 2.43 (m, 4H) and 1.11 (t, J = 6.8 Hz, 3H) |
| 109 | 563.25 | (DMSO-d6) δ 10.97 (br s, 1H), 9.38 (s, 2H), 8.69 (br s, 1H), 8.41 (s, 1H), 8.14 (s, 1H), 7.66 (br s, 1H), 7.22 (m, 1H), 5.29 (m, 1H), 4.88 (m, 1H), 4.28 (m, 2H), 3.20 (m, 2H), 2.06 (m, 2H), 1.48 (d, J = 6.40 Hz, 3H), 1.33 (m, 2H), 1.22 (m, 2H) and 1.09-1.12 (m, 6H) |
| 110 | 562.22 | (DMSO-d6) δ 12.29 (br s, 1H), 10.55 (br s, 1H), 9.32 (s, 2H), 8.37 (d, J = 6.0 Hz, 1H), 8.32 (s, 1H), 8.06 (s, 1H), 7.74 (br s, 1H), 6.91 (m, 2H), 5.14 (br s, 1H), 4.08-4.11 (m, 2H), 3.16-3.22 (m, 2H), 3.02-3.07 (m, 2H), 2.55 (m, 1H), 1.91-1.94 (m, 2H), 1.60-1.62 (m, 2H), 1.57 (s, 6H) and 1.11 (t, J = 7.20 Hz, 3H) |
| 111 | 477.09 | (DMSO-d6) δ 10.62 (s, 1H), 9.39 (s, 2H), 8.92-8.76 (m, 1H), 8.55 (d, J = 8.3 Hz, 1H), 8.42 (d, J = 1.5 Hz, 1H), 8.17 (d, J = 1.1 Hz, 1H), 8.04 (td, J = 7.8, 1.8 Hz, 1H), 7.48 (ddd, J = 7.4, 4.9, 0.8 Hz, 1H), 6.87 (t, J = 5.4 Hz, 1H), 5.30 (s, 1H), 3.84 (td, J = 11.0, 2.2 Hz, 2H), 3.79-3.69 (m, 2H), 3.29-3.18 (m, 2H), 2.33-2.21 (m, 2H), 1.78 (d, J = 12.1 Hz, 2H), 1.14 (t, J = 7.2 Hz, 3H). |
| 112 | 560.17 | (DMSO-d6) δ 10.62 (s, 1H), 9.33 (s, 2H), 8.76 (d, J = 5.0 Hz, 1H), 8.44-8.32 (m, 2H), 8.14 (s, 1H), 7.42 (d, J = 4.9 Hz, 1H), 6.88 (t, J = 5.3 Hz, 1H), 5.30 (d, J = 5.6 Hz, 1H), 4.89 (p, J = 6.5 Hz, 1H), 4.28 (d, J = 5.6 |

TABLE 1-continued

Compounds and characterisation data

| No. | Observed LCMS [M + H]⁺ | ¹H NMR |
|---|---|---|
| | | 4H), 3.60 (s, 2H), 3.24 (dt, J = 14.0, 7.0 Hz, 2H), 2.34 (s, 4H), 1.83 (d, J = 4.9 Hz, 4H), 1.50 (d, J = 6.6 Hz, 3H), 1.14 (t, J = 7.2 Hz, 3H). |
| 113 | 449.05 | (DMSO-$d_6$) δ 10.63 (s, 1H), 9.45 (s, 2H), 8.89-8.80 (ddd, J = 4.8, 1.7, 0.6 Hz 1H), 8.55 (d, J = 8.0 Hz, 1H), 8.44 (d, J = 1.4 Hz, 1H), 8.20 (d, J = 1.4 Hz, 1H), 8.04 (td, J = 8.0, 1.7 Hz, 1H), 7.56-7.44 (ddd, J = 12.2, 4.8, 0.6 Hz, 1H), 6.87 (t, J = 5.2 Hz, 1H), 6.42 (s, 1H), 5.08 (d, J = 6.7 Hz, 2H), 4.77 (d, J = 6.7 Hz, 2H), 3.28-3.20 (m, 2H), 1.14 (t, J = 7.2 Hz, 3H). |
| 114 | 546.21 [M − H]⁻ | (DMSO-$d_6$) δ 10.61 (br s, 1H), 9.33 (s, 2H), 8.73 (m, 1H), 8.38 (d, J = 6.40 Hz, 2H), 8.13 (s, 1H), 7.37 (m, 1H), 6.85 (m, 1H), 5.15 (s, 1H), 3.75 (s, 2H), 3.18-3.23 (m, 4H), 3.10 (s, 3H), 3.06 (m, 2H), 1.57 (s, 6H), 1.40 (s, 3H) and 1.09 (t, J = 7.20 Hz, 3H). |
| 115 | 422.2 | (DMSO-$d_6$) δ 10.74 (br s, 1H), 9.23 (s, 2H), 9.09 (d, J = 4.80 Hz, 2H), 8.71 (s, 1H), 8.23 (s, 1H), 7.57 (t, J = 4.80 Hz, 1H), 6.86 (m, 1H), 5.33 (d, J = 5.60 Hz, 1H), 4.87 (m, 1H), 3.22 (m, 2H), 1.48 (d, J = 6.40 Hz, 3H) and 1.12 (t, J = 7.20 Hz, 3H) |
| 116 | 603.3 | (DMSO-$d_6$) δ 10.64 (br s, 1H), 9.11 (s, 1H), 8.74 (d, J = 4.0 Hz, 1H), 8.42 (m, 2H), 8.38 (s, 1H), 8.06 (m, 1H), 7.76 (d, J = 7.6 Hz, 1H), 7.36 (m, 1H), 7.12 (m, 1H), 6.86 (m, 1H), 5.22 (m, 1H), 4.02 (m, 1H), 3.76 (s, 2H), 3.58 (br s, 2H), 3.21 (m, 2H), 3.15 (s, 3H), 2.95 (br s, 2H) and 1.11 (t, J = 7.20 Hz, 3H) |
| 117 | 563.31 | (DMSO-$d_6$) δ 12.70 (br s, 1H), 10.92 (br s, 1H), 9.35 (s, 2H), 8.72 (br s, 1H), 8.45 (m, 1H), 8.35 (s, 1H), 7.12 (m, 1H), 7.02 (m, 1H), 4.88 (m, 1H), 3.54 (m, 2H), 3.22 (m, 2H), 2.53 (m, 3H), 2.20 (m, 2H), 1.57 (m, 2H), 1.49 (d, J = 6.40 Hz, 3H), 1.24 (s, 3H) and 1.12 (t, J = 7.20 Hz, 3H) |
| 118 | 451.1 | (DMSO-$d_6$) δ 10.62 (s, 1H), 9.33 (s, 2H), 8.83 (d, J = 4.2 Hz, 1H), 8.53 (d, J = 8.0 Hz, 1H), 8.39 (s, 1H), 8.14 (s, 1H), 8.02 (t, J = 7.6 Hz, 1H), 7.54-7.40 (m, 1H), 6.80 (d, J = 54.2 Hz, 1H), 5.06 (d, J = 6.5 Hz, 1H), 4.54 (d, J = 5.6 Hz, 1H), 4.49 (t, J = 5.7 Hz, 1H), 4.09 (dd, J = 11.5, 5.6 Hz, 1H), 3.28-3.16 (m, 2H), 1.12 (t, J = 7.1 Hz, 3H), 1.07 (d, J = 6.3 Hz, 3H). |
| 119 | 461.12 | (DMSO-$d_6$) δ 10.61 (s, 1H), 9.32 (s, 2H), 8.83 (d, J = 4.1 Hz, 1H), 8.52 (d, J = 8.2 Hz, 1H), 8.39 (d, J = 1.4 Hz, 1H), 8.14 (s, 1H), 8.02 (td, J = 7.9, 1.7 Hz, 1H), 7.46 (dd, J = 7.2, 5.1 Hz, 1H), 6.87 (t, J = 5.4 Hz, 1H), 5.08 (s, 1H), 3.26 |
| 120 | 535.22 | (DMSO-$d_6$) δ 10.72 (br s, 1H), 9.24 (s, 2H), 8.99 (s, 2H), 8.69 (s, 1H), 8.22 (s, 1H), 6.83 (m, 1H), 5.16 (s, 1H), 3.60-3.63 (m, 6H), 3.22 (m, 2H), 2.44 (br s, 4H), 1.56 (s, 6H) and 1.10 (t, J = 7.20 Hz, 3H). |
| 121 | 520.13 | (DMSO-$d_6$) δ 10.62 (s, 1H), 9.32 (s, 2H), 8.76 (d, J = 5.2 Hz, 1H), 8.42 (s, 1H), 8.36 (d, J = 1.6 Hz, 1H), 8.12 (d, J = 1.4 Hz, 1H), 7.44 (dd, J = 5.1, 1.0 Hz, 1H), 6.89 (t, J = 5.3 Hz, 1H), 5.28 (d, J = 5.6 Hz, 1H), 4.94-4.82 (m, 1H), 3.65 (s, 2H), 3.64-3.58 (m, 4H), 3.29-3.14 (m, 2H), 2.47-2.41 (m, 4H), 1.49 (d, J = 6.6 Hz, 3H), 1.12 (t, J = 7.2 Hz, 3H). |
| 122 | 520.13 | (DMSO-$d_6$) δ 10.64 (s, 1H), 9.32 (s, 2H), 8.76 (d, J = 4.9 Hz, 1H), 8.42 (s, 1H), 8.36 (d, J = 1.6 Hz, 1H), 8.12 (d, J = 1.5 Hz, 1H), 7.44 (dd, J = 5.1, 1.0 Hz, 1H), 6.92 (s, 1H), 5.28 (d, J = 5.6 Hz, 1H), 4.88 (p, J = 6.5 Hz, 1H), 3.65 (s, 2H), 3.64-3.59 (m, 4H), 3.21 (dt, J = 12.8, 6.5 Hz, 2H), 2.47-2.40 (m, 4H), 1.49 (d, J = 6.6 Hz, 3H), 1.12 (t, J = 7.2 Hz, 3H). |
| 123 | 549.09 | (DMSO-$d_6$) δ 10.67 (s, 1H), 9.43 (s, 2H), 8.85 (dd, J = 5.0, 0.9 Hz, 1H), 8.56 (d, J = 8.1 Hz, 1H), 8.44 (d, J = 1.4 Hz, 1H), 8.19 (d, J = 1.4 Hz, 1H), 8.04 (td, J = 8.1, 1.8 Hz, 1H), 7.48 (dd, J = 7.0, 5.0 Hz, 1H), 6.88 (s, 1H), 5.14 (d, J = 7.4 Hz, 2H), 4.93 (d, J = 7.4 Hz, 2H), 3.24 (m, 2H), 2.75 (t, J = 6.7 Hz, 2H), 2.57 (t, J = 6.7 Hz, 2H), 1.14 (t, J = 7.2 Hz, 3H). |
| 124 | 551.12 | (DMSO-$d_6$) δ 12.18 (s, 1H), 10.64 (s, 1H), 9.38 (s, 2H), 8.85 (ddd, J = 4.9, 1.7, 0.9 Hz, 1H), 8.55 (d, J = 8.4 Hz, 1H), 8.43 (d, J = 1.6 Hz, 1H), 8.18 (d, J = 1.6 Hz, 1H), 8.10-7.97 (m, 1H), 7.48 (ddd, J = 7.5, 4.9, 0.9 Hz, 1H), 6.88 (t, J = 5.2 Hz, 1H), 5.47 (s, 1H), 4.50 (d, J = 10.6 Hz, 1H), 4.37 (d, J = 10.6 Hz, 1H), 3.23 (m, 2H), 2.50-2.38 (m, 4H), 1.58 (s, 3H), 1.14 (t, J = 7.2 Hz, 3H). |
| 125 | 576.18 | (DMSO-$d_6$) δ 10.60 (s, 1H), 9.39 (s, 2H), 8.78 (d, J = 4.9 Hz, 1H), 8.45 (s, 1H), 8.41 (d, J = 1.6 Hz, 1H), 8.16 (d, J = 1.2 Hz, 1H), 7.46 (dd, J = 5.1, 1.0 Hz, 1H), 6.87 (t, J = 5.4 Hz, 1H), 5.30 (s, 1H), 3.84 (td, J = 11.0, 2.2 Hz, 2H), 3.77-3.70 (m, 2H), 3.66 (s, 2H), 3.65-3.60 (m, 4H), 3.24 (dd, J = 7.1, 5.8 Hz, 2H), 2.49-2.41 (m, 4H), 2.29 (td, J = 13.6, 4.8 Hz, 2H), 1.79 (d, J = 12.2 Hz, 2H), 1.14 (t, J = 7.2 Hz, 3H). |
| 126 | 478.02 | (DMSO-$d_6$) δ 9.38 (s, 2H), 8.84 (d, J = 3.7 Hz, 1H), 8.59-8.43 (m, 4H), 8.39 (s, 1H), 8.16 (s, 1H), 8.04 (t, J = 7.4 Hz, 1H), 7.54-7.42 (m, 1H), 7.34 (brs, 1H), 6.08-5.92 (m, 1H), 4.01-3.86 (m, 2H), 3.27-3.18 (m, 2H), 1.70 (d, J = 6.6 Hz, 3H), 1.13 (t, J = 7.1 Hz, 3H). |
| 127 | 493.11 | (DMSO-$d_6$) δ 10.62 (s, 1H), 9.37 (s, 2H), 8.83 (d, J = 4.0 Hz, 1H), 8.53 (d, J = 8.3 Hz, 1H), 8.40 (d, J = 1.5 Hz, 1H), 8.15 (br s, 1H), 8.02 (td, J = 7.9, 1.8 Hz, 1H), 7.47 (dd, J = 7.1, 5.2 Hz, 1H), 6.87 (t, J = 5.4 Hz, 1H), 5.23 (s, 1H), 3.28-3.18 (m, 2H), 3.14-2.97 (m, 2H), 2.55-2.51 (m, 2H), 2.36-2.25 (m, 2H), 2.09-1.99 (m, 2H), 1.12 (t, J = 7.2 Hz, 3H). |
| 128 | 490.1 | (DMSO-$d_6$) δ 10.71 (br s, 1H), 9.38 (s, 2H), 8.87-8.83 (m, 1H), 8.55 (m, J = 8.4 Hz, 1H), 8.42 (d, J = 1.6 Hz, 1H), 8.23 (br s, 1H), 8.17 (d, J = 1.6 Hz, |

TABLE 1-continued

Compounds and characterisation data

| No. | Observed LCMS [M + H]+ | 1H NMR |
|---|---|---|
| | | 1H), 8.06-8.01 (m, 1H), 7.48 (ddd, J = 7.5, 4.9, 0.9 Hz, 1H), 6.96 (t, J = 5.5 Hz, 1H), 5.21 (s, 1H), 3.28-3.16 (m, 4H), 2.71-2.61 (m, 2H), 2.36-2.23 (m, 5H), 1.83 (br d, J = 12.3 Hz, 2H), 1.14 (t, J = 7.2 Hz, 3H). |
| 129 | 535.11 | (DMSO-$d_6$) δ 10.80 (br s, 1H), 9.60 (br s, 2H), 9.36 (s, 2H), 8.85 (d, J = 4.7 Hz, 1H), 8.54 (d, J = 7.8 Hz, 1H), 8.40 (s, 1H), 8.26 (br s, 3H), 8.16 (s, 1H), 8.04 (t, J = 7.8 Hz, 1H), 7.49 (dd, J = 7.0, 4.7 Hz, 1H), 7.11 (br s, 1H), 4.19 (s, 2H), 3.29-3.16 (m, 6H), 1.87 (s, 6H), 1.13 (t, J = 7.1 Hz, 3H). |
| 130 | 487.1 | (CDCl$_3$) δ 8.98 (s, 2H), 8.63 (d, J = 23.2 Hz, 1H), 8.01-7.64 (m, 4H), 7.24-7.19 (m, 1H), 6.14-5.66 (m, 1H), 4.92 (d, J = 55.8 Hz, 1H), 4.29-4.10 (m, 1H), 3.29-3.23 (m, 2H), 1.11 (t, J = 6.7 Hz, 3H). |
| 131 | 505.1 | (CDCl$_3$) δ 9.08 (s, 2H), 8.78 (d, J = 4.4 Hz, 1H), 8.07-7.76 (m, 4H), 7.34-7.27 (m, 1H), 5.20 (s, 1H), 4.67 (d, J = 7.1 Hz, 1H), 3.48-3.36 (m, 2H), 1.26 (t, J = 7.2 Hz, 3H). |
| 132 | 505.88 | (DMSO-$d_6$) δ 10.81 (bs, 1H), 9.37 (s, 2H), 8.84 (d, J = 4.1 Hz, 1H), 8.54 (d, J = 8.2 Hz, 1H), 8.47-8.29 (m, 4H), 8.16 (d, J = 1.3 Hz, 1H), 8.04 (t, J = 7.7 Hz, 1H), 7.49 (dd, J = 7.1, 4.9 Hz, 1H), 7.11 (bs, 1H), 4.25-4.06 (m, 1H), 3.29-3.13 (m, 2H), 1.91 (s, 3H), 1.81 (s, 3H), 1.54 (d, J = 7.1 Hz, 3H), 1.13 (t, J = 7.1 Hz, 3H). |
| 133 | 521.09 | (DMSO-$d_6$) δ 10.75 (s, 1H), 9.33 (s, 2H), 8.86-8.79 (m, 1H), 8.53 (d, J = 8.4 Hz, 1H), 8.39 (d, J = 1.6 Hz, 1H), 8.14 (d, J = 1.6 Hz, 1H), 8.06-7.97 (m, 1H), 7.50-7.42 (m, 1H), 6.99 (s, 1H), 5.85 (q, J = 6.7 Hz, 1H), 3.22 (dd, J = 7.1, 5.7 Hz, 2H), 2.69-2.59 (m, 2H), 2.55 (dd, J = 13.1, 6.8 Hz, 2H), 1.61 (d, J = 6.8 Hz, 3H), 1.12 (t, J = 7.2 Hz, 3H). |
| 134 | 521.1 | (DMSO-$d_6$) δ 10.80 (s, 1H), 9.33 (s, 2H), 8.82 (ddd, J = 4.8, 1.7, 0.9 Hz, 1H), 8.53 (d, J = 8.4 Hz, 1H), 8.39 (d, J = 1.6 Hz, 1H), 8.14 (d, J = 1.6 Hz, 1H), 8.06-7.97 (m, 1H), 7.50-7.42 (m, 1H), 7.03 (s, 1H), 5.85 (q, J = 6.7 Hz, 1H), 3.22 (dd, J = 7.1, 5.7 Hz, 2H), 2.67-2.59 (m, 2H), 2.47-2.40 (m, 2H), 1.61 (d, J = 6.8 Hz, 3H), 1.12 (t, J = 7.2 Hz, 3H). |
| 135 | 550.18 | (DMSO-$d_6$) δ 10.62 (s, 1H), 9.35 (s, 2H), 8.78 (d, J = 4.8 Hz, 1H), 8.44 (s, 1H), 8.39 (s, 1H), 8.15 (s, 1H), 7.45 (d, J = 4.8 Hz, 1H), 6.88 (m, 1H), 5.04 (s, 1H), 4.68 (t, J = 6.0 Hz, 1H), 3.82-3.70 (m, 2H), 3.66 (s, 2H), 3.63 (s, 4H), 3.24 (dd, J = 12.9, 6.8 Hz, 2H), 2.45 (s, 4H), 1.52 (s, 3H), 1.14 (t, J = 6.8 Hz, 3H). |
| 136 | 506.06 | (DMSO-$d_6$) δ 9.39 (s, 2H), 8.84 (d, J = 4.1 Hz, 1H), 8.69 (s, 3H), 8.54 (d, J = 8.1 Hz, 1H), 8.40 (d, J = 1.2 Hz, 1H), 8.17 (d, J = 1.3 Hz, 1H), 8.04 (t, J = 7.2 Hz, 1H), 7.49 (dd, J = 7.1, 4.9 Hz, 1H), 7.21 (s, 1H), 5.95 (q, J = 6.7 Hz, 1H), 3.28-3.17 (m, 2H), 1.70 (d, J = 6.7 Hz, 3H), 1.62 (s, 6H), 1.13 (t, J = 7.2 Hz, 3H). |
| 137 | 492.05 | (DMSO-$d_6$) δ 9.39 (s, 2H), 8.84 (d, J = 4.1 Hz, 1H), 8.69 (s, 3H), 8.54 (d, J = 8.1 Hz, 1H), 8.40 (d, J = 1.2 Hz, 1H), 8.17 (d, J = 1.3 Hz, 1H), 8.04 (t, J = 7.2 Hz, 1H), 7.49 (dd, J = 7.1, 4.9 Hz, 1H), 7.21 (s, 1H), 5.95 (q, J = 6.7 Hz, 1H), 3.28-3.17 (m, 2H), 1.70 (d, J = 6.7 Hz, 3H), 1.62 (s, 6H), 1.13 (t, J = 7.2 Hz, 3H). |
| 138 | 576.2 | (DMSO-$d_6$) δ 10.61 (s, 1H), 9.36 (s, 2H), 8.84-8.81 (m, 1H), 8.52 (d, J = 8.3 Hz, 1H), 8.40 (d, J = 1.6 Hz, 1H), 8.15 (d, J = 1.4 Hz, 1H), 8.04-7.99 (m, 1H), 7.48-7.44 (m, 1H), 6.87 (t, J = 5.4 Hz, 1H), 5.32 (s, 1H), 3.79 (d, J = 12.6 Hz, 2H), 3.30-3.18 (m, 4H), 2.10 (td, J = 13.0, 4.4 Hz, 2H), 1.79 (d, J = 12.7 Hz, 2H), 1.43 (s, 9H), 1.12 (t, J = 7.2 Hz, 3H). |
| 139 | 509.1 | (DMSO-$d_6$) δ 10.62 (br s, 1H), 9.38 (s, 2H), 8.85-8.81 (m, 1H), 8.52 (d, J = 8.3 Hz, 1H), 8.40 (d, J = 1.5 Hz, 1H), 8.15 (d, J = 1.5 Hz, 1H), 8.04-7.99 (m, 1H), 7.46 (ddd, J = 7.5, 4.9, 0.8 Hz, 1H), 6.92-6.86 (m, 1H), 5.60 (s, 1H), 3.27-3.18 (m, 2H), 3.03-2.94 (m, 4H), 2.48-2.41 (m, 2H), 2.35-2.23 (m, 2H), 1.12 (t, J = 7.2 Hz, 3H). |
| 140 | 520.07 | (DMSO-$d_6$) δ 10.63 (s, 1H), 9.33 (s, 2H), 8.84 (ddd, J = 4.9, 1.8, 0.9 Hz, 1H), 8.56 (d, J = 8.4 Hz, 1H), 8.42 (d, J = 1.5 Hz, 1H), 8.16 (d, J = 1.5 Hz, 1H), 8.03 (dt, J = 7.6, 1.8 Hz 1H), 7.48 (ddd, J = 7.6, 4.9, 0.9 Hz, 1H), 6.87 (t, J = 5.4 Hz, 1H), 3.27-3.20 (m, 2H), 3.18 (s, 2H), 2.27 (s, 6H), 1.80 (s, 6H), 1.14 (t, J = 7.2 Hz, 3H). |
| 141 | 562.13 | (DMSO-$d_6$) δ 10.63 (s, 1H), 9.33 (s, 2H), 8.84 (ddd, J = 4.9, 1.7, 0.8 Hz, 1H), 8.56 (d, J = 8.3 Hz, 1H), 8.42 (d, J = 1.5 Hz, 1H), 8.16 (d, J = 1.5 Hz, 1H), 8.03 (td, J = 7.7, 1.7 Hz, 1H), 7.48 (ddd, J = 7.7, 4.9, 0.8 Hz, 1H), 6.86 (t, J = 5.4 Hz, 1H), 3.61-3.54 (m, 4H), 3.25 (s, 2H), 3.23 (m, 2H), 2.54 (m, 4H), 1.80 (s, 6H), 1.14 (t, J = 7.2 Hz, 3H). |
| 142 | 548.29 | (DMSO-$d_6$) δ 10.60 (s, 1H) 9.32 (s, 2H), 8.75 (d, J = 5.2 Hz, 1H), 8.41 (s, 1H), 8.38 (d, J = 1.2 Hz, 1H), 8.12 (s, 1H), 7.42 (d, J = 5.2 Hz, 1H), 6.90 (t, J = 5.2 Hz, 1H), 5.30 (d, J = 5.6 Hz, 1H), 4.88 (p, J = 6.4 Hz, 1H), 3.61 (m, 4H), 3.22 (m, 2H), 2.72 (d, J = 10.8 Hz, 2H), 1.73 (t, J = 10.8 Hz, 2H), 1.48 (d, J = 6.4 Hz, 3H), 1.12 (t, J = 7.2 Hz, 3H), 1.03 (d, J = 6.4 Hz, 6H). |
| 143 | 548.27 | (DMSO-$d_6$) δ 10.60 (s, 1H) 9.32 (s, 2H), 8.75 (d, J = 5.2 Hz, 1H), 8.41 (s, 1H), 8.38 (d, J = 1.2 Hz, 1H), 8.12 (s, 1H), 7.42 (d, J = 5.2 Hz, 1H), 6.90 (t, J = 5.2 Hz, 1H), 5.30 (d, J = 5.6 Hz, 1H), 4.88 (p, J = 6.4 Hz, 1H), 3.61 (m, 4H), 3.22 (m, 2H), 2.72 (d, J = 10.8 Hz, 2H), 1.73 (t, J = 10.8 Hz, 2H), 1.48 (d, J = 6.4 Hz, 3H), 1.12 (t, J = 7.2 Hz, 3H), 1.03 (d, J = 6.4 Hz, 6H). |

TABLE 1-continued

Compounds and characterisation data

| No. | Observed LCMS [M + H]+ | 1H NMR |
|---|---|---|
| 144 | 534 | (DMSO-d$_6$) δ 10.86 (bs, 1H), 9.33 (s, 2H), 8.91-8.78 (m, 1H), 8.57 (d, J = 8.3 Hz, 1H), 8.41 (d, J = 1.6 Hz, 1H), 8.16 (d, J = 1.6 Hz, 1H), 8.10-7.99 (m, 1H), 7.91 (s, 2H), 7.56-7.42 (m, 1H), 7.17 (bs, 1H), 3.32-3.14 (m, 2H), 2.80 (dd, J = 12.8, 6.5 Hz, 2H), 2.39 (t, J = 6.7 Hz, 2H), 1.79 (s, 6H), 1.69-1.50 (m, 4H), 1.14 (t, J = 7.2 Hz, 3H). |
| 145 | 562.18 | (DMSO-d$_6$) δ 10.83 (bs, 1H), 10.22 (bs, 1H), 9.34 (s, 2H), 8.85 (d, J = 4.0 Hz, 1H), 8.57 (d, J = 8.2 Hz, 1H), 8.41 (d, J = 1.5 Hz, 1H), 8.16 (d, J = 1.5 Hz, 1H), 8.09-7.97 (m, 1H), 7.49 (dd, J = 7.2, 5.0 Hz, 1H), 7.15 (bs, 1H), 3.22 (dd, J = 12.3, 6.9 Hz, 2H), 3.11-2.97 (m, 2H), 2.74 (d, J = 4.9 Hz, 6H), 2.41 (t, J = 7.1 Hz, 2H), 1.79 (s, 6H), 1.77-1.67 (m, 2H), 1.64-1.48 (m, 2H), 1.14 (t, J = 7.2 Hz, 3H). |
| 146 | 492.07 | (DMSO-d$_6$) δ 10.87 (bs, 1H), 9.36 (s, 2H), 8.85 (d, J = 4.2 Hz, 1H), 8.54 (d, J = 8.1 Hz, 1H), 8.39 (d, J = 1.3 Hz, 1H), 8.33 (s, 2H), 8.16 (d, J = 1.3 Hz, 1H), 8.04 (t, J = 7.2 Hz, 1H), 7.49 (dd, J = 7.1, 5.0 Hz, 1H), 7.21 (bs, 1H), 3.89 (d, J = 5.5 Hz, 2H), 3.32-3.11 (m, 2H), 1.86 (s, 6H), 1.13 (t, J = 7.1 Hz, 3H). |
| 147 | 540.22 | (DMSO-d$_6$) δ 10.63 (br s, 1H), 9.33 (s, 2H), 8.76 (d, J = 4.40 Hz, 1H), 8.38-8.41 (m, 2H), 8.13 (s, 1H), 7.40 (m, 1H), 6.86 (m, 1H), 5.16 (s, 1H), 3.89 (s, 2H), 3.69-3.76 (m, 4H), 3.21 (m, 2H), 1.57 (s, 6H) and 1.09 (t, J = 7.20 Hz, 3H) |
| 148 | 576.18 | (DMSO-d$_6$) δ 10.63 (s, 1H), 9.44 (s, 2H), 8.78 (d, J = 5.0 Hz, 1H), 8.48-8.37 (m, 2H), 8.19 (d, J = 1.0 Hz, 1H), 7.45 (dd, J = 5.0, 1.0 Hz, 1H), 6.88 (t, J = 5.4 Hz, 1H), 6.42 (s, 1H), 5.08 (d, J = 6.7 Hz, 2H), 4.78 (d, J = 6.7 Hz, 2H), 3.69-3.59 (m, 4H), 3.29-3.18 (m, 2H), 2.75 (d, J = 10.5 Hz, 2H), 1.76 (t, J = 10.5 Hz, 2H), 1.14 (t, J = 7.2 Hz, 3H), 1.05 (d, J = 6.3 Hz, 6H). |
| 149[a] | 498.97 [M − H]− | (DMSO-d$_6$) δ 9.08 (s, 2H), 8.61 (d, J = 4.2 Hz, 1H), 8.07 (d, J = 8.2 Hz, 1H), 7.86 (s, 1H), 7.82 (s, 1H), 7.71 (t, J = 7.2 Hz, 1H), 7.49 (s, 1H), 7.21 (dd, J = 7.0, 5.1 Hz, 1H), 5.35-5.19 (m, 1H), 3.14 (dd, J = 13.2, 6.9 Hz, 2H), 1.44 (d, J = 6.6 Hz, 3H), 1.06 (t, J = 7.2 Hz, 3H). |
| 154 | 548.18 | (DMSO-d$_6$): δ 10.62 (s, 1H), 9.44 (s, 2H), 8.78 (d, J = 5.0 Hz, 1H), 8.55-8.33 (m, 2H), 8.19 (d, J = 1.1 Hz, 1H), 7.46 (d, J = 5.0 Hz, 1H), 6.88 (t, J = 5.5 Hz, 1H), 6.42 (s, 1H), 5.08 (d, J = 6.7 Hz, 2H), 4.78 (d, J = 6.7 Hz, 2H), 3.67 (s, 2H), 3.64 (t, J = 4.5 Hz, 4H), 3.28-3.19 (m, 2H), 2.48-2.42 (m, 4H), 1.14 (t, J = 7.2 Hz, 3H). |
| 155 | 573.26 | (DMSO-d$_6$): δ 10.64 (br s, 1H), 9.11 (s, 2H), 8.74 (d, J = 4.0 Hz, 1H), 8.42 (m, 2H), 8.38 (s, 1H), 8.06 (m, 1H), 7.76 (d, J = 7.6 Hz, 1H), 7.36 (m, 1H), 7.12 (m, 1H), 6.86 (m, 1H), 5.22 (m, 1H), 4.02 (m, 1H), 3.76 (s, 2H), 3.58 (br s, 2H), 3.21 (m, 2H), 3.15 (s, 3H), 2.95 (br s, 2H) and 1.11 (t, J = 7.20 Hz, 3H) |
| 156 | 568.28 | (DMSO-d$_6$): δ 10.62 (br s, 1H), 9.33 (s, 2H), 8.77 (d, J = 4.80 Hz, 1H), 8.43 (s, 1H), 8.38 (s, 1H), 8.13 (s, 1H), 7.45 (d, J = 4.80 Hz, 1H), 6.85 (m, 1H), 5.15 (s, 1H), 3.72 (s, 2H), 3.21 (m, 2H), 2.56 (m, 4H), 2.04 (m, 4H), 1.57 (s, 6H) and 1.11 (t, J = 7.2 Hz, 3H) |
| 157 | 451.09 | (DMSO-d$_6$) δ 10.62 (s, 1H), 9.36 (s, 2H), 8.91-8.78 (m, 1H), 8.55 (d, J = 8.3 Hz, 1H), 8.41 (d, J = 1.4 Hz, 1H), 8.16 (d, J = 1.4 Hz, 1H), 8.09-7.97 (m, 1H), 7.48 (ddd, J = 7.5, 4.9, 0.8 Hz, 1H), 6.88 (t, J = 5.3 Hz, 1H), 5.04 (s, 1H), 4.66 (t, J = 6.1 Hz, 1H), 3.81-3.66 (m, 2H), 3.29-3.17 (m, 2H), 1.52 (s, 3H), 1.14 (t, J = 7.2 Hz, 3H). |
| 158 | 435.17 | (DMSO-d$_6$) δ 10.64 (br s, 1H), 9.31 (s, 2H), 8.65 (s, 1H), 8.43 (d, J = 8.40 Hz, 1H), 8.34 (s, 1H), 8.10 (s, 1H), 7.84 (d, J = 8.0 Hz, 1H), 6.90 (m, 1H), 5.31 (d, J = 5.60 Hz, 1H), 4.86 (m, 1H), 3.21 (m, 2H), 2.40 (s, 3H), 1.48 (d, J = 6.40 Hz, 3H) and 1.11 (t, J = 7.20 Hz, 3H) |
| 159 | 547.31 | (DMSO-d$_6$): δ 10.62 (br s, 1H), 9.33 (s, 2H), 8.75 (d, J = 4.80 Hz, 1H), 8.40 (m, 2H), 8.13 (s, 1H), 7.41 (d, J = 4.8 Hz, 1H), 6.88 (br s, 1H), 5.15 (s, 1H), 3.62 (s, 2H), 3.21 (m, 2H), 2.35-2.50 (m, 8H), 2.15 (s, 3H), 1.57 (s, 6H) and 1.11 (t, J = 7.20 Hz, 3H) |
| 160 | 518.22 | (DMSO-d$_6$): δ 10.16 (d, J = 4.8 Hz, 1H), 9.39 (s, 2H), 9.03 (d, J = 4.7 Hz, 1H), 8.85 (d, J = 4.0 Hz, 1H), 8.54 (d, J = 8.2 Hz, 1H), 8.41 (d, J = 1.5 Hz, 1H), 8.18 (d, J = 1.5 Hz, 1H), 8.04 (td, J = 8.0, 1.6 Hz, 1H), 7.49 (dd, J = 7.1, 4.9 Hz, 1H), 7.18 (s, 1H), 6.01 (q, J = 6.7 Hz, 1H), 4.61-4.44 (m, 1H), 3.37-3.17 (m, 4H), 2.45-2.28 (m, 1H), 2.18 (dq, J = 14.2, 7.3 Hz, 1H), 2.07-1.91 (m, 2H), 1.72 (d, J = 6.7 Hz, 3H), 1.13 (t, J = 7.2 Hz, 3H). |
| 161 | 518.15 | (DMSO-d$_6$): δ 10.16 (d, J = 4.8 Hz, 1H), 9.39 (s, 2H), 9.03 (d, J = 4.7 Hz, 1H), 8.85 (d, J = 4.0 Hz, 1H), 8.54 (d, J = 8.2 Hz, 1H), 8.41 (d, J = 1.5 Hz, 1H), 8.18 (d, J = 1.5 Hz, 1H), 8.04 (td, J = 8.0, 1.6 Hz, 1H), 7.49 (dd, J = 7.1, 4.9 Hz, 1H), 7.18 (s, 1H), 6.01 (q, J = 6.7 Hz, 1H), 4.61-4.44 (m, 1H), 3.37-3.17 (m, 4H), 2.45-2.28 (m, 1H), 2.18 (dq, J = 14.2, 7.3 Hz, 1H), 2.07-1.91 (m, 2H), 1.72 (d, J = 6.7 Hz, 3H), 1.13 (t, J = 7.2 Hz, 3H). |
| 162 | 548.14 | (DMSO-d$_6$): δ 10.41 (br s, 1H), 9.41 (s, 2H), 8.83 (dd, J = 4.8, 0.9 Hz, 1H), 8.53 (d, J = 8.3 Hz, 1H), 8.42 (d, J = 1.6 Hz, 1H), 8.17 (d, J = 1.4 Hz, 1H), 8.03 (td, J = 7.9, 1.8 Hz, 1H), 7.51-7.44 (m, 1H), 6.86 (t, J = 5.3 Hz, 1H), 6.44 (s, 1H), 4.40 (br s, 2H), 4.01 (d, J = 8.3 Hz, 2H), 3.28-3.17 (m, 2H), 1.42 (s, 9H), 1.12 (t, J = 7.2 Hz, 3H). |

TABLE 1-continued

Compounds and characterisation data

| No. | Observed LCMS [M + H]+ | 1H NMR |
|---|---|---|
| 163 | 448.1 | (DMSO-d6): δ 10.64 (s, 1H), 9.49 (s, 2H), 9.19 (s, 1H), 8.84 (ddd, J = 4.8, 1.7, 0.9 Hz, 2H), 8.53 (d, J = 8.3 Hz, 1H), 8.43 (d, J = 1.6 Hz, 1H), 8.21 (d, J = 1.5 Hz, 1H), 8.08-7.99 (m, 1H), 7.48 (ddd, J = 7.5, 4.9, 0.9 Hz, 1H), 6.92 (t, J = 5.5 Hz, 1H), 4.64-4.52 (m, 2H), 4.23-4.11 (m, 2H), 3.29-3.14 (m, 2H), 1.12 (t, J = 7.2 Hz, 3H). |
| 164 | 562.2 | (DMSO-d6): δ 10.63 (bs, 1H), 9.35 (s, 2H), 8.78 (d, J = 4.9 Hz, 1H), 8.43 (s, 1H), 8.39 (d, J = 1.6 Hz, 1H), 8.15 (d, J = 1.4 Hz, 1H), 7.44 (dd, J = 5.1, 1.0 Hz, 1H), 6.89 (t, J = 5.4 Hz, 1H), 5.15 (s, 1H), 3.76-3.52 (m, 4H), 3.29-3.17 (m, 2H), 2.75 (d, J = 10.2 Hz, 2H), 1.75 (t, J = 10.7 Hz, 2H), 1.59 (s, 6H), 1.14 (t, J = 7.2 Hz, 3H), 1.05 (d, J = 6.3 Hz, 6H). |
| 165 | 589.05 | HCl salt (DMSO-d6): δ 10.84 (bs, 1H), 9.82 (bs, 1H), 9.33 (s, 2H), 9.00 (t, J = 5.8 Hz, 1H), 8.85 (d, J = 4.1 Hz, 1H), 8.55 (d, J = 8.1 Hz, 2H), 8.40 (d, J = 1.3 Hz, 1H), 8.16 (d, J = 1.3 Hz, 1H), 8.04 (t, J = 7.1 Hz, 1H), 7.49 (dd, J = 7.1, 4.9 Hz, 1H), 7.17 (bs, 1H), 4.24-4.16 (m, 2H), 4.03 (qd, J = 17.8, 5.9 Hz, 2H), 3.22 (dd, J = 17.0, 10.5 Hz, 4H), 2.30 (dd, J = 17.4, 9.5 Hz, 1H), 1.87 (t, J = 7.9 Hz, 2H), 1.81 (d, J = 3.1 Hz, 6H), 1.13 (t, J = 7.2 Hz, 3H). |
| 166 | 531.92 | HCl salt (DMSO-d6): δ 10.87 (bs, 1H), 10.07 (bs, 1H), 9.37 (s, 2H), 8.85 (d, J = 4.1 Hz, 2H), 8.59-8.50 (m, 1H), 8.41 (d, J = 1.0 Hz, 1H), 8.17 (d, J = 1.1 Hz, 1H), 8.04 (t, J = 7.3 Hz, 1H), 7.49 (dd, J = 7.0, 4.8 Hz, 1H), 7.20 (s, 1H), 4.56-4.40 (m, 1H), 3.32-3.13 (m, 4H), 2.45-2.21 (m, 2H), 1.98 (dd, J = 13.1, 6.7 Hz, 2H), 1.92 (s, 3H), 1.81 (s, 3H), 1.13 (t, J = 7.1 Hz, 3H). |
| 167 | 676.25 | (DMSO-d6): δ 12.35 (s, 1H), 10.70 (s, 1H), 9.44 (s, 2H), 8.78 (d, J = 5.5 Hz, 1H), 8.46 (s, 1H), 8.42 (d, J = 1.4 Hz, 1H), 8.18 (d, J = 1.4 Hz, 1H), 7.45 (d, J = 5.5 Hz, 1H), 6.93 (s, 1H), 5.14 (d, J = 7.5 Hz, 2H), 4.94 (d, J = 7.5 Hz, 2H), 3.68-3.59 (m, 4H), 3.27-3.19 (m, 2H), 2.74 (m, 4H), 2.57 (m, 2H), 1.76 (t, J = 10.7 Hz, 2H), 1.14 (t, J = 7.2 Hz, 3H), 1.05 (d, J = 6.3 Hz, 6H). |
| 168 | 465.21 | (Acetone) δ 9.26 (s, 2H), 8.85 (d, J = 2.2 Hz, 1H), 8.85 (d, J = 2.2 Hz, 1H), 8.42 (d, J = 8.2 Hz, 1H), 8.35 (d, J = 1.6 Hz, 1H), 8.05 (d, J = 1.6 Hz, 1H), 8.01 (dd, J = 8.6, 2.0 Hz, 1H), 7.21 (d, J = 24.2 Hz, 1H), 5.05 (q, J = 6.7 Hz, 1H), 4.96-4.89 (m, 1H), 4.53 (s, 1H), 4.38 (d, J = 5.2 Hz, 1H), 1.54 (dd, J = 6.6, 4.4 Hz, 6H), 1.21 (t, J = 7.2 Hz, 3H). |
| 169 | 605.12 | (DMSO-d6): δ 10.63 (s, 1H), 9.33 (s, 2H), 8.84 (ddd, J = 4.8, 1.7, 0.8 Hz, 1H), 8.55 (d, J = 7.9 Hz, 1H), 8.40 (d, J = 1.5 Hz, 1H), 8.14 (d, J = 1.5 Hz, 1H), 8.08-7.98 (m, 1H), 7.48 (ddd, J = 7.9, 4.8, 0.8 Hz, 1H), 6.90 (t, J = 5.4 Hz, 1H), 3.56-3.52 (m, 4H), 3.39 (s, 2H), 3.28-3.20 (m, 2H), 2.63 (t, J = 6.2 Hz, 2H), 2.40-2.30 (m, 6H), 1.80 (s, 6H), 1.14 (t, J = 7.2 Hz, 3H). |
| 170 | 549.95 | (DMSO-d6): δ 10.86 (bs, 1H), 9.61 (bs, 2H), 9.36 (s, 2H), 8.84 (s, 1H), 8.53 (d, J = 7.8 Hz, 1H), 8.40 (s, 1H), 8.16 (s, 1H), 8.04 (t, J = 7.2 Hz, 1H), 7.49 (s, 1H), 7.22 (s, 1H), 3.91 (s, 2H), 3.22 (bs, 2H), 1.86 (s, 6H), 1.13 (t, J = 6.9 Hz, 3H). |
| 171 | 549.93 | HCl salt - (DMSO-d6): δ 10.83 (bs, 1H), 9.33 (s, 2H), 8.84 (s, 1H), 8.53 (d, J = 7.7 Hz, 1H), 8.46 (s, 3H), 8.39 (s, 1H), 8.15 (s, 1H), 8.03 (t, J = 6.9 Hz, 1H), 7.48 (s, 1H), 7.18 (s, 1H), 4.20 (s, 1H), 3.22 (s, 2H), 3.01 (qd, J = 17.5, 5.3 Hz, 2H), 1.81 (d, J = 7.2 Hz, 6H), 1.13 (t, J = 6.1 Hz, 3H). (COOH signal obscured by H2O) |
| 172 | 519.97 | HCl salt - (DMSO-d6): δ 10.88 (bs, 1H), 9.34 (s, 2H), 8.85 (dd, J = 4.8, 0.8 Hz, 1H), 8.58 (d, J = 8.3 Hz, 1H), 8.42 (d, J = 1.6 Hz, 1H), 8.16 (d, J = 1.5 Hz, 1H), 8.07-7.90 (m, 4H), 7.53-7.46 (m, 1H), 7.20 (bs, 1H), 3.23 (dd, J = 6.8, 4.9 Hz, 2H), 2.87 (dd, J = 14.8, 6.0 Hz, 2H), 2.48 (d, J = 7.4 Hz, 2H), 1.86-1.79 (m, 8H), 1.14 (t, J = 7.2 Hz, 3H). |
| 173 | 525.15 | (DMSO-d6): δ 10.62 (br s, 1H), 9.40 (s, 2H), 8.86-8.80 (m, 1H), 8.53 (d, J = 8.3 Hz, 1H), 8.41 (d, J = 1.5 Hz, 1H), 8.17 (d, J = 1.2 Hz, 1H), 8.02 (td, J = 7.8, 1.8 Hz, 1H), 7.47 (dd, J = 7.1, 5.2 Hz, 1H), 6.91-6.81 (m, 1H), 5.81 (s, 1H), 3.43-3.33 (m, 2H), 3.26-3.17 (m, 2H), 3.17-3.05 (m, 2H), 2.64 (t, J = 11.5 Hz, 2H), 2.39-2.21 (m, 2H), 1.12 (t, J = 7.2 Hz, 3H) |
| 174 | 476.07 | (DMSO-d6): δ 10.61 (br s, 1H), 9.41 (s, 2H), 8.85-8.82 (m, 1H), 8.54-8.50 (m, 2H), 8.41 (d, J = 1.5 Hz, 1H), 8.39-8.29 (m, 1H), 8.18 (d, J = 1.5 Hz, 1H), 8.05-8.00 (m, 1H), 7.50-7.45 (m, 1H), 6.90-6.84 (m, 1H), 5.70 (s, 1H), 3.28-3.14 (m, 6H), 2.41-2.29 (m, 2H), 2.12-2.00 (m, 2H), 1.12 (t, J = 7.2 Hz, 3H). |
| 175 | 548.25 | (DMSO-d6) δ 10.62 (br s, 1H), 9.33 (s, 2H), 8.73 (d, J = 4.40 Hz, 1H), 8.39 (m, 2H), 8.13 (s, 1H), 7.36 (d, J = 4.0 Hz, 1H), 6.86 (m, 1H), 5.16 (s, 1H), 4.08 (m, 1H), 3.74 (s, 2H), 3.58 (m, 2H), 3.35 (m, 2H), 3.19-3.23 (m, 2H), 2.93 (m, 2H), 1.57 (s, 6H) and 1.06-1.13 (m, 6H) |
| 176 | 388.14 | (DMSO-d6) δ 10.62 (br s, 1H), 8.95 (s, 2H), 7.73 (s, 1H), 7.69 (s, 1H), 6.68 (m, 1H), 5.09 (s, 1H), 3.84 (s, 3H), 3.15-3.22 (m, 2H), 1.54 (s, 6H) and 1.09 (t, J = 7.20 Hz, 3H) |
| 177 | 376.11 | (DMSO-d6) δ 10.80 (br s, 1H), 9.04 (s, 2H), 7.89-8.01 (m, 2H), 6.71 (m, 1H), 5.14 (s, 1H), 3.16-3.22 (m, 2H), 1.54 (s, 6H) and 1.09 (t, J = 7.20 Hz, 3H) |

TABLE 1-continued

Compounds and characterisation data

| No. | Observed LCMS [M + H]+ | 1H NMR |
|---|---|---|
| 178 | 469.08 | (DMSO/Acetone) δ 9.20 (s, 2H), 8.54 (d, J = 5.5 Hz, 1H), 8.48 (s, 1H), 8.14 (d, J = 1.6 Hz, 1H), 8.11 (s, 1H), 7.56-7.31 (m, 1H), 7.29 (t, J = 4.6 Hz, 1H), 5.30 (s, 1H), 4.90-4.81 (m, 1H), 4.02 (s, 3H), 3.24-3.14 (m, 2H), 1.47 (d, J = 6.6 Hz, 3H), 1.10 (t, J = 7.2 Hz, 3H). |
| 179 | 563.98 | HCl salt - (DMSO-$d_6$): δ 11.03 (s, 1H), 9.36 (s, 2H), 9.34 (s, 2H), 8.85 (d, J = 4.6 Hz, 1H), 8.55 (d, J = 8.0 Hz, 1H), 8.40 (d, J = 1.3 Hz, 1H), 8.16 (d, J = 1.3 Hz, 1H), 8.05 (dt, J = 8.0, 1.2 Hz, 1H), 7.50 (dd, J = 7.2, 4.6 Hz, 1H), 7.38 (s, 1H), 4.10 (s, 2H), 3.58 (s, 1H), 3.32-3.08 (m, 4H), 2.73 (t, J = 7.3 Hz, 2H), 1.86 (s, 6H), 1.13 (t, J = 7.3 Hz, 3H). |
| 180 | 531.94 | HCl salt - (DMSO-$d_6$): δ = 10.85 (bs, 1H), 9.40 (bs, 1H), 9.35 (s, 2H), 9.26 (bs, 1H), 8.85 (d, J = 4.1 Hz, 1H), 8.57 (d, J = 8.2 Hz, 1H), 8.42 (d, J = 1.4 Hz, 1H), 8.17 (d, J = 1.4 Hz, 1H), 8.03 (dd, J = 11.1, 4.4 Hz, 1H), 7.49 (dd, J = 7.1, 4.9 Hz, 1H), 7.15 (bs, 1H), 3.45-3.31 (m, 3H), 3.26-3.14 (m, 4H), 2.24 (q, J = 6.9 Hz, 2H), 1.82 (d, J = 16.6 Hz, 6H), 1.13 (t, J = 7.2 Hz, 3H). |
| 181 | 547.97 | HCl salt - (DMSO-$d_6$): δ 10.87 (bs, 1H), 10.02 (bs, 1H), 9.63 (s, 1H), 9.39 (s, 2H), 8.85 (d, J = 4.2 Hz, 1H), 8.56 (d, J = 8.2 Hz, 1H), 8.42 (d, J = 1.2 Hz, 1H), 8.18 (d, J = 1.3 Hz, 1H), 8.05 (t, J = 7.7 Hz, 1H), 7.49 (dd, J = 7.1, 5.0 Hz, 1H), 7.19 (bs, 1H), 4.46 (s, 2H), 4.01-3.88 (m, 2H), 3.76 (t, J = 9.8 Hz, 1H), 3.24 (dd, J = 17.6, 11.7 Hz, 3H), 3.15 (bs, 1H), 1.87 (d, J = 32.2 Hz, 6H), 1.13 (t, J = 7.2 Hz, 3H). |
| 182 | 428.19 | (DMSO-$d_6$) δ 10.62 (br s, 1H), 9.02 (s, 2H), 7.69-7.70 (m, 2H), 6.68 (m, 1H), 5.14 (s, 1H), 3.92 (d, J = 6.80 Hz, 2H), 3.14-3.21 (m, 2H), 1.54 (s, 6H), 1.18-1.20 (m, 1H), 1.08 (t, J = 7.20 Hz, 3H), 0.50-0.55 (m, 2H) and 0.27-0.31 (m, 2H) |
| 183 | 432.13 | (DMSO-$d_6$) δ 10.63 (br s, 1H), 9.01 (s, 2H), 7.71-7.74 (m, 2H), 6.68 (m, 1H), 5.11 (s, 1H), 4.20 (t, J = 4.80 Hz, 2H), 3.64 (t, J = 4.80 Hz, 2H), 3.24 (s, 3H), 3.16-3.20 (m, 2H), 1.53 (s, 6H), and 1.09 (t, J = 7.20 Hz, 3H) |
| 184 | 616 | (DMSO-$d_6$): δ 10.96 (s, 1H), 9.78-9.06 (m, 2H), 9.34 (s, 2H), 8.85 (d, J = 4.5 Hz, 1H), 8.55 (d, J = 8.1 Hz, 1H), 8.41 (d, J = 1.4 Hz, 1H), 8.17 (d, J = 1.4 Hz, 1H), 8.05 (td, J = 8.1, 1.7 Hz, 1H), 7.50 (dd, J = 7.1, 4.5 Hz, 1H), 7.26 (s, 1H), 4.12 (s, 4H), 3.58 (s, 2H), 3.32-3.15 (m, 4H), 1.87 (s, 6H), 1.13 (t, J = 7.2 Hz, 3H). |
| 185 | 536.12 | (DMSO-$d_6$): δ 10.69 (s, 1H), 9.33 (s, 2H), 8.77 (d, J = 5.0 Hz, 1H), 8.45-8.33 (m, 2H), 8.14 (d, J = 1.4 Hz, 1H), 7.44 (d, J = 5.0 Hz, 1H), 7.02-6.89 (m, 1H), 5.30 (s, 1H), 4.90 (d, J = 5.8 Hz, 1H), 3.70 (s, 2H), 3.23 (dd, J = 13.3, 6.5 Hz, 2H), 2.70 (dd, J = 18.3, 6.0 Hz, 8H), 1.51 (d, J = 6.6 Hz, 3H), 1.14 (t, J = 7.2 Hz, 3H). |
| 186 | 418.2 | (DMSO-$d_6$) δ 10.68 (br s, 1H), 9.06 (s, 2H), 7.71-7.73 (m, 2H), 6.78 (m, 1H), 5.12 (s, 1H), 4.88 (t, J = 5.20 Hz, 1H), 4.12 (t, J = 5.20 Hz, 2H), 3.70 (t, J = 4.80 Hz, 2H), 3.14-3.21 (m, 2H), 1.54 (s, 6H), and 1.08 (t, J = 7.20 Hz, 3H) |
| 187 | 550.23 | (DMSO-$d_6$) δ 10.60 (br s, 1H), 9.32 (s, 2H), 8.76 (d, J = 4.80 Hz, 1H), 8.36-8.40 (m, 2H), 8.13 (s, 1H), 7.42 (d, J = 4.40 Hz, 1H), 6.85 (m, 1H), 5.13 (s, 1H), 3.67 (s, 2H), 3.20-3.23 (m, 2H), 2.66-2.69 (m, 8H), 1.57 (s, 6H) and 1.11 (t, J = 7.20 Hz, 3H) |
| 188 | 566.23 | (DMSO-$d_6$) δ 10.62 (br s, 1H), 9.32 (s, 2H), 8.78 (d, J = 4.80 Hz, 1H), 8.44 (s, 1H), 8.37 (s, 1H), 8.13 (s, 1H), 7.45 (d, J = 4.80 Hz, 1H), 6.86 (m, 1H), 5.15 (s, 1H), 3.75 (s, 2H), 3.18-3.25 (m, 2H), 2.93 (m, 4H), 2.69-2.79 (m, 4H), 1.57 (s, 6H) and 1.11 (t, J = 7.60 Hz, 3H) |
| 189 | 445.22 | (DMSO-$d_6$) δ 10.68 (br s, 1H), 8.98 (s, 2H), 7.83 (s, 1H), 7.58 (s, 1H), 6.70 (m, 1H), 5.11 (br s, 1H), 3.18 (m, 4H), 3.07 (s, 3H), 2.89 (m, 2H), 2.54 (s, 3H), 1.53 (s, 6H), and 1.08 (t, J = 7.20 Hz, 3H) |
| 190 | 514.98 | (DMSO-$d_6$) δ 10.60 (br s, 1H), 9.39 (s, 2H), 8.85 (d, J = 4.6 Hz, 1H), 8.61-8.49 (m, 1H), 8.47-8.38 (m, 1H), 8.22-8.15 (m, 1H), 8.04 (t, J = 7.8 Hz, 1H), 7.49 (dd, J = 7.3, 4.9 Hz, 1H), 6.98-6.88 (m, 1H), 5.09 (d, J = 7.5 Hz, 2H), 3.25-3.21 (m, 2H), 1.88 (s 6H), 1.16-1.11 (m, 3H). |
| 191 | 582.23 | (DMSO-$d_6$ + $D_2O$) δ 9.25 (s, 2H), 8.74 (d, J = 4.80 Hz, 1H), 8.35 (s, 1H), 8.30 (s, 1H), 8.06 (s, 1H), 7.45 (d, J = 5.20 Hz, 1H), 3.84 (s, 2H), 3.11-3.21 (m, 6H), 2.94 (m, 4H), 1.54 (s, 6H) and 1.07 (t, J = 7.20 Hz, 3H) |
| 192 | 524.22 | (DMSO-$d_6$) δ 10.64 (br s, 1H), 9.01 (s, 2H), 7.85 (s, 1H), 7.71 (s, 1H), 6.98 (s, 1H), 6.90 (m, 2H), 6.69 (m, 1H), 5.08-5.10 (m, 3H), 3.73 (s, 3H), 3.71 (s, 3H), 3.17-3.20 (m, 2H), 1.51 (s, 6H), and 1.09 (t, J = 7.20 Hz, 3H) |
| 193 | 444.16 | (DMSO-$d_6$) δ 10.62 (br s, 1H), 8.99 (s, 2H), 7.72 (s, 1H), 7.70 (s, 1H), 6.68 (m, 1H), 5.27 (d, J = 5.20 Hz, 1H), 4.82 (m, 1H), 3.99-4.13 (m, 3H), 3.63-3.70 (m, 2H), 3.16-3.20 (m, 2H), 1.90-1.96 (m, 1H), 1.64-1.80 (m, 2H), 1.59-1.64 (m, 1H), 1.46 (d, J = 6.80 Hz, 3H) and 1.09 (t, J = 7.20 Hz, 3H) |
| 194 | 429.24 | (DMSO-$d_6$) δ 10.68 (br s, 1H), 9.05 (s, 2H), 7.79 (s, 1H), 7.61 (s, 1H), 6.70 (m, 1H), 5.27 (d, J = 5.60 Hz, 1H), 4.82 (m, 1H), 3.48 (m, 4H), 3.16-3.19 (m, 2H), 2.73 (m, 4H), 1.45 (d, J = 6.40 Hz, 3H) and 1.08 (t, J = 7.20 Hz, 3H) |
| 195 | 442.31 | (DMSO-$d_6$) δ 9.11 (s, 2H), 7.69 (m, 1H), 7.30 (s, 1H), 7.05 (m, 1H), 6.57 (m, 1H), 5.14 (s, 1H), 3.19 (m, 5H), 1.98-2.01 (m, 2H), 1.53 (s, 6H), 1.27-1.35 (m, 4H) and 1.08 (m, 3H) |

TABLE 1-continued

Compounds and characterisation data

| No. | Observed LCMS $[M + H]^+$ | $^1$H NMR |
|---|---|---|
| 196 | 508.09 | (DMSO-$d_6$): δ 9.32 (s, 2H), 8.75 (d, J = 5.0 Hz, 1H), 8.47 (s, 1H), 8.36 (d, J = 1.5 Hz, 1H), 8.20 (s, 1H), 8.13 (d, J = 1.5 Hz, 1H), 7.45 (d, J = 5.0 Hz, 1H), 6.99 (t, J = 5.5 Hz, 1H), 3.94 (s, 3H), 3.53 (t, J = 5.7 Hz, 2H), 3.21 (tt, J = 13.0, 6.5 Hz, 2H), 2.68 (t, J = 5.7 Hz, 2H), 2.54 (s, 1H), 1.57 (s, 6H), 1.12 (t, J = 7.2 Hz, 3H). |
| 197 | 420 | (CD$_3$OD) δ 8.80 (d, J = 5.2 Hz, 2H), 8.56 (s, 1H), 8.15-8.11 (m, 2H), 8.04 (s, 1H), 7.94-7.88 (m, 2H), 7.43 (s, 2H), 7.35 (t, J = 7.2 Hz, 1H), 5.03 (q, J = 6.0 Hz, 1H), 3.42-3.38 (m, 2H), 1.60 (d, J = 6.4 Hz, 3H), 1.26 (t, J = 7.2 Hz, 3H). |
| 198 | 542.3 | (DMSO-$d_6$): δ 10.61 (s, 1H), 9.33 (s, 2H), 8.76 (d, J = 5.2 Hz, 1H), 8.42 (s, 1H), 8.37 (d, J = 1.3 Hz, 1H), 8.13 (d, J = 0.7 Hz, 1H), 7.44 (dd, J = 5.0, 1.1 Hz, 1H), 6.88 (t, J = 5.1 Hz, 1H), 5.75 (s, 1H), 5.13 (s, 1H), 3.64 (s, 2H), 3.26-3.17 (m, 2H), 1.57 (s, 6H), 1.12 (t, J = 7.2 Hz, 3H). |
| 199 | 487.21 | (DMSO-$d_6$) δ 10.63 (br s, 1H), 9.04 (s, 2H), 7.75 (s, 1H), 7.70 (s, 1H), 6.68 (m, 1H), 5.10 (s, 1H), 4.17 (t, J = 5.20 Hz, 2H), 3.53 (m, 4H), 3.15-3.21 (m, 2H), 2.64 (t, J = 5.20 Hz, 2H), 2.37 (m, 4H), 1.53 (s, 6H) and 1.08 (t, J = 7.20 Hz, 3H) |
| 200 | 448.14 | (DMSO-$d_6$) δ 10.84 (br s, 1H), 8.93 (s, 2H), 7.63-7.69 (m, 2H), 6.72 (m, 1H), 5.21 (br s, 1H), 3.37 (t, J = 6.40 Hz, 2H), 3.11-3.15 (m, 5H), 2.98 (t, J = 6.40 Hz, 2H), 1.58 (s, 6H), and 1.04 (t, J = 6.80 Hz, 3H) |
| 201 | 464.14 | (DMSO-$d_6$) δ 11.06 (br s, 1H), 9.03 (s, 2H), 7.92-7.98 (m, 2H), 6.79 (m, 1H), 5.27 (br s, 1H), 3.65 (m, 1H), 3.45 (m, 1H), 3.02-3.15 (m, 6H), 2.85-2.89 (m, 1H), 1.57 (s, 6H), and 1.05 (t, J = 7.20 Hz, 3H) |
| 202 | 451.21 | (DMSO-$d_6$): δ 10.59 (s, 1H), 9.33 (s, 2H), 8.63 (d, J = 6 Hz, 1H), 8.38 (d, J = 0.8 Hz, 1H), 8.12 (s, 1H), 8.02 (d, J = 1.2 Hz, 1H), 7.05 (dd, J = 5.6, 2 Hz, 1H), 6.87 (br t, J = 5.2 Hz, 1H), 5.30 (d, J = 5.2 Hz, 1H), 4.88 (p, J = 6 Hz, 1H), 3.99 (s, 3H), 3.21 (p, J = 6.4 Hz, 2H), 1.49 (d, J = 6.4 Hz, 3H), 1.12 (t, J = 7.2 Hz, 3H). |

$^a$Compound 149 was prepared by coupling Precursor 81 with Intermediate 1 under Suzuki coupling conditions as previously described then was subsequently converted to the target compound as follows. Zinc (177 mg) was added to a solution of 1-[5-[2-(ethylcarbamoylamino)-7-(2-pyridyl)-1,3-benzothiazol-5-yl]pyrimidin-2-yl]ethyl bis(2,2,2-trichloroethyl) phosphate (230 mg) in a mixture of pyridine (1.5 mL) and acetic acid (0.3 mL) and the mixture stirred at RT for 2 h. The mixture was filtered through celite, washing with pyridine (3 × 10 mL) and concentrated in vacuo. The residue was treated with MeOH (30 mL) to give a solid, which was collected by filtration. This was purified by reverse phase chromatography eluting with 0-100% ACN/H$_2$O, followed by 50% MeOH/H$_2$O 50% ammonia) to give Compound 149 as the bis ammonium salt (50 mg).

ADME Assays

The following assay(s) may be used to assess the properties of a prodrug and the potential suitability of the prodrug to deliver a compound in vivo.

Chemical Stability Assay

Compounds may be tested for chemical stability across four pH values i.e. 2.1, 4.5, 7.4 and 9.1 and in water. Stress solutions are prepared with 10% acetonitrile and samples introduced from DMSO stocks (2 mM) to give a final concentration of 16 µM. Test samples are analysed by HPLC using a C8 reverse phase column (Phenomenex Kinetex™ 2.6 µm C8 100 Å LC Column 50×3 mm or similar) with an elution gradient of 5-100% acetonitrile:water+0.1% formic acid. The assay is conducted over 24 hrs with 2-hourly injections. Data analysis is performed using peak areas at 254 nm and LCMS for mass determination.

In an alternative method, compounds are dissolved in DMSO are diluted to produce triplicate 10 µM solutions in HEPES pH 7.4 containing 5% DMSO. The samples are incubated for 24 h at 37° C. and analysed by LCMS following the addition of 2 volumes of methanol. The percentage of compound remaining is determined by comparing peak areas to a T0 sample.

The chemical stability of representative Compounds 19, 123, 133 and 134 were tested and determined to be chemically stable at pH 7.4 with ≥95% of the compound remaining at 24 hours.

Thermodynamic Solubility

In a 1.5 mL eppendorf tube, approximately 2 mg of compound is resuspended in a volume of HEPES buffer pH 7.4 to achieve a 5 mg/mL suspension. The tubes are placed on an orbital shaker at room temperature and following shaking for 24 hours the tubes are spun at 1400 rpm in a bench top centrifuge to pellet the undissolved compound. Duplicate 150 µL aliquots of the supernatant are then transferred into two ultracentrifuge tubes and spun at 357440 g for 4 hours at 20° C. 50 µL of the supernatant from each tube is then diluted with 100 µL of methanol and analysed by HPLC or LCMS to determine the concentration of compound in solution by comparing to a standard curve. The thermodynamic solubility of representative Compounds 19, 123, 134 and 153 were tested and determined to be highly soluble, at ≥2 mg/mL, at pH 7.4.

Microsomal Stability

In a 96 well polypropylene plate, 10 µM compound is prepared in 100 mM KPO$_4$ buffer pH 7.4, 5 mM MgCl$_2$, 25 µg/ml Alamethicin, 1 mg/ml (protein) liver microsomes (mouse) and a final DMSO concentration of 0.1% in 100 µl in duplicate. The plate is pre-incubated at 37° C. for 10 minutes after which reactions are initiated by the addition of NADPH and UDPGA to a final concentration of 1 mM and 5 mM respectively. Reactions are incubated at 37° C. and terminated by the addition of 100 µl DMSO at 0, 10, 30 and 60 minutes. Samples of 100 µl are withdrawn and added to 50 µl ice cold methanol and mixed on an orbital shaker for 10 minutes to precipitate the proteins. The samples are then centrifuged at 4000 rpm and 10° C. for 30 minutes and supernatants are analysed by LCMS. The T1/2 and clearance are determined by linear regression from the peak areas. The microsomal stability of representative Compounds 19, 123, 133 and 134 were tested and determined to be unstable, in each case the major metabolite being the parent alcohol, with a half-life less than 20 mins.

Plasma Stability

Compounds dissolved in DMSO are diluted to produce duplicate 50 µl aliquots of 10 µM solutions in neat plasma containing 1% DMSO in 96 well polypropylene plates. Following incubation at 37° C. for 5 hours, 100 µl ice cold acetonitrile is added to the samples and mixed on an orbital shaker for 10 minutes to precipitate the proteins. The samples are then centrifuged at 4000 rpm and 10° C. for 30 minutes and supernatants are analysed by LCMS. The recovery and percentage of compound remaining is determined by comparing peak areas to a DMSO stock and T0 sample respectively.

Biological Data

The in vitro and in vivo antiviral activity of the compounds of the invention may be determined using the following protocols.

On-Target Enzyme Assay: Determination of Gyrase ATPase Activity

Gyrase converts ATP into ADP and inorganic phosphate. The released phosphate can be detected by the addition of malachite green solution and measured by monitoring the increase in absorbance at 600 nm. The ATPase assay is carried out in a buffer containing 2 mU/µL Gyrase enzyme ($A_2B_2$ complex from *Staphylococcus aureus*), 0.08 mg/mL double-stranded DNA, 8 mM HEPES.KOH pH 7.6, 100 mM K glutamate, 2 mM Mg acetate, 2 mM DTT, 0.01 mg/mL BSA, and 5% DMSO solution containing the inhibitor. Alternatively, the ATPase assay is carried out in a buffer containing 4.8 µg/mL Gyrase enzyme ($A_2B_2$ complex from *Escherichia coli*), 0.08 µg/mL ssDNA, 35 mM Tris pH 7.5, 24 mM KCl, 2 mM $MgCl_2$, 6.5% Glycerol, 2 mM DTT, 1.8 mM Spermidine, 0.5 mg/mL BSA and 5% DMSO solution containing the inhibitor. The reaction is started by adding ATP to a final concentration of 1 mM and allowed to incubate at 30° C. for 60 minutes. The reaction is stopped by adding 200 µL of malachite green solution (0.034% malachite green, 10 mM ammonium molybdate, 1 M HCl, 3.4% ethanol, 0.01% tween 20). Colour is allowed to develop for 5 minutes and the absorbance at 600 nm is measured spectrophotometrically. The $IC_{50}$ values are determined from the absorbance readings using no compound and no enzyme controls.

The compounds of the invention demonstrated on target enzyme activity with the majority of compounds tested showing Gyrase ATPase activity $IC_{50}$ values less than 1 µg/mL, with most of these being less than 0.1 µg/mL.

Bacterial Assay Determination of Antibacterial Activity

Compounds of the invention were tested for antimicrobial activity by susceptibility testing in liquid or on solid media. MICs for compounds against each strain were determined by the broth microdilution or agar dilution method according to the guidelines of the Clinical Laboratories and Standards Institute, formerly the National Committee for Clinical Laboratory Standards (Clinical Laboratories and Standards Institute. *Methods for Dilution Antimicrobial Susceptibility Tests for Bacteria That Grow Aerobically; Approved Standard—Seventh Edition*. Document M7-A7. CLSI, Wayne, Pa., 2006; Clinical Laboratories and Standards Institute. The Gram positive bacterial strains tested include *S. aureus* (*Staphylococcus aureus* (Isolate ID ATCC 29213)), *S. epidermidis* (*Staphylococcus epidermidis* (Isolate ID ATCC 12228)), *E. faecalis* (*Enterococcus faecalis* (Isolate ID ATCC 29212)), *E. faecium* (*Enterococcus faecium* (Isolate ID ATCC 700221)), *S. pyogenes* (*Streptococcus pyogenes* (Isolate ID ATCC 51339)) and *S. pneumoniae* (*Streptococcus pneumoniae* (Isolate ID ATCC 49619)). The Gram negative bacterial strains tested include *H. influenzae* (*Haemophilus influenzae* (Isolate ID ATCC 49247)), *A. baumannii* (*Acinetobacter baumannii* (Isolate ID ATCC 19606)), *E. coli* (*Escherichia coli* (Isolate ID ATCC 25922)), *K. pneumoniae* (*Klebsiella pneumoniae* (Isolate ID ATCC 13882)), *L. pneumophila* (*Legionella pneumophila* (Isolate ID ATCC 33152)), *M. catarrhalis* (*Moraxella catarrhalis* (Isolate ID ATCC 25240)) and *N. gonorrhoeae* (*Neisseria gonorrhoeae* (Isolate ID ATCC 49226)).

Gram Positive Antibacterial Activity

Representative compounds of the invention were tested for activity against one or more Gram positive bacterial strains and the results are presented in Tables 1 and 2.

TABLE 1

*S. aureus* (ATCC 29213) minimal inhibitory concentration (MIC)

| MIC (µg/mL) | Representative compound example number |
|---|---|
| ≤1 | 1, 2, 3, 4, 6, 7, 8, 10, 12, 13, 14, 15, 17, 18, 22, 23, 24, 25, 26, 27, 28, 29, 30, 31, 32, 33, 34, 35, 36, 37, 38, 39, 40, 42, 43, 48, 49, 50, 53, 54, 55, 56, 57, 58, 59, 60, 61, 62, 63, 64, 67, 68, 69, 70, 71, 73, 74, 75, 76, 77, 78, 80, 81, 82, 83, 84, 87, 88, 92, 93, 94, 95, 96, 98, 100, 101, 104, 106, 107, 108, 111, 112, 113, 114, 115, 116, 118, 119, 120, 121, 122, 125, 127, 128, 130, 131, 154, 155, 156, 157, 158, 162, 164, 168, 173, 175, 176, 177, 178, 182, 183, 185, 187, 188, 191, 192, 193, 197, 198, 202 |
| 2 | 16, 20, 45, 52, 65, 66, 79, 85, 91, 99, 103, 109, 110, 150, 151, 159, 196, 199 |
| 4 | 11, 21, 46, 51, 97, 186 |
| 8 | 9, 47, 72, 86, 89, 174 |
| 16 | 5, 41, 44, 90, 102, 105, 117, 194 |

TABLE 2

*S. pyogenes* (ATCC 51339) minimal inhibitory concentration (MIC)

| MIC (µg/mL) | Representative compound example number |
|---|---|
| ≤1 | 1, 2, 3, 4, 5, 6, 7, 8, 9, 10, 11, 12, 14, 15, 16, 17, 18, 20, 21, 22, 23, 24, 25, 26, 27, 28, 29, 30, 31, 32, 33, 34, 35, 36, 37, 38, 39, 40, 42, 43, 45, 48, 49, 50, 51, 52, 53, 54, 55, 56, 58, 59, 60, 61, 62, 63, 64, 65, 66, 67, 68, 69, 70, 71, 73, 74, 75, 76, 77, 78, 80, 81, 82, 83, 84, 85, 86, 87, 88, 91, 92, 93, 94, 95, 96, 97, 98, 99, 100, 101, 103, 104, 105, 106, 107, 108, 109, 110, 111, 112, 113, 114, 115, 116, 117, 118, 119, 120, 121, 122, 125, 127, 128, 130, 131, 154, 155, 156, 157, 158, 159, 162, 164, 168, 173, 175, 176, 178, 182, 183, 185, 187, 188, 191, 192, 197 |
| 2 | 13, 57, 79, 89, 90, 151, 174, 177, 186, 193, 199 |
| 4 | 46 |
| 8 | 47, 72, 150, 163 |
| 16 | 41, 44, 102 |

Gram Negative Antibacterial Activity

Selected compounds of the invention were also tested for activity against the Gram negative bacterial strain *H. influenzae* (ATCC 49247) and the results are presented in Table 3.

TABLE 3

*H. influenzae* (ATCC 49247) minimal inhibitory concentration (MIC)

| MIC (µg/mL) | Representative compound example number |
|---|---|
| ≤2 | 1, 6, 7, 8, 10, 15, 17, 22, 23, 27, 28, 30, 31, 32, 35, 36, 38, 39, 40, 43, 53, 55, 56, 58, 59, 61, 62, 63, 64, 68, 69, 70, 71, 73, 74, 75, 76, 80, 81, 82, 83, 87, 88, 92, 95, 96, 99, 100, 104, 111, 113, 114, 115, 116, 118, 119, 121, 122, 125, 127, 130, 131, 154, 155, 157, 158, 168, 173, 175, 178, 185, 187, 198, 202 |

Pharmacokinetic Assays: Determination of PK Profile

The pharmacokinetic profiles of compounds are determined by measuring the compound concentration in plasma by LC/MS/MS following a single intravenous or peroral administration of the compounds at a dose of 1 or 3 mg/kg individually or in a cassette of up to 5 compounds. The concentrations are described as the mean plasma concentrations at each time point from three animals. Intravenous dose formulation is administered as a single bolus dose through the tail vein. Oral dose formulation is administered to animals by an oral gavage needle. In both cases the dose volume is 5.0 mL/kg. Blood is collected from rats using a jugular vein catheter and from anesthetized mice through a capillary guided into the retro-orbital plexus. The collected blood is then centrifuged to obtain plasma and the compounds extracted into methanol prior to determining the compound concentration by LC/MS/MS.

The pharmacokinetic profiles of selected compounds of the invention were compared directly with their primary alcohol analogues, Compounds A and B below, in the rat assay (IV).

1-Ethyl-3-[5-[2-(hydroxymethyl)pyrimidin-5-yl]-7-(2-pyridyl)-1,3-benzothiazol-2-yl]urea (Compound A)

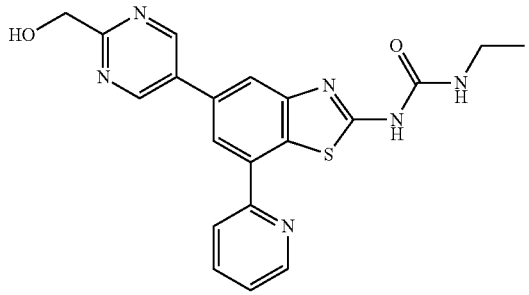 [SMILES: CCNC(=O)Nc1nc2cc(-c3cnc(CO)nc3)cc(-c3ccccn3)c2s1]

MS: 406.99 [M+H]$^+$. $^1$H NMR (400 MHz, DMSO-d$_6$) δ 10.66 (s, 1H), 9.34 (s, 2H), 8.84 (d, J=4.1 Hz, 1H), 8.54 (d, J=8.2 Hz, 1H), 8.40 (d, J=1.1 Hz, 1H), 8.16 (s, 1H), 8.03 (td, J=8.0, 1.6 Hz, 1H), 7.48 (dd, J=7.0, 5.0 Hz, 1H), 6.91 (s, 1H), 5.39 (t, J=6.1 Hz, 1H), 4.72 (d, J=5.9 Hz, 2H), 3.26-3.21 (m, 2H), 1.14 (t, J=7.2 Hz, 3H).

1-Ethyl-3-[5-[6-(hydroxymethyl)-3-pyridyl]-7-(2-pyridyl)-1,3-benzothiazol-2-yl]urea (Compound B)

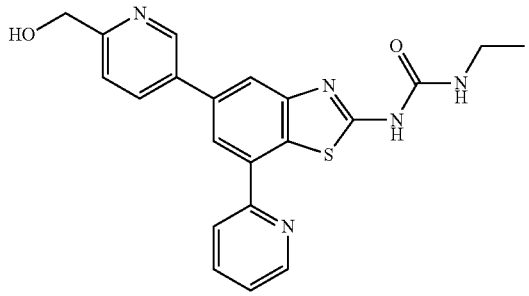 [SMILES: CCNC(=O)Nc1nc2cc(-c3ccc(CO)nc3)cc(-c3ccccn3)c2s1]

MS: 406.15 [M+H]$^+$. $^1$H NMR (400 MHz, DMSO-d$_6$): d 10.62 (br s, 1H), 9.0 (d, J=2.0 Hz, 1H), 8.82 (d, J=4.40 Hz, 1H), 8.50 (d, J=8.0 Hz, 1H), 8.30-8.32 (m, 2H), 7.98-8.03 (m, 2H), 7.60 (d, J=8.40 Hz, 1H), 7.44-7.47 (m, 1H), 6.87 (m, 1H), 5.49 (t, J=5.60 Hz, 1H), 4.65 (d, J=5.60 Hz, 2H).

The results are shown in Table 4 and presented graphically in FIGS. 1A and 1B where the X axis denotes time (hours) and the Y axis denotes plasma concentration (μg/mL). The AUC$_{iv}$, clearance and T$_{1/2}$ values are provided in the following table where AUC$_{iv}$ is area under the curve for intravenous (IV) and T$_{1/2}$ represents the compound half-life. Surprisingly, the compounds of the invention demonstrated improved clearance and an increase in AUC$_{iv}$ and half-life when compared with Compounds A and B.

TABLE 4

AUC$_{iv}$, clearance and half-life values for selected compounds compared against their primary alcohol substituted analogue compounds A and B in the rat assay.

| Cpd No. | Dose (mg/kg) | AUC$_{iv}$ (μg · hr/mL) | Clearance (mL · min/kg) | T$_{1/2}$ (min) |
|---|---|---|---|---|
| A | 3 | 2 | 25 | 81 |
| B | 3 | 1.8 | 28 | 60 |
| 1 | 1 | 3.1 | 4.3 | 203 |
| 17 | 3 | 4 | 12 | 107 |
| 27 | 1 | 1.13 | 13 | 158 |

Animal Models of Infection

Suitable models of infection will be familiar to those skilled in the art and include the following suitable for intravenous (IV) or oral (PO) dosing.

Thigh Infection Model(s)

Mouse:

The thighs of female CD-1 mice (18-22 g), rendered neutropenic by the intraperitoneal administration of cyclophosphamide (150 mg/kg at day −4 and 100 mg/kg at day −1), were inoculated with approximately 2×10$^5$ cfus of S. aureus Smith prepared from a fresh overnight culture. Compounds were administered as indicated 2 hours later and the cfus enumerated at various times post dosing by harvesting the thighs, homogenising in saline on ice and plating serial dilutions onto charcoal containing plates for growth overnight and colony counting. For example, when dosed IV at 30 mg/kg Compounds 1 and 17 demonstrated a ≥3 log drop in colony forming units compared to the control. Similarly, when dosed PO at 100 mg/kg Compound 1 demonstrated a ≥3 log drop in colony forming units compared to the control.

Rat:

The thighs of Sprague-Dawley rats (250-275 g), rendered neutropenic by the intraperitoneal administration of cyclophosphamide (75 mg/kg on days −4 and −1), were inoculated with approximately 1×10$^7$ cfus of S. aureus ATCC29213. Compounds were administered as indicated 2 hours later and the cfus enumerated at various times post dosing by harvesting the thighs, homogenising in PBS on ice and plating serial dilutions onto CLED agar plates for growth at 37° C. and colony counting. For example, when dosed IV at ≤40 mg/kg Compound 1 demonstrated a ≥3 log drop in colony forming units compared to the control.

Lung Infection Model(s)

Mouse (Gram Positive):

Anaesthetised female CD-1 mice (18-22 g) were inoculated intranasally with approximately 10$^6$ cfus of S. pneumoniae ATCC6301 prepared from a fresh overnight culture by placing 50 μl of inoculum on the nares and allowing the mice to inhale. Compounds were administered as indicated at 24 hours post inoculation and the cfus enumerated at 48 hours post inoculation by harvesting the lungs, homogenising in PBS on ice and plating serial dilutions onto TSA+5% blood plates for growth overnight at 37° C. and colony counting. For example, when dosed IV at 30 mg/kg Compound 1 demonstrated a ≥3 log drop in colony forming units compared to the control.

Rat (Gram Negative):

Anaesthetised Sprague-Dawley rats (180-200 g), rendered neutropenic by the intraperitoneal administration of cyclophosphamide, were inoculated intratracheally with approximately 5×10$^7$ cfus of H. influenzae prepared from a fresh culture by delivering 0.5 ml of inoculum in molten agar. Compounds were administered as indicated at 5 hours post inoculation followed by additional daily treatments and the cfus enumerated at 96 hours post inoculation by harvesting the lungs, homogenising in PBS on ice and plating serial dilutions onto bacterial growth medium for cfu determination.

Figure 2:
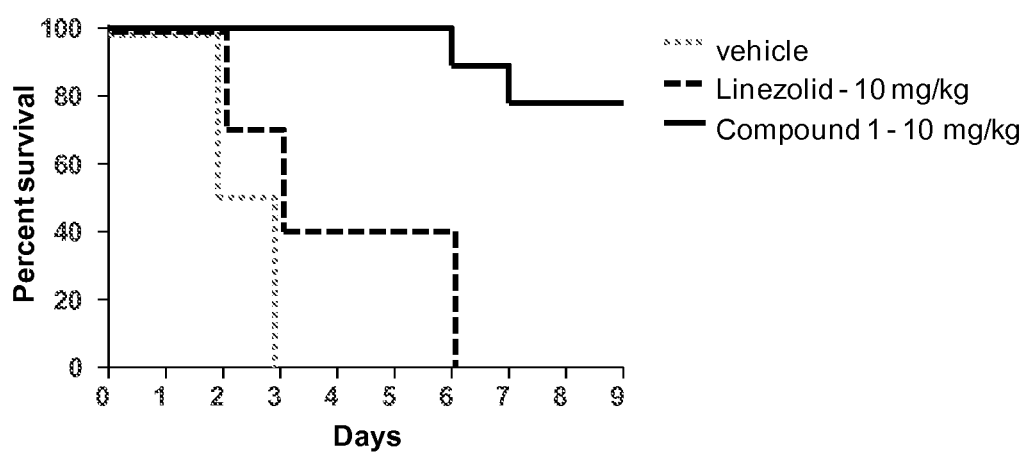
FIG. 2: Shows the comparative survival of mice dosed IV at 10 mg/kg with Compound 1 or Linezolid in the S. pneumoniae 9 day lung infection model where the X axis denotes the number of days and the Y axis denotes the percentage survival.

Mouse Survival Model:

Anaesthetised female CD-1 mice (18-22 g) were inoculated intranasally with approximately 10$^6$ cfus of S. pneumoniae ATCC6301 prepared from a fresh overnight culture by placing 50 µl of inoculum on the nares and allowing the mice to inhale. Compounds are administered as indicated at 24, 48 and 72 hours post inoculation and the mice monitored for survival for seven or nine days after infection. For example, Compound 1 was dosed IV at 10 mg/kg and the results are shown in FIG. 2. Compound 1 demonstrated improved efficacy with 80% of mice surviving at seven or nine days. In comparison, mice dosed with 10 mg/kg Linezolid were dead by day six. Similarly, when Compound 17 was dosed IV at 30 mg/kg 90% of mice survived at day seven.

Skin Infection Model(s)
Mouse:

An area of the skin was stripped from the back dorsal surface of anaesthetised female CD-1 mice (18-22 g) by abrading with a fine emery board following removal of the fur by shaving. An infection was initiated by placing 5 µl of inoculum, containing approximately 10$^7$ cfus of S. aureus Smith prepared from a fresh overnight culture, onto the damaged skin. Compounds were administered as indicated at 4, 20, 28, 44, 52, 68 and 76 hours post inoculation and the cfus enumerated after 5 days post inoculation by harvesting the wounds, homogenising in PBS on ice and plating serial dilutions onto charcoal containing plates for growth overnight and colony counting.

Septicaemia Infection Model(s)
Mouse:

Female CD-1 mice (18-22 g) were inoculated intraperitoneally with approximately 5×10$^5$ cfus of S. aureus Smith prepared from a fresh overnight culture suspended in 5% hog gastric mucin. Compounds were administered as indicated at 2 hours post inoculation and the mice monitored for survival for five days after infection.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication, or information derived from it, or to any matter which is known, is not, and should not be taken as an acknowledgement or admission or any form of suggestion that that prior publication, or information derived from it, or known matter forms part of the common general knowledge in the field of endeavour to which this specification relates.

The invention claimed is:
1. A compound of Formula (I)

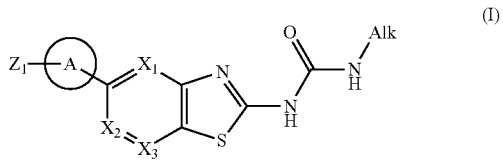

salts, racemates, diastereomers, enantiomers, esters, carbamates, phosphates, sulfates, deuterated forms and prodrugs thereof
wherein
X$_1$ is N or C—R$_1$ where R$_1$ is selected from H, OH, optionally substituted C$_{1-3}$alkyl, optionally substituted C$_{2-3}$alkenyl, optionally substituted C$_{2-3}$alkynyl, optionally substituted C$_{1-3}$alkoxyl, halo, haloC$_{1-3}$alkyl, NH$_2$, optionally substituted NHC$_{1-3}$alkyl, optionally substituted N(C$_{1-3}$alkyl)$_2$, optionally substituted SC$_{1-3}$alkyl and CN;

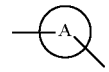

represents Ring A which is selected from saturated or unsaturated monocyclic C$_{3-7}$cycloalkyl, saturated or unsaturated monocyclic 3-7 membered heterocycle, saturated or unsaturated fused bicyclic C$_{8-10}$cycloalkyl, saturated or unsaturated fused bicyclic 8-10 membered-heterocyclyl, C$_{6-10}$aryl and 5-10 membered heteroaryl and may be optionally substituted;

Z$_1$ is a secondary or tertiary alcohol of general formula

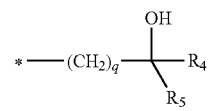

an ester, carbamate, phosphate, sulfate or prodrug thereof as defined below or Z$_1$ is selected from H, OH, optionally substituted C$_{1-6}$alkyl, optionally substituted C$_{2-6}$alkenyl, optionally substituted C$_{2-6}$alkynyl, optionally substituted (CH$_2$)$_m$OC$_{1-6}$alkyl, optionally substituted (CH$_2$)$_m$SC$_{1-6}$alkyl, optionally substituted (CH$_2$)$_m$S(═O)C$_{1-6}$alkyl, halo, optionally substituted haloC$_{1-3}$alkyl, CN and optionally substituted (CH$_2$)$_m$NR$^a$R$^b$ where each R$^a$ and R$^b$ is independently selected from H, optionally substituted C$_{1-6}$alkyl, optionally substituted C$_{3-6}$cycloalkyl and optionally substituted 4-6-membered heterocycle or R$^a$ and R$^b$ join together to form an optionally substituted 4-6-membered heterocyclyl where each m is an integer independently selected from 0, 1, 2 and 3;

X$_2$ is N or C—R$_2$ where R$_2$ is selected from H, OH, optionally substituted C$_{1-6}$alkyl, optionally substituted C$_{2-6}$alkenyl, optionally substituted C$_{2-6}$alkynyl, optionally substituted (CH$_2$)$_m$OC$_{1-6}$alkyl, optionally substituted (CH$_2$)$_m$SC$_{1-6}$alkyl, optionally substituted (CH$_2$)$_m$S(═O)C$_{1-6}$alkyl, optionally substituted (CH$_2$)$_m$O(CH$_2$)$_m$ C$_{3-7}$cycloalkyl, optionally substituted (CH$_2$)$_m$ C$_{3-7}$cycloalkyl, optionally substituted (CH$_2$)$_m$O(CH$_2$)$_m$phenyl, optionally substituted (CH$_2$)$_m$phenyl, optionally substituted (CH$_2$)$_m$O(CH$_2$)$_m$-5-10-membered heterocycle, optionally substituted $(CH_2)_m$-5-10-membered heterocycle, halo, optionally substituted $haloC_{1-3}$alkyl, CN, and optionally substituted $(CH_2)_m NR^a R^b$;

$X_3$ is N or C—$R_3$ where $R_3$ is selected from H, OH, optionally substituted $C_{1-6}$alkyl, optionally substituted $C_{2-6}$alkenyl, optionally substituted $C_{2-6}$alkynyl, optionally substituted $(CH_2)_m OC_{1-6}$alkyl, optionally substituted $(CH_2)_m SC_{1-6}$alkyl, optionally substituted $(CH_2)_m S(\!=\!O)C_{1-6}$alkyl, optionally substituted $(CH_2)_m O(CH_2)_m$ $C_{3-7}$cycloalkyl, optionally substituted $(CH_2)_m$ $C_{3-7}$cycloalkyl, optionally substituted $(CH_2)_m O(CH_2)_m$ phenyl, optionally substituted $(CH_2)_m$phenyl, optionally substituted $(CH_2)_m O(CH_2)_m$-5-10-membered heterocycle, optionally substituted $(CH_2)_m$-5-10-membered heterocycle, halo, $haloC_{1-3}$ alkyl, CN and optionally substituted $(CH_2)_m NR^a R^b$ or $R_3$ is a group of formula

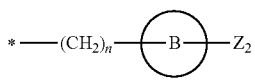

where * represents the point of attachment to the carbon ring atom; n is an integer selected from 0, 1, 2 and 3;

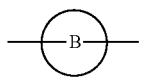

represents Ring B which is selected from saturated or unsaturated monocyclic $C_{3-7}$cycloalkyl, saturated or unsaturated monocyclic 3-7 membered heterocycle, saturated or unsaturated fused bicyclic $C_{8-10}$cycloalkyl, saturated or unsaturated fused bicyclic 8-10 membered-heterocyclyl, $C_{6-10}$aryl and 5-10 membered heteroaryl and may be optionally substituted; and $Z_2$ is a secondary or tertiary alcohol of general formula

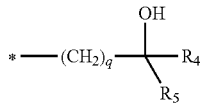

an ester, carbamate, phosphate, sulfate or prodrug thereof as defined below or $Z_2$ is selected from H, OH, optionally substituted $C_{1-6}$alkyl, optionally substituted $C_{2-6}$alkenyl, optionally substituted $C_{2-6}$alkynyl, $(CH_2)_m OC_{1-6}$alkyl, optionally substituted $(CH_2)_m SC_{1-6}$alkyl, optionally substituted $(CH_2)_m S(\!=\!O)C_{1-6}$alkyl, halo, optionally substituted $haloC_{1-3}$alkyl, CN, optionally substituted $(CH_2)_m NR^a R^b$, optionally substituted $(CH_2)_p$-4-6-membered heterocycylic ring, optionally substituted $(CH_2)_p$-spiro-bicyclic-7-11-membered heterocycylic ring and optionally substituted

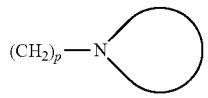

where p is an integer selected from 0, 1, 2 and 3 and

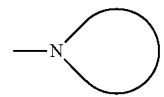

represents an optionally substituted 4-6 membered heterocyclic ring or an optionally substituted spiro bicyclic 7-11-membered heterocyclic ring; and Alk is optionally substituted $C_{1-6}$alkyl, $C_{2-6}$alkenyl, $C_{2-6}$alkynyl, $C_{3-6}$cycloalkyl; and with the proviso that at least one of $Z_1$ or $Z_2$ is present and is a secondary or tertiary alcohol of general formula

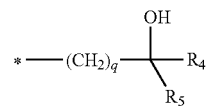

an ester, carbamate, phosphate, sulfate or prodrug thereof wherein q is an integer selected from 0, 1, 2 and 3;

$R_4$ is H or is selected from optionally substituted $C_{1-6}$alkyl, optionally substituted $C_{2-6}$alkenyl, optionally substituted $C_{2-6}$alkynyl, optionally substituted $(CH_2)_t OC_{1-6}$alkyl, optionally substituted $(CH_2)_t OC(\!=\!O)C_{1-6}$alkyl, optionally substituted $(CH_2)_t SC_{1-6}$alkyl, optionally substituted $(CH_2)_t S(\!=\!O)C_{1-6}$alkyl, halo, optionally substituted $haloC_{1-3}$alkyl and optionally substituted $(CH_2)_t NR^a R^b$;

$R_5$ is selected from optionally substituted $C_{1-6}$alkyl, optionally substituted $C_{2-6}$alkenyl, optionally substituted $C_{2-6}$alkynyl, optionally substituted $C_{3-7}$cycloalkyl ring, optionally substituted phenyl, optionally substituted 4-6-membered heterocyclyl ring, optionally substituted 5-6-membered heteroaryl ring, optionally substituted $(CH_2)_t OC_{1-6}$alkyl, optionally substituted $(CH_2)_t OC(\!=\!O)C_{1-6}$alkyl, optionally substituted $(CH_2)_t SC_{1-6}$alkyl, optionally substituted $(CH_2)_t S(\!=\!O)C_{1-6}$alkyl, halo, optionally substituted $haloC_{1-3}$alkyl and optionally substituted $(CH_2)_m NR^a R^b$;

t is an integer selected from 1, 2, 3, 4, 5 and 6;

or $R_4$ and $R_5$ together with the carbon atom to which they are attached form an optionally substituted 4-6-membered heterocyclic ring or $C_{3-7}$cycloalkyl ring; and

* represents the point of attachment to Ring A or Ring B respectively; and further wherein each $(CH_2)$ entity when present may be independently optionally substituted.

2. A compound according to claim 1 wherein $Z_1$ is a secondary or tertiary alcohol of general formula

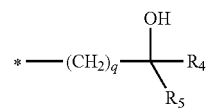

or an ester, carbamate, phosphate, sulfate or prodrug thereof wherein q, $R_4$, $R_5$ and * are as defined in claim 1.

3. A compound according to claim 1 wherein $Z_1$ is a chiral alcohol of general formula

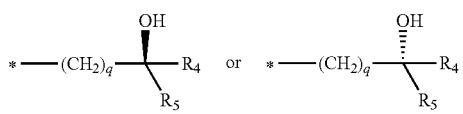

or an ester, carbamate, phosphate, sulfate or prodrug thereof wherein q, $R_4$, $R_5$ and * are as defined in claim 1 provided that $R_4$ and $R_5$ are different.

4. A compound according to claim 1 wherein $X_1$ is C—$R_1$, $X_2$ is C—$R_2$ and $X_3$ is C—$R_3$.

5. A compound according to claim 1 wherein ring A is an optionally substituted 5-6-membered heteroaryl.

6. A compound according to claim 1 wherein $X_1$ is C—$R_1$ and $R_1$ is H or halo.

7. A compound according to claim 1 wherein $X_2$ is C—$R_2$ where $R_2$ is selected from H, OH, optionally substituted $C_{1-6}$alkyl, optionally substituted $C_{2-6}$alkenyl, optionally substituted $OC_{1-6}$alkyl, optionally substituted $SC_{1-6}$alkyl, optionally substituted $S(=O)C_{1-6}$alkyl, an optionally substituted 5-6-membered heterocycle, halo, halo$C_{1-3}$alkyl, CN and optionally substituted $(CH_2)_m NR^a R^b$.

8. A compound according to claim 1 wherein $X_3$ is C—$R_3$ and $R_3$ is H.

9. A compound according to claim 1 wherein $X_3$ is C—$R_3$ and $R_3$ is selected from optionally substituted $C_{1-3}$alkyl, optionally substituted $OC_{1-3}$alkyl, optionally substituted $(CH_2)_m NH_2$, optionally substituted $(CH_2)_m NHC_{1-3}$alkyl and optionally substituted $(CH_2)_m N(C_{1-3}alkyl)_2$ where m is as defined in claim 1.

10. A compound according to claim 1 wherein $X_3$ is C—$R_3$ and $R_3$ is a group of formula

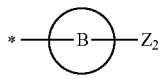

as defined in claim 1.

11. A compound according to claim 10 wherein the compound is of Formula (II):

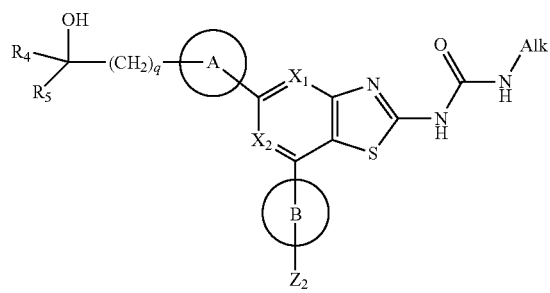

(II)

salts, racemates, diastereomers, enantiomers, esters, carbamates, phosphates, sulfates, deuterated forms and prodrugs thereof
wherein $X_1$, $X_2$, Alk, Ring A, Ring B, $Z_2$, $R_4$, $R_5$ and q are as defined in claim 1.

12. A compound according to claim 11 wherein ring B is an optionally substituted 5-6 membered heteroaryl.

13. A compound according to claim 11 wherein $Z_2$ is H.

14. A compound according to claim 11 wherein $Z_2$ is selected from OH, optionally substituted $C_{1-6}$alkyl, optionally substituted $C_{2-6}$alkenyl, optionally substituted $C_{2-6}$alkynyl, optionally substituted $(CH_2)_m OC_{1-6}$alkyl, optionally substituted $(CH_2)_m SC_{1-6}$alkyl, optionally substituted $(CH_2)_m S(=O)C_{1-6}$alkyl, halo, optionally substituted halo$C_{1-3}$ alkyl, $(CH_2)_m NH_2$, optionally substituted $(CH_2)_m NHC_{1-6}$ alkyl, optionally substituted $(CH_2)_m N(C_{1-6}alkyl)_2$, optionally substituted $(CH_2)_p$-4-6-membered heterocyclic ring, optionally substituted $(CH_2)_p$-spiro-bicyclic-7-11-membered heterocyclic ring and optionally substituted

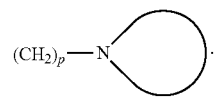

15. A compound according to claim 1 wherein the compound is of general formula (III):

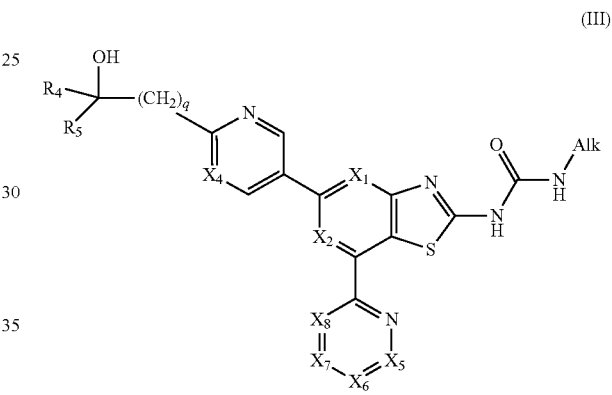

(III)

salts, racemates, diastereomers, enantiomers, esters, carbamates, phosphates, sulfates, deuterated forms and prodrugs thereof
wherein $X_1$, $X_2$, Alk, $R_4$, $R_5$ and q are as defined in claim 1;
$X_4$ is N, CH, C-halo or C—$C_{1-3}$alkoxy;
$X_5$, $X_6$, $X_7$ and $X_8$ are each independently selected from N, C—H or C—$Z_2$ where $Z_2$ is as defined in claim 1 provided that no more than one of $X_5$, $X_6$, $X_7$ or $X_8$ is N.

16. A compound according to claim 1 wherein q is 0.

17. A compound according to claim 1 selected from the group consisting of:
1) 1-ethyl-3-[5-[2-(1-hydroxy-1-methyl-ethyl)pyrimidin-5-yl]-7-(2-pyridyl)-1,3-benzothiazol-2-yl]urea;
2) 1-ethyl-3-[7-[4-[(3-hydroxy-3-methyl-azetidin-1-yl)methyl]-2-pyridyl]-5-[2-(1-hydroxy-1-methyl-ethyl)pyrimidin-5-yl]-1,3-benzothiazol-2-yl]urea;
3) 1-ethyl-3-[5-[2-(1-hydroxy-1-methyl-ethyl)pyrimidin-5-yl]-6-(tetrahydrofuran-2-ylmethoxy)-1,3-benzothiazol-2-yl]urea;
4) 1-ethyl-3-[6-fluoro-5-[6-[hydroxy(3-pyridyl)methyl]-3-pyridyl]-1,3-benzothiazol-2-yl]urea;
5) 1-(2-hydroxyethyl)-3-[5-[2-(1-hydroxy-1-methyl-ethyl)pyrimidin-5-yl]-7-(2-pyridyl)-1,3-benzothiazol-2-yl]urea;
6) 1-ethyl-3-[5-[5-(1-hydroxyethyl)pyrazin-2-yl]-7-(2-pyridyl)-1,3-benzothiazol-2-yl]urea;
7) 1-[5-[2-[(1S*,2R*)-1,2-dihydroxypropyl]pyrimidin-5-yl]-7-(2-pyridyl)-1,3-benzothiazol-2-yl]-3-ethyl-urea (mixture 1-[5-[2-[(1S,2R)-1,2-dihydroxypropyl]pyrimidin-5-yl]-7-(2-pyridyl)-1,3-benzothiazol-2-yl]-3-ethyl-urea; and 1-[5-[2-[(1R,2S)-1,2-dihydroxypropyl]pyrimidin-5-yl]-7-(2-pyridyl)-1,3-benzothiazol-2-yl]-3-ethyl-urea);

8) 1-[5-[2-[(3R*,4S*)-3,4-dihydroxytetrahydropyran-4-yl]pyrimidin-5-yl]-7-(2-pyridyl)-1,3-benzothiazol-2-yl]-3-ethyl-urea (mixture 1-[5-[2-[(3R,4S)-3,4-dihydroxytetrahydropyran-4-yl]pyrimidin-5-yl]-7-(2-pyridyl)-1,3-benzothiazol-2-yl]-3-ethyl-urea; and 1-[5-[2-[(3S,4R)-3,4-dihydroxytetrahydropyran-4-yl]pyrimidin-5-yl]-7-(2-pyridyl)-1,3-benzothiazol-2-yl]-3-ethyl-urea);

9) 1-ethyl-3-[5-[4-(1-hydroxyethyl)triazol-1-yl]-7-(2-pyridyl)-1,3-benzothiazol-2-yl]urea;

10) 1-ethyl-3-[5-[2-(1-hydroxy-1-methyl-ethyl)pyrimidin-5-yl]-7-pyrimidin-2-yl-1,3-benzothiazol-2-yl]urea;

11) 1-ethyl-3-[5-[4-(1-hydroxy-1-methyl-ethyl)imidazol-1-yl]-7-(2-pyridyl)-1,3-benzothiazol-2-yl]urea;

12) 1-ethyl-3-[5-[2-(1-hydroxy-1-methyl-ethyl)pyrimidin-5-yl]-7-methoxy-1,3-benzothiazol-2-yl]urea;

13) 1-ethyl-3-[5-[2-(1-hydroxy-1-methyl-ethyl)pyrimidin-5-yl]-7-(methoxymethyl)-1,3-benzothiazol-2-yl]urea;

14) 1-ethyl-3-[5-[2-(1-hydroxyethyl)pyrimidin-5-yl]-7-[(6-methyl-3-pyridyl)methoxy]-1,3-benzothiazol-2-yl]urea;

15) 1-ethyl-3-[5-[2-(1-hydroxyethyl)pyrimidin-5-yl]-7-[4-(methylsulfanylmethyl)-2-pyridyl]-1,3-benzothiazol-2-yl]urea;

16) 1-ethyl-3-[5-[2-(1-hydroxyethyl)pyrimidin-5-yl]-7-[4-(methylsulfinylmethyl)-2-pyridyl]-1,3-benzothiazol-2-yl]urea;

17) 1-ethyl-3-[5-[2-(1-hydroxyethyl)pyrimidin-5-yl]-7-(2-pyridyl)-1,3-benzothiazol-2-yl]urea;

18) 1-[5-[2-(ethylcarbamoylamino)-7-(2-pyridyl)-1,3-benzothiazol-5-yl]pyrimidin-2-yl]ethyl 4-methylpiperazine-1-carboxylate;

19) 4-[1-[5-[2-(ethylcarbamoylamino)-7-(2-pyridyl)-1,3-benzothiazol-5-yl]pyrimidin-2-yl]ethoxy]-4-oxo-butanoic acid;

20) O4-[1-[5-[2-(ethylcarbamoylamino)-7-(2-pyridyl)-1,3-benzothiazol-5-yl]pyrimidin-2-yl]-1-methyl-ethyl] O1-methyl butanedioate;

21) 4-[1-[5-[2-(ethylcarbamoylamino)-7-(2-pyridyl)-1,3-benzothiazol-5-yl]pyrimidin-2-yl]-1-methyl-ethoxy]-4-oxo-butanoic acid;

22) 1-ethyl-3-[5-[2-[(1R)-1-hydroxyethyl]pyrimidin-5-yl]-7-(2-pyridyl)-1,3-benzothiazol-2-yl]urea;

23) 1-ethyl-3-[5-[2-[(1S)-1-hydroxyethyl]pyrimidin-5-yl]-7-(2-pyridyl)-1,3-benzothiazol-2-yl]urea;

24) 1-ethyl-3-[5-[6-[hydroxy-(1-methylimidazol-2-yl)methyl]-3-pyridyl]-7-(2-pyridyl)-1,3-benzothiazol-2-yl]urea;

25) 1-ethyl-3-[5-[2-(1-hydroxy-1-methyl-ethyl)pyrimidin-5-yl]-7-[5-(morpholinomethyl)-2-pyridyl]-1,3-benzothiazol-2-yl]urea;

26) 1-ethyl-3-[5-[2-(1-hydroxy-1-methyl-ethyl)pyrimidin-5-yl]-7-[4-(pyrrolidin-1-ylmethyl)-2-pyridyl]-1,3-benzothiazol-2-yl]urea;

27) 1-ethyl-3-[5-[6-(1-hydroxy-1-methyl-ethyl)-3-pyridyl]-7-(2-pyridyl)-1,3-benzothiazol-2-yl]urea;

28) 1-ethyl-3-[5-[2-(1-hydroxy-1-methyl-ethyl)pyrimidin-5-yl]-7-[4-(morpholinomethyl)-2-pyridyl]-1,3-benzothiazol-2-yl]urea;

29) 1-ethyl-3-[5-[2-(1-hydroxy-1-methyl-ethyl)pyrimidin-5-yl]-7-[4-[(3-hydroxypyrrolidin-1-yl)methyl]-2-pyridyl]-1,3-benzothiazol-2-yl]urea;

30) 1-ethyl-3-[7-[4-[(3-hydroxyazetidin-1-yl)methyl]-2-pyridyl]-5-[2-(1-hydroxy-1-methyl-ethyl)pyrimidin-5-yl]-1,3-benzothiazol-2-yl]urea;

31) 1-ethyl-3-[5-[2-(1-hydroxy-1-methyl-ethyl)pyrimidin-5-yl]-7-[4-[(3-methoxyazetidin-1-yl)methyl]-2-pyridyl]-1,3-benzothiazol-2-yl]urea;

32) 1-ethyl-3-[5-[2-(1-hydroxy-1-methyl-ethyl)pyrimidin-5-yl]-7-[4-(2-morpholinoethoxy)-2-pyridyl]-1,3-benzothiazol-2-yl]urea;

33) 1-ethyl-3-[5-[2-(1-hydroxy-1-methyl-ethyl)pyrimidin-5-yl]-7-[4-(1-morpholinoethyl)-2-pyridyl]-1,3-benzothiazol-2-yl]urea;

34) 1-[7-[4-[(3,3-difluoropyrrolidin-1-yl)methyl]-2-pyridyl]-5-[2-(1-hydroxy-1-methyl-ethyl)pyrimidin-5-yl]-1,3-benzothiazol-2-yl]-3-ethyl-urea;

35) 1-ethyl-3-[7-[4-[[(3S)-3-fluoropyrrolidin-1-yl]methyl]-2-pyridyl]-5-[2-(1-hydroxy-1-methyl-ethyl)pyrimidin-5-yl]-1,3-benzothiazol-2-yl]urea;

36) 1-ethyl-3-[7-[4-[[(3R)-3-fluoropyrrolidin-1-yl]methyl]-2-pyridyl]-5-[2-(1-hydroxy-1-methyl-ethyl)pyrimidin-5-yl]-1,3-benzothiazol-2-yl]urea;

37) 1-[7-[4-[(3,3-difluoro-1-piperidyl)methyl]-2-pyridyl]-5-[2-(1-hydroxy-1-methyl-ethyl)pyrimidin-5-yl]-1,3-benzothiazol-2-yl]-3-ethyl-urea;

38) 1-ethyl-3-[5-[2-(1-hydroxy-1-methyl-ethyl)pyrimidin-5-yl]-7-[4-(3-morpholinopropoxy)-2-pyridyl]-1,3-benzothiazol-2-yl]urea;

39) 1-ethyl-3-[5-[2-(1-hydroxy-1-methyl-ethyl)pyrimidin-5-yl]-7-pyrazin-2-yl-1,3-benzothiazol-2-yl]urea;

40) 1-[5-[2-(1,2-dihydroxyethyl)pyrimidin-5-yl]-7-(2-pyridyl)-1,3-benzothiazol-2-yl]-3-ethyl-urea;

41) 1-[7-(dimethylaminomethyl)-6-hydroxy-5-[6-(1-hydroxy-1-methyl-ethyl)-3-pyridyl]-1,3-benzothiazol-2-yl]-3-ethyl-urea;

42) 1-ethyl-3-[5-[2-(1-hydroxy-1-methyl-ethyl)pyrimidin-5-yl]-7-[4-[[(3R)-3-methoxypyrrolidin-1-yl]methyl]-2-pyridyl]-1,3-benzothiazol-2-yl]urea;

43) 1-ethyl-3-[5-[2-(1-hydroxy-1-methyl-ethyl)pyrimidin-5-yl]-7-(6-methylpyrimidin-4-yl)-1,3-benzothiazol-2-yl]urea;

44) 1-ethyl-3-[6-hydroxy-5-[6-(1-hydroxy-1-methyl-ethyl)-3-pyridyl]-7-(morpholinomethyl)-1,3-benzothiazol-2-yl]urea;

45) 1-[6-[2-(ethylcarbamoylamino)-5-[2-(1-hydroxy-1-methyl-ethyl)pyrimidin-5-yl]-1,3-benzothiazol-7-yl]-3-pyridyl]-4-methyl-piperidine-4-carboxylic acid;

46) 2-[6-[2-(ethylcarbamoylamino)-5-[2-(1-hydroxy-1-methyl-ethyl)pyrimidin-5-yl]-1,3-benzothiazol-7-yl]-3-pyridyl]acetic acid;

47) 1-ethyl-3-[5-[2-(1-hydroxycyclohexyl)pyrimidin-5-yl]-7-(2-pyridyl)-1,3-benzothiazol-2-yl]urea;

48) 1-ethyl-3-[5-[2-(1-hydroxy-1-methyl-ethyl)thiazol-5-yl]-7-(2-pyridyl)-1,3-benzothiazol-2-yl]urea;

49) 1-ethyl-3-[5-[5-(1-hydroxy-1-methyl-ethyl)pyrazin-2-yl]-7-(2-pyridyl)-1,3-benzothiazol-2-yl]urea;

50) 1-[2-[2-(ethylcarbamoylamino)-5-[2-(1-hydroxy-1-methyl-ethyl)pyrimidin-5-yl]-1,3-benzothiazol-7-yl]-4-pyridyl]-4-methyl-piperidine-4-carboxylic acid;

51) 1-[6-[2-(ethylcarbamoylamino)-5-[2-(1-hydroxy-1-methyl-ethyl)pyrimidin-5-yl]-1,3-benzothiazol-7-yl]-2-pyridyl]-4-methyl-piperidine-4-carboxylic acid;

52) 1-[4-[2-(ethylcarbamoylamino)-5-[2-(1-hydroxy-1-methyl-ethyl)pyrimidin-5-yl]-1,3-benzothiazol-7-yl]pyrimidin-2-yl]-4-methyl-piperidine-4-carboxylic acid;
53) 1-[7-[4-[(cyclopropylamino)methyl]-2-pyridyl]-5-[2-(1-hydroxy-1-methyl-ethyl)pyrimidin-5-yl]-1,3-benzothiazol-2-yl]-3-ethyl-urea;
54) 4-[[2-[2-(ethylcarbamoylamino)-5-[2-(1-hydroxy-1-methyl-ethyl)pyrimidin-5-yl]-1,3-benzothiazol-7-yl]-4-pyridyl]amino]-1-methyl-cyclohexanecarboxylic acid;
55) 1-ethyl-3-[5-[2-(1-hydroxyethyl)pyrimidin-5-yl]-7-[4-(morpholinomethyl)-2-pyridyl]-1,3-benzothiazol-2-yl]urea;
56) 1-ethyl-3-[5-[2-(1-hydroxy-1-methyl-ethyl)pyrimidin-5-yl]-7-[5-(2-morpholinoethoxy)-2-pyridyl]-1,3-benzothiazol-2-yl]urea;
57) 1-[5-[2-(1-hydroxy-1-methyl-ethyl)pyrimidin-5-yl]-7-(2-pyridyl)-1,3-benzothiazol-2-yl]-3-propyl-urea;
58) 1-[5-[2-[cyclopropyl(hydroxy)methyl]pyrimidin-5-yl]-7-(2-pyridyl)-1,3-benzothiazol-2-yl]-3-ethyl-urea;
59) 1-ethyl-3-[5-[2-(1-hydroxypropyl)pyrimidin-5-yl]-7-(2-pyridyl)-1,3-benzothiazol-2-yl]urea;
60) 1-ethyl-3-[5-[2-(1-hydroxy-2,2-dimethyl-propyl)pyrimidin-5-yl]-7-(2-pyridyl)-1,3-benzothiazol-2-yl]urea;
61) 1-ethyl-3-[5-[2-(1-hydroxybutyl)pyrimidin-5-yl]-7-(2-pyridyl)-1,3-benzothiazol-2-yl]urea
62) [(1R)-1-[5-[2-(ethylcarbamoylamino)-7-(2-pyridyl)-1,3-benzothiazol-5-yl]pyrimidin-2-yl]ethyl](2R)-2-amino-3-methyl-butanoate;
63) [(1S)-1-[5-[2-(ethylcarbamoylamino)-7-(2-pyridyl)-1,3-benzothiazol-5-yl]pyrimidin-2-yl]ethyl](2R)-2-amino-3-methyl-butanoate;
64) 1-ethyl-3-[7-[4-[[(3S)-3-fluoropyrrolidin-1-yl]methyl]-2-pyridyl]-5-[2-(1-hydroxyethyl)pyrimidin-5-yl]-1,3-benzothiazol-2-yl]urea;
65) 1-ethyl-3-[7-[4-[(3-hydroxyazetidin-1-yl)methyl]-2-pyridyl]-5-[2-(1-hydroxyethyl)pyrimidin-5-yl]-1,3-benzothiazol-2-yl]urea;
66) 1-ethyl-3-[5-[2-(1-hydroxyethyl)pyrimidin-5-yl]-7-[4-[(3-hydroxy-3-methyl-azetidin-1-yl)methyl]-2-pyridyl]-1,3-benzothiazol-2-yl]urea;
67) 1-ethyl-3-[5-[2-(1-hydroxy-1-methyl-ethyl)pyrimidin-5-yl]-7-[4-[(3-hydroxy-3-methyl-pyrrolidin-1-yl)methyl]-2-pyridyl]-1,3-benzothiazol-2-yl]urea;
68) 1-ethyl-3-[5-[2-(1-hydroxyethyl)pyrimidin-5-yl]-7-[4-[(3-methylmorpholin-4-yl)methyl]-2-pyridyl]-1,3-benzothiazol-2-yl]urea;
69) 1-[7-[4-[[(2R,6S)-2,6-dimethylmorpholin-4-yl]methyl]-2-pyridyl]-5-[2-(1-hydroxyethyl)pyrimidin-5-yl]-1,3-benzothiazol-2-yl]-3-ethyl-urea;
70) 1-ethyl-3-[5-[2-(1-hydroxyethyl)pyrimidin-5-yl]-7-[4-[(2,2,3,3,5,5,6,6-octadeuteriomorpholin-4-yl)methyl]-2-pyridyl]-1,3-benzothiazol-2-yl]urea;
71) 1-[7-[4-[(2,5-dimethylmorpholin-4-yl)methyl]-2-pyridyl]-5-[2-(1-hydroxyethyl)pyrimidin-5-yl]-1,3-benzothiazol-2-yl]-3-ethyl-urea;
72) (2S)-1-[[2-[2-(ethylcarbamoylamino)-5-[2-(1-hydroxyethyl)pyrimidin-5-yl]-1,3-benzothiazol-7-yl]-4-pyridyl]methyl]pyrrolidine-2-carboxylic acid;
73) 1-ethyl-3-[5-[2-(1-hydroxyethyl)pyrimidin-5-yl]-7-[4-(6-oxa-2-azaspiro[3.3]heptan-2-ylmethyl)-2-pyridyl]-1,3-benzothiazol-2-yl]urea;
74) 1-[5-[2-(ethylcarbamoylamino)-7-[4-(1-hydroxy-1-methyl-ethyl)-2-pyridyl]-1,3-benzothiazol-5-yl]pyrimidin-2-yl]-4-methyl-piperidine-4-carboxylic acid;
75) 1-ethyl-3-[5-[2-(1-hydroxyethyl)pyrimidin-5-yl]-7-[4-(2-morpholinoethoxy)-2-pyridyl]-1,3-benzothiazol-2-yl]urea;
76) 1-ethyl-3-[5-[2-(1-hydroxyethyl)pyrimidin-5-yl]-7-[4-[(3-methoxyazetidin-1-yl)methyl]-2-pyridyl]-1,3-benzothiazol-2-yl]urea;
77) 1-ethyl-3-[5-[2-(1-hydroxyethyl)pyrimidin-5-yl]-7-[4-[[(3R)-3-hydroxypyrrolidin-1-yl]methyl]-2-pyridyl]-1,3-benzothiazol-2-yl]urea;
78) 1-ethyl-3-[5-[2-(1-hydroxy-1-methyl-ethyl)pyrimidin-5-yl]-7-[4-(2-methoxyethylamino)pyrimidin-2-yl]-1,3-benzothiazol-2-yl]urea;
79) 1-ethyl-3-[7-[4-(4-ethylpiperazin-1-yl)pyrimidin-2-yl]-5-[2-(1-hydroxy-1-methyl-ethyl)pyrimidin-5-yl]-1,3-benzothiazol-2-yl]urea;
80) 1-ethyl-3-[5-[2-(1-hydroxy-1-methyl-ethyl)pyrimidin-5-yl]-7-[4-(2-methoxyethoxy)-2-pyridyl]-1,3-benzothiazol-2-yl]urea;
81) 1-ethyl-3-[5-[2-(1-hydroxy-2-morpholino-ethyl)pyrimidin-5-yl]-7-(2-pyridyl)-1,3-benzothiazol-2-yl]urea;
82) 1-[5-[2-(1-hydroxy-1-methyl-ethyl)pyrimidin-5-yl]-7-(2-pyridyl)-1,3-benzothiazol-2-yl]-3-methyl-urea;
83) 1-[5-[2-(1-hydroxyethyl)pyrimidin-5-yl]-7-(2-pyridyl)-1,3-benzothiazol-2-yl]-3-methyl-urea;
84) 1-ethyl-3-[5-[2-(1-hydroxyethyl)pyrimidin-5-yl]-7-[4-[(3-hydroxy-3-methyl-pyrrolidin-1-yl)methyl]-2-pyridyl]-1,3-benzothiazol-2-yl]urea;
85) 1-ethyl-3-[7-[4-(2-hydroxyethylamino)pyrimidin-2-yl]-5-[2-(1-hydroxy-1-methyl-ethyl)pyrimidin-5-yl]-1,3-benzothiazol-2-yl]urea;
86) 1-ethyl-3-[7-[4-(3-hydroxy-3-methyl-azetidin-1-yl)pyrimidin-2-yl]-5-[2-(1-hydroxy-1-methyl-ethyl)pyrimidin-5-yl]-1,3-benzothiazol-2-yl]urea;
87) 1-[6-[2-(ethylcarbamoylamino)-5-[2-(1-hydroxy-1-methyl-ethyl)pyrimidin-5-yl]-1,3-benzothiazol-7-yl]pyrimidin-4-yl]-4-methyl-piperidine-4-carboxylic acid;
88) 1-[5-[2-(ethylcarbamoylamino)-7-[4-(1-hydroxyethyl)-2-pyridyl]-1,3-benzothiazol-5-yl]pyrimidin-2-yl]-4-methyl-piperidine-4-carboxylic acid;
89) [1-[5-[2-(ethylcarbamoylamino)-7-(2-pyridyl)-1,3-benzothiazol-5-yl]pyrimidin-2-yl]-1-methyl-ethyl]-4-methylpiperazine-1-carboxylate;
90) 1-ethyl-3-[5-[2-(1-hydroxyethyl)pyrimidin-5-yl]-7-(4-hydroxy-2-pyridyl)-1,3-benzothiazol-2-yl]urea;
91) 1-ethyl-3-[5-[2-(1-hydroxy-1-methyl-ethyl)pyrimidin-5-yl]-7-[4-(2-morpholinoethylamino)pyrimidin-2-yl]-1,3-benzothiazol-2-yl]urea;
92) 1-ethyl-3-[5-[2-(1-hydroxyethyl)pyrimidin-5-yl]-7-[4-(2-methoxyethoxy)-2-pyridyl]-1,3-benzothiazol-2-yl]urea;
93) 1-ethyl-3-[5-[2-(1-hydroxyethyl)pyrimidin-5-yl]-7-[4-(3-methoxyazetidin-1-yl)pyrimidin-2-yl]-1,3-benzothiazol-2-yl]urea;
94) 1-ethyl-3-[5-[2-(1-hydroxyethyl)pyrimidin-5-yl]-7-(4-morpholinopyrimidin-2-yl)-1,3-benzothiazol-2-yl]urea;
95) 1-ethyl-3-[5-[6-(1-hydroxyethyl)-3-pyridyl]-7-(2-pyridyl)-1,3-benzothiazol-2-yl]urea;
96) 1-ethyl-3-[7-(2-pyridyl)-5-[6-(2,2,2-trifluoro-1-hydroxy-ethyl)-3-pyridyl]-1,3-benzothiazol-2-yl]urea;
97) 1-[2-[2-(ethylcarbamoylamino)-5-[2-(1-hydroxy-1-methyl-ethyl)pyrimidin-5-yl]-1,3-benzothiazol-7-yl]pyrimidin-4-yl]-4-methyl-piperidine-4-carboxylic acid;
98) 1-ethyl-3-[5-[2-(1-ethyl-1-hydroxy-propyl)pyrimidin-5-yl]-7-(2-pyridyl)-1,3-benzothiazol-2-yl]urea;

99) 1-[5-[2-(ethylcarbamoylamino)-7-[5-(1-hydroxy-1-methyl-ethyl)-2-pyridyl]-1,3-benzothiazol-5-yl]pyrimidin-2-yl]-4-methyl-piperidine-4-carboxylic acid;
100) 1-[7-[4-(diethoxyphosphorylmethyl)-2-pyridyl]-5-[2-(1-hydroxyethyl)pyrimidin-5-yl]-1,3-benzothiazol-2-yl]-3-ethyl-urea;
101) 1-ethyl-3-[5-[2-(1-hydroxy-1-methyl-ethyl)pyrimidin-5-yl]-7-[4-(morpholinomethyl)-2-pyridyl]-1,3-benzothiazol-2-yl]urea;
102) 1-ethyl-3-[5-[2-(1-hydroxy-1-methyl-ethyl)pyrimidin-5-yl]-7-[6-(morpholinomethyl)pyrazin-2-yl]-1,3-benzothiazol-2-yl]urea;
103) 1-ethyl-3-[5-[2-(1-hydroxy-1-methyl-ethyl)pyrimidin-5-yl]-7-[4-[(2-hydroxy-2-methyl-propyl)amino]pyrimidin-2-yl]-1,3-benzothiazol-2-yl]urea;
104) 1-ethyl-3-[5-[2-(1-hydroxyethyl)pyrimidin-5-yl]-7-[4-(tetrahydrofuran-2-ylmethoxy)-2-pyridyl]-1,3-benzothiazol-2-yl]urea;
105) 1-ethyl-3-[7-[4-(3-hydroxyazetidin-1-yl)pyrimidin-2-yl]-5-[2-(1-hydroxyethyl)pyrimidin-5-yl]-1,3-benzothiazol-2-yl]urea;
106) 1-ethyl-3-[7-(5-fluoro-4-morpholino-pyrimidin-2-yl)-5-[2-(1-hydroxyethyl)pyrimidin-5-yl]-1,3-benzothiazol-2-yl]urea;
107) 1-ethyl-3-[5-[2-(1-hydroxy-1-methyl-ethyl)pyrimidin-5-yl]-7-[4-[4-(2-methoxyethyl)piperazin-1-yl]pyrimidin-2-yl]-1,3-benzothiazol-2-yl]urea;
108) 1-ethyl-3-[7-[4-(morpholinomethyl)-2-pyridyl]-5-[6-(2,2,2-trifluoro-1-hydroxy-ethyl)-3-pyridyl]-1,3-benzothiazol-2-yl]urea;
109) 1-[6-[2-(ethylcarbamoylamino)-5-[2-(1-hydroxyethyl)pyrimidin-5-yl]-1,3-benzothiazol-7-yl]pyridin-4-yl]-4-methyl-piperidine-4-carboxylic acid;
110) 1-[2-[2-(ethylcarbamoylamino)-5-[2-(1-hydroxy-1-methyl-ethyl)pyrimidin-5-yl]-1,3-benzothiazol-7-yl]-4-pyridyl]piperidine-4-carboxylic acid;
111) 1-ethyl-3-[5-[2-(4-hydroxytetrahydropyran-4-yl)pyrimidin-5-yl]-7-(2-pyridyl)-1,3-benzothiazol-2-yl]urea;
112) 1-ethyl-3-[5-[2-(1-hydroxyethyl)pyrimidin-5-yl]-7-[4-(2-oxa-7-azaspiro[3.5]nonan-7-ylmethyl)-2-pyridyl]-1,3-benzothiazol-2-yl]urea;
113) 1-ethyl-3-[5-[2-(3-hydroxyoxetan-3-yl)pyrimidin-5-yl]-7-(2-pyridyl)-1,3-benzothiazol-2-yl]urea;
114) 1-ethyl-3-[5-[2-(1-hydroxy-1-methyl-ethyl)pyrimidin-5-yl]-7-[4-[(3-methoxy-3-methyl-azetidin-1-yl)methyl]-2-pyridyl]-1,3-benzothiazol-2-yl]urea;
115) 1-ethyl-3-[5-[2-(1-hydroxyethyl)pyrimidin-5-yl]-7-pyrimidin-2-yl-1,3-benzothiazol-2-yl]urea;
116) 1-ethyl-3-[7-[4-(2-morpholino ethoxy)-2-pyridyl]-5-[6-(2,2,2-trifluoro-1-hydroxy-ethyl)-3-pyridyl]-1,3-benzothiazol-2-yl]urea;
117) 1-[2-[2-(ethylcarbamoylamino)-5-[2-(1-hydroxyethyl)pyrimidin-5-yl]-1,3-benzothiazol-7-yl]pyrimidin-4-yl]-4-methyl-piperidine-4-carboxylic acid;
118) 1-[5-[2-[(1R*,2R*)-1,2-dihydroxypropyl]pyrimidin-5-yl]-7-(2-pyridyl)-1,3-benzothiazol-2-yl]-3-ethyl-urea (mixture 1-[5-[2-[(1R,2R)-1,2-dihydroxypropyl]pyrimidin-5-yl]-7-(2-pyridyl)-1,3-benzothiazol-2-yl]-3-ethyl-urea; and 1-[5-[2-[(1S,2S)-1,2-dihydroxypropyl]pyrimidin-5-yl]-7-(2-pyridyl)-1,3-benzothiazol-2-yl]-3-ethyl-urea);
119) 1-ethyl-3-[5-[2-(1-hydroxycyclopentyl)pyrimidin-5-yl]-7-(2-pyridyl)-1,3-benzothiazol-2-yl]urea;
120) 1-ethyl-3-[5-[2-(1-hydroxy-1-methyl-ethyl)pyrimidin-5-yl]-7-[5-(morpholinomethyl)pyrimidin-2-yl]-1,3-benzothiazol-2-yl]urea;
121) 1-ethyl-3-[5-[2-[(1R)-1-hydroxyethyl]pyrimidin-5-yl]-7-[4-(morpholinomethyl)-2-pyridyl]-1,3-benzothiazol-2-yl]urea;
122) 1-ethyl-3-[5-[2-[(1S)-1-hydroxyethyl]pyrimidin-5-yl]-7-[4-(morpholinomethyl)-2-pyridyl]-1,3-benzothiazol-2-yl]urea;
123) 4-[3-[5-[2-(ethylcarbamoylamino)-7-(2-pyridyl)-1,3-benzothiazol-5-yl]pyrimidin-2-yl]oxetan-3-yl]oxy-4-oxo-butanoic acid;
124) 4-[2-[5-[2-(ethylcarbamoylamino)-7-(2-pyridyl)-1,3-benzothiazol-5-yl]pyrimidin-2-yl]-2-hydroxy-propoxy]-4-oxo-butanoic acid;
125) 1-ethyl-3-[5-[2-(4-hydroxytetrahydropyran-4-yl)pyrimidin-5-yl]-7-[4-(morpholinomethyl)-2-pyridyl]-1,3-benzothiazol-2-yl]urea;
126) 1-[5-[2-(ethylcarbamoylamino)-7-(2-pyridyl)-1,3-benzothiazol-5-yl]pyrimidin-2-yl]ethyl 2-aminoacetate;
127) 1-ethyl-3-[5-[2-(4-hydroxytetrahydrothiopyran-4-yl)pyrimidin-5-yl]-7-(2-pyridyl)-1,3-benzothiazol-2-yl]urea;
128) 1-ethyl-3-[5-[2-(4-hydroxy-1-methyl-4-piperidyl)pyrimidin-5-yl]-7-(2-pyridyl)-1,3-benzothiazol-2-yl]urea;
129) [1-[5-[2-(ethylcarbamoylamino)-7-(2-pyridyl)-1,3-benzothiazol-5-yl]pyrimidin-2-yl]-1-methyl-ethyl]2-(2-aminoethylamino)acetate;
130) 1-[5-[2-[(1R*,2S*)-3,3-difluoro-1,2-dihydroxy-propyl]pyrimidin-5-yl]-7-(2-pyridyl)-1,3-benzothiazol-2-yl]-3-ethyl-urea (mixture 1-[5-[2-[(1R,2S)-3,3-difluoro-1,2-dihydroxy-propyl]pyrimidin-5-yl]-7-(2-pyridyl)-1,3-benzothiazol-2-yl]-3-ethyl-urea; and 1-[5-[2-[(1S,2R)-3,3-difluoro-1,2-dihydroxy-propyl]pyrimidin-5-yl]-7-(2-pyridyl)-1,3-benzothiazol-2-yl]-3-ethyl-urea);
131) 1-ethyl-3-[7-(2-pyridyl)-5-[2-[(1R*,2S*)-3,3,3-trifluoro-1,2-dihydroxy-propyl]pyrimidin-5-yl]-1,3-benzothiazol-2-yl]urea (mixture 1-ethyl-3-[7-(2-pyridyl)-5-[2-[(1R,2S)-3,3,3-trifluoro-1,2-dihydroxy-propyl]pyrimidin-5-yl]-1,3-benzothiazol-2-yl]urea; and 1-ethyl-3-[7-(2-pyridyl)-5-[2-[(1S,2R)-3,3,3-trifluoro-1,2-dihydroxy-propyl]pyrimidin-5-yl]-1,3-benzothiazol-2-yl]urea);
132) [1-[5-[2-(ethylcarbamoylamino)-7-(2-pyridyl)-1,3-benzothiazol-5-yl]pyrimidin-2-yl]-1-methyl-ethyl] (2S)-2-aminopropanoate;
133) 4-[(1S)-1-[5-[2-(ethylcarbamoylamino)-7-(2-pyridyl)-1,3-benzothiazol-5-yl]pyrimidin-2-yl]ethoxy]-4-oxo-butanoic acid;
134) 4-[(1R)-1-[5-[2-(ethylcarbamoylamino)-7-(2-pyridyl)-1,3-benzothiazol-5-yl]pyrimidin-2-yl]ethoxy]-4-oxo-butanoic acid;
135) 1-[5-[2-(1,2-dihydroxy-1-methyl-ethyl)pyrimidin-5-yl]-7-[4-(morpholinomethyl)-2-pyridyl]-1,3-benzothiazol-2-yl]-3-ethyl-urea;
136) 1-[5-[2-(ethylcarbamoylamino)-7-(2-pyridyl)-1,3-benzothiazol-5-yl]pyrimidin-2-yl]ethyl 2-amino-2-methyl-propanoate;
137) 1-[5-[2-(ethylcarbamoylamino)-7-(2-pyridyl)-1,3-benzothiazol-5-yl]pyrimidin-2-yl]ethyl 3-aminopropanoate;
138) tert-butyl 4-[5-[2-(ethylcarbamoylamino)-7-(2-pyridyl)-1,3-benzothiazol-5-yl]pyrimidin-2-yl]-4-hydroxy-piperidine-1-carboxylate;
139) 1-ethyl-3-[5-[2-(4-hydroxy-1-oxo-thian-4-yl)pyrimidin-5-yl]-7-(2-pyridyl)-1,3-benzothiazol-2-yl]urea;

140) [1-[5-[2-(ethylcarbamoylamino)-7-(2-pyridyl)-1,3-benzothiazol-5-yl]pyrimidin-2-yl]-1-methyl-ethyl]2-(dimethylamino)acetate;
141) [1-[5-[2-(ethylcarbamoylamino)-7-(2-pyridyl)-1,3-benzothiazol-5-yl]pyrimidin-2-yl]-1-methyl-ethyl]2-morpholinoacetate;
142) 1-[7-[4-[[(2R,6S)-2,6-dimethylmorpholin-4-yl]methyl]-2-pyridyl]-5-[2-[(1R)-1-hydroxyethyl]pyrimidin-5-yl]-1,3-benzothiazol-2-yl]-3-ethyl-urea;
143) 1-[7-[4-[[(2R,6S)-2,6-dimethylmorpholin-4-yl]methyl]-2-pyridyl]-5-[2-[(1S)-1-hydroxyethyl]pyrimidin-5-yl]-1,3-benzothiazol-2-yl]-3-ethyl-urea;
144) [1-[5-[2-(ethylcarbamoylamino)-7-(2-pyridyl)-1,3-benzothiazol-5-yl]pyrimidin-2-yl]-1-methyl-ethyl]5-aminopentanoate;
145) [1-[5-[2-(ethylcarbamoylamino)-7-(2-pyridyl)-1,3-benzothiazol-5-yl]pyrimidin-2-yl]-1-methyl-ethyl]5-(dimethylamino)pentanoate;
146) [1-[5-[2-(ethylcarbamoylamino)-7-(2-pyridyl)-1,3-benzothiazol-5-yl]pyrimidin-2-yl]-1-methyl-ethyl]2-aminoacetate;
147) 1-[7-[4-[(3,3-difluoroazetidin-1-yl)methyl]-2-pyridyl]-5-[2-(1-hydroxy-1-methyl-ethyl)pyrimidin-5-yl]-1,3-benzothiazol-2-yl]-3-ethyl-urea;
148) 1-[7-[4-[[(2R,6S)-2,6-dimethylmorpholin-4-yl]methyl]-2-pyridyl]-5-[2-(3-hydroxyoxetan-3-yl)pyrimidin-5-yl]-1,3-benzothiazol-2-yl]-3-ethyl-urea;
149) 1-[5-[2-(ethylcarbamoylamino)-7-(2-pyridyl)-1,3-benzothiazol-5-yl]pyrimidin-2-yl]ethyl dihydrogen phosphate;
150) 1-ethyl-3-[5-[2-(1-hydroxy-1-methyl-ethyl)pyrimidin-5-yl]-6-(2-methoxyethylamino)-1,3-benzothiazol-2-yl]urea;
151) 1-ethyl-3-[5-[2-(1-hydroxy-1-methyl-ethyl)pyrimidin-5-yl]-7-morpholino-1,3-benzothiazol-2-yl]urea;
152) [(1R)-1-[5-[2-(ethylcarbamoylamino)-7-(2-pyridyl)-1,3-benzothiazol-5-yl]pyrimidin-2-yl]ethyl]dihydrogen phosphate;
153) [(1S)-1-[5-[2-(ethylcarbamoylamino)-7-(2-pyridyl)-1,3-benzothiazol-5-yl]pyrimidin-2-yl]ethyl]dihydrogen phosphate;
154) 1-ethyl-3-[5-[2-(3-hydroxyoxetan-3-yl)pyrimidin-5-yl]-7-[4-(morpholinomethyl)-2-pyridyl]-1,3-benzothiazol-2-yl]urea;
155) 1-ethyl-3-[7-[4-[(3-methoxyazetidin-1-yl)methyl]-2-pyridyl]-5-[6-[2,2,2-trifluoro-1-hydroxy-ethyl]-3-pyridyl]-1,3-benzothiazol-2-yl]urea;
156) 1-[7-[4-[(4,4-difluoro-1-piperidyl)methyl]-2-pyridyl]-5-[2-(1-hydroxy-1-methyl-ethyl)pyrimidin-5-yl]-1,3-benzothiazol-2-yl]-3-ethyl-urea;
157) 1-[5-[2-[1,2-dihydroxy-1-methyl-ethyl]pyrimidin-5-yl]-7-(2-pyridyl)-1,3-benzothiazol-2-yl]-3-ethyl-urea;
158) 1-ethyl-3-[5-[2-[1-hydroxyethyl]pyrimidin-5-yl]-7-(5-methyl-2-pyridyl)-1,3-benzothiazol-2-yl]urea;
159) 1-ethyl-3-[5-[2-(1-hydroxy-1-methyl-ethyl)pyrimidin-5-yl]-7-[4-[(4-methylpiperazin-1-yl)methyl]-2-pyridyl]-1,3-benzothiazol-2-yl]urea;
160) [(1S)-1-[5-[2-(ethylcarbamoylamino)-7-(2-pyridyl)-1,3-benzothiazol-5-yl]pyrimidin-2-yl]ethyl](2S)-pyrrolidine-2-carboxylate;
161) [(1R)-1-[5-[2-(ethylcarbamoylamino)-7-(2-pyridyl)-1,3-benzothiazol-5-yl]pyrimidin-2-yl]ethyl](2S)-pyrrolidine-2-carboxylate;
162) tert-butyl 3-[5-[2-(ethylcarbamoylamino)-7-(2-pyridyl)-1,3-benzothiazol-5-yl]pyrimidin-2-yl]-3-hydroxy-azetidine-1-carboxylate;
163) 1-ethyl-3-[5-[2-(3-hydroxyazetidin-3-yl)pyrimidin-5-yl]-7-(2-pyridyl)-1,3-benzothiazol-2-yl]urea;
164) 1-[7-[4-[[(2R,6S)-2,6-dimethylmorpholin-4-yl]methyl]-2-pyridyl]-5-[2-(1-hydroxy-1-methyl-ethyl)pyrimidin-5-yl]-1,3-benzothiazol-2-yl]-3-ethyl-urea;
165) [1-[5-[2-(ethylcarbamoylamino)-7-(2-pyridyl)-1,3-benzothiazol-5-yl]pyrimidin-2-yl]-1-methyl-ethyl]2-[[(2S)-pyrrolidine-2-carbonyl]amino]acetate;
166) [1-[5-[2-(ethylcarbamoylamino)-7-(2-pyridyl)-1,3-benzothiazol-5-yl]pyrimidin-2-yl]-1-methyl-ethyl](2S)-pyrrolidine-2-carboxylate;
167) 4-[3-[5-[7-[4-[[(2R,6S)-2,6-dimethylmorpholin-4-yl]methyl]-2-pyridyl]-2-(ethylcarbamoylamino)-1,3-benzothiazol-5-yl]pyrimidin-2-yl]oxetan-3-yl]oxy-4-oxo-butanoic acid;
168) 1-ethyl-3-[7-[5-(1-hydroxyethyl)-2-pyridyl]-5-[2-(1-hydroxyethyl)pyrimidin-5-yl]-1,3-benzothiazol-2-yl]urea;
169) [1-[5-[2-(ethylcarbamoylamino)-7-(2-pyridyl)-1,3-benzothiazol-5-yl]pyrimidin-2-yl]-1-methyl-ethyl]2-(2-morpholinoethylamino)acetate;
170) 2-[[2-[1-[5-[2-(ethylcarbamoylamino)-7-(2-pyridyl)-1,3-benzothiazol-5-yl]pyrimidin-2-yl]-1-methyl-ethoxy]-2-oxo-ethyl]amino]acetic acid;
171) (2S)-2-amino-4-[1-[5-[2-(ethylcarbamoylamino)-7-(2-pyridyl)-1,3-benzothiazol-5-yl]pyrimidin-2-yl]-1-methyl-ethoxy]-4-oxo-butanoic acid;
172) [1-[5-[2-(ethylcarbamoylamino)-7-(2-pyridyl)-1,3-benzothiazol-5-yl]pyrimidin-2-yl]-1-methyl-ethyl]-4-aminobutanoate;
173) 1-ethyl-3-[5-[2-(4-hydroxy-1,1-dioxo-thian-4-yl)pyrimidin-5-yl]-7-(2-pyridyl)-1,3-benzothiazol-2-yl]urea;
174) 1-ethyl-3-[5-[2-(4-hydroxy-4-piperidyl)pyrimidin-5-yl]-7-(2-pyridyl)-1,3-benzothiazol-2-yl]urea;
175) 1-[7-[4-[(3-ethoxyazetidin-1-yl)methyl]-2-pyridyl]-5-[2-(1-hydroxy-1-methyl-ethyl)pyrimidin-5-yl]-1,3-benzothiazol-2-yl]-3-ethyl-urea;
176) 1-ethyl-3-[5-[2-(1-hydroxy-1-methyl-ethyl)pyrimidin-5-yl]-6-methoxy-1,3-benzothiazol-2-yl]urea;
177) 1-ethyl-3-[6-fluoro-5-[2-(1-hydroxy-1-methyl-ethyl)pyrimidin-5-yl]-1,3-benzothiazol-2-yl]urea;
178) 1-ethyl-3-[7-(3-fluoro-4-methoxy-2-pyridyl)-5-[2-[1-hydroxyethyl]pyrimidin-5-yl]-1,3-benzothiazol-2-yl]urea;
179) 3-[[2-[1-[5-[2-(ethylcarbamoylamino)-7-(2-pyridyl)-1,3-benzothiazol-5-yl]pyrimidin-2-yl]-1-methyl-ethoxy]-2-oxo-ethyl]amino]propanoic acid;
180) [1-[5-[2-(ethylcarbamoylamino)-7-(2-pyridyl)-1,3-benzothiazol-5-yl]pyrimidin-2-yl]-1-methyl-ethyl](3R)-pyrrolidine-3-carboxylate;
181) [1-[5-[2-(ethylcarbamoylamino)-7-(2-pyridyl)-1,3-benzothiazol-5-yl]pyrimidin-2-yl]-1-methyl-ethyl](3R)-morpholine-3-carboxylate;
182) 1-[6-(cyclopropylmethoxy)-5-[2-(1-hydroxy-1-methyl-ethyl)pyrimidin-5-yl]-1,3-benzothiazol-2-yl]-3-ethyl-urea;
183) 1-ethyl-3-[5-[2-(1-hydroxy-1-methyl-ethyl)pyrimidin-5-yl]-6-(2-methoxyethoxy)-1,3-benzothiazol-2-yl]urea;
184) [1-[5-[2-(ethylcarbamoylamino)-7-(2-pyridyl)-1,3-benzothiazol-5-yl]pyrimidin-2-yl]-1-methyl-ethyl]2-(2-phosphonooxyethylamino)acetate;
185) 1-ethyl-3-[5-[2-[1-hydroxyethyl]pyrimidin-5-yl]-7-[4-(thiomorpholinomethyl)-2-pyridyl]-1,3-benzothiazol-2-yl]urea;

186) 1-ethyl-3-[6-(2-hydroxyethoxy)-5-[2-(1-hydroxy-1-methyl-ethyl)pyrimidin-5-yl]-1,3-benzothiazol-2-yl] urea;
187) 1-ethyl-3-[5-[2-(1-hydroxy-1-methyl-ethyl)pyrimidin-5-yl]-7-[4-(thiomorpholinomethyl)-2-pyridyl]-1,3-benzothiazol-2-yl]urea;
188) 1-ethyl-3-[5-[2-(1-hydroxy-1-methyl-ethyl)pyrimidin-5-yl]-7-[4-[(1-oxo-1,4-thiazinan-4-yl)methyl]-2-pyridyl]-1,3-benzothiazol-2-yl]urea;
189) 1-ethyl-3-[5-[2-(1-hydroxy-1-methyl-ethyl)pyrimidin-5-yl]-6-[2-methoxyethyl(methyl)amino]-1,3-benzothiazol-2-yl]urea;
190) [1-[5-[2-(ethylcarbamoylamino)-7-(2-pyridyl)-1,3-benzothiazol-5-yl]pyrimidin-2-yl]-1-methyl-ethyl]dihydrogen phosphate;
191) 1-[7-[4-[(1,1-dioxo-1,4-thiazinan-4-yl)methyl]-2-pyridyl]-5-[2-(1-hydroxy-1-methyl-ethyl)pyrimidin-5-yl]-1,3-benzothiazol-2-yl]-3-ethyl-urea;
192) 1-[6-[(3,4-dimethoxyphenyl)methoxy]-5-[2-(1-hydroxy-1-methyl-ethyl)pyrimidin-5-yl]-1,3-benzothiazol-2-yl]-3-ethyl-urea;
193) 1-ethyl-3-[5-[2-[1-hydroxyethyl]pyrimidin-5-yl]-6-(tetrahydrofuran-2-ylmethoxy)-1,3-benzothiazol-2-yl] urea;
194) 1-ethyl-3-[5-[2-[1-hydroxyethyl]pyrimidin-5-yl]-6-morpholino-1,3-benzothiazol-2-yl]urea;
195) 1-[7-[(3S)-3-aminopyrrolidin-1-yl]-5-[2-(1-hydroxy-1-methyl-ethyl)pyrimidin-5-yl]-1,3-benzothiazol-2-yl]-3-ethyl-urea;
196) 1-ethyl-3-[7-[4-[(2-hydroxyethylamino)methyl]-2-pyridyl]-5-[2-(1-hydroxy-1-methyl-ethyl)pyrimidin-5-yl]-1,3-benzothiazol-2-yl]urea;
197) 1-ethyl-3-[5-[5-(1-hydroxyethyl)-3-pyridyl]-7-(2-pyridyl)-1,3-benzothiazol-2-yl]urea;
198) 1-ethyl-3-[5-[2-(1-hydroxy-1-methyl-ethyl)pyrimidin-5-yl]-7-[4-[(2,2,3,3,5,5,6,6-octadeuteriomorpholin-4-yl)methyl]-2-pyridyl]-1,3-benzothiazol-2-yl] urea;
199) 1-ethyl-3-[5-[2-(1-hydroxy-1-methyl-ethyl)pyrimidin-5-yl]-6-(2-morpholinoethoxy)-1,3-benzothiazol-2-yl]urea;
200) 1-ethyl-3-[5-[2-(1-hydroxy-1-methyl-ethyl)pyrimidin-5-yl]-6-(2-methoxyethylsulfanyl)-1,3-benzothiazol-2-yl]urea;
201) 1-ethyl-3-[5-[2-(1-hydroxy-1-methyl-ethyl)pyrimidin-5-yl]-6-(2-methoxyethylsulfinyl)-1,3-benzothiazol-2-yl]urea; and
202) 1-ethyl-3-[5-[2-[(1R)-1-hydroxyethyl]pyrimidin-5-yl]-7-(5-methoxy-2-pyridyl)-1,3-benzothiazol-2-yl] urea;

salts, racemates, diastereomers, enantiomers, esters, carbamates, phosphates, sulfates, deuterated forms and prodrugs thereof.

18. A method for the treatment of a bacterial infection comprising administration of a compound as defined in claim 1 or a pharmaceutically acceptable salt, racemate, diastereomer, enantiomer, ester, carbamate, phosphate, sulfate, deuterated form or prodrug thereof to a subject suffering from said infection.

19. A method according to claim 18 wherein the bacterial infection is a Gram-positive infection, Gram-negative infection, community acquired bacterial pneumonia (CABP), hospital acquired bacterial pneumonia (HABP), or ventilator acquired bacterial pneumonia (VABP).

20. A method according to claim 18 wherein the bacterial infection is a respiratory infection, a skin or skin structure infection, a urinary tract infection, an intra-abdominal infection or a blood stream infection.

21. A pharmaceutical composition comprising a compound as defined in claim 1 or a pharmaceutically acceptable salt, racemate, diastereomer, enantiomer, ester, carbamate, phosphate, sulfate, deuterated form or prodrug thereof and an excipient or carrier.

22. A process for the manufacture of a compound as defined in claim 1 comprising the step(s) of:
coupling an intermediate of formula (i-a) with a precursor of formula (ii-a):

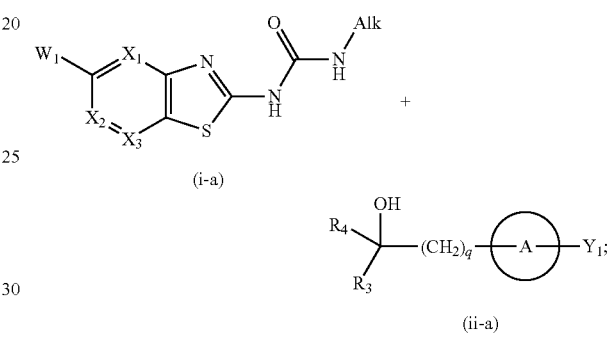

or alternatively coupling an intermediate of formula (i-b) with a precursor of formula (ii-b):

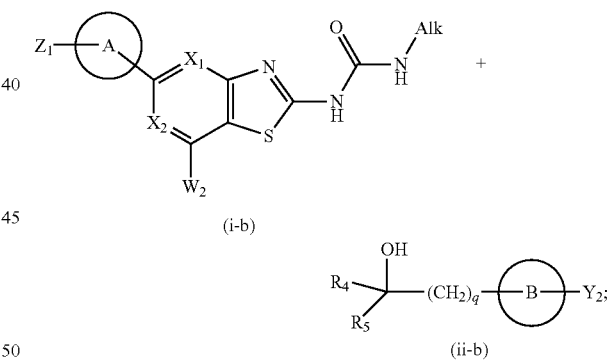

under coupling conditions wherein
$W_1$ and $W_2$ are selected from halo, boronic acid or a boronate ester thereof, a stannylated moiety and triflate;
$Y_1$ and $Y_2$ are selected from H, halo, boronic acid or a boronate ester thereof, a stannylated moiety and triflate; and
ring A, ring B, Alk, $X_1$, $X_2$, $X_3$, $R_4$, $R_5$ and q are as defined in claim 1.